US012502439B2

(12) United States Patent
Lowman et al.

(10) Patent No.: US 12,502,439 B2
(45) **Date of Patent: *Dec. 23, 2025**

(54) ACTIVATABLE ANTIBODIES THAT BIND EPIDERMAL GROWTH FACTOR RECEPTOR AND METHODS OF USE THEREOF

(71) Applicant: CytomX Therapeutics, Inc., South San Francisco, CA (US)

(72) Inventors: Henry Bernard Lowman, El Granada, CA (US); Luc Roland Desnoyers, San Francisco, CA (US); Shouchun Liu, Burlingame, CA (US); James William West, Bend, OR (US); Jason Gary Sagert, San Mateo, CA (US); Olga Vasiljeva, Cupertino, CA (US); Elizabeth-Edna Mary Menendez, San Mateo, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/396,187

(22) Filed: Dec. 26, 2023

(65) Prior Publication Data

US 2024/0398998 A1 Dec. 5, 2024

Related U.S. Application Data

(62) Division of application No. 16/892,973, filed on Jun. 4, 2020, now Pat. No. 11,890,354, which is a division of application No. 15/875,947, filed on Jan. 19, 2018, now Pat. No. 10,709,799, which is a division of application No. 15/381,972, filed on Dec. 16, 2016, now Pat. No. 9,889,211, which is a division of application No. 14/815,111, filed on Jul. 31, 2015, now Pat. No. 9,545,442, which is a division of application No. 13/872,052, filed on Apr. 26, 2013, now Pat. No. 9,120,853.

(60) Provisional application No. 61/639,796, filed on Apr. 27, 2012, provisional application No. 61/662,204, filed on Jun. 20, 2012, provisional application No. 61/749,220, filed on Jan. 4, 2013, provisional application No. 61/749,529, filed on Jan. 7, 2013, provisional application No. 61/763,237, filed on Feb. 11, 2013.

(51) Int. Cl.

| | |
|---|---|
| ***C12N 5/09*** | (2010.01) |
| ***A61K 39/395*** | (2006.01) |
| ***A61K 47/68*** | (2017.01) |
| ***A61K 49/00*** | (2006.01) |
| ***C07K 16/28*** | (2006.01) |
| ***C07K 16/30*** | (2006.01) |
| ***C12N 5/06*** | (2006.01) |
| ***C12N 15/00*** | (2006.01) |
| ***G01N 33/574*** | (2006.01) |
| ***G01N 33/58*** | (2006.01) |
| ***G01N 33/68*** | (2006.01) |
| *A61K 39/00* | (2006.01) |

(52) U.S. Cl.

CPC ...... *A61K 49/0058* (2013.01); *A61K 39/3955* (2013.01); *A61K 47/68031* (2023.08); *A61K 47/6849* (2017.08); *C07K 16/2863* (2013.01); *C07K 16/2866* (2013.01); *C07K 16/30* (2013.01); *G01N 33/57492* (2013.01); *G01N 33/58* (2013.01); *G01N 33/6872* (2013.01); *A61K 2039/505* (2013.01); *C07K 2317/14* (2013.01); *C07K 2317/24* (2013.01); *C07K 2317/56* (2013.01); *C07K 2317/90* (2013.01); *C07K 2317/92* (2013.01); *C07K 2317/94* (2013.01); *G01N 2333/71* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell et al. |
| 4,522,811 | A | 6/1985 | Eppstein et al. |
| 5,030,719 | A | 7/1991 | Umemoto et al. |
| 5,151,510 | A | 9/1992 | Stec et al. |
| 5,525,491 | A | 6/1996 | Hton et al. |
| 7,465,790 | B2 | 12/2008 | Waldmann et al. |
| 7,666,817 | B2 | 2/2010 | Daugherty et al. |
| 8,034,959 | B2 | 10/2011 | Ng et al. |
| 8,226,945 | B2 | 7/2012 | Ebens, Jr. et al. |
| 8,513,390 | B2 | 8/2013 | Stagliano et al. |

(Continued)

FOREIGN PATENT DOCUMENTS

| | | |
|---|---|---|
| EA | 2010/00704 | 12/2010 |
| EP | 1324771 | 6/2011 |

(Continued)

OTHER PUBLICATIONS

Affara et al., "Delineating protease functions during cancer development" Proteases and Cancer, 2009, 539:1-32.

(Continued)

*Primary Examiner* — Elizabeth C. Kemmerer
*Assistant Examiner* — Regina M DeBerry
(74) *Attorney, Agent, or Firm* — Fish & Richardson P.C.

(57) ABSTRACT

The invention relates generally to activatable antibodies that include a masking moiety (MM), a cleavable moiety (CM), and an antibody (AB) that specifically binds to epidermal growth factor receptor (EGFR), and to methods of making and using these anti-EGFR activatable antibodies in a variety of therapeutic, diagnostic and prophylactic indications.

20 Claims, 27 Drawing Sheets

Specification includes a Sequence Listing.

(56) References Cited

U.S. PATENT DOCUMENTS

| | | | |
|---|---|---|---|
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,809,504 | B2 | 8/2014 | Lauermann |
| 8,895,702 | B2 | 11/2014 | Williams et al. |
| 9,120,853 | B2 | 9/2015 | Lowman et al. |
| 9,169,321 | B2 | 10/2015 | Daugherty et al. |
| 9,453,078 | B2 | 9/2016 | Stagliano et al. |
| 9,540,440 | B2 | 1/2017 | Lowman et al. |
| 9,545,442 | B2 | 1/2017 | Lowman et al. |
| 9,737,623 | B2 | 8/2017 | Desnoyers et al. |
| 9,889,211 | B2 | 2/2018 | Lowman et al. |
| 10,059,762 | B2 | 8/2018 | Stagliano et al. |
| 10,077,300 | B2 | 9/2018 | Daugherty et al. |
| 10,118,961 | B2 | 11/2018 | Stagliano et al. |
| 10,533,053 | B2 | 1/2020 | Lowman et al. |
| 10,568,977 | B2 | 2/2020 | Desnoyers et al. |
| 10,709,799 | B2 | 7/2020 | Lowman et al. |
| 11,890,354 | B2 | 2/2024 | Lowman et al. |
| 2002/0016481 | A1 | 2/2002 | Sasaki et al. |
| 2002/0127564 | A1 | 9/2002 | Nolan |
| 2004/0109855 | A1 | 6/2004 | Waldmann et al. |
| 2004/0111757 | A1 | 6/2004 | Zhang et al. |
| 2007/0213511 | A1 | 9/2007 | Kunz et al. |
| 2008/0114153 | A1 | 5/2008 | Steeves et al. |
| 2008/0175847 | A1 | 7/2008 | Yan et al. |
| 2009/0062142 | A1 | 3/2009 | Daugherty et al. |
| 2009/0148905 | A1 | 6/2009 | Ashman et al. |
| 2009/0304719 | A1 | 12/2009 | Daugherty et al. |
| 2010/0189651 | A1 | 7/2010 | Stagliano et al. |
| 2010/0189727 | A1 | 7/2010 | Rodeck et al. |
| 2011/0178279 | A1 | 7/2011 | Williams et al. |
| 2013/0004481 | A1 | 1/2013 | Solca et al. |
| 2013/0060010 | A1 | 3/2013 | Williams et al. |
| 2013/0315906 | A1 | 11/2013 | Lowman et al. |
| 2016/0193332 | A1 | 7/2016 | Lowman et al. |
| 2017/0196996 | A1 | 7/2017 | Lowman et al. |
| 2018/0333507 | A1 | 11/2018 | Lowman et al. |
| 2020/0270350 | A1 | 8/2020 | Lowman et al. |
| 2021/0023243 | A1 | 1/2021 | Lowman et al. |

FOREIGN PATENT DOCUMENTS

| | | |
|---|---|---|
| WO | WO 1994/11026 | 5/1994 |
| WO | WO 1997/31024 | 8/1997 |
| WO | WO 1998/11126 | 3/1998 |
| WO | WO 2001/79271 | 10/2001 |
| WO | WO 2001/079480 | 10/2001 |
| WO | WO 2001/91798 | 12/2001 |
| WO | WO 2004/009638 | 1/2004 |
| WO | WO 2007/008712 | 1/2007 |
| WO | WO 2007/105027 | 9/2007 |
| WO | WO 2008/101177 | 8/2008 |
| WO | WO 2009/011572 | 1/2009 |
| WO | WO 2009/025846 | 2/2009 |
| WO | WO 2009/068649 | 6/2009 |
| WO | WO 2009/140242 | 11/2009 |
| WO | WO 2010/081173 | 7/2010 |
| WO | WO 2010/129609 | 11/2010 |
| WO | WO 2011/109789 | 9/2011 |
| WO | WO 2013/043071 | 3/2013 |
| WO | WO 2013/163631 | 10/2013 |
| WO | WO 2014/197612 | 12/2014 |
| WO | WO 2015/013671 | 1/2015 |

OTHER PUBLICATIONS

Azzopardi et al.,"Cetuximab pharmacokinetics influences progression-free survival of metastatic colorectal cancer patients" Clinical Cancer Research, Oct. 2011, 17(19):6329-37.

Bagshawe, "Antibody-directed enzyme prodrug therapy (ADEPT) for cancer" Expert review of anticancer therapy, Oct. 2006, 6(10):1421-31.

Baldrick, "Pharmaceutical excipient development: the need for preclinical guidance" Regulatory toxicology and pharmacology, Oct. 2000, 32(2):210-8.

Baselga et al., "Phase I studies of anti-epidermal growth factor receptor chimeric antibody C225 alone and in combination with cisplatin" Journal of Clinical Oncology, Feb. 14, 2000, 18(4):904-914.

Benjamin et al., "Tolerance to rat monoclonal antibodies. Implications for serotherapy" The Journal of experimental medicine, Jun. 1986, 163(6):1539-52.

Bhattacharya et al., "Impact of genetic variation on three dimensional structure and function of proteins," PLoS One, Mar. 15, 2017 12(3):e0171355.

Boulware et al., "Evolutionary optimization of peptide substrates for proteases that exhibit rapid hydrolysis kinetics" Biotechnology and bioengineering Jun. 15, 2010, 106(3):339-46.

Bowie et al., "A method to identify protein sequences that fold into a known three-dimensional structure" Science, Jul. 12, 1991, 253(5016):164-70.

Brinks et al., "Preclinical models used for immunogenicity prediction of therapeutic proteins", Pharmaceutical research, Jul. 2013, 30(7):1719-28.

cancer.gov [online], "Cetuximab" NCI Cancer Drug Information, 2006, retrieved on Jul. 18, 2014, retrieved from URL<http://www.cancer.gov/cancertopics/druginfo/cetuximab>, 3 pages.

Cancerres.aacrjournals.org [online], Desnoyers et al., "Abstract 4570: Development of a proteolytically activatable EGFR Probody for cancer therapy", Apr. 15, 2013, retrieved on Oct. 15, 2015, retrieved from URL http://cancerres.aacrjournals.org/content/73/8 Supplement/4570, 2 pages.

Charman, "Lipids, lipophilic drugs, and oral drug delivery—some emerging concepts" Journal of pharmaceutical sciences, Aug. 2000, 89(8):967-78.

Chiller et al., "Cellular events during induction of immunologic unresponsiveness in adult mice" The Journal of Immunology, Jun. 1971, 106(6):1647-53.

Chirinos-Rojas et al., "Use of a solid-phase random peptide library to identify inhibitors of TNF-α mediated cytotoxicity in vitro" Cytokine, Apr. 1997, 9(4):226-32.

Chothia et al., "Canonical structures for the hypervariable regions of immunoglobulins" Journal of molecular biology, Aug. 20, 1987, 196(4):901-17.

Chothia et al., "Conformations of immunoglobulin hypervariable regions" Nature, Dec. 1989, 342(6252):877-83.

Chung et al., "Cetuximab-induced anaphylaxis and IgE specific for galactose-α-1, 3- galactose" New England journal of medicine, Mar. 13, 2008, 358(11):1109-17.

Cwirla et al., "Peptides on phage: a vast library of peptides for identifying ligands" Proceedings of the National Academy of Sciences, Aug. 1990, 87(16):6378-82.

Darragh et al., "Tumor detection by imaging proteolytic activity" Cancer research, Feb. 15, 2010, 70(4):1505-12.

Davies et al., "Antibody-antigen complexes" Annual review of biochemistry, Jul. 1990, 59(1):439-73.

Donaldson et al., "Design and development of masked therapeutic antibodies to limit off-target effects: application to anti-EGFR antibodies" Cancer biology & therapy, Nov. 15, 2009, 8(22):2147-52.

drugbank.Ca, [online] "Cetuximab" DrugBank Accession No. DB00002, retrieved on Dec. 16, 2016, retrieved from URL <http://www.drugbank.ca/drugs/DB00002>10 pages.

Edwards et al., "The remarkable flexibility of the human antibody repertoire; isolation of over one thousand different antibodies to a single protein, BLyS" Journal of molecular biology, Nov. 14, 2003, 334(1):103-18.

Extended European Search Report in European Appln. No. 13780884.6, dated Mar. 3, 2016, 15 pages.

Fenton et al., "Rheostat positions: A new classification of protein positions relevant to pharmacogenomics," Medicinal Chemistry Research, Jul. 2020, 29:1133-1146.

(56) References Cited

OTHER PUBLICATIONS

Francisco et al., "cAC10-vcMMAE, an anti-CD30-monomethyl auristatin E conjugate with potent and selective antitumor activity" Blood, Aug. 15, 2003, 102(4):1458-65.
Fv Structure and Diversity in Three Dimensions, 3rd ed., New York: Raven Press, Paul (ed)., 1993, pp. 292-295.
Geysen et al., "Strategies for epitope analysis using peptide synthesis" Journal of immunological methods, Sep. 24, 1987, 102(2):259-74.
Gilliland et al., "Elimination of the immunogenicity of therapeutic antibodies" The Journal of Immunology, Mar. 15, 1999, 162(6):3663-71.
Goldstein et al., "Biological efficacy of a chimeric antibody to the epidermal growth factor receptor in a human tumor xenograft model" Clinical Cancer Research, Nov. 1995, 1(11):1311-8.
Gravanis et al., "The European Medicines Agency review of ofatumumab (Arzerra®) for the treatment of chronic lymphocytic leukemia in patients refractory to fludarabine and alemtuzumab: summary of the scientific assessment of the European medicines agency committee for medicinal products for human use" The oncologist, Dec. 2010, 15(12):1335-43.
Guo et al., "Protein tolerance to random amino acid change," PNAS USA, Jun. 22, 2004, 101(25):9205-10.
Hale, "Synthetic peptide mimotope of the CAMPATH-1 (CD52) antigen, a small glycosylphosphatidylinositol-anchored glycoprotein" Immunotechnology, Dec. 1995, 1(3-4):175-87.
Handbook of Therapeutic Antibodies, WILEY-VCH Verlag GmbH & Co. KGaA, Weinheim, Dübel (ed)., vol. 1, 2007, pp. 95-102 and 119-126.
Holliger et al., "Diabodies": small bivalent and bispecific antibody fragments Proceedings of the National Academy of Sciences, Jul. 15, 1993, 90(14):6444-8.
Huston, et al., "Protein engineering of antibody binding sites: recovery of specific activity in an anti-digoxin single-chain Fv analogue produced in *Escherichia coli*" Proceedings of the National Academy of Sciences, Aug. 1988, 85(16):5879-83.
Hutchinson, "Ezzie Developing patterns" Nature Rev Cancer, 2005, 5:341.
Hynes et al., "ErbB receptors and signaling pathways in cancer" Current opinion in cell biology, Apr. 2009, 21(2):177-84.
International Preliminary Report on Patentability in International Appln. No. PCT/US2013/038540, mailed Nov. 6, 2014, 6 pages.
International Search Report and Written Opinion in International Appln. No. PCT/US2013/038540, mailed Nov. 15, 2013, 10 pages.
Invitation to Pay Additional Fees in International Appln. No. PCT/US2013/038540, mailed Sep. 11, 2013, 2 pages.
Irving, "Probodies Empower a New Generation of Antibody Immunotherapies" InCytomX Therapeutics Inc. presentation at Keystone Symposia™ on Molecular and Cellular Biology, Feb. 8, 2015 , 25 pages.
James et al., "1.9 Å structure of the therapeutic antibody CAMPATH-1H fab in complex with a synthetic peptide antigen" Journal of molecular biology, Jun. 4, 1999, 289(2):293-301.
Jansen et al., "Immunotoxins: hybrid molecules combining high specificity and potent cytotoxicity" Immunological reviews, Feb. 1982, 62(1): 185-216.
Jensen-Jarolim et al., "Peptide mimotopes displayed by phage inhibit antibody binding to bet v 1, the major birch pollen allergen, and induce specific IgG response in mice" The FASEB journal, Dec. 1998, 12(15):1635-42.
Sequences of proteins of immunological interest, 5th ed., Kabat (ed)., NIH Publication 91-3242, 1991, p. 310.
Katz, "Structural and mechanistic determinants of affinity and specificity of ligands discovered or engineered by phage display" Annual review of biophysics and biomolecular structure, Jun. 1997, 26(1):27-45.
Killen et al., "Specific killing of lymphocytes that cause experimental autoimmune myasthenia gravis by ricin toxin-acetylcholine receptor conjugates" The Journal of Immunology, Nov. 1984, 133(5):2549-53.
Krieckaert et al., "Immunogenicity of biologic therapies—we need tolerance" Nature Reviews Rheumatology, Oct. 2010, 6(10):558-9.
Krieckaert et al., "Methotrexate reduces immunogenicity in adalimumab treated rheumatoid arthritis patients in a dose dependent manner" Annals of the rheumatic diseases, Nov. 2012, 71(11): 1914-5.
LaPlanche et al., "Phosphorothioate-modified oligodeoxyribonucleotides. III. NMR and UV spectroscoptc studies of the R p-R p, S p-S p, and R p-S p duplexes, [d (GGSAATTCC)] 2, derived from diastereomeric O-ethyl phosphorothioates" Nucleic acids research, Nov. 11, 1986, 14(22):9081-93.
Leibiger et al., "Variable domain-linked oligosaccharides of a human monoclonal IgG: structure and influence on antigen binding" Biochemical Journal, Mar. 1999, 338(2):529-38.
Leitner et al., "A mimotope defined by phage display inhibits IgE binding to the plant panallergen profiling" European journal of immunology, Sep. 1998, 28(9):2921-7.
Li et al., "Structural basis for inhibition of the epidermal growth factor receptor by cetuximab" Cancer cell, Apr. 2005, 7(4):301-11.
Lichtenstein, "Comprehensive review: antitumor necrosis factor agents in inflammatory bowel disease and factors implicated in treatment response" Therapeutic advances in gastroenterology, Jul. 2013, 6(4):269-93.
Lloyd et al., "Modelling the human immune response: performance of a 1011 human antibody repertoire against a broad panel of therapeutically relevant antigens" Protein Engineering, Design & Selection, Mar. 2009, 22(3):159-68.
ludger.com, [online] "Designing Biobetter Monoclonal Antibody Therapeutics by Glycoengineering," Oct. 2, 2009, retrieved from URL <http://www.ludger.com/articles/ludger-m-00308-intpharmind-2009-biobetter-mAbs.pdf>, 5 pages.
Malmqvist, "Biospecific interaction analysis using biosensor technology" Nature, Jan. 1993, 361(6408):186-7.
Marasco et al., "Design, intracellular expression, and activity of a human anti-human immunodeficiency virus type 1 gp120 single-chain antibody" Proceedings of the National Academy of Sciences, Aug. 15, 1993, 90(16):7889-93.
Mitchison, The dosage requirements for immunological paralysis by soluble proteins. Immunology, Oct. 1968, 15(4):509-530.
Mitra et al., "Reagents for the crosslinking of proteins by equilibrium transfer alkylation" Journal of the American Chemical Society, May 1979, 101(11):3097-110.
Mook et al., "In situ localization of gelatinolytic activity in the extracellular matrix of metastases of colon cancer in rat liver using quenched fluorogenic DQ-gelatin" Journal of Histochemistry & Cytochemistry, Jun. 2003, 51(6):821-9.
Moore et al., "Antibodies to discontinuous or conformationally sensitive epitopes on the gp120 glycoprotein of human immunodeficiency virus type 1 are highly prevalent in sera of infected humans" Journal of Virology, Feb. 1993, 67(2):863-75.
Morris "Epitope mapping: B-cell epitopes" Encyclopedia of life sciences, 2007:1-3.
Murthy et al., "Legumain expression in relation to clinicopathologic and biological variables in colorectal cancer" Clinical cancer research, Mar. 2005, 11(6):2293-9.
neb.com [online], retrieved on Jan. 11, 2012, retrieved from URL<http://www.neb.com/neb/products/phd/phd.html>, 5 pages.
Nelson et al., "Development trends for human monoclonal antibody therapeutics" Nature reviews drug discovery, Oct. 2010, 9(10):767-74.
Nielsen et al., "Urokinase plasminogen activator is localized in stromal cells in ductal breast cancer" Laboratory investigation, Nov. 2001, 81(11):1485-501.
Oligonucleotides and analogues: A Practical Approach, Oxford University Press, Eckstein (ed)., 1991, pp. 87-108.
Pirker et al., "Cetuximab plus chemotherapy in patients with advanced non-small-cell lung cancer (FLEX): an open-label randomised phase III trial" The Lancet, May 2, 2009, 373(9674):1525-31.
Powell et al., "Compendium of excipients for parenteral formulations" PDA Journal of Pharmaceutical Science and Technology, Sep. 1998, 52(5):238-311.

(56) References Cited

OTHER PUBLICATIONS

Ramakrishnan et al., "Comparison of the selective cytotoxic effects of immunotoxins containing ricin A chain or pokeweed antiviral protein and anti-Thy 1.1 monoclonal antibodies" Cancer research, Jan. 1984, 44(1):201-8.
Roitt's Essential Immunology, 10th ed., Immunochemical Techniques, Roitt (ed)., 2001, Chapter 6, pp. 108, 118-120.
Rudikoff et al., "Single amino acid substitution altering antigen-binding specificity" Proceedings of the National Academy of Sciences, Mar. 1982, 79(6):1979-83.
Schwarz et al., "Mechanisms and principles of N-linked protein glycosylation" Current opinion in structural biology, Oct. 2011, 21(5):576-82.
Sciencetranslationalmedicine.org [online], Desnoyers et al., "Tumor-specific activation of an EGFR-targeting probody enhances therapeutic index" Oct. 16, 2013, retrieved on Oct. 16, 2013, retrieved from URL http://www.sciencetranslationalmedicine.org, 5(207):207ra144, 10 pages.
Scott et al., "Searching for peptide ligands with an epitope library" Science, Jul. 27, 1990 249(4967):386-90.
Segaert et al., "Clinical signs, pathophysiology and management of skin toxicity during therapy with epidermal growth factor receptor inhibitors" Annals of oncology, Sep. 2005, 16(9):1425-33.
Sethu et al., "Immunogenicity to biologics: mechanisms, prediction and reduction" Archivum immunologiae et therapiae experimentalis, Oct. 2012, 60(5):331-44.
Smith et al., "Phage display" Chemical reviews, Apr. 1997, 97(2):391-410.
Stec et al., "Automated solid-phase synthesis, separation, and stereochemistry of phosphorothioate analogs of oligodeoxyribonucleotides" Journal of the American Chemical Society, Oct. 1984, 106(20):6077-9.
Stein et al., "Physicochemical properties of phospborothioate oligodeoxynucleotides" Nucleic acids research, Apr. 25, 1988 16(8):3209-21.
Tabernero et al., "Pharmacogenomic and pharmacoproteomic studies of cetuximab in metastatic colorectal cancer: biomarker analysis of a phase I dose-escalation study" Journal of clinical oncology, Mar. 2010, 28(7):1181-9.
Thornton et al., "Prediction of progress at last" Nature, Nov. 1991, 354(6349):105-6.
Tokuriki et al., Stability effects of mutations and protein evolvability, Curr. Opin. Struc. Biol, Oct. 2009, 19:596-604.
Uhlmann et al., "Antisense oligonucleotides: a new therapeutic principle" Chemical Reviews, Jun. 1990, 90(4):543-84.
Vitetta et al., "Redesigning nature's poisons to create anti-tumor reagents" Science, Nov. 20, 1987, 238(4830):1098-104.
Wang, "Lyophilization and development of solid protein pharmaceuticals" International journal of pharmaceutics, Aug. 2000, 203(1-2):1-60.
Weigle, "Recent observations and concepts in immunological unresponsiveness and autoimmunity" Clinical and experimental immunology, Oct. 1971, 9(4):437.
Wolbink et al., "Dealing with immunogenicity of biologicals: assessment and clinical relevance" Current opinion in rheumatology, May 2009, 21(3):211-5.
Wright et al., "Antibody variable region glycosylation: position effects on antigen binding and carbohydrate structure" The EMBO journal, Oct. 1991, 10(10):2717-23.
Yan et al., "Antibody-based therapy for solid tumors" The Cancer Journal, May 2008, 14(3):178-83.
Yang et al., "Generation and characterization of a target-selectively activated antibody against epidermal growth factor receptor with enhanced anti-tumor potency" InMAbs, Mar. 4, 2015, 7(2):440-450.
Yu et al., "Interaction between bevacizumab and murine VEGF-A: a reassessment" Investigative ophthalmology & visual science, Feb. 2008, 49(2):522-7.
Zeitlin et al., "Enhanced potency of a fucose-free monoclonal antibody being developed as an Ebola virus immunoprotectant" Proceedings of the National Academy of Sciences, Dec. 20, 2011, 108(51):20690-4.
Zhong et al., "Recent advances in glycosylation modifications in the context of therapeutic glycoproteins" Integrative Proteomics, Feb. 2012, 24:183-96.
Zon et al., "Phosphorothioate oligonucleotides: chemistry, purification, analysis, scale-up and future directions" Anti-cancer drug design, Dec. 1991, 6(6):539-68.

Pb-1204 in liver

Pb-NSUB in liver

FIGURE 9A
| Protease | $k_{cat}/K_m$ $M^{-1}s^{-1}$ |
|---|---|
| Human uPA | 2236 |
| Mouse uPA | 82 |
| Human MT-SP1 | 8442 |
| Mouse MT-SP1 | 22655 |
| Legumain | 75000 (pH 4.0) |
| tPA | 43.8 |
| Thrombin | 2.3 |
FIGURE 9B
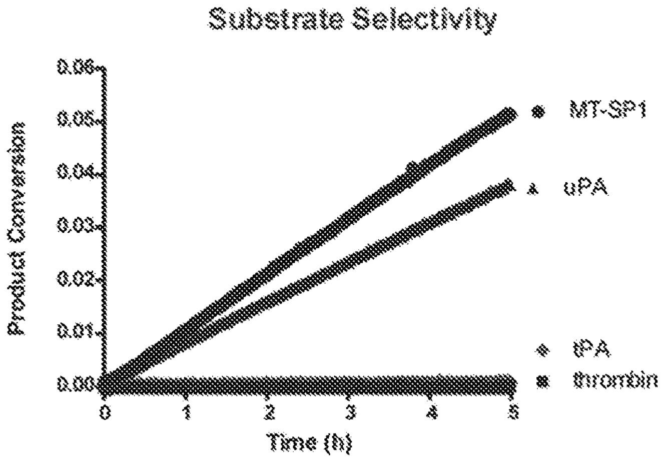
FIGURE 9C
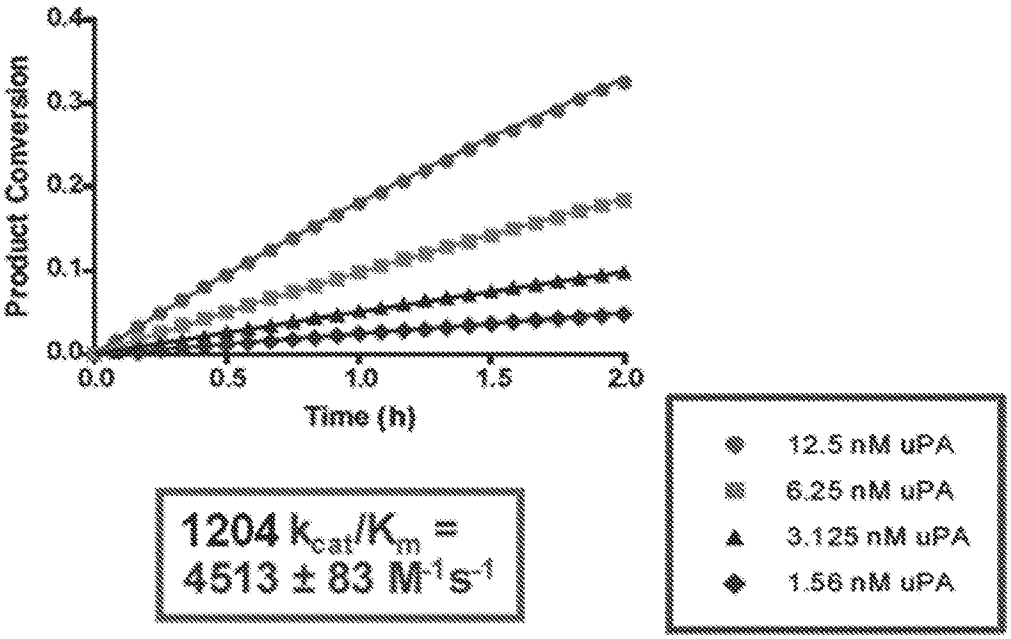

FIGURE 17

Lung Tumor

| Patient # | EGFR | MT-SP1 | Cetux | 3954-1204-C225v5 |
|---|---|---|---|---|
| 5608 | - | +++ | | |
| 5610 | - | - | | |
| 5613 | + | - | ++ | + |
| 5615 | - | - | | |
| 5621 | +++ | ++ | +++ | ++ |
| 5625 | +++ | ++ | +++ | ++ |
| 5627 | - | - | | |
| 5646 | +/- | + | + | + |
| 5648 | - | - | | |
| 5654 | +/- | ++ | | |

Colon Cancer

| Patient # | EGFR | MT-SP1 | Cetux | 3954-1204 C225v5 |
|---|---|---|---|---|
| 5577 | +++ | +++ | | |
| 5579 | +++ | - | ++ | ++ |
| 5638 | ++ | + | ++ | + |
| 5642 | +++ | +++ | | |
| 5650 | ++ | + | +/++ | + |
| 5652 | +++ | +++ | +++ | +++ |
| 5656 | +++ | ++ | | |
| 5658 | - | +++ | | |
| 5660 | ++ | +++ | | |

* - scoring is based on comparison with Cetuximab staining

| Patient # | EGFR | MT-SP1 | Cetuximab | 3954-1204-C225 | Cancer Type |
|---|---|---|---|---|---|
| 5594 | +++ | ++ | +++ | ~90% | Esophageal |

ACTIVATABLE ANTIBODIES THAT BIND EPIDERMAL GROWTH FACTOR RECEPTOR AND METHODS OF USE THEREOF

RELATED APPLICATIONS

This application is a divisional of U.S. patent application Ser. No. 16/892,973, filed on Jun. 4, 2020, which is a divisional of U.S. patent application Ser. No. 15/875,947, filed Jan. 19, 2018 and now U.S. Pat. No. 10,709,799, which is a divisional of U.S. patent application Ser. No. 15/381,972, filed Dec. 16, 2016 and now U.S. Pat. No. 9,889,211, which is a divisional of U.S. patent application Ser. No. 14/815,111, filed Jul. 31, 2015 and now issued as U.S. Pat. No. 9,545,442, which is a divisional of U.S. patent application Ser. No. 13/872,052, filed Apr. 26, 2013 and now issued as U.S. Pat. No. 9,120,853, which claims the benefit of U.S. Provisional Application No. 61/639,796, filed Apr. 27, 2012; U.S. Provisional Application No. 61/662,204, filed Jun. 20, 2012; U.S. Provisional Application No. 61/749,220, filed Jan. 4, 2013; U.S. Provisional Application No. 61/749,529, filed Jan. 7, 2013; and U.S. Provisional Application No. 61/763,237, filed Feb. 11, 2013; each of which is incorporated herein by reference in its entirety.

INCORPORATION OF SEQUENCE LISTING

This application contains a Sequence Listing that has been submitted electronically as an XML file named 45325-0031006_SL_ST26.xml. The XML file, created on Dec. 21, 2023, is 76,109 bytes in size. The material in the XML file is hereby incorporated by reference in its entirety.

FIELD OF THE INVENTION

The invention relates generally to activatable antibodies that specifically bind to epidermal growth factor receptor (EGFR), conjugated activatable antibodies that specifically bind to EGFR, and methods of making and using these anti-EGFR activatable antibodies and/or conjugated anti-EGFR activatable antibodies in a variety of therapeutic, diagnostic and prophylactic indications.

BACKGROUND OF THE INVENTION

Antibody-based therapies have proven effective treatments for some diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

The invention provides activatable antibodies that include an antibody or antigen-binding fragment thereof that specifically binds epidermal growth factor receptor (EGFR) coupled to a masking moiety (MM), such that coupling of the MM reduces the ability of the antibody or antigen-binding fragment thereof to bind EGFR. In a preferred embodiment, the MM is coupled via a sequence that includes a substrate for a protease, for example, a protease that is co-localized with EGFR at a treatment site in a subject. The activatable anti-EGFR antibodies provided herein are stable in circulation, activated at intended sites of therapy and/or diagnosis but not in normal, i.e., healthy tissue, and, when activated, exhibit binding to EGFR that is at least comparable to the corresponding, unmodified antibody.

The invention provides conjugated activatable antibodies that include an antibody or antigen-binding fragment thereof that specifically binds epidermal growth factor receptor (EGFR) coupled to a masking moiety (MM), such that coupling of the MM reduces the ability of the antibody or antigen-binding fragment thereof to bind EGFR, and wherein the activatable antibody is conjugated to one or more additional agents. In a preferred embodiment of the conjugated activatable antibodies, the MM is coupled via a sequence that includes a substrate for a protease, for example, a protease that is co-localized with EGFR at a treatment site in a subject. The conjugated, activatable anti-EGFR antibodies provided herein are stable in circulation, activated at intended sites of therapy and/or diagnosis but not in normal, i.e., healthy tissue, and, when activated, exhibit binding to EGFR that is at least comparable to the corresponding, unmodified antibody.

The invention provides methods of treating, preventing and/or delaying the onset or progression of, or alleviating a symptom of an indication, e.g., disease or disorder, associated with aberrant expression and/or activity of EGFR, e.g., an EGFR-related disorder, in a subject using a therapeutic molecule, e.g., activatable antibodies that in an activated state bind EGFR and/or conjugated activatable antibodies that in an activated state bind EGFR, particularly activatable antibodies and/or conjugated activatable antibodies that when activated bind and neutralize or otherwise inhibit at least one biological activity of EGFR and/or EGFR-mediated signaling.

The activatable antibodies described herein in an activated state bind EGFR and include (i) an antibody or an antigen binding fragment thereof (AB) that specifically binds to EGFR, wherein the AB is or is derived from cetuximab; (ii) a masking moiety (MM) that inhibits the binding of the AB of the activatable antibody in an uncleaved state to EGFR; and (c) a cleavable moiety (CM) coupled to the AB, wherein the CM is a polypeptide that functions as a substrate for a protease.

In some embodiments, the MM has an equilibrium dissociation constant for binding to the AB which is greater than the equilibrium dissociation constant of the AB to EGFR.

In some embodiments, the MM has an equilibrium dissociation constant for binding to the AB which is no more than the equilibrium dissociation constant of the AB to EGFR.

In some embodiments, the MM does not interfere or compete with the AB of the activatable antibody in a cleaved state for binding to EGFR.

In some embodiments, the protease is co-localized with EGFR in a tissue, and the protease cleaves the CM in the activatable antibody when the activatable antibody is exposed to the protease. In some embodiments, the protease is not active or is significantly less active in tissues that do not significantly express EGFR. In some embodiments, the protease is not active or is significantly less active in healthy, e.g., non-diseased tissues.

In some embodiments, the activatable antibody in the uncleaved state has the structural arrangement from N-terminus to C-terminus as follows: MM-CM-AB or AB-CM-MM.

In some embodiments, the activatable antibody includes a linking peptide between the MM and the CM.

In some embodiments, the activatable antibody includes a linking peptide between the CM and the AB.

In some embodiments, the activatable antibody includes a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other.

In some embodiments, the AB has an equilibrium dissociation constant of about 100 nM or less for binding to EGFR.

In some embodiments, the MM is a polypeptide of about 2 to 40 amino acids in length, for example, no more than 40 amino acids long.

In some embodiments, the MM polypeptide sequence is different from that of EGFR, and the MM polypeptide sequence is no more than 50% identical to any natural binding partner of the AB.

In some embodiments, the CM is positioned in the activatable antibody such that in the uncleaved state, binding of the activatable antibody to EGFR is reduced to occur with an equilibrium dissociation constant that is at least 20-fold greater than the equilibrium dissociation constant of an unmodified AB binding to EGFR, and whereas the AB of the activatable antibody in the cleaved state binds EGFR.

In some embodiments, the CM is positioned in the activatable antibody such that in the uncleaved state, binding of the activatable antibody to EGFR is reduced to occur with an equilibrium dissociation constant that is at least 100-fold greater than the equilibrium dissociation constant of an unmodified AB binding to EGFR, and whereas the AB of the activatable antibody in the cleaved state binds EGFR.

In some embodiments, the CM is positioned in the activatable antibody such that in the uncleaved state, binding of the activatable antibody to EGFR is reduced to occur with an equilibrium dissociation constant that is at least 200-fold greater than the equilibrium dissociation constant of an unmodified AB binding to EGFR, and whereas the AB of the activatable antibody in the cleaved state binds EGFR.

In some embodiments, the coupling of the MM reduces the ability of the AB to bind EGFR such that the dissociation constant ($K_d$) of the AB when coupled to the MM towards EGFR is at least 20 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 100 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 1000 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 10,000 times greater than the $K_d$ of the AB when not coupled to the MM towards EGFR.

In some embodiments, the CM is a polypeptide of up to 15 amino acids in length.

In some embodiments, in the presence of EGFR, the MM reduces the ability of the AB to bind EGFR by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the activatable antibody includes an antibody or antigen-binding fragment thereof that specifically binds EGFR. In some embodiments, the antibody or immunologically active fragment thereof that binds EGFR is a monoclonal antibody, domain antibody, single chain, Fab fragment, a $F(ab')_2$ fragment, a scFv, a scab, a dAb, a single domain heavy chain antibody, and a single domain light chain antibody. In some embodiments, such an antibody or immunologically active fragment thereof that binds EGFR is a mouse, chimeric, humanized or fully human monoclonal antibody.

In some embodiments, the activatable antibody that in an activated state binds Epidermal Growth Factor Receptor (EGFR) includes an antibody or an antigen binding fragment thereof (AB) that specifically binds to EGFR, wherein the AB includes a heavy chain amino acid sequence selected from the group consisting of SEQ ID NO: 2, SEQ ID NO: 6 and SEQ ID NO: 10, and a light chain amino acid that includes SEQ ID NO: 68; a masking moiety (MM) that inhibits the binding of the AB of the activatable antibody in an uncleaved state to EGFR, wherein the masking moiety includes the amino acid sequence CISPRGCPDGPYVMY (SEQ ID NO: 14); and a cleavable moiety (CM) coupled to the AB, wherein the CM is a polypeptide that functions as a substrate for a protease, and wherein the CM includes the amino acid sequence LSGRSDNH (SEQ ID NO: 13), wherein the activatable antibody in the uncleaved state has the structural arrangement from N-terminus to C-terminus as follows: MM-CM-AB or AB-CM-MM. In some embodiments, the AB of the activatable antibody includes a heavy chain amino acid sequence selected from the group consisting of SEQ ID NO: 2, SEQ ID NO: 6, and SEQ ID NO: 10, and a light chain amino acid sequence including SEQ ID NO: 68. In some embodiments, the AB of the activatable antibody includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 68.

In some embodiments, the activatable antibody includes a heavy chain amino acid sequence selected from the group consisting of SEQ ID NO: 2, SEQ ID NO: 6, and SEQ ID NO: 10, and a light chain amino acid sequence including SEQ ID NO: 28. In some embodiments, the activatable antibody includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 28.

In some embodiments, the activatable antibody includes a heavy chain amino acid sequence selected from the group consisting of SEQ ID NO: 2, SEQ ID NO: 6, and SEQ ID NO: 10, and a light chain amino acid sequence including SEQ ID NO: 4. In some embodiments, the activatable antibody includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 4.

In some embodiments, the activatable antibody that in an activated state binds Epidermal Growth Factor Receptor (EGFR) includes an antibody or an antigen binding fragment thereof (AB) that specifically binds to EGFR, wherein the AB includes a heavy chain amino acid sequence selected from the group consisting of SEQ ID NO: 2, SEQ ID NO: 6 and SEQ ID NO: 10, and a light chain amino acid that includes SEQ ID NO: 68; a masking moiety (MM) that inhibits the binding of the AB of the activatable antibody in an uncleaved state to EGFR, wherein the masking moiety includes the amino acid sequence CISPRGCPDGPYVMY (SEQ ID NO: 14); and a cleavable moiety (CM) coupled to the AB, wherein the CM is a polypeptide that functions as a substrate for a protease, and wherein the CM includes the amino acid sequence LSGRSDNH (SEQ ID NO: 13), wherein the activatable antibody in the uncleaved state has the structural arrangement from N-terminus to C-terminus as follows: MM-CM-AB or AB-CM-MM. In some embodiments, the AB of the activatable antibody includes a heavy chain amino acid sequence selected from the group consisting of SEQ ID NO: 2, SEQ ID NO: 6, and SEQ ID NO: 10, and a light chain amino acid sequence including SEQ ID NO: 68. In some embodiments, the AB of the activatable antibody is encoded by a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence including SEQ ID NO: 68. In some embodiments, the AB of the activatable antibody is encoded by a nucleic acid sequence encoding a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence encoding a light chain amino acid that is at least 90%, 91%, 92%, 93%, 94%, 95%, 96%, 97%, 98% or 99% identical to an amino acid sequence including SEQ ID NO: 68.

In some embodiments, the activatable antibody is encoded by a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence including SEQ ID NO: 28. In some embodiments, the activatable antibody is encoded by a nucleic acid sequence encoding a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence encoding a light chain amino acid that is at least 90%, 91%, 92%, 93%, 94%, 95%, 96%, 97%, 98% or 99% identical to an amino acid sequence including SEQ ID NO: 28.

In some embodiments, the activatable antibody is encoded by a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence including SEQ ID NO: 4. In some embodiments, the activatable antibody is encoded by a nucleic acid sequence encoding a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence encoding a light chain amino acid that is at least 90%, 91%, 92%, 93%, 94%, 95%, 96%, 97%, 98% or 99% identical to an amino acid sequence including SEQ ID NO: 4.

In some embodiments, the AB of the activatable antibody is encoded by a nucleic acid including a heavy chain nucleic acid sequence selected from the group consisting of SEQ ID NO: 1, SEQ ID NO: 5, and SEQ ID NO: 9, and a light chain nucleic acid sequence including SEQ ID NO: 67. In some embodiments, the AB of the activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence encoding a light chain nucleic acid that is at least 90%, 91%, 92%, 93%, 94%, 95%, 96%, 97%, 98% or 99% identical to a nucleic acid sequence including SEQ ID NO: 67.

In some embodiments, the activatable antibody is encoded by a nucleic acid including a heavy chain nucleic acid sequence selected from the group consisting of SEQ ID NO: 1, SEQ ID NO: 5, and SEQ ID NO: 9, and a light chain nucleic acid sequence including SEQ ID NO: 27. In some embodiments, the activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence encoding a light chain nucleic acid that is at least 90%, 91%, 92%, 93%, 94%, 95%, 96%, 97%, 98% or 99% identical to a nucleic acid sequence including SEQ ID NO: 27.

In some embodiments, the activatable antibody is encoded by a nucleic acid including a heavy chain nucleic acid sequence selected from the group consisting of SEQ ID NO: 1, SEQ ID NO: 5, and SEQ ID NO: 9, and a light chain nucleic acid sequence including SEQ ID NO: 3. In some embodiments, the activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence encoding a light chain nucleic acid that is at least 90%, 91%, 92%, 93%, 94%, 95%, 96%, 97%, 98% or 99% identical to a nucleic acid sequence including SEQ ID NO: 3.

In some embodiments, the AB of the activatable antibody includes a heavy chain amino acid sequence selected from the group consisting of SEQ ID NO: 26, SEQ ID NO: 30 and SEQ ID NO: 34, and a light chain amino acid sequence including SEQ ID NO: 68. In some embodiments, the AB of the activatable antibody includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 68.

In some embodiments, the activatable antibody includes a heavy chain amino acid sequence selected from the group consisting of SEQ ID NO: 26, SEQ ID NO: 30 and SEQ ID NO: 34, and a light chain amino acid sequence including SEQ ID NO: 28. In some embodiments, the activatable antibody includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 28.

In some embodiments, the activatable antibody includes a heavy chain amino acid sequence selected from the group consisting of SEQ ID NO: 26, SEQ ID NO: 30 and SEQ ID NO: 34, and a light chain amino acid sequence including SEQ ID NO: 4. In some embodiments, the activatable antibody includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 4.

In some embodiments, the AB of the activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence including SEQ ID NO: 68. In some embodiments, the AB of the activatable antibody is encoded by a nucleic acid sequence that includes a nucleic acid sequence encoding a includes a heavy chain amino acid sequence that is at least 90%, 91%, 92%, 93%, 94%, 95%, 96%, 97%, 98% or 99% identical to an amino acid selected from the group consisting of SEQ ID NO: 26, SEQ ID NO: 30, and SEQ ID NO: 34, and a nucleic acid sequence encoding a light chain amino acid that is at least 90%, 91%, 92%, 93%, 94%, 95%, 96%, 97%, 98% or 99% identical to an amino acid sequence including SEQ ID NO: 68.

In some embodiments, the activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence including SEQ ID NO: 28. In some embodiments, the activatable antibody is encoded by a nucleic acid sequence that includes a nucleic acid sequence encoding a includes a heavy chain amino acid sequence that is at least 90%, 91%, 92%, 93%, 94%, 95%, 96%, 97%, 98% or 99% identical to an amino acid including SEQ ID NO: 68, and a nucleic acid sequence encoding a light chain amino acid that is at least 90%, 91%, 92%, 93%, 94%, 95%, 96%, 97%, 98% or 99% identical to an amino acid sequence including SEQ ID NO: 28.

In some embodiments, the activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence including SEQ ID NO: 4. In some embodiments, the activatable antibody is encoded by a nucleic acid sequence that includes a nucleic acid sequence encoding a includes a heavy chain amino acid sequence that is at least 90%, 91%, 92%, 93%, 94%, 95%, 96%, 97%, 98% or 99% identical to an amino acid including SEQ ID NO: 68, and a nucleic acid sequence encoding a light chain amino acid that is at least 90%, 91%, 92%, 93%, 94%, 95%, 96%, 97%, 98% or 99% identical to an amino acid sequence including SEQ ID NO: 4.

In some embodiments, the AB of the activatable antibody is encoded by a nucleic acid including a heavy chain nucleic acid sequence selected from the group consisting of SEQ ID NO: 25, SEQ ID NO: 29, and SEQ ID NO: 33, and a light chain nucleic acid sequence including SEQ ID NO: 67. In some embodiments, the AB of the activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to a nucleic acid sequence including SEQ ID NO: 67.

In some embodiments, the activatable antibody is encoded by a nucleic acid including a heavy chain nucleic acid sequence selected from the group consisting of SEQ ID NO: 25, SEQ ID NO: 29, and SEQ ID NO: 33, and a light chain nucleic acid sequence including SEQ ID NO: 27. In some embodiments, the activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to a nucleic acid sequence including SEQ ID NO: 27.

In some embodiments, the activatable antibody is encoded by a nucleic acid including a heavy chain nucleic acid sequence selected from the group consisting of SEQ ID NO: 25, SEQ ID NO: 29, and SEQ ID NO: 33, and a light chain nucleic acid sequence including SEQ ID NO: 3. In some embodiments, the activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to a nucleic acid sequence including SEQ ID NO: 3.

In some embodiments, the AB of the activatable antibody includes a heavy chain including the amino acid sequence of SEQ ID NO: 26, and a light chain including the amino acid sequence of SEQ ID NO: 68. In some embodiments, the AB of the activatable antibody includes a heavy chain including an amino acid sequence that is at least 90%, 91%, 92%, 93%, 94%, 95%, 96%, 97%, 98% or 99% identical to the amino acid sequence of SEQ ID NO: 26, and a light chain including an amino acid sequence that is at least 90%, 91%, 92%, 93%, 94%, 95%, 96%, 97%, 98% or 99% identical to the amino acid sequence of SEQ ID NO: 68.

In some embodiments, the activatable antibody includes a heavy chain including the amino acid sequence of SEQ ID NO: 26, and a light chain including the amino acid sequence of SEQ ID NO: 28. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 26, and a light chain including an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody includes a heavy chain including the amino acid sequence of SEQ ID NO: 26, and a light chain including the amino acid sequence of SEQ ID NO: 4. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 26, and a light chain including an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody includes a heavy chain including the amino acid sequence of SEQ ID NO: 2, and a light chain including the amino acid sequence of SEQ ID NO: 68. In some embodiments, the AB of the activatable antibody includes a heavy chain including an amino acid sequence that is at least 90%, 91%, 92%, 93%, 94%, 95%, 96%, 97%, 98% or 99% identical to the amino acid sequence of SEQ ID NO: 2, and a light chain including an amino acid sequence that is at least 90%, 91%, 92%, 93%, 94%, 95%, 96%, 97%, 98% or 99% identical to the amino acid sequence of SEQ ID NO: 68.

In some embodiments, the activatable antibody includes a heavy chain including the amino acid sequence of SEQ ID NO: 2, and a light chain including the amino acid sequence of SEQ ID NO: 28. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 2, and a light chain including an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody includes a heavy chain including the amino acid sequence of SEQ ID NO: 2, and a light chain including the amino acid sequence of SEQ ID NO: 4. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 2, and a light chain including an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody includes a heavy chain including the amino acid sequence of SEQ ID NO: 6, and a light chain including the amino acid sequence of SEQ ID NO: 68. In some embodiments, the AB of the activatable antibody includes a heavy chain including an amino acid sequence that is at least 90%, 91%, 92%, 93%, 94%, 95%, 96%, 97%, 98% or 99% identical to the amino acid sequence of SEQ ID NO: 6, and a light chain including an amino acid sequence that is at least 90%, 91%, 92%, 93%, 94%, 95%, 96%, 97%, 98% or 99% identical to the amino acid sequence of SEQ ID NO: 68.

In some embodiments, the activatable antibody includes a heavy chain including the amino acid sequence of SEQ ID NO: 6, and a light chain including the amino acid sequence of SEQ ID NO: 28. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 6, and a light chain including an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody includes a heavy chain including the amino acid sequence of SEQ ID NO: 6, and a light chain including the amino acid sequence of SEQ ID NO: 4. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 6, and a light chain including an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody includes a heavy chain including the amino acid sequence of SEQ ID NO: 30, and a light chain including the amino acid sequence of SEQ ID NO: 68. In some embodiments, the AB of the activatable antibody includes a heavy chain including an amino acid sequence that is at least 90%, 91%, 92%, 93%, 94%, 95%, 96%, 97%, 98% or 99% identical to the amino acid sequence of SEQ ID NO: 30, and a light chain including an amino acid sequence that is at least 90%, 91%, 92%, 93%, 94%, 95%, 96%, 97%, 98% or 99% identical to the amino acid sequence of SEQ ID NO: 68.

In some embodiments, the activatable antibody includes a heavy chain including the amino acid sequence of SEQ ID NO: 30, and a light chain including the amino acid sequence of SEQ ID NO: 28. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 30, and a light chain including an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody includes a heavy chain including the amino acid sequence of SEQ ID NO: 30, and a light chain including the amino acid sequence of SEQ ID NO: 4. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 30, and a light chain including an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody includes a heavy chain including the amino acid sequence of SEQ ID NO: 10, and a light chain including the amino acid sequence of SEQ ID NO: 68. In some embodiments, the AB of the activatable antibody includes a heavy chain including an amino acid sequence that is at least 90%, 91%, 92%, 93%, 94%, 95%, 96%, 97%, 98% or 99% identical to the amino acid sequence of SEQ ID NO: 10, and a light chain including an amino acid sequence that is at least 90%, 91%, 92%, 93%, 94%, 95%, 96%, 97%, 98% or 99% identical to the amino acid sequence of SEQ ID NO: 68.

In some embodiments, the activatable antibody includes a heavy chain including the amino acid sequence of SEQ ID NO: 10, and a light chain including the amino acid sequence of SEQ ID NO: 28. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 10, and a light chain including an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody includes a heavy chain including the amino acid sequence of SEQ ID NO: 10, and a light chain including the amino acid sequence of SEQ ID NO: 4. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 10, and a light chain including an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody includes a heavy chain including the amino acid sequence of SEQ ID NO: 34, and a light chain including the amino acid sequence of SEQ ID NO: 68. In some embodiments, the AB of the activatable antibody includes a heavy chain including an amino acid sequence that is at least 90%, 91%, 92%, 93%, 94%, 95%, 96%, 97%, 98% or 99% identical to the amino acid sequence of SEQ ID NO: 34, and a light chain including an amino acid sequence that is at least 90%, 91%, 92%, 93%, 94%, 95%, 96%, 97%, 98% or 99% identical to the amino acid sequence of SEQ ID NO: 68.

In some embodiments, the activatable antibody includes a heavy chain including the amino acid sequence of SEQ ID NO: 34, and a light chain including the amino acid sequence of SEQ ID NO: 28. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 34, and a light chain including an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody includes a heavy chain including the amino acid sequence of SEQ ID NO: 34, and a light chain including the amino acid sequence of SEQ ID NO: 4. In some embodiments, the activatable antibody includes a heavy chain including an amino acid sequence that is at least 90%, 91%, 92%, 93%, 94%, 95%, 96%, 97%, 98% or 99% identical to the amino acid sequence of SEQ ID NO: 34, and a light chain including an amino acid sequence that is at least 90%, 91%, 92%, 93%, 94%, 95%, 96%, 97%, 98% or 99% identical to the amino acid sequence of SEQ ID NO: 4.

In some embodiments, the CM is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1.

In some embodiments, the CM includes the amino acid sequence LSGRSDNH (SEQ ID NO: 13).

In some embodiments, the MM does not include more than 25% amino acid sequence identity to EGFR. In some embodiments, the MM does not include more than 10% amino acid sequence identity to EGFR.

In some embodiments, the MM includes the amino acid sequence CISPRGCPDGPYVMY (SEQ ID NO: 14).

In some embodiments, at least one of LP1 or LP2 includes an amino acid sequence selected from the group consisting of $(GS)_n$, $(GGS)_n$, $(GSGGS)_n$ (SEQ ID NO: 15) and $(GGGS)_n$ (SEQ ID NO: 16), where n is an integer of at least one. In some embodiments, at least one of LP1 or LP2 includes an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), and GSSSG (SEQ ID NO: 22).

In some embodiments, LP1 includes the amino acid sequence GSSGGSGGSGGSG (SEQ ID NO: 23).

In some embodiments, LP2 includes the amino acid sequence GSSGT (SEQ ID NO: 24) or GSSG (SEQ ID NO: 37).

In some embodiments, the anti-EGFR activatable antibody is exposed to and cleaved by uPA or MT-SP1 such that, in the activated or cleaved state, the activated antibody includes the light chain amino acid sequence of SEQ ID NO: 69. In some embodiments, the anti-EGFR activatable antibody is exposed to and cleaved by legumain such that, in the activated or cleaved state, the activated antibody includes the light chain amino acid sequence of SEQ ID NO: 70.

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is an agent selected from the group listed in Table 1. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is conjugated to the AB via a linker. In some embodiments, the linker is a cleavable linker. In some embodiments, the linker is selected from the group consisting of the linkers shown in Tables 2 and 3.

In some embodiments, the activatable antibody also includes a detectable moiety. In some embodiments, the detectable moiety is a diagnostic agent. In some embodiments, the detectable moiety is a conjugatable detection reagent. In some embodiments, the detectable moiety is, for example, a fluorescein derivative such as fluorescein isothiocyanate (FITC).

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer includes at least the amino acid sequence QGQSGQ (SEQ ID NO: 38). In some embodiments, an activatable antibody includes a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, an activatable antibody includes a spacer joined directly to a MM sequence and includes the amino acid sequence QGQSGQCISPRGCPDGPYVMY (SEQ ID NO: 59) in the structural arrangement from N-terminus to C-terminus of spacer-MM-CM-AB.

In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable anti-EGFR antibody is monospecific. In some embodiments, the activatable anti-EGFR antibody is multispecific, e.g., by way of non-limiting example, bispecific or trifunctional. In some embodiments, the activatable anti-EGFR antibody is formulated as part of a pro-Bispecific T Cell Engager (BITE) molecule. In some embodiments, the activatable anti-EGFR antibody is formulated as part of a pro-Chimeric Antigen Receptor (CAR) modified T cell or other engineered receptor.

In some embodiments, the activatable antibody that in an activated state binds Epidermal Growth Factor Receptor (EGFR) includes an antibody or an antigen binding fragment thereof (AB) that specifically binds to EGFR, wherein the AB includes a heavy chain amino acid sequence selected from the group consisting of SEQ ID NO: 26, SEQ ID NO: 30 and SEQ ID NO: 34, and a light chain amino acid that includes SEQ ID NO: 68; a masking moiety (MM) that inhibits the binding of the AB of the activatable antibody in an uncleaved state to EGFR, wherein the masking moiety includes the amino acid sequence CISPRGCPDGPYVMY (SEQ ID NO: 14); and a cleavable moiety (CM) coupled to the AB, wherein the CM is a polypeptide that functions as a substrate for a protease, and wherein the CM includes the amino acid sequence LSGRSDNH (SEQ ID NO: 13), wherein the activatable antibody in the uncleaved state has the structural arrangement from N-terminus to C-terminus as follows: MM-CM-AB or AB-CM-MM. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes the light chain amino acid sequence of SEQ ID NO: 68 joined directly to a spacer amino acid sequence that includes the amino acid sequence QGQSGQ (SEQ ID NO: 38).

In some embodiments, the activatable antibody that in an activated state binds Epidermal Growth Factor Receptor (EGFR) includes an antibody or an antigen binding fragment thereof (AB) that specifically binds to EGFR, wherein the AB includes a heavy chain amino acid sequence selected from the group consisting of SEQ ID NO: 2, SEQ ID NO: 6 and SEQ ID NO: 10, and a light chain amino acid that includes SEQ ID NO: 68; a masking moiety (MM) that inhibits the binding of the AB of the activatable antibody in an uncleaved state to EGFR, wherein the masking moiety includes the amino acid sequence CISPRGCPDGPYVMY (SEQ ID NO: 14); and a cleavable moiety (CM) coupled to the AB, wherein the CM is a polypeptide that functions as a substrate for a protease, and wherein the CM includes the amino acid sequence LSGRSDNH (SEQ ID NO: 13), wherein the activatable antibody in the uncleaved state has the structural arrangement from N-terminus to C-terminus as follows: MM-CM-AB or AB-CM-MM. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes the light chain amino acid sequence of SEQ ID NO: 68 joined directly to a spacer amino acid sequence that includes the amino acid sequence QGQSGQ (SEQ ID NO: 38).

In some embodiments, the antigen binding fragment thereof is selected from the group consisting of a Fab fragment, a $F(ab')_2$ fragment, a scFv, and a scAb.

In some embodiments, the AB of the activatable antibody includes a combination of heavy and light chains selected from the group consisting of: a heavy chain including amino acid sequence of SEQ ID NO: 2 and a light chain including the amino acid sequence of SEQ ID NO: 68; a heavy chain including amino acid sequence of SEQ ID NO: 26 and a light chain including the amino acid sequence of SEQ ID NO: 68; a heavy chain including amino acid sequence of SEQ ID NO: 6 and a light chain including the amino acid sequence of SEQ ID NO: 68; a heavy chain including amino acid sequence of SEQ ID NO: 30 and a light chain including the amino acid sequence of SEQ ID NO: 68; a heavy chain including amino acid sequence of SEQ ID NO: 10 and a light chain including the amino acid sequence of SEQ ID NO: 68; and a heavy chain including amino acid sequence of SEQ ID NO: 34 and a light chain including the amino acid sequence of SEQ ID NO: 68.

In some embodiments, the AB of the activatable antibody includes a heavy chain including amino acid sequence of SEQ ID NO: 2 and a light chain including the amino acid sequence of SEQ ID NO: 68. In some embodiments, the AB of the activatable antibody includes a heavy chain including amino acid sequence that is at least 90%, 91%, 92%, 93%, 94%, 95%, 96%, 97%, 98% or 99% identical to the sequence of SEQ ID NO: 2 and a light chain including the amino acid sequence that is at least 90%, 91%, 92%, 93%, 94%, 95%, 96%, 97%, 98% or 99% identical to the sequence of SEQ ID NO: 68.

In some embodiments, the activatable antibody includes a heavy chain including amino acid sequence of SEQ ID NO: 2 and a light chain including the amino acid sequence of SEQ ID NO: 4. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 2 and a light chain including the amino acid sequence that is at least 90%, 91%, 92%, 93%, 94%, 95%, 96%, 97%, 98% or 99% identical to the sequence of SEQ ID NO: 4.

In some embodiments, the activatable antibody includes a heavy chain including amino acid sequence of SEQ ID NO: 2 and a light chain including the amino acid sequence of SEQ ID NO: 28. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 2 and a light chain including the amino acid sequence that is at least 90%, 91%, 92%, 93%, 94%, 95%, 96%, 97%, 98% or 99% identical to the sequence of SEQ ID NO: 28.

In some embodiments, the AB of the activatable antibody includes a heavy chain including amino acid sequence of SEQ ID NO: 26 and a light chain including the amino acid sequence of SEQ ID NO: 68. In some embodiments, the AB of the activatable antibody includes a heavy chain including amino acid sequence that is at least 90%, 91%, 92%, 93%, 94%, 95%, 96%, 97%, 98% or 99% identical to the sequence of SEQ ID NO: 26 and a light chain including the amino acid sequence that is at least 90%, 91%, 92%, 93%, 94%, 95%, 96%, 97%, 98% or 99% identical to the sequence of SEQ ID NO: 68.

In some embodiments, the activatable antibody includes a heavy chain including amino acid sequence of SEQ ID NO: 26 and a light chain including the amino acid sequence of SEQ ID NO: 4. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 26 and a light chain including the amino acid sequence that is at least 90%, 91%, 92%, 93%, 94%, 95%, 96%, 97%, 98% or 99% identical to the sequence of SEQ ID NO: 4.

In some embodiments, the activatable antibody includes a heavy chain including amino acid sequence of SEQ ID NO: 26 and a light chain including the amino acid sequence of SEQ ID NO: 28. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 26 and a light chain including the amino acid sequence that is at least 90%, 91%, 92%, 93%, 94%, 95%, 96%, 97%, 98% or 99% identical to the sequence of SEQ ID NO: 28.

In some embodiments, the AB of the activatable antibody includes a heavy chain including amino acid sequence of SEQ ID NO: 6 and a light chain including the amino acid sequence of SEQ ID NO: 68. In some embodiments, the AB of the activatable antibody includes a heavy chain including amino acid sequence that is at least 90%, 91%, 92%, 93%, 94%, 95%, 96%, 97%, 98% or 99% identical to the sequence of SEQ ID NO: 6 and a light chain including the amino acid sequence that is at least 90%, 91%, 92%, 93%, 94%, 95%, 96%, 97%, 98% or 99% identical to the sequence of SEQ ID NO: 68.

In some embodiments, the activatable antibody includes a heavy chain including amino acid sequence of SEQ ID NO: 6 and a light chain including the amino acid sequence of SEQ ID NO: 4. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 6 and a light chain including the amino acid sequence that is at least 90%, 91%, 92%, 93%, 94%, 95%, 96%, 97%, 98% or 99% identical to the sequence of SEQ ID NO: 4.

In some embodiments, the activatable antibody includes a heavy chain including amino acid sequence of SEQ ID NO: 6 and a light chain including the amino acid sequence of SEQ ID NO: 28. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 6 and a light chain including the amino acid sequence that is at least 90%, 91%, 92%, 93%, 94%, 95%, 96%, 97%, 98% or 99% identical to the sequence of SEQ ID NO: 28.

In some embodiments, the AB of the activatable antibody includes a heavy chain including amino acid sequence of SEQ ID NO: 30 and a light chain including the amino acid sequence of SEQ ID NO: 68. In some embodiments, the AB of the activatable antibody includes a heavy chain including amino acid sequence that is at least 90%, 91%, 92%, 93%, 94%, 95%, 96%, 97%, 98% or 99% identical to the sequence of SEQ ID NO: 30 and a light chain including the amino acid sequence that is at least 90%, 91%, 92%, 93%, 94%, 95%, 96%, 97%, 98% or 99% identical to the sequence of SEQ ID NO: 68.

In some embodiments, the activatable antibody includes a heavy chain including amino acid sequence of SEQ ID NO: 30 and a light chain including the amino acid sequence of SEQ ID NO: 4. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 30 and a light chain including the amino acid sequence that is at least 90%, 91%, 92%, 93%, 94%, 95%, 96%, 97%, 98% or 99% identical to the sequence of SEQ ID NO: 4.

In some embodiments, the activatable antibody includes a heavy chain including amino acid sequence of SEQ ID NO: 30 and a light chain including the amino acid sequence of SEQ ID NO: 28. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 30 and a light chain including the amino acid sequence that is at least 90%, 91%, 92%, 93%, 94%, 95%, 96%, 97%, 98% or 99% identical to the sequence of SEQ ID NO: 28.

In some embodiments, the AB of the activatable antibody includes a heavy chain including amino acid sequence of SEQ ID NO: 10 and a light chain including the amino acid sequence of SEQ ID NO: 68. In some embodiments, the AB of the activatable antibody includes a heavy chain including amino acid sequence that is at least 90%, 91%, 92%, 93%, 94%, 95%, 96%, 97%, 98% or 99% identical to the sequence of SEQ ID NO: 10 and a light chain including the amino acid sequence that is at least 90%, 91%, 92%, 93%, 94%, 95%, 96%, 97%, 98% or 99% identical to the sequence of SEQ ID NO: 68.

In some embodiments, the activatable antibody includes a heavy chain including amino acid sequence of SEQ ID NO: 10 and a light chain including the amino acid sequence of SEQ ID NO: 4. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 10 and a light chain including the amino acid sequence that is at least 90%, 91%, 92%, 93%, 94%, 95%, 96%, 97%, 98% or 99% identical to the sequence of SEQ ID NO: 4.

In some embodiments, the activatable antibody includes a heavy chain including amino acid sequence of SEQ ID NO: 10 and a light chain including the amino acid sequence of SEQ ID NO: 28. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 10 and a light chain including the amino acid sequence that is at least 90%, 91%, 92%, 93%, 94%, 95%, 96%, 97%, 98% or 99% identical to the sequence of SEQ ID NO: 28.

In some embodiments, the AB of the activatable antibody includes and a heavy chain including amino acid sequence of SEQ ID NO: 34 and a light chain including the amino acid sequence of SEQ ID NO: 68. In some embodiments, the AB of the activatable antibody includes a heavy chain including amino acid sequence that is at least 90%, 91%, 92%, 93%, 94%, 95%, 96%, 97%, 98% or 99% identical to the sequence of SEQ ID NO: 34 and a light chain including the amino acid sequence that is at least 90%, 91%, 92%, 93%, 94%, 95%, 96%, 97%, 98% or 99% identical to the sequence of SEQ ID NO: 68.

In some embodiments, the activatable antibody includes a heavy chain including amino acid sequence of SEQ ID NO: 34 and a light chain including the amino acid sequence of SEQ ID NO: 4. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 34 and a light chain including the amino acid sequence that is at least 90%, 91%, 92%, 93%, 94%, 95%, 96%, 97%, 98% or 99% identical to the sequence of SEQ ID NO: 4.

In some embodiments, the activatable antibody includes a heavy chain including amino acid sequence of SEQ ID NO: 34 and a light chain including the amino acid sequence of SEQ ID NO: 28. In some embodiments, the activatable antibody includes a heavy chain including amino acid sequence that is at least 90%, 91%, 92%, 93%, 94%, 95%, 96%, 97%, 98% or 99% identical to the sequence of SEQ ID NO: 34 and a light chain including the amino acid sequence that is at least 90%, 91%, 92%, 93%, 94%, 95%, 96%, 97%, 98% or 99% identical to the sequence of SEQ ID NO: 28.

In some embodiments, the AB has an equilibrium dissociation constant of about 100 nM or less for binding to EGFR.

In some embodiments, the MM has an equilibrium dissociation constant for binding to the AB which is greater than the equilibrium dissociation constant of the AB to EGFR. In some embodiments, the MM does not interfere or compete with the AB of the activatable antibody in a cleaved state for binding to EGFR.

In some embodiments, the MM is a polypeptide of no more than 40 amino acids in length. In some embodiments, the MM polypeptide sequence is different from that of EGFR, and the MM polypeptide sequence is no more than 50% identical to any natural binding partner of the AB. In some embodiments, the MM does not include more than 25% amino acid sequence identity to EGFR. In some embodiments, the MM does not include more than 10% amino acid sequence identity to EGFR.

In some embodiments, the CM is a polypeptide of up to 15 amino acids in length. In some embodiments, the CM is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1. In some embodiments, the protease is co-localized with EGFR in a tissue, and wherein the protease cleaves the CM in the activatable antibody when the activatable antibody is exposed to the protease.

In some embodiments, the activatable antibody includes a linking peptide between the MM and the CM. In some embodiments, the activatable antibody includes a linking peptide between the CM and the AB. In some embodiments, the activatable antibody includes a first linking peptide (LP1) and a second linking peptide (LP2), and the activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 15) and $(GGGS)_n$ (SEQ ID NO: 16), where n is an integer of at least one. In some embodiments, at least one of LP1 or LP2 includes an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), and GSSSG (SEQ ID NO: 22). In some embodiments, LP1 includes the amino acid sequence GSSGGSGGSGGSG (SEQ ID NO: 23). In some embodiments, LP2 includes the amino acid sequence GSSGT (SEQ ID NO: 24) or GSSG (SEQ ID NO: 37).

In some embodiments, the anti-EGFR activatable antibody is exposed to and cleaved by uPA or MT-SP1 such that, in the activated or cleaved state, the activated antibody includes the light chain amino acid sequence of SEQ ID NO: 69. In some embodiments, the anti-EGFR activatable antibody is exposed to and cleaved by legumain such that, in the activated or cleaved state, the activated antibody includes the light chain amino acid sequence of SEQ ID NO: 70.

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is an agent selected from the group listed in Table 1. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is conjugated to the AB via a linker. In some embodiments, the linker is a cleavable linker. In some embodiments, the linker is selected from the group consisting of the linkers shown in Tables 2 and 3.

In some embodiments, the activatable antibody also includes a detectable moiety. In some embodiments, the detectable moiety is a diagnostic agent. In some embodiments, the detectable moiety is a conjugatable detection reagent. In some embodiments, the detectable moiety is, for example, a fluorescein derivative such as fluorescein isothiocyanate (FITC).

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer includes at least the amino acid sequence QGQSGQ (SEQ ID NO: 38). In some embodiments, an activatable antibody includes a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, an activatable antibody includes a spacer joined directly to a MM sequence and includes the amino acid sequence QGQSGQCISPRGCPDGPYVMY (SEQ ID NO: 59) in the structural arrangement from N-terminus to C-terminus of spacer-MM-CM-AB.

In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable anti-EGFR antibody is monospecific. In some embodiments, the activatable anti-EGFR antibody is multispecific, e.g., by way of non-limiting example, bispecific or trifunctional. In some embodiments, the activatable anti-EGFR antibody is formulated as part of a pro-Bispecific T Cell Engager (BITE) molecule. In some embodiments, the activatable anti-EGFR antibody is formulated as part of a pro-Chimeric Antigen Receptor (CAR) modified T cell or other engineered receptor.

The invention also provides conjugated activatable antibodies that bind Epidermal Growth Factor Receptor (EGFR) in an activated state and include an antibody or an antigen binding fragment thereof (AB) that specifically binds to EGFR; a masking moiety (MM) that inhibits the binding of the AB of the activatable antibody in an uncleaved state to EGFR; a cleavable moiety (CM) coupled to the AB, wherein the CM is a polypeptide that functions as a substrate for a protease, and a cytotoxic agent.

In some embodiments, the AB is or is derived from cetuximab.

In some embodiments of the conjugated activatable antibodies, the antigen binding fragment thereof is selected from the group consisting of a Fab fragment, a $F(ab')_2$ fragment, a scFv, a scAb, a dAb, a single domain heavy chain antibody, and a single domain light chain antibody.

In some embodiments, the AB of the conjugated activatable antibody includes a heavy chain amino acid sequence selected from the group consisting of SEQ ID NO: 26, SEQ ID NO: 30 and SEQ ID NO: 34, and a light chain amino acid that includes SEQ ID NO: 68. In some embodiments, the AB of the conjugated activatable antibody includes a heavy chain amino acid sequence selected from the group consisting of SEQ ID NO: 2, SEQ ID NO: 6 and SEQ ID NO: 10, and a light chain amino acid that includes SEQ ID NO: 68. In some embodiments, the AB of the conjugated activatable antibody includes a heavy chain including amino acid sequence of SEQ ID NO: 2, and a light chain including the amino acid sequence of SEQ ID NO: 68. In some embodiments, the AB of the conjugated activatable antibody includes a heavy chain including amino acid sequence of SEQ ID NO: 26, and a light chain including the amino acid sequence of SEQ ID NO: 68. In some embodiments, the AB of the conjugated activatable antibody includes a heavy chain including amino acid sequence of SEQ ID NO: 6, and a light chain including the amino acid sequence of SEQ ID NO: 68. In some embodiments, the AB of the conjugated activatable antibody includes a heavy chain including amino acid sequence of SEQ ID NO: 30, and a light chain including the amino acid sequence of SEQ ID NO: 68. In some embodiments, the AB of the conjugated activatable antibody includes a heavy chain including amino acid sequence of SEQ ID NO: 10, and a light chain including the amino acid sequence of SEQ ID NO: 68. In some embodiments, the AB of the conjugated activatable antibody includes a heavy chain including amino acid sequence of SEQ ID NO: 34, and a light chain including the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody includes a heavy chain including amino acid sequence of SEQ ID NO: 2 and a light chain including the amino acid sequence of SEQ ID NO: 68. In some embodiments, the activatable antibody includes a heavy chain including amino acid sequence of SEQ ID NO: 2 and a light chain including the amino acid sequence of SEQ ID NO: 4. In some embodiments, the activatable antibody includes a heavy chain including amino acid sequence of SEQ ID NO: 2 and a light chain including the amino acid sequence of SEQ ID NO: 28.

In some embodiments, the AB of the activatable antibody includes a heavy chain including amino acid sequence of SEQ ID NO: 26 and a light chain including the amino acid sequence of SEQ ID NO: 68. In some embodiments, the activatable antibody includes a heavy chain including amino acid sequence of SEQ ID NO: 26 and a light chain including the amino acid sequence of SEQ ID NO: 4. In some embodiments, the activatable antibody includes a heavy chain including amino acid sequence of SEQ ID NO: 26 and a light chain including the amino acid sequence of SEQ ID NO: 28.

In some embodiments, the AB of the activatable antibody includes a heavy chain including amino acid sequence of SEQ ID NO: 6 and a light chain including the amino acid sequence of SEQ ID NO: 68. In some embodiments, the activatable antibody includes a heavy chain including amino acid sequence of SEQ ID NO: 6 and a light chain including the amino acid sequence of SEQ ID NO: 4. In some embodiments, the activatable antibody includes a heavy chain including amino acid sequence of SEQ ID NO: 6 and a light chain including the amino acid sequence of SEQ ID NO: 28.

In some embodiments, the AB of the activatable antibody includes a heavy chain including amino acid sequence of SEQ ID NO: 30 and a light chain including the amino acid sequence of SEQ ID NO: 68. In some embodiments, the activatable antibody includes a heavy chain including amino acid sequence of SEQ ID NO: 30 and a light chain including the amino acid sequence of SEQ ID NO: 4. In some embodiments, the activatable antibody includes a heavy chain including amino acid sequence of SEQ ID NO: 30 and a light chain including the amino acid sequence of SEQ ID NO: 28.

In some embodiments, the AB of the activatable antibody includes a heavy chain including amino acid sequence of SEQ ID NO: 10 and a light chain including the amino acid sequence of SEQ ID NO: 68. In some embodiments, the activatable antibody includes a heavy chain including amino acid sequence of SEQ ID NO: 10 and a light chain including the amino acid sequence of SEQ ID NO: 4. In some embodiments, the activatable antibody includes a heavy chain including amino acid sequence of SEQ ID NO: 10 and a light chain including the amino acid sequence of SEQ ID NO: 28.

In some embodiments, the AB of the activatable antibody includes and a heavy chain including amino acid sequence of SEQ ID NO: 34 and a light chain including the amino acid sequence of SEQ ID NO: 68. In some embodiments, the activatable antibody includes a heavy chain including amino acid sequence of SEQ ID NO: 34 and a light chain including the amino acid sequence of SEQ ID NO: 4. In some embodiments, the activatable antibody includes a heavy chain including amino acid sequence of SEQ ID NO: 34 and a light chain including the amino acid sequence of SEQ ID NO: 28.

In some embodiments of the conjugated activatable antibody, the AB has an equilibrium dissociation constant of about 100 nM or less for binding to EGFR.

In some embodiments of the conjugated activatable antibody, the MM has an equilibrium dissociation constant for binding to the AB which is greater than the equilibrium dissociation constant of the AB to EGFR. In some embodiments of the conjugated activatable antibody, the MM does not interfere or compete with the AB of the activatable antibody in a cleaved state for binding to EGFR. In some embodiments of the conjugated activatable antibody, the MM is a polypeptide of no more than 40 amino acids in length. In some embodiments of the conjugated activatable antibody, the MM polypeptide sequence is different from that of EGFR, and the MM polypeptide sequence is no more than 50% identical to any natural binding partner of the AB. In some embodiments of the conjugated activatable antibody, the MM does not include more than 25% amino acid sequence identity to EGFR. In some embodiments of the conjugated activatable antibody, the MM does not include more than 10% amino acid sequence identity to EGFR. In some embodiments of the conjugated activatable antibody, the MM includes the amino acid sequence CISPRGCPDGPYVMY (SEQ ID NO: 14).

In some embodiments of the conjugated activatable antibody, the CM is a polypeptide of up to 15 amino acids in length. In some embodiments of the conjugated activatable antibody, the CM is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1. In some embodiments of the conjugated activatable antibody, the CM includes the amino acid sequence LSGRSDNH (SEQ ID NO: 13).

In some embodiments, the conjugated activatable antibody includes a linking peptide between the MM and the CM. In some embodiments, the conjugated activatable antibody includes a linking peptide between the CM and the AB. In some embodiments, the conjugated activatable antibody includes a first linking peptide (LP1) and a second linking peptide (LP2), and wherein the conjugated activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments of the conjugated activatable antibody, at least one of LP1 or LP2 includes an amino acid sequence selected from the group consisting of $(GS)_n$, $(GGS)_n$, (GSGGS), (SEQ ID NO: 15) and (GGGS), (SEQ ID NO: 16), where n is an integer of at least one. In some embodiments of the conjugated activatable antibody, at least one of LP1 or LP2 includes an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), and GSSSG (SEQ ID NO: 22). In some embodiments of the conjugated activatable antibody, LP1 includes the amino acid sequence GSSGGSGGSGGSG (SEQ ID NO: 23). In some embodiments of the conjugated activatable antibody, LP2 includes the amino acid sequence GSSGT (SEQ ID NO: 24) or GSSG (SEQ ID NO: 37).

In some embodiments, the anti-EGFR activatable antibody is exposed to and cleaved by uPA or MT-SP1 such that, in the activated or cleaved state, the activated antibody includes the light chain amino acid sequence of SEQ ID NO: 69. In some embodiments, the anti-EGFR activatable antibody is exposed to and cleaved by legumain such that, in the activated or cleaved state, the activated antibody includes the light chain amino acid sequence of SEQ ID NO: 70.

In some embodiments, the cytotoxic agent included in the conjugated activatable antibody is an agent that is conjugated to the AB. In some embodiments of the conjugated activatable antibody, the agent is a therapeutic agent. In some embodiments, the agent is an antineoplastic agent. In some embodiments of the conjugated activatable antibody, the agent is a toxin or fragment thereof. In some embodiments of the conjugated activatable antibody, the agent is an agent selected from the group listed in Table 1. In some embodiments of the conjugated activatable antibody, the agent is a dolastatin. In some embodiments, the agent is an auristatin or derivative thereof. In some embodiments, the agent is auristatin E or a derivative thereof. In some embodiments of the conjugated activatable antibody, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments of the conjugated activatable antibody, the agent is conjugated to the AB via a linker. In some embodiments of the conjugated activatable antibody, the linker is a cleavable linker. In some embodiments of the conjugated activatable antibody, the linker is selected from the group consisting of the linkers shown in Tables 2 and 3.

In some embodiments, the conjugated activatable antibody also includes a detectable moiety. In some embodiments of the conjugated activatable antibody, the detectable moiety is a diagnostic agent. In some embodiments, the detectable moiety is a conjugatable detection reagent. In some embodiments, the detectable moiety is, for example, a fluorescein derivative such as fluorescein isothiocyanate (FITC).

In some embodiments, the conjugated activatable antibody also includes a signal peptide. In some embodiments, the signal peptide is conjugated to the conjugated activatable antibody via a spacer. In some embodiments, the spacer is conjugated to the conjugated activatable antibody in the absence of a signal peptide. In some embodiments, the spacer is joined directly to the MM of the conjugated activatable antibody. In some embodiments, the spacer includes at least the amino acid sequence QGQSGQ (SEQ ID NO: 38). In some embodiments, an activatable antibody includes a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, an activatable antibody includes a spacer joined directly to a MM sequence and includes the amino acid sequence QGQSGQCISPRGCPDGPYVMY (SEQ ID NO: 59) in the structural arrangement from N-terminus to C-terminus of spacer-MM-CM-AB.

In some embodiments, the serum half-life of the conjugated activatable antibody is at least 5 days when administered to an organism. In some embodiments, the serum half-life of the conjugated activatable antibody is at least 4 days when administered to an organism. In some embodiments, the serum half-life of the conjugated activatable antibody is at least 3 days when administered to an organism. In some embodiments, the serum half-life of the conjugated activatable antibody is at least 2 days when administered to an organism. In some embodiments, the serum half-life of the conjugated activatable antibody is at least 24 hours when administered to an organism. In some embodiments, the serum half-life of the conjugated activatable antibody is at least 20 hours when administered to an organism. In some embodiments, the serum half-life of the conjugated activatable antibody is at least 18 hours when administered to an organism. In some embodiments, the serum half-life of the conjugated activatable antibody is at least 16 hours when administered to an organism. In some embodiments, the serum half-life of the conjugated activatable antibody is at least 14 hours when administered to an organism. In some embodiments, the serum half-life of the conjugated activatable antibody is at least 12 hours when administered to an organism. In some embodiments, the serum half-life of the conjugated activatable antibody is at least 10 hours when administered to an organism. In some embodiments, the serum half-life of the conjugated activatable antibody is at least 8 hours when administered to an organism. In some embodiments, the serum half-life of the conjugated activatable antibody is at least 6 hours when administered to an organism. In some embodiments, the serum half-life of the conjugated activatable antibody is at least 4 hours when administered to an organism. In some embodiments, the serum half-life of the conjugated activatable antibody is at least 3 hours when administered to an organism.

In some embodiments, the conjugated activatable anti-EGFR antibody is monospecific. In some embodiments, the conjugated activatable anti-EGFR antibody is multispecific, e.g., by way of non-limiting example, bispecific or trifunctional. In some embodiments, the conjugated activatable anti-EGFR antibody is formulated as part of a pro-Bispecific T Cell Engager (BITE) molecule. In some embodiments, the conjugated activatable anti-EGFR antibody is formulated as part of a pro-Chimeric Antigen Receptor (CAR) modified T cell or other engineered receptor.

The invention also provides an isolated nucleic acid molecule encoding an activatable anti-EGFR antibody described herein, as well as vectors that include these isolated nucleic acid sequences. The invention provides methods of producing an activatable antibody by culturing a cell under conditions that lead to expression of the activatable antibody, wherein the cell includes such a vector.

In some embodiments, the nucleic acid encodes a MM that has an equilibrium dissociation constant for binding to the AB which is greater than the equilibrium dissociation constant of the AB to EGFR. In some embodiments, the nucleic acid encodes a MM that has an equilibrium dissociation constant for binding to the AB which is no more than the equilibrium dissociation constant of the AB to EGFR. In some embodiments, the nucleic acid encodes a MM that does not interfere or compete with the AB of the activatable antibody in a cleaved state for binding to EGFR.

In some embodiments, the nucleic acid encodes a CM that is cleaved by a protease that is co-localized with EGFR in a tissue, and the protease cleaves the CM in the activatable antibody when the activatable antibody is exposed to the protease. In some embodiments, the protease is not active or is significantly less active in tissues that do not significantly express EGFR. In some embodiments, the protease is not active or is significantly less active in healthy, e.g., non-diseased tissues.

In some embodiments, the nucleic acid encodes an activatable antibody that has the structural arrangement from N-terminus to C-terminus as follows in the uncleaved state: MM-CM-AB or AB-CM-MM.

In some embodiments, the nucleic acid encodes an activatable antibody that includes a linking peptide between the MM and the CM.

In some embodiments, the nucleic acid encodes an activatable antibody that includes a linking peptide between the CM and the AB.

In some embodiments, the nucleic acid encodes an activatable antibody that includes a first linking peptide (LP1) and a second linking peptide (LP2), and wherein the activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, the nucleic acid that encodes the AB of an activatable antibody includes a heavy chain including amino acid sequence of SEQ ID NO: 2 and a light chain including the amino acid sequence of SEQ ID NO: 68. In some embodiments, the nucleic acid that encodes an activatable antibody includes a heavy chain including amino acid sequence of SEQ ID NO: 2 and a light chain including the amino acid sequence of SEQ ID NO: 4. In some embodiments, the nucleic acid that encodes an activatable antibody includes a heavy chain including amino acid sequence of SEQ ID NO: 2 and a light chain including the amino acid sequence of SEQ ID NO: 28.

In some embodiments, the nucleic acid that encodes the AB of an activatable antibody includes a heavy chain including amino acid sequence of SEQ ID NO: 26 and a light chain including the amino acid sequence of SEQ ID NO: 68. In some embodiments, the nucleic acid that encodes an activatable antibody includes a heavy chain including amino acid sequence of SEQ ID NO: 26 and a light chain including the amino acid sequence of SEQ ID NO: 4. In some embodiments, the nucleic acid that encodes an activatable antibody includes a heavy chain including amino acid sequence of SEQ ID NO: 26 and a light chain including the amino acid sequence of SEQ ID NO: 28.

In some embodiments, the nucleic acid that encodes the AB of an activatable antibody includes a heavy chain including amino acid sequence of SEQ ID NO: 6 and a light chain including the amino acid sequence of SEQ ID NO: 68. In some embodiments, the nucleic acid that encodes an activatable antibody includes a heavy chain including amino acid sequence of SEQ ID NO: 6 and a light chain including the amino acid sequence of SEQ ID NO: 4. In some embodiments, the nucleic acid that encodes an activatable antibody includes a heavy chain including amino acid sequence of SEQ ID NO: 6 and a light chain including the amino acid sequence of SEQ ID NO: 28.

In some embodiments, the nucleic acid that encodes the AB of an activatable antibody includes a heavy chain including amino acid sequence of SEQ ID NO: 30 and a light chain including the amino acid sequence of SEQ ID NO: 68. In some embodiments, the nucleic acid that encodes an activatable antibody includes a heavy chain including amino acid sequence of SEQ ID NO: 30 and a light chain including the amino acid sequence of SEQ ID NO: 4. In some embodiments, the nucleic acid that encodes an activatable antibody includes a heavy chain including amino acid sequence of SEQ ID NO: 30 and a light chain including the amino acid sequence of SEQ ID NO: 28.

In some embodiments, the nucleic acid that encodes the AB of an activatable antibody includes a heavy chain including amino acid sequence of SEQ ID NO: 10 and a light chain including the amino acid sequence of SEQ ID NO: 68. In some embodiments, the nucleic acid that encodes an activatable antibody includes a heavy chain including amino acid sequence of SEQ ID NO: 10 and a light chain including the amino acid sequence of SEQ ID NO: 4. In some embodiments, the nucleic acid that encodes an activatable antibody includes a heavy chain including amino acid sequence of SEQ ID NO: 10 and a light chain including the amino acid sequence of SEQ ID NO: 28.

In some embodiments, the nucleic acid that encodes the AB of an activatable antibody includes a heavy chain including amino acid sequence of SEQ ID NO: 34 and a light chain including the amino acid sequence of SEQ ID NO: 68. In some embodiments, the nucleic acid that encodes an activatable antibody includes a heavy chain including amino acid sequence of SEQ ID NO: 34 and a light chain including the amino acid sequence of SEQ ID NO: 4. In some embodiments, the nucleic acid that encodes an activatable antibody includes a heavy chain including amino acid sequence of SEQ ID NO: 34 and a light chain including the amino acid sequence of SEQ ID NO: 28.

In some embodiments, the nucleic acid includes an AB that includes a heavy chain including nucleic acid sequence of SEQ ID NO: 1 and a light chain including the nucleic acid sequence of SEQ ID NO: 67. In some embodiments, the nucleic acid includes a heavy chain including nucleic acid sequence of SEQ ID NO: 1 and a light chain including the nucleic acid sequence of SEQ ID NO: 3. In some embodiments, the nucleic acid includes a heavy chain including nucleic acid sequence of SEQ ID NO: 1 and a light chain including the nucleic acid sequence of SEQ ID NO: 27.

In some embodiments, the nucleic acid includes an AB that includes a heavy chain including nucleic acid sequence of SEQ ID NO: 25 and a light chain including the nucleic acid sequence of SEQ ID NO: 67. In some embodiments, the nucleic acid includes a heavy chain including nucleic acid sequence of SEQ ID NO: 25 and a light chain including the nucleic acid sequence of SEQ ID NO: 3. In some embodiments, the nucleic acid includes a heavy chain including nucleic acid sequence of SEQ ID NO: 25 and a light chain including the nucleic acid sequence of SEQ ID NO: 27.

In some embodiments, the nucleic acid includes an AB that includes a heavy chain including nucleic acid sequence of SEQ ID NO: 5 and a light chain including the nucleic acid sequence of SEQ ID NO: 67. In some embodiments, the nucleic acid includes a heavy chain including nucleic acid sequence of SEQ ID NO: 5 and a light chain including the nucleic acid sequence of SEQ ID NO: 3. In some embodiments, the nucleic acid includes a heavy chain including nucleic acid sequence of SEQ ID NO: 5 and a light chain including the nucleic acid sequence of SEQ ID NO: 27.

In some embodiments, the nucleic acid includes an AB that includes a heavy chain including nucleic acid sequence of SEQ ID NO: 29 and a light chain including the nucleic acid sequence of SEQ ID NO: 67. In some embodiments, the nucleic acid includes a heavy chain including nucleic acid sequence of SEQ ID NO: 29 and a light chain including the nucleic acid sequence of SEQ ID NO: 3. In some embodiments, the nucleic acid includes a heavy chain including nucleic acid sequence of SEQ ID NO: 29 and a light chain including the nucleic acid sequence of SEQ ID NO: 27.

In some embodiments, the nucleic acid includes an AB that includes a heavy chain including nucleic acid sequence of SEQ ID NO: 9 and a light chain including the nucleic acid sequence of SEQ ID NO: 67. In some embodiments, the nucleic acid includes a heavy chain including nucleic acid sequence of SEQ ID NO: 9 and a light chain including the nucleic acid sequence of SEQ ID NO: 3. In some embodiments, the nucleic acid includes a heavy chain including nucleic acid sequence of SEQ ID NO: 9 and a light chain including the nucleic acid sequence of SEQ ID NO: 27.

In some embodiments, the nucleic acid includes an AB that includes a heavy chain including nucleic acid sequence of SEQ ID NO: 33 and a light chain including the nucleic acid sequence of SEQ ID NO: 67. In some embodiments, the nucleic acid includes a heavy chain including nucleic acid sequence of SEQ ID NO: 33 and a light chain including the nucleic acid sequence of SEQ ID NO: 3. In some embodiments, the nucleic acid includes a heavy chain including nucleic acid sequence of SEQ ID NO: 33 and a light chain including the nucleic acid sequence of SEQ ID NO: 27.

In some embodiments, the nucleic acid encodes an AB that has an equilibrium dissociation constant of about 100 nM or less for binding to EGFR.

In some embodiments, the nucleic acid encodes a MM that is a polypeptide of about 2 to 40 amino acids in length, for example, no more than 40 amino acids long.

In some embodiments, the nucleic acid encodes a MM polypeptide sequence that is different from that of EGFR, and the MM polypeptide sequence is no more than 50% identical to any natural binding partner of the AB.

In some embodiments, the nucleic acid encodes a CM that is positioned in the activatable antibody such that in the uncleaved state, binding of the activatable antibody to EGFR is reduced to occur with an equilibrium dissociation constant that is at least 20-fold greater than the equilibrium dissociation constant of an unmodified AB binding to EGFR, and whereas the AB of the activatable antibody in the cleaved state binds EGFR.

In some embodiments, the nucleic acid encodes a CM that is positioned in the activatable antibody such that in the uncleaved state, binding of the activatable antibody to EGFR is reduced to occur with an equilibrium dissociation constant that is at least 100-fold greater than the equilibrium dissociation constant of an unmodified AB binding to EGFR, and whereas the AB of the activatable antibody in the cleaved state binds EGFR.

In some embodiments, the nucleic acid encodes a CM that is positioned in the activatable antibody such that in the uncleaved state, binding of the activatable antibody to EGFR is reduced to occur with an equilibrium dissociation constant that is at least 200-fold greater than the equilibrium dissociation constant of an unmodified AB binding to EGFR, and whereas the AB of the activatable antibody in the cleaved state binds EGFR.

In some embodiments, the nucleic acid encodes a CM that is a polypeptide of up to 15 amino acids in length.

In some embodiments, nucleic acid encodes a MM, that in the presence of EGFR, reduces the ability of the AB to bind EGFR by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the nucleic acid encodes an activatable antibody that includes an antibody or antigen-binding fragment thereof that specifically binds EGFR. In some embodiments, the nucleic acid encodes an antibody or immunologically active fragment thereof that binds EGFR and is a monoclonal antibody, domain antibody, single chain, Fab fragment, a $F(ab')_2$ fragment, a scFv, a scab, a dAb, a single domain heavy chain antibody, and a single domain light chain antibody. In some embodiments, the nucleic acid encodes an antibody or immunologically active fragment thereof that binds EGFR and is a mouse, chimeric, humanized or fully human monoclonal antibody.

In some embodiments, the nucleic acid encodes the AB of an activatable antibody that includes a heavy chain amino acid sequence selected from the group consisting of SEQ ID NO: 2, SEQ ID NO: 6, and SEQ ID NO: 10, and a light chain amino acid sequence including SEQ ID NO: 68. In some embodiments, the nucleic acid encodes the AB of an activatable antibody that includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the nucleic acid encodes an activatable antibody that includes a heavy chain amino acid sequence selected from the group consisting of SEQ ID NO: 2, SEQ ID NO: 6, and SEQ ID NO: 10, and a light chain amino acid sequence including SEQ ID NO: 28. In some embodiments, the nucleic acid encodes an activatable antibody that includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 28.

In some embodiments, the nucleic acid encodes an activatable antibody that includes a heavy chain amino acid sequence selected from the group consisting of SEQ ID NO: 2, SEQ ID NO: 6, and SEQ ID NO: 10, and a light chain amino acid sequence including SEQ ID NO: 4. In some embodiments, the nucleic acid encodes an activatable antibody that includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 4.

In some embodiments, the nucleic acid includes an AB that includes a heavy chain nucleic acid sequence selected from the group consisting of SEQ ID NO: 1, SEQ ID NO: 5, and SEQ ID NO: 9, and a light chain nucleic acid sequence that includes SEQ ID NO: 67. In some embodiments, the nucleic acid sequence includes an AB that includes a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a light chain nucleic acid that is at least 90%, 91%, 92%, 93%, 94%, 95%, 96%, 97%, 98% or 99% identical to a nucleic acid sequence including SEQ ID NO: 67.

In some embodiments, the nucleic acid includes a heavy chain nucleic acid sequence selected from the group consisting of SEQ ID NO: 1, SEQ ID NO: 5, and SEQ ID NO: 9, and a light chain nucleic acid sequence that includes SEQ ID NO: 27. In some embodiments, the nucleic acid sequence includes a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a light chain nucleic acid that is at least 90%, 91%, 92%, 93%, 94%, 95%, 96%, 97%, 98% or 99% identical to a nucleic acid sequence including SEQ ID NO: 27.

In some embodiments, the nucleic acid includes a heavy chain nucleic acid sequence selected from the group consisting of SEQ ID NO: 1, SEQ ID NO: 5, and SEQ ID NO: 9, and a light chain nucleic acid sequence that includes SEQ ID NO: 3. In some embodiments, the nucleic acid sequence includes a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a light chain nucleic acid that is at least 90%, 91%, 92%, 93%, 94%, 95%, 96%, 97%, 98% or 99% identical to a nucleic acid sequence including SEQ ID NO: 3.

In some embodiments, the nucleic acid that encodes an activatable antibody includes an AB that includes a heavy chain amino acid sequence selected from the group consisting of SEQ ID NO: 26, SEQ ID NO: 30 and SEQ ID NO: 34, and a light chain amino acid sequence including SEQ ID NO: 68. In some embodiments, the activatable antibody includes an AB that includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the nucleic acid that encodes an activatable antibody includes a heavy chain amino acid sequence selected from the group consisting of SEQ ID NO: 26, SEQ ID NO: 30 and SEQ ID NO: 34, and a light chain amino acid sequence including SEQ ID NO: 28. In some embodiments, the activatable antibody includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 28.

In some embodiments, the nucleic acid that encodes an activatable antibody includes a heavy chain amino acid sequence selected from the group consisting of SEQ ID NO: 26, SEQ ID NO: 30 and SEQ ID NO: 34, and a light chain amino acid sequence including SEQ ID NO: 4. In some embodiments, the activatable antibody includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 4.

In some embodiments, the nucleic acid includes an AB that includes a heavy chain nucleic acid sequence selected from the group consisting of SEQ ID NO: 25, SEQ ID NO: 29, and SEQ ID NO: 33, and a light chain nucleic acid sequence that includes SEQ ID NO: 67. In some embodiments, the nucleic acid sequence includes an AB that includes a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a light chain nucleic acid that is at least 90%, 91%, 92%, 93%, 94%, 95%, 96%, 97%, 98% or 99% identical to a nucleic acid sequence including SEQ ID NO: 67.

In some embodiments, the nucleic acid includes a heavy chain nucleic acid sequence selected from the group consisting of SEQ ID NO: 25, SEQ ID NO: 29, and SEQ ID NO: 33, and a light chain nucleic acid sequence that includes SEQ ID NO: 27. In some embodiments, the nucleic acid sequence includes a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a light chain nucleic acid that is at least 90%, 91%, 92%, 93%, 94%, 95%, 96%, 97%, 98% or 99% identical to a nucleic acid sequence including SEQ ID NO: 27.

In some embodiments, the nucleic acid includes a heavy chain nucleic acid sequence selected from the group consisting of SEQ ID NO: 25, SEQ ID NO: 29, and SEQ ID NO: 33, and a light chain nucleic acid sequence that includes SEQ ID NO: 4. In some embodiments, the nucleic acid sequence includes a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a light chain nucleic acid that is at least 90%, 91%, 92%, 93%, 94%, 95%, 96%, 97%, 98% or 99% identical to a nucleic acid sequence including SEQ ID NO: 4.

In some embodiments, the nucleic acid encodes a CM that is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1.

In some embodiments, the nucleic acid encodes a CM that includes the amino acid sequence LSGRSDNH (SEQ ID NO: 13).

In some embodiments, the nucleic acid encodes a MM that does not include more than 25% amino acid sequence identity to EGFR. In some embodiments, the nucleic acid encodes a MM that does not include more than 10% amino acid sequence identity to EGFR.

In some embodiments, the nucleic acid encodes a MM that includes the amino acid sequence CISPRGCPDGPYVMY (SEQ ID NO: 14).

In some embodiments, the nucleic acid encodes an LP1 and/or LP2, wherein ta least one of LP1 or LP2 includes an amino acid sequence selected from the group consisting of $(GS)_n$, $(GGS)_n$, $(GSGGS)_n$ (SEQ ID NO: 15) and $(GGGS)_n$ (SEQ ID NO: 16), where n is an integer of at least one.

In some embodiments, the nucleic acid encodes an LP1 and/or LP2, wherein at least one of LP1 or LP2 includes an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), and GSSSG (SEQ ID NO: 22).

In some embodiments, the nucleic acid encodes an LP1 that includes the amino acid sequence GSSGGSGGSGGSG (SEQ ID NO: 23).

In some embodiments, the nucleic acid encodes an LP2 that includes the amino acid sequence GSSGT (SEQ ID NO: 24) or GSSG (SEQ ID NO: 37).

In some embodiments, the nucleic acid encodes an activatable antibody that also includes a signal peptide. In some embodiments, the nucleic acid encodes a signal peptide that is conjugated to the activatable antibody via a spacer. In some embodiments, the nucleic acid encodes a spacer that is conjugated to the activatable antibody in the absence of a signal peptide. In some embodiments, the nucleic acid encodes a spacer that is joined directly to the MM of the activatable antibody. In some embodiments, the nucleic acid encodes a spacer that includes at least the amino acid sequence QGQSGQ (SEQ ID NO: 38). In some embodiments, the nucleic acid encodes an activatable antibody that includes a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, the nucleic acid encodes an activatable antibody that includes a spacer joined directly to a MM sequence and includes the amino acid sequence QGQSGQ-CISPRGCPDGPYVMY (SEQ ID NO: 59) in the structural arrangement from N-terminus to C-terminus of spacer-MM-CM-AB.

The invention also provides a method of manufacturing activatable antibodies that in an activated state binds Epidermal Growth Factor Receptor (EGFR) by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds EGFR, (i) wherein the CM is a polypeptide that functions as a substrate for a protease; and (ii) wherein the CM is positioned in the activatable antibody such that, in an uncleaved state, the MM interferes with specific binding of the AB to EGFR and, when the activatable antibody is in a cleaved state, the MM does not interfere or compete with specific binding of the AB to EGFR; and (b) recovering the activatable antibody.

In some embodiments, the AB is or is derived from cetuximab,

In some embodiments, the MM has an equilibrium dissociation constant for binding to the AB which is greater than the equilibrium dissociation constant of the AB to EGFR.

In some embodiments, the MM has an equilibrium dissociation constant for binding to the AB which is no more than the equilibrium dissociation constant of the AB to EGFR.

In some embodiments, the MM does not interfere or compete with the AB of the activatable antibody in a cleaved state for binding to EGFR.

In some embodiments, the protease is co-localized with EGFR in a tissue, and the protease cleaves the CM in the activatable antibody when the activatable antibody is exposed to the protease. In some embodiments, the protease is not active or is significantly less active in tissues that do not significantly express EGFR. In some embodiments, the protease is not active or is significantly less active in healthy, e.g., non-diseased tissues.

In some embodiments, the activatable antibody has the structural arrangement from N-terminus to C-terminus as follows in the uncleaved state: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody has the structural arrangement from N-terminus to C-terminus as follows in the uncleaved state: MM-LP1-CM-LP2-AB or AB-LP2-CM-LP1-MM.

In some embodiments, the two linking peptides need not be identical to each other.

In some embodiments, the AB has an equilibrium dissociation constant of about 100 nM or less for binding to EGFR.

In some embodiments, the MM is a polypeptide of about 2 to 40 amino acids in length, for example, no more than 40 amino acids long.

In some embodiments, the MM polypeptide sequence is different from that of EGFR, and the MM polypeptide sequence is no more than 50% identical to any natural binding partner of the AB.

In some embodiments, the CM is positioned in the activatable antibody such that in the uncleaved state, binding of the activatable antibody to EGFR is reduced to occur with an equilibrium dissociation constant that is at least 20-fold greater than the equilibrium dissociation constant of an unmodified AB binding to EGFR, and whereas the AB of the activatable antibody in the cleaved state binds EGFR.

In some embodiments, the CM is positioned in the activatable antibody such that in the uncleaved state, binding of the activatable antibody to EGFR is reduced to occur with an equilibrium dissociation constant that is at least 100-fold greater than the equilibrium dissociation constant of an unmodified AB binding to EGFR, and whereas the AB of the activatable antibody in the cleaved state binds EGFR.

In some embodiments, the CM is positioned in the activatable antibody such that in the uncleaved state, binding of the activatable antibody to EGFR is reduced to occur with an equilibrium dissociation constant that is at least 200-fold greater than the equilibrium dissociation constant of an unmodified AB binding to EGFR, and whereas the AB of the activatable antibody in the cleaved state binds EGFR.

In some embodiments, the coupling of the MM reduces the ability of the AB to bind EGFR such that the dissociation constant ($K_d$) of the AB when coupled to the MM towards EGFR is at least 20 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 100 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 1000 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 10,000 times greater than the $K_d$ of the AB when not coupled to the MM towards EGFR.

In some embodiments, the CM is a polypeptide of up to 15 amino acids in length.

In some embodiments, in the presence of EGFR, the MM reduces the ability of the AB to bind EGFR by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the activatable antibody includes an antibody or antigen-binding fragment thereof that specifically binds EGFR. In some embodiments, the antibody or immunologically active fragment thereof that binds EGFR is a monoclonal antibody, domain antibody, single chain, Fab fragment, a $F(ab')_2$ fragment, a scFv, a scab, a dAb, a single domain heavy chain antibody, and a single domain light chain antibody. In some embodiments, such an antibody or immunologically active fragment thereof that binds EGFR is a mouse, chimeric, humanized or fully human monoclonal antibody.

In some embodiments, the AB of the activatable antibody comprises a heavy chain amino acid sequence selected from the group consisting of SEQ ID NO: 2, SEQ ID NO: 6, and SEQ ID NO: 10, and a light chain amino acid sequence comprising SEQ ID NO: 68. In some embodiments, the AB of the activatable antibody comprises a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence comprising SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain amino acid sequence selected from the group consisting of SEQ ID NO: 2, SEQ ID NO: 6, and SEQ ID NO: 10, and a light chain amino acid sequence comprising SEQ ID NO: 28. In some embodiments, the activatable antibody comprises a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence comprising SEQ ID NO: 28.

In some embodiments, the activatable antibody comprises a heavy chain amino acid sequence selected from the group consisting of SEQ ID NO: 2, SEQ ID NO: 6, and SEQ ID NO: 10, and a light chain amino acid sequence comprising SEQ ID NO: 4. In some embodiments, the activatable antibody comprises a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence comprising SEQ ID NO: 4.

In some embodiments, the AB of the activatable antibody is encoded by a nucleic acid sequence that comprises a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence comprising SEQ ID NO: 68. In some embodiments, the AB of the activatable antibody is encoded by a nucleic acid sequence encoding a comprises a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence encoding a light chain amino acid that is at least 90%, 91%, 92%, 93%, 94%, 95%, 96%, 97%, 98% or 99% identical to an amino acid sequence comprising SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody is encoded by a nucleic acid sequence that comprises a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence comprising SEQ ID NO: 67. In some embodiments, the AB of the activatable antibody is encoded by a nucleic acid sequence encoding a comprises a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence encoding a light chain amino acid that is at least 90%, 91%, 92%, 93%, 94%, 95%, 96%, 97%, 98% or 99% identical to an amino acid sequence comprising SEQ ID NO: 67.

In some embodiments, the activatable antibody is encoded by a nucleic acid sequence that comprises a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence comprising SEQ ID NO: 4. In some embodiments, the activatable antibody is encoded by a nucleic acid sequence encoding a comprises a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence encoding a light chain amino acid that is at least 90%, 91%, 92%, 93%, 94%, 95%, 96%, 97%, 98% or 99% identical to an amino acid sequence comprising SEQ ID NO: 4.

In some embodiments, the AB of the activatable antibody is encoded by a nucleic acid comprising a heavy chain nucleic acid sequence selected from the group consisting of SEQ ID NO: 1, SEQ ID NO: 5, and SEQ ID NO: 9, and a light chain nucleic acid sequence comprising SEQ ID NO: 67. In some embodiments, the AB of the activatable antibody is encoded by a nucleic acid sequence comprising a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence that comprises a nucleic acid sequence encoding a light chain nucleic acid that is at least 90%, 91%, 92%, 93%, 94%, 95%, 96%, 97%, 98% or 99% identical to a nucleic acid sequence selected comprising SEQ ID NO: 67.

In some embodiments, the activatable antibody is encoded by a nucleic acid comprising a heavy chain nucleic acid sequence selected from the group consisting of SEQ ID NO: 1, SEQ ID NO: 5, and SEQ ID NO: 9, and a light chain nucleic acid sequence comprising SEQ ID NO: 27. In some embodiments, the activatable antibody is encoded by a nucleic acid sequence comprising a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence that comprises a nucleic acid sequence encoding a light chain nucleic acid that is at least 90%, 91%, 92%, 93%, 94%, 95%, 96%, 97%, 98% or 99% identical to a nucleic acid sequence selected comprising SEQ ID NO: 27.

In some embodiments, the activatable antibody is encoded by a nucleic acid comprising a heavy chain nucleic acid sequence selected from the group consisting of SEQ ID NO: 1, SEQ ID NO: 5, and SEQ ID NO: 9, and a light chain nucleic acid sequence comprising SEQ ID NO: 4. In some embodiments, the activatable antibody is encoded by a nucleic acid sequence comprising a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence that comprises a nucleic acid sequence encoding a light chain nucleic acid that is at least 90%, 91%, 92%, 93%, 94%, 95%, 96%, 97%, 98% or 99% identical to a nucleic acid sequence selected comprising SEQ ID NO: 4.

In some embodiments, the AB of the activatable antibody comprises a heavy chain amino acid sequence selected from the group consisting of SEQ ID NO: 26, SEQ ID NO: 30 and SEQ ID NO: 34, and a light chain amino acid sequence comprising SEQ ID NO: 68. In some embodiments, the AB of the activatable antibody comprises a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence comprising SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain amino acid sequence selected from the group consisting of SEQ ID NO: 26, SEQ ID NO: 30 and SEQ ID NO: 34, and a light chain amino acid sequence comprising SEQ ID NO: 28. In some embodiments, the activatable antibody comprises a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence comprising SEQ ID NO: 28.

In some embodiments, the activatable antibody comprises a heavy chain amino acid sequence selected from the group consisting of SEQ ID NO: 26, SEQ ID NO: 30 and SEQ ID NO: 34, and a light chain amino acid sequence comprising SEQ ID NO: 4. In some embodiments, the activatable antibody comprises a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence comprising SEQ ID NO: 4.

In some embodiments, the AB of the activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence comprising SEQ ID NO: 68. In some embodiments, the AB of the activatable antibody is encoded by a nucleic acid encoding a heavy chain amino acid sequence that is at least 90%, 91%, 92%, 93%, 94%, 95%, 96%, 97%, 98% or 99% identical to an amino acid selected from the group consisting of SEQ ID NO: 26, SEQ ID NO: 30, and SEQ ID NO: 34, and a nucleic acid sequence encoding a light chain amino acid that is at least 90%, 91%, 92%, 93%, 94%, 95%, 96%, 97%, 98% or 99% identical to an amino acid sequence comprising SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence comprising SEQ ID NO: 28. In some embodiments, the activatable antibody is encoded by a nucleic acid encoding a heavy chain amino acid sequence that is at least 90%, 91%, 92%, 93%, 94%, 95%, 96%, 97%, 98% or 99% identical to an amino acid selected from the group consisting of SEQ ID NO: 26, SEQ ID NO: 30, and SEQ ID NO: 34, and a nucleic acid sequence encoding a light chain amino acid that is at least 90%, 91%, 92%, 93%, 94%, 95%, 96%, 97%, 98% or 99% identical to an amino acid sequence comprising SEQ ID NO: 68.

In some embodiments, the activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence comprising SEQ ID NO: 4. In some embodiments, the activatable antibody is encoded by a nucleic acid encoding a heavy chain amino acid sequence that is at least 90%, 91%, 92%, 93%, 94%, 95%, 96%, 97%, 98% or 99% identical to an amino acid selected from the group consisting of SEQ ID NO: 26, SEQ ID NO: 30, and SEQ ID NO: 34, and a nucleic acid sequence encoding a light chain amino acid that is at least 90%, 91%, 92%, 93%, 94%, 95%, 96%, 97%, 98% or 99% identical to an amino acid sequence comprising SEQ ID NO: 4.

In some embodiments, the AB of the activatable antibody is encoded by a nucleic acid comprising a heavy chain nucleic acid sequence selected from the group consisting of SEQ ID NO: 25, SEQ ID NO: 29, and SEQ ID NO: 33, and a light chain nucleic acid sequence comprising SEQ ID NO: 67. In some embodiments, the AB of the activatable antibody is encoded by a nucleic acid sequence comprising a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to an nucleic acid sequence comprising SEQ ID NO: 67.

In some embodiments, the activatable antibody is encoded by a nucleic acid comprising a heavy chain nucleic acid sequence selected from the group consisting of SEQ ID NO: 25, SEQ ID NO: 29, and SEQ ID NO: 33, and a light chain nucleic acid sequence comprising SEQ ID NO: 27. In some embodiments, the activatable antibody is encoded by a nucleic acid sequence comprising a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to an nucleic acid sequence comprising SEQ ID NO: 27.

In some embodiments, the activatable antibody is encoded by a nucleic acid comprising a heavy chain nucleic acid sequence selected from the group consisting of SEQ ID NO: 25, SEQ ID NO: 29, and SEQ ID NO: 33, and a light chain nucleic acid sequence comprising SEQ ID NO: 3. In some embodiments, the activatable antibody is encoded by a nucleic acid sequence comprising a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to an nucleic acid sequence comprising SEQ ID NO: 3.

In some embodiments, the AB of the activatable antibody comprises a heavy chain comprising the amino acid sequence of SEQ ID NO: 2, and a light chain comprising the amino acid sequence of SEQ ID NO: 68. In some embodiments, the AB of the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 2, and a light chain comprising an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain comprising the amino acid sequence of SEQ ID NO: 2, and a light chain comprising the amino acid sequence of SEQ ID NO: 28. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 2, and a light chain comprising an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody comprises a heavy chain comprising the amino acid sequence of SEQ ID NO: 2, and a light chain comprising the amino acid sequence of SEQ ID NO: 4. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 2, and a light chain comprising an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody comprises a heavy chain comprising the amino acid sequence of SEQ ID NO: 26, and a light chain comprising the amino acid sequence of SEQ ID NO: 68. In some embodiments, the AB of the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 26, and a light chain comprising an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain comprising the amino acid sequence of SEQ ID NO: 26, and a light chain comprising the amino acid sequence of SEQ ID NO: 28. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 26, and a light chain comprising an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody comprises a heavy chain comprising the amino acid sequence of SEQ ID NO: 26, and a light chain comprising the amino acid sequence of SEQ ID NO: 4. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 26, and a light chain comprising an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody comprises a heavy chain comprising the amino acid sequence of SEQ ID NO: 6, and a light chain comprising the amino acid sequence of SEQ ID NO: 68. In some embodiments, the AB of the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 6, and a light chain comprising an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain comprising the amino acid sequence of SEQ ID NO: 6, and a light chain comprising the amino acid sequence of SEQ ID NO: 28. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 6, and a light chain comprising an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody comprises a heavy chain comprising the amino acid sequence of SEQ ID NO: 6, and a light chain comprising the amino acid sequence of SEQ ID NO: 4. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 6, and a light chain comprising an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody comprises a heavy chain comprising the amino acid sequence of SEQ ID NO: 30, and a light chain comprising the amino acid sequence of SEQ ID NO: 68. In some embodiments, the AB of the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 30, and a light chain comprising an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain comprising the amino acid sequence of SEQ ID NO: 30, and a light chain comprising the amino acid sequence of SEQ ID NO: 28. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 30, and a light chain comprising an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody comprises a heavy chain comprising the amino acid sequence of SEQ ID NO: 30, and a light chain comprising the amino acid sequence of SEQ ID NO: 4. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 30, and a light chain comprising an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody comprises a heavy chain comprising the amino acid sequence of SEQ ID NO: 10, and a light chain comprising the amino acid sequence of SEQ ID NO: 68. In some embodiments, the AB of the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 10, and a light chain comprising an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain comprising the amino acid sequence of SEQ ID NO: 10, and a light chain comprising the amino acid sequence of SEQ ID NO: 28. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 10, and a light chain comprising an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody comprises a heavy chain comprising the amino acid sequence of SEQ ID NO: 10, and a light chain comprising the amino acid sequence of SEQ ID NO: 4. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 10, and a light chain comprising an amino acid sequence that is at least 90%, 91%, 92%, 93%, 94%, 95%, 96%, 97%, 98% or 99% identical to the amino acid sequence of SEQ ID NO: 4.

In some embodiments, the AB of the activatable antibody comprises a heavy chain comprising the amino acid sequence of SEQ ID NO: 34, and a light chain comprising the amino acid sequence of SEQ ID NO: 68. In some embodiments, the AB of the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 34, and a light chain comprising an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the activatable antibody comprises a heavy chain comprising the amino acid sequence of SEQ ID NO: 34, and a light chain comprising the amino acid sequence of SEQ ID NO: 28. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 34, and a light chain comprising an amino acid sequence that is at least 90%, 91%, 92%, 93%, 94%, 95%, 96%, 97%, 98% or 99% identical to the amino acid sequence of SEQ ID NO: 28.

In some embodiments, the activatable antibody comprises a heavy chain comprising the amino acid sequence of SEQ ID NO: 34, and a light chain comprising the amino acid sequence of SEQ ID NO: 4. In some embodiments, the activatable antibody comprises a heavy chain comprising an amino acid sequence that is at least 90%, 91%, 92%, 93%, 94%, 95%, 96%, 97%, 98% or 99% identical to the amino acid sequence of SEQ ID NO: 34, and a light chain comprising an amino acid sequence that is at least 90%, 91%, 92%, 93%, 94%, 95%, 96%, 97%, 98% or 99% identical to the amino acid sequence of SEQ ID NO: 4.

In some embodiments, the CM is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1.

In some embodiments, the CM comprises the amino acid sequence LSGRSDNH (SEQ ID NO: 13).

In some embodiments, the MM does not comprise more than 25% amino acid sequence identity to EGFR.

In some embodiments, the MM does not comprise more than 10% amino acid sequence identity to EGFR.

In some embodiments, the MM comprises the amino acid sequence CISPRGCPDGPYVMY (SEQ ID NO: 14).

In some embodiments, at least one of LP1 or LP2 comprises an amino acid sequence selected from the group consisting of $(GS)_n$, $(GGS)_n$, $(GSGGS)_n$ (SEQ ID NO: 15) and $(GGGS)_n$ (SEQ ID NO: 16), where n is an integer of at least one.

In some embodiments, at least one of LP1 or LP2 comprises an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), and GSSSG (SEQ ID NO: 22).

In some embodiments, LP1 comprises the amino acid sequence GSSGGSGGSGGSG (SEQ ID NO: 23).

In some embodiments, LP2 comprises the amino acid sequence GSSGT (SEQ ID NO: 24) or GSSG (SEQ ID NO: 37).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker.

In some embodiments, the activatable antibody also includes a detectable moiety. In some embodiments, the detectable moiety is a diagnostic agent. In some embodiments, the detectable moiety is a conjugatable detection reagent. In some embodiments, the detectable moiety is, for example, a fluorescein derivative such as fluorescein isothiocyanate (FITC).

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer includes at least the amino acid sequence QGQSGQ (SEQ ID NO: 38). In some embodiments, an activatable antibody comprises a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, an activatable antibody includes a spacer of sequence: joined directly to a MM sequence and includes the amino acid sequence QGQSGQ-CISPRGCPDGPYVMY (SEQ ID NO: 59) in the structural arrangement from N-terminus to C-terminus of spacer-MM-CM-AB.

The invention provides methods of treating, preventing and/or delaying the onset or progression of, or alleviating a symptom of an indication, e.g., disease or disorder, associated with aberrant expression and/or activity of EGFR, e.g., an EGFR-related disorder or EGFR-related disease, in a subject using a therapeutic molecule, e.g., activatable antibodies that bind EGFR and/or conjugated activatable antibodies that bind EGFR, particularly activatable antibodies and/or conjugated activatable antibodies that bind and neutralize or otherwise inhibit at least one biological activity of EGFR and/or EGFR-mediated signaling.

In some embodiments, the indication, e.g., disease or disorder, associated with aberrant expression and/or activity of EGFR is a cancer. In some embodiments, the cancer is a breast cancer, e.g., by way of non-limiting example, the breast cancer is a triple-negative breast cancer. In some embodiments, the cancer is a triple-negative breast cancer. In some embodiments, the cancer is colorectal cancer. In some embodiments, the cancer is gastric cancer. In some embodiments, the cancer is glioblastoma. In some embodiments, the cancer is a head and neck cancer, e.g., by way of non-limiting example, esophageal cancer. In some embodiments, the cancer is an esophageal cancer. In some embodiments, the cancer is a lung cancer, e.g., by way of non-limiting example, non-small cell lung cancer. In some embodiments, the cancer is a non-small cell lung cancer. In some embodiments, the cancer is ovarian/endometrial cancer. In some embodiments, the cancer is pancreatic cancer. In some embodiments, the cancer is prostate cancer. In some embodiments, the cancer is a renal cancer. In some embodiments, the cancer is a sarcoma, e.g., by way of non-limiting example, osteosarcoma. In some embodiments, the cancer is an osteosarcoma. In some embodiments, the cancer is a skin cancer, e.g., by way of non-limiting example, squamous cell cancer, basal cell carcinoma, and/or melanoma. In some embodiments, the cancer is a squamous cell cancer. In some embodiments, the cancer is a basal cell carcinoma. In some embodiments, the cancer is a melanoma.

In some embodiments, the indication, e.g., disease or disorder, associated with aberrant expression and/or activity of EGFR is an inflammatory disorder and/or an autoimmune disease. In some embodiments, the inflammatory and/or autoimmune disease is psoriasis.

The therapeutic molecule, e.g., activatable anti-EGFR antibody and/or conjugated anti-EGFR activatable antibody, can be administered at any stage of the disease. For example, a therapeutic molecule can be administered to a patient suffering cancer of any stage, from early to metastatic. For example, therapeutic molecule can be administered to a patient suffering from an inflammatory disorder and/or autoimmune disease of any stage, from early onset to an advanced stage. It is to be understood that the terms subject and patient are used interchangeably herein.

The therapeutic molecules, e.g. activatable anti-EGFR antibodies and/or conjugated activatable anti-EGFR antibodies, are also useful in other therapeutic indications and treatment regimens. For example, the therapeutic molecules of the embodiments provided herein can be used in a treatment regimen that includes neoadjuvant therapy.

In some embodiments, the therapeutic molecules, e.g. activatable anti-EGFR antibodies and/or conjugated activatable anti-EGFR antibodies, are administered during and/or after treatment in combination with one or more additional agents such as, by way of non-limiting example, a chemotherapeutic agent. In some embodiments, the therapeutic molecule and the additional agent(s) are administered simultaneously. For example, the therapeutic molecule and the additional agent(s) can be formulated in a single composition or administered as two or more separate compositions. In some embodiments, the therapeutic molecule and the additional agent(s) are administered sequentially.

The invention also provides methods of preventing, delaying the progression of, treating, alleviating a symptom of, or otherwise ameliorating an EGFR-related disorder, for example, cancer, in a subject by administering a therapeutically effective amount of an activatable anti-EGFR antibody described herein to a subject in need thereof.

The invention also provides methods of inhibiting angiogenesis in a subject by administering a therapeutically effective amount of an activatable anti-EGFR antibody described herein to a subject in need thereof.

In some embodiments, the subject is a mammal. In some embodiments, the subject is a human. In some embodiments, the subject is a non-human mammal, such as a non-human primate, companion animal (e.g., cat, dog, horse), farm animal, work animal, or zoo animal.

The activatable anti-EGFR antibody and therapeutic formulations thereof are administered to a subject suffering from or susceptible to a disease or disorder associated with aberrant EGFR expression and/or activity. A subject suffering from or susceptible to a disease or disorder associated with aberrant EGFR expression and/or activity is identified using any of a variety of methods known in the art. For example, subjects suffering from cancer or other neoplastic condition are identified using any of a variety of clinical and/or laboratory tests such as, physical examination and blood, urine and stool analysis to evaluate health status.

Administration of an activatable anti-EGFR antibody to a patient suffering from a disease or disorder associated with aberrant EGFR expression and/or activity is considered successful if any of a variety of laboratory or clinical objectives is achieved. For example, administration of an activatable anti-EGFR antibody to a patient suffering from a disease or disorder associated with aberrant EGFR expression and/or activity is considered successful if one or more of the symptoms associated with the disease or disorder is alleviated, reduced, inhibited or does not progress to a further, i.e., worse, state. Administration of an activatable anti-EGFR antibody to a patient suffering from a disease or disorder associated with aberrant EGFR expression and/or activity is considered successful if the diabetes enters remission or does not progress to a further, i.e., worse, state.

In some embodiments, the activatable anti-EGFR antibody is administered during and/or after treatment in combination with one or more additional agents such as, for example, a chemotherapeutic agent. In some embodiments, the activatable anti-EGFR antibody and the additional agent(s) are administered simultaneously. For example, the activatable anti-EGFR antibody and the additional agent(s) can be formulated in a single composition or administered as two or more separate compositions. In some embodiments, the activatable anti-EGFR antibody and the additional agent(s) are administered sequentially.

The invention also provides methods of using activatable antibodies that bind EGFR (i.e., activatable anti-EGFR antibodies, also referred to herein as anti-EGFR activatable antibodies) in a variety of diagnostic and/or prophylactic indications, as well as kits for use in these methods. For example, the invention provides methods of detecting presence or absence of a cleaving agent and EGFR in a subject or a sample by (i) contacting a subject or sample with an anti-EGFR activatable antibody, and (ii) measuring a level of activated anti-EGFR activatable antibody in the subject or sample, wherein a detectable level of activated anti-EGFR activatable antibody in the subject or sample indicates that the cleaving agent and EGFR are present in the subject or sample and wherein no detectable level of activated anti-EGFR activatable antibody in the subject or sample indicates that the cleaving agent, EGFR or both the cleaving agent and EGFR are absent in the subject or sample. Such an anti-EGFR activatable antibody includes a masking moiety (MM), a cleavable moiety (CM) that is cleaved by the cleaving agent, and an antigen binding domain or fragment thereof (AB) that specifically binds EGFR, wherein the anti-EGFR activatable antibody in an uncleaved (i.e., non-activated) state comprises a structural arrangement from N-terminus to C-terminus as follows: MM-CM-AB or AB-CM-MM; (ii) wherein the MM is a peptide that inhibits binding of the AB to EGFR, and wherein the MM does not have an amino acid sequence of a naturally occurring binding partner of the AB; and (iii) wherein the MM of the activatable antibody in an uncleaved state interferes with specific binding of the AB to EGFR, and wherein the MM of an activatable antibody in a cleaved (i.e., activated) state does not interfere or compete with specific binding of the AB to EGFR.

The invention also provides kits for use in methods of detecting presence or absence of a cleaving agent and a target of interest (EGFR) in a subject or a sample, where the kits include at least an anti-EGFR activatable antibody and/or conjugated anti-EGFR activatable antibody described herein for use in contacting a subject or sample and means for detecting the level of activated anti-EGFR activatable antibody and/or conjugated anti-EGFR activatable antibody in the subject or sample, wherein a detectable level of activated anti-EGFR activatable antibody in the subject or sample indicates that the cleaving agent and EGFR are present in the subject or sample and wherein no detectable level of activated anti-EGFR activatable antibody in the subject or sample indicates that the cleaving agent, EGFR or both the cleaving agent and EGFR are absent in the subject or sample.

The invention also provides methods of detecting presence or absence of a cleaving agent in a subject or a sample by (i) contacting a subject or sample with an anti-EGFR activatable antibody in the presence of EGFR, and (ii) measuring a level of activated anti-EGFR activatable antibody in the subject or sample, wherein a detectable level of activated anti-EGFR activatable antibody in the subject or sample indicates that the cleaving agent is present in the subject or sample and wherein no detectable level of activated anti-EGFR activatable antibody in the subject or sample indicates that the cleaving agent is absent in the subject or sample. Such an anti-EGFR activatable antibody includes a masking moiety (MM), a cleavable moiety (CM) that is cleaved by the cleaving agent, and an antigen binding domain or fragment thereof (AB) that specifically binds EGFR, wherein the anti-EGFR activatable antibody in an uncleaved (i.e., non-activated) state comprises a structural arrangement from N-terminus to C-terminus as follows: MM-CM-AB or AB-CM-MM; (ii) wherein the MM is a peptide that inhibits binding of the AB to EGFR, and wherein the MM does not have an amino acid sequence of a naturally occurring binding partner of the AB; and (iii) wherein the MM of the activatable antibody in an uncleaved state interferes with specific binding of the AB to EGFR, and wherein the MM of an activatable antibody in a cleaved (i.e., activated) state does not interfere or compete with specific binding of the AB to EGFR.

The invention also provides kits for use in methods of detecting presence or absence of a cleaving agent in a subject or a sample, where the kits include at least an anti-EGFR activatable antibody and/or conjugated anti-EGFR activatable antibody described herein for use in contacting a subject or sample and means for detecting the level of activated anti-EGFR activatable antibody and/or conjugated anti-EGFR activatable antibody in the subject or sample, wherein a detectable level of activated anti-EGFR activatable antibody in the subject or sample indicates that the cleaving agent is present in the subject or sample and wherein no detectable level of activated anti-EGFR activatable antibody in the subject or sample indicates that the cleaving agent is absent in the subject or sample.

The invention provides methods of detecting presence or absence of a cleaving agent and EGFR in a subject or a sample by (i) contacting a subject or sample with an anti-EGFR activatable antibody, wherein the anti-EGFR activatable antibody includes a detectable label that is positioned on a portion of the anti-EGFR activatable antibody that is released following cleavage of the CM and (ii) measuring a level of activated anti-EGFR activatable antibody in the subject or sample, wherein a detectable level of activated anti-EGFR activatable antibody in the subject or sample indicates that the cleaving agent and EGFR are present in the subject or sample and wherein no detectable level of activated anti-EGFR activatable antibody in the subject or sample indicates that the cleaving agent, EGFR or both the cleaving agent and EGFR are absent in the subject or sample. Such an anti-EGFR activatable antibody includes a masking moiety (MM), a cleavable moiety (CM) that is cleaved by the cleaving agent, and an antigen binding domain or fragment thereof (AB) that specifically binds EGFR, wherein the anti-EGFR activatable antibody in an uncleaved (i.e., non-activated) state comprises a structural arrangement from N-terminus to C-terminus as follows: MM-CM-AB or AB-CM-MM; (ii) wherein the MM is a peptide that inhibits binding of the AB to EGFR, and wherein the MM does not have an amino acid sequence of a naturally occurring binding partner of the AB; and (iii) wherein the MM of the activatable antibody in an uncleaved state interferes with specific binding of the AB to EGFR, and wherein the MM of an activatable antibody in a cleaved (i.e., activated) state does not interfere or compete with specific binding of the AB to EGFR.

The invention also provides methods of detecting presence or absence of a cleaving agent in a subject or a sample by (i) contacting a subject or sample with an anti-EGFR activatable antibody, wherein the anti-EGFR activatable antibody includes a detectable label that is positioned on a portion of the anti-EGFR activatable antibody that is released following cleavage of the CM; and (ii) measuring a level of detectable label in the subject or sample, wherein a detectable level of the detectable label in the subject or sample indicates that the cleaving agent is absent in the subject or sample and wherein no detectable level of the detectable label in the subject or sample indicates that the cleaving agent is present in the subject or sample. Such an anti-EGFR activatable antibody includes a masking moiety (MM), a cleavable moiety (CM) that is cleaved by the cleaving agent, and an antigen binding domain or fragment thereof (AB) that specifically binds EGFR, wherein the anti-EGFR activatable antibody in an uncleaved (i.e., non-activated) state comprises a structural arrangement from N-terminus to C-terminus as follows: MM-CM-AB or AB-CM-MM; (ii) wherein the MM is a peptide that inhibits binding of the AB to EGFR, and wherein the MM does not have an amino acid sequence of a naturally occurring binding partner of the AB; and (iii) wherein the MM of the activatable antibody in an uncleaved state interferes with specific binding of the AB to EGFR, and wherein the MM of an activatable antibody in a cleaved (i.e., activated) state does not interfere or compete with specific binding of the AB to EGFR.

The invention also provides kits for use in methods of detecting presence or absence of a cleaving agent and a target of interest (EGFR) in a subject or a sample, where the kits include at least an anti-EGFR activatable antibody and/or conjugated anti-EGFR activatable antibody described herein for use in contacting a subject or sample and means for detecting the level of activated anti-EGFR activatable antibody and/or conjugated anti-EGFR activatable antibody in the subject or sample, wherein a detectable level of the detectable label in the subject or sample indicates that the cleaving agent is absent in the subject or sample and wherein no detectable level of the detectable label in the subject or sample indicates that the cleaving agent is present in the subject or sample.

In some embodiments of these methods and/or kits, the anti-EGFR activatable antibody includes a detectable label. In some embodiments of these methods and/or kits, the detectable label includes an imaging agent, a contrasting agent, an enzyme, a fluorescent label, a chromophore, a dye, one or more metal ions, or a ligand-based label. In some embodiments of these methods and/or kits, the imaging agent comprises a radioisotope. In some embodiments of these methods, the radioisotope is indium or technetium. In some embodiments of these methods, the radioisotope is or is derived from iodine. In some embodiments of these methods, the radioisotope is $^{125}I$ or $^{133}I$. In some embodiments of these methods and/or kits, the contrasting agent comprises iodine, gadolinium or iron oxide. In some embodiments of these methods and/or kits, the enzyme comprises horseradish peroxidase, alkaline phosphatase, or β-galactosidase. In some embodiments of these methods and/or kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and/or kits, the luminescent label comprises an N-methylacrydium derivative. In some embodiments of these methods and/or kits, the label comprises an Alexa Fluor® label, such as Alex Fluor® 680 or Alexa Fluor® 750. In some embodiments of these methods and/or kits, the ligand-based label comprises biotin, avidin, streptavidin or one or more haptens.

In some embodiments of these methods and/or kits, the subject is a mammal. In some embodiments of these methods and/or kits, the subject is a human. In some embodiments, the subject is a non-human mammal, such as a non-human primate, companion animal (e.g., cat, dog, horse), farm animal, work animal, or zoo animal.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods and/or kits, the method and/or kit is used to identify or otherwise refine, e.g., stratify, a patient population suitable for treatment with an anti-EGFR activatable antibody of the disclosure. For example, patients that test positive for both the target (e.g., EGFR) and a protease that cleaves the substrate in the cleavable moiety (CM) of the anti-EGFR activatable antibody being tested in these methods are identified as suitable candidates for treatment with such an anti-EGFR activatable antibody comprising such a CM. Likewise, patients that test negative for either or both of the target (e.g., EGFR) and the protease that cleaves the substrate in the CM in the activatable antibody being tested using these methods are identified as suitable candidates for another form of therapy (i.e., not suitable for treatment with the anti-EGFR activatable antibody being tested). In some embodiments, such patients can be tested with other anti-EGFR activatable antibodies until a suitable anti-EGFR activatable antibody for treatment is identified (e.g., an anti-EGFR activatable antibody comprising a CM that is cleaved by the patient at the site of disease).

The invention also provides kits for use in methods of identifying or otherwise refining a patient population, where the kits include at least (i) an anti-EGFR activatable antibody and/or conjugated anti-EGFR activatable antibody described herein for use in contacting a subject or sample, (ii) means for detecting the level of activated anti-EGFR activatable antibody and/or conjugated anti-EGFR activatable antibody in the subject or sample, wherein a detectable level of activated anti-EGFR activatable antibody in the sample indicates that the sample is positive for the presence of EGFR and a cleaving agent that cleaves the substrate in the cleavable moiety (CM) of the anti-EGFR activatable antibody and/or conjugated anti-EGFR activatable antibody and (iii) means for identifying and selecting one or more subjects that test positive for the presence of EGFR and the cleaving agent thereby identifying or refining a patient population. In some embodiments, the kit also includes instructions for administering a therapeutically effective amount of an anti-EGFR activatable antibody and/or conjugated anti-EGFR activatable antibody described herein to the one or more subjects in the patient population that test positive for the presence of EGFR and the cleaving agent. In some embodiments, the kit also includes instructions for administering a therapeutically effective amount of another anti-EGFR therapeutic agent described herein to the one or more subjects in the patient population that did not test positive for the presence of both EGFR and the cleaving agent. In some embodiments, the anti-EGFR activatable antibody comprises a detectable label. In some embodiments, the detectable label comprises an imaging agent, a contrasting agent, an enzyme, a fluorescent label, a chromophore, a dye, one or more metal ions, or a ligand-based label. In some embodiments, the EGFR-related disorder is cancer. In some embodiments, the cancer is breast cancer, colorectal cancer, gastric cancer, glioblastoma, head and neck cancer, lung cancer, ovarian cancer, endometrial cancer, pancreatic cancer, prostate cancer, renal cancer, sarcoma, or skin cancer. In some embodiments, the EGFR-related disorder is psoriasis.

In some embodiments of these methods, the MM is a peptide having a length from about 2 to 40 amino acids. In some embodiments of these methods, the anti-EGFR activatable antibody comprises a linker peptide, wherein the linker peptide is positioned between the MM and the CM. In some embodiments of these methods, the anti-EGFR activatable antibody comprises a linker peptide, where the linker peptide is positioned between the AB and the CM. In some embodiments of these methods, the anti-EGFR activatable antibody comprises a first linker peptide (L1) and a second linker peptide (L2), wherein the first linker peptide is positioned between the MM and the CM and the second linker peptide is positioned between the AB and the CM. In some embodiments of these methods, each of L1 and L2 is a peptide of about 1 to 20 amino acids in length, and wherein each of L1 and L2 need not be the same linker. In some embodiments of these methods, one or both of L1 and L2 comprises a glycine-serine polymer.

In some embodiments of these methods, at least one of LP1 or LP2 comprises an amino acid sequence selected from the group consisting of $(GS)_n$, $(GGS)_n$, $(GSGGS)_n$ (SEQ ID NO: 15) and $(GGGS)_n$ (SEQ ID NO: 16), where n is an integer of at least one. In some embodiments of these methods, at least one of LP1 or LP2 comprises an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), and GSSSG (SEQ ID NO: 22). In some embodiments of these methods, LP1 comprises the amino acid sequence GSSGGSGGSGGSG (SEQ ID NO: 23). In some embodiments of these methods, LP2 comprises the amino acid sequence GSSGT (SEQ ID NO: 24) or GSSG (SEQ ID NO: 37).

In some embodiments of these methods, the AB comprises an antibody or antibody fragment sequence selected from the anti-EGFR antibody sequences presented herein. In some embodiments of these methods, the AB comprises a Fab fragment, a scFv or a single chain antibody (SCAB).

In some embodiments of these methods, the cleaving agent is a protease that is co-localized in the subject or sample with EGFR and the CM is a polypeptide that functions as a substrate for the protease, wherein the protease cleaves the CM in the anti-EGFR activatable antibody when the anti-EGFR activatable antibody is exposed to the protease. In some embodiments of these methods, the CM is a polypeptide of up to 15 amino acids in length. In some embodiments of these methods, the CM is coupled to the N-terminus of the AB. In some embodiments of these methods, the CM is coupled to the C-terminus of the AB. In some embodiments of these methods, the CM is coupled to the N-terminus of a VL chain of the AB.

In some embodiments of these methods, the cleaving agent is an enzyme and the CM is a substrate for the enzyme. In some embodiments of these methods, the enzyme is a protease disclosed herein. In some embodiments of these methods, the protease is one of the proteases disclosed herein. In some embodiments of these methods, the protease is selected from the group consisting of uPA, legumain, MT-SP1, ADAM17, BMP-1, TMPRSS3, TMPRSS4, MMP-9, MMP-12, MMP-13, and MMP-14. In some embodiments, the enzyme comprises uPA. In some embodiments, the enzyme comprises legumain. In some embodiments, the enzyme comprises MT-SP1. In some embodiments, the protease is not active or is significantly less active in tissues that do not significantly express EGFR. In some embodiments, the protease is not active or is significantly less active in healthy, e.g., non-diseased tissues.

The invention also provides methods of using the anti-EGFR antibodies and/or conjugated activatable anti-EGFR antibodies (i.e., activatable anti-EGFR antibody conjugates, also referred to herein as conjugated activatable anti-EGFR antibodies and/or conjugated anti-EGFR activatable antibodies) in a variety of diagnostic and/or prophylactic indications. For example, the invention provides methods of detecting presence or absence of a cleaving agent and a target of interest (EGFR) in a subject or a sample by (i) contacting a subject or sample with an anti-EGFR antibody and/or conjugated activatable anti-EGFR antibody and (ii) measuring a level of anti-EGFR antibody and/or conjugated activatable anti-EGFR antibody in the subject or sample, wherein a detectable level of activated anti-EGFR antibody and/or conjugated activatable anti-EGFR antibody in the subject or sample indicates that the cleaving agent and EGFR are present in the subject or sample and wherein no detectable level of activated anti-EGFR antibody and/or conjugated activatable anti-EGFR antibody in the subject or sample indicates that the cleaving agent, EGFR or both the cleaving agent and EGFR are absent in the subject or sample.

The invention also provides methods of detecting presence or absence of a cleaving agent in a subject or a sample by (i) contacting a subject or sample with an anti-EGFR antibody and/or conjugated activatable anti-EGFR antibody in the presence of EGFR, and (ii) measuring a level of activated anti-EGFR antibody and/or conjugated activatable anti-EGFR antibody in the subject or sample, wherein a detectable level of activated anti-EGFR antibody and/or conjugated activatable anti-EGFR antibody in the subject or sample indicates that the cleaving agent is present in the subject or sample and wherein no detectable level of anti-EGFR antibody and/or conjugated activatable anti-EGFR antibody in the subject or sample indicates that the cleaving agent is absent in the subject or sample.

The invention also provides methods of detecting presence or absence of a cleaving agent in a subject or a sample by (i) contacting a subject or sample with an anti-EGFR antibody and/or conjugated activatable anti-EGFR antibody; and (ii) measuring a level of detectable label in the subject or sample, wherein a detectable level of the detectable label in the subject or sample indicates that the cleaving agent is absent in the subject or sample and wherein no detectable level of the detectable label in the subject or sample indicates that the cleaving agent is present in the subject or sample.

In some embodiments of these methods, the anti-EGFR antibody and/or conjugated activatable anti-EGFR antibody includes a detectable label selected from the group consisting of an imaging agent, a contrasting agent, an enzyme, a fluorescent label, a chromophore, a dye, one or more metal ions, and a ligand-based label. In some embodiments of these methods, the imaging agent comprises a radioisotope. In some embodiments of these methods, the radioisotope is indium or technetium. In some embodiments of these methods, the contrasting agent comprises iodine, gadolinium or iron oxide. In some embodiments of these methods, the enzyme comprises horseradish peroxidase, alkaline phosphatase, or β-galactosidase. In some embodiments of these methods, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods, the luminescent label comprises an N-methylacrydium derivative. In some embodiments of these methods, the label comprises an Alexa FluorR label, such as Alex FluorR 680 or Alexa Fluor 750. In some embodiments of these methods, the ligand-based label comprises biotin, avidin, streptavidin or one or more haptens.

In some embodiments of these methods, the subject is a mammal. In some embodiments of these methods, the subject is a human. In some embodiments, the subject is a non-human mammal, such as a non-human primate, companion animal (e.g., cat, dog, horse), farm animal, work animal, or zoo animal.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods, the method is used to identify or otherwise refine a patient population suitable for treatment with an anti-EGFR antibody and/or conjugated activatable anti-EGFR antibody of the disclosure. For example, patients that test positive for both the target (e.g., EGFR) and a protease that cleaves the substrate in the cleavable moiety (CM) of the anti-EGFR antibody and/or conjugated activatable anti-EGFR antibody being tested in these methods are identified as suitable candidates for treatment with such anti-EGFR antibody and/or such a conjugated activatable anti-EGFR antibody comprising such a CM. Likewise, patients that test negative for either or both of the target (e.g., EGFR) and the protease that cleaves the substrate in the CM in the activatable antibody being tested using these methods are identified as suitable candidates for another form of therapy (i.e., not suitable for treatment with the anti-EGFR antibody and/or conjugated activatable anti-EGFR antibody being tested). In some embodiments, such patients can be tested with other anti-EGFR antibody and/or conjugated activatable anti-EGFR antibody until a suitable anti-EGFR antibody and/or conjugated activatable anti-EGFR antibody for treatment is identified (e.g., an anti-EGFR antibody and/or conjugated activatable anti-EGFR antibody comprising a CM that is cleaved by the patient at the site of disease).

In some embodiments, the activatable antibody binds EGFR in an activated state and includes (i) an antibody or an antigen binding fragment thereof (AB) that specifically binds to EGFR, wherein the AB is or is derived from cetuximab; (ii) a masking moiety (MM) that inhibits the binding of the AB of the activatable antibody in an uncleaved state to EGFR; and (c) a cleavable moiety (CM) coupled to the AB, wherein the CM is a polypeptide that functions as a substrate for a protease.

In some embodiments, the MM has an equilibrium dissociation constant for binding to the AB which is greater than the equilibrium dissociation constant of the AB to EGFR. In some embodiments, the MM has an equilibrium dissociation constant for binding to the AB which is no more than the equilibrium dissociation constant of the AB to EGFR. In some embodiments, the MM does not interfere or compete with the AB of the activatable antibody in a cleaved state for binding to EGFR when the activatable antibody is.

In some embodiments, the protease is co-localized with EGFR in a tissue, and the protease cleaves the CM in the activatable antibody when the activatable antibody is exposed to the protease. In some embodiments, the protease is not active or is significantly less active in tissues that do not significantly express EGFR. In some embodiments, the protease is not active or is significantly less active in healthy, e.g., non-diseased tissues.

In some embodiments, the activatable antibody and/or conjugated activatable antibody has the structural arrangement from N-terminus to C-terminus as follows in the uncleaved state: MM-CM-AB or AB-CM-MM.

In some embodiments, the activatable antibody and/or conjugated activatable antibody includes a linking peptide between the MM and the CM.

In some embodiments, the activatable antibody and/or conjugated activatable antibody includes a linking peptide between the CM and the AB.

In some embodiments, the activatable antibody and/or conjugated activatable antibody includes a first linking peptide (LP1) and a second linking peptide (LP2), and wherein the activatable antibody and/or conjugated activatable antibody has the structural arrangement from N-terminus to C-terminus as follows in the uncleaved state: MM-LP1-CM-LP2-AB or AB-LP2-CM-LP1-MM. In some embodiments, the two linking peptides need not be identical to each other.

In some embodiments, the AB has an equilibrium dissociation constant of about 100 nM or less for binding to EGFR.

In some embodiments, the MM is a polypeptide of about 2 to 40 amino acids in length, for example, no more than 40 amino acids long.

In some embodiments, the MM polypeptide sequence is different from that of EGFR, and the MM polypeptide sequence is no more than 50% identical to any natural binding partner of the AB.

In some embodiments, the CM is positioned in the activatable antibody and/or conjugated activatable antibody such that in the uncleaved state, binding of the activatable antibody and/or conjugated activatable antibody to EGFR is reduced to occur with an equilibrium dissociation constant that is at least 20-fold greater than the equilibrium dissociation constant of an unmodified AB binding to EGFR, and whereas the AB of the activatable antibody in the cleaved state binds EGFR.

In some embodiments, the CM is positioned in the activatable antibody and/or conjugated activatable antibody such that in the uncleaved state, binding of the activatable antibody and/or conjugated activatable antibody to EGFR is reduced to occur with an equilibrium dissociation constant that is at least 100-fold greater than the equilibrium dissociation constant of an unmodified AB binding to EGFR, and whereas the AB of the activatable antibody in the cleaved state binds EGFR.

In some embodiments, the CM is positioned in the activatable antibody and/or conjugated activatable antibody such that in the uncleaved state, binding of the activatable antibody and/or conjugated activatable antibody to EGFR is reduced to occur with an equilibrium dissociation constant that is at least 200-fold greater than the equilibrium dissociation constant of an unmodified AB binding to EGFR, and whereas the AB of the activatable antibody in the cleaved state binds EGFR.

In some embodiments, the coupling of the MM reduces the ability of the AB to bind EGFR such that the dissociation constant ($K_d$) of the AB when coupled to the MM towards EGFR is at least 20 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 100 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 1000 times greater than the $K_d$ of the AB when not coupled to the MM towards EGFR. In some embodiments, the coupling of the MM reduces the ability of the AB to bind EGFR such that the $K_d$ of the AB when coupled to the MM towards EGFR is at least 10,000 times greater than the $K_d$ of the AB when not coupled to the MM towards EGFR.

In some embodiments, the CM is a polypeptide of up to 15 amino acids in length.

In some embodiments, in the presence of EGFR, the MM reduces the ability of the AB to bind EGFR by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the activatable antibody and/or conjugated activatable antibody includes an antibody or antigen-binding fragment thereof that specifically binds EGFR. In some embodiments, the antibody or immunologically active fragment thereof that binds EGFR is a monoclonal antibody, domain antibody, single chain, Fab fragment, a $F(ab')_2$ fragment, a scFv, a scab, a dAb, a single domain heavy chain antibody, and a single domain light chain antibody. In some embodiments, such an antibody or immunologically active fragment thereof that binds EGFR is a mouse, chimeric, humanized or fully human monoclonal antibody.

In some embodiments, the AB of the activatable antibody and/or conjugated activatable antibody includes a heavy chain amino acid sequence selected from the group consisting of SEQ ID NO: 2, SEQ ID NO: 6, and SEQ ID NO: 10, and a light chain amino acid sequence including SEQ ID NO: 68. In some embodiments, the AB of the activatable antibody and/or conjugated activatable antibody includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a light chain amino acid that is at least 90%, 91%, 92%, 93%, 94%, 95%, 96%, 97%, 98% or 99% identical to an amino acid sequence including SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody is encoded by a nucleic acid sequence that includes a nucleic acid sequence encoding a heavy chain amino acid sequence selected from the group consisting of SEQ ID NO: 2, SEQ ID NO: 6, and SEQ ID NO: 10, and a nucleic acid encoding a light chain amino acid sequence including SEQ ID NO: 68. In some embodiments, the AB of the activatable antibody and/or conjugated activatable antibody is encoded by a nucleic acid sequence encoding a includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 6, and SEQ ID NO: 10, and a nucleic acid sequence that includes a nucleic acid sequence encoding a light chain amino acid that is at least 90%, 91%, 92%, 93%, 94%, 95%, 96%, 97%, 98% or 99% identical to an amino acid sequence including SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody is encoded by a nucleic acid including a heavy chain nucleic acid sequence selected from the group consisting of SEQ ID NO: 1, SEQ ID NO: 5, and SEQ ID NO: 9, and a light chain nucleic acid sequence of SEQ ID NO: 67. In some embodiments, the AB of the activatable antibody and/or conjugated activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 1, SEQ ID NO: 5, and SEQ ID NO: 9, and a nucleic acid sequence that includes a nucleic acid sequence encoding a light chain nucleic acid that is at least 90%, 91%, 92%, 93%, 94%, 95%, 96%, 97%, 98% or 99% identical to a nucleic acid sequence including SEQ ID NO: 67.

In some embodiments, the AB of the activatable antibody and/or conjugated activatable antibody includes a heavy chain amino acid sequence selected from the group consisting of SEQ ID NO: 26, SEQ ID NO: 30 and SEQ ID NO: 34, and a light chain amino acid sequence including SEQ ID NO: 68. In some embodiments, the AB of the activatable antibody and/or conjugated activatable antibody includes a heavy chain amino acid sequence that is at least 90%, 91%, 92%, 93%, 94%, 95%, 96%, 97%, 98% or 99% identical to an amino acid sequence selected from the group consisting of SEQ ID NO: 26, SEQ ID NO: 30 and SEQ ID NO: 34, and a light chain amino acid sequence that is at least 90%, 91%, 92%, 93%, 94%, 95%, 96%, 97%, 98% or 99% identical to an amino acid sequence s including SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody is encoded by a nucleic acid sequence encoding a heavy chain amino acid sequence selected from the group consisting of SEQ ID NO: 26, SEQ ID NO: 30, and SEQ ID NO: 34, and a nucleic acid sequence encoding a light chain amino acid sequence including SEQ ID NO: 68. In some embodiments, the AB of the activatable antibody and/or conjugated activatable antibody is encoded by a nucleic acid sequence that includes a nucleic acid sequence encoding a includes a heavy chain amino acid sequence that is at least 90%, 91%, 92%, 93%, 94%, 95%, 96%, 97%, 98% or 99% identical to an amino acid including SEQ ID NO: 26, SEQ ID NO: 30, and SEQ ID NO: 34, and a nucleic acid sequence encoding a light chain amino acid that is at least 90%, 91%, 92%, 93%, 94%, 95%, 96%, 97%, 98% or 99% identical to an amino acid sequence including SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody is encoded by a nucleic acid including a heavy chain nucleic acid sequence selected from the group consisting of SEQ ID NO: 25, SEQ ID NO: 29, and SEQ ID NO: 33, and a light chain nucleic acid sequence including SEQ ID NO: 67. In some embodiments, the AB of the activatable antibody and/or conjugated activatable antibody is encoded by a nucleic acid sequence including a heavy chain nucleic acid sequence that is at least 90%, 91%, 92%, 93%, 94%, 95%, 96%, 97%, 98% or 99% identical to an nucleic acid sequence selected from the group consisting of SEQ ID NO: 25, SEQ ID NO: 29, and SEQ ID NO: 33, and a nucleic acid sequence encoding a light chain amino acid that is at least 90%, 91%, 92%, 93%, 94%, 95%, 96%, 97%, 98% or 99% identical to a nucleic acid sequence including SEQ ID NO: 67.

In some embodiments, the AB of the activatable antibody and/or conjugated activatable antibody includes a heavy chain including the amino acid sequence of SEQ ID NO: 2, and a light chain including the amino acid sequence of SEQ ID NO: 68. In some embodiments, the AB of the activatable antibody and/or conjugated activatable antibody includes a heavy chain including an amino acid sequence that is at least 90%, 91%, 92%, 93%, 94%, 95%, 96%, 97%, 98% or 99% identical to the amino acid sequence of SEQ ID NO: 2, and a light chain including an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody includes a heavy chain including the amino acid sequence of SEQ ID NO: 26, and a light chain including the amino acid sequence of SEQ ID NO: 68. In some embodiments, the AB of the activatable antibody and/or conjugated activatable antibody includes a heavy chain including an amino acid sequence that is at least 90%, 91%, 92%, 93%, 94%, 95%, 96%, 97%, 98% or 99% identical to the amino acid sequence of SEQ ID NO: 26, and a light chain including an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody includes a heavy chain including the amino acid sequence of SEQ ID NO: 6, and a light chain including the amino acid sequence of SEQ ID NO: 68. In some embodiments, the AB of the activatable antibody and/or conjugated activatable antibody includes a heavy chain including an amino acid sequence that is at least 90%, 91%, 92%, 93%, 94%, 95%, 96%, 97%, 98% or 99% identical to the amino acid sequence of SEQ ID NO: 6, and a light chain including an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody includes a heavy chain including the amino acid sequence of SEQ ID NO: 30, and a light chain including the amino acid sequence of SEQ ID NO: 68. In some embodiments, the AB of the activatable antibody and/or conjugated activatable antibody includes a heavy chain including an amino acid sequence that is at least 90%, 91%, 92%, 93%, 94%, 95%, 96%, 97%, 98% or 99% identical to the amino acid sequence of SEQ ID NO: 30, and a light chain including an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody includes a heavy chain including the amino acid sequence of SEQ ID NO: 10, and a light chain including the amino acid sequence of SEQ ID NO: 68. In some embodiments, the AB of the activatable antibody and/or conjugated activatable antibody includes a heavy chain including an amino acid sequence that is at least 90%, 91%, 92%, 93%, 94%, 95%, 96%, 97%, 98% or 99% identical to the amino acid sequence of SEQ ID NO: 10, and a light chain including an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the AB of the activatable antibody and/or conjugated activatable antibody includes a heavy chain including the amino acid sequence of SEQ ID NO: 34, and a light chain including the amino acid sequence of SEQ ID NO: 68. In some embodiments, the AB of the activatable antibody and/or conjugated activatable antibody includes a heavy chain including an amino acid sequence that is at least 90%, 91%, 92%, 93%, 94%, 95%, 96%, 97%, 98% or 99% identical to the amino acid sequence of SEQ ID NO: 34, and a light chain including an amino acid sequence that is at least 90%, 91%, 92%, 93%, 94%, 95%, 96%, 97%, 98% or 99% identical to the amino acid sequence of SEQ ID NO: 68. In some embodiments, the activatable antibody includes the light chain amino acid sequence of SEQ ID NO: 68 and a spacer amino acid sequence. In some embodiments, the activatable antibody includes the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid of SEQ ID NO: 68 and a spacer amino acid sequence that includes the amino acid sequence QGQSGQ (SEQ ID NO: 38). In some embodiments, the activatable antibody includes a light chain amino acid that is at least 90%, 91%, 92%, 93%, 94%, 95%, 96%, 97%, 98% or 99% identical to the light chain amino acid sequence of SEQ ID NO: 68 joined directly to a spacer amino acid sequence that includes the amino acid sequence QGQSGQ (SEQ ID NO: 38).

In some embodiments, the CM is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1.

In some embodiments, the CM includes the amino acid sequence LSGRSDNH (SEQ ID NO: 13).

In some embodiments, the MM does not include more than 25% amino acid sequence identity to EGFR. In some embodiments, the MM does not include more than 10% amino acid sequence identity to EGFR.

In some embodiments, the MM includes the amino acid sequence CISPRGCPDGPYVMY (SEQ ID NO: 14).

In some embodiments, at least one of LP1 or LP2 includes an amino acid sequence selected from the group consisting of $(GS)_n$, $(GGS)_n$, $(GSGGS)_n$ (SEQ ID NO: 15) and $(GGGS)_n$ (SEQ ID NO: 16), where n is an integer of at least one. In some embodiments, at least one of LP1 or LP2 includes an amino acid sequence selected from the group consisting of GGSG (SEQ ID NO: 17), GGSGG (SEQ ID NO: 18), GSGSG (SEQ ID NO: 19), GSGGG (SEQ ID NO:

20), GGGSG (SEQ ID NO: 21), and GSSSG (SEQ ID NO: 22). In some embodiments, LP1 includes the amino acid sequence GSSGGSGGSGGSG (SEQ ID NO: 23). In some embodiments, LP2 includes the amino acid sequence GSSGT (SEQ ID NO: 24) or GSSG (SEQ ID NO: 37).

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is an agent selected from the group listed in Table 1. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof.

In some embodiments, the agent is conjugated to the AB via a linker. In some embodiments, the linker is a cleavable linker. In some embodiments, the linker is selected from the group consisting of the linkers shown in Tables 2 and 3.

In some embodiments, the activatable antibody and/or conjugated activatable antibody also includes a signal peptide. In some embodiments, the signal peptide is conjugated to the activatable antibody and/or conjugated activatable antibody via a spacer. In some embodiments, the spacer is conjugated to the activatable antibody and/or conjugated activatable antibody in the absence of a signal peptide. In some embodiments, the spacer is joined directly to the MM of the activatable antibody and/or conjugated activatable antibody. In some embodiments, the spacer includes at least the amino acid sequence QGQSGQ (SEQ ID NO: 38). In some embodiments, an activatable antibody and/or conjugated activatable antibody includes a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, an activatable antibody and/or conjugated activatable antibody includes a spacer joined directly to a MM sequence and includes the amino acid sequence QGQSGQCISPRGCPDGPYVMY (SEQ ID NO: 59) in the structural arrangement from N-terminus to C-terminus of spacer-MM-CM-AB.

In some embodiments, the activatable anti-EGFR antibody and/or conjugated activatable anti-EGFR antibody is monospecific. In some embodiments, the activatable anti-EGFR antibody and/or conjugated activatable anti-EGFR antibody is multispecific, e.g., by way of non-limiting example, bispecific or trifunctional. In some embodiments, the activatable anti-EGFR antibody and/or conjugated activatable anti-EGFR antibody is formulated as part of a pro-Bispecific T Cell Engager (BITE) molecule. In some embodiments, the activatable anti-EGFR antibody and/or conjugated activatable anti-EGFR antibody is formulated as part of a pro-Chimeric Antigen Receptor (CAR) modified T cell or other engineered receptor.

Pharmaceutical compositions according to the invention can include an antibody and/or conjugated antibody of the invention and a carrier. These pharmaceutical compositions can be included in kits, such as, for example, diagnostic kits.

BRIEF DESCRIPTION OF THE DRAWINGS

FIG. 2B is a graph depicting the enzymatic efficiency of two proteases, MT-SP1 and uPA, at cleaving Pb-1204. FIG. 2C is a graph depicting capillary electrophoretic analysis of Pb-1204 before and after digestion with the proteases uPA, MT-SP1 and legumain.

FIG. 2D is a graph depicting the effect of the anti-EGFR antibody cetuximab, Pb-1204 and uPA-activated Pb-1204 on the proliferation of H292 cells.

FIG. 3B is an illustration depicting the optical imaging of HT29 xenograft tumor bearing mice injected intraperitoneally with either of Alexa Fluor 750-conjugated Pb-NSUB (red) and quenched probe Cy5-NSUB-Q, referred to herein as “IQ-NSUB” (blue; left panel), where NSUB represents an amino acid sequence that is not susceptible to protease cleavage, or Alexa Fluor 750-conjugated Pb-1204 (red) and quenched probe Cy5.5-1204-Q, referred to herein as “IQ-1204” (blue; right panel), where 1204 is the substrate sequence 1204: LSGRSDNH (SEQ ID NO: 13), which is susceptible to cleavage by at least uPA. A high-intensity overlapping fluorescent signal was detected only in the tumor of mouse administered with activatable anti-EGFR antibody and probe containing 1204 substrate. FIGS. 3C and 3D are illustrations depicting immunofluorescent detection of activatable anti-EGFR antibodies in HT29 xenograft tumors 7 days after the mice were injected with Alexa Fluor 750-conjugated Pb-1204 (FIG. 3C) or Alexa Fluor 750-conjugated Pb-NSUB (FIG. 3D). FIGS. 3E and 3F are a series of photographs the optical imaging of H292 xenograft tumor bearing mice injected intraperitoneally with Pb-NSUB, 3954-1204-C225v4 or cetuximab (i.e., unmodified cetuximab). The 3954-1204-C225v4 activatable antibody localizes to the tumor site in the H292 xenograft mouse model.

FIG. 3G is a series of photographs that depict the three dimensional optical and computed tomography (3D/CT tomography) of animals in the H292 xenograft mouse model that were administered cetuximab, Pb-NSUB or 3954-1204-C225v4. FIG. 3H is a series of photographs depicting human IgG immunohistochemistry staining on representative H292 tumors from in vivo imaging studies.

FIG. 4A is a graph depicting the effects seen in H292 xenograft tumor-bearing mice that were treated weekly using cetuximab (25 mg/kg, blue line), Pb-1204 (25 mg/kg, red line), Pb-NSUB (25 mg/kg, green line), or vehicle (black line), where Pb-NSUB represents an activatable anti-EGFR antibody construct that has an antibody portion that binds EGFR and also includes the NSUB amino acid sequence, which is not susceptible to protease cleavage. Data are presented as mean tumor volume±SEM. Percent tumor growth inhibition (TGI) was evaluated at Day 20.

FIGS. 4B and 4C are graphs depicting the level of IgG concentration and the level of EGFR-binding IgG in samples of plasma (1, 8, 24, 72 h post-dose) (FIG. 4B) and tumor (72 h post-dose) (FIG. 4C) collected from H292 xenograft tumor-bearing mice injected with 25 mg/kg of cetuximab, Pb-NSUB or Pb-1204. IgG concentration (blue) and EGFR binding (red) were measured by ELISA. FIG. 4D is a graph depicting the tumor volume observed in LXFA677 tumor-bearing mice that were injected intraperitoneally (IP) once with cetuximab (25 mg/kg, blue line), Pb-1204 (25 mg/kg, red line), vehicle (black line). Data are presented as mean tumor volume±SEM. Percent tumor growth inhibition (TGI) was evaluated at Day 25. FIGS. 4E and 4F are graphs depicting the level of IgG concentration and the level of EGFR-binding IgG in samples of plasma (day 1, 7, 14, 21, 28 post-dose) (FIG. 4E) and tumor (72 h post-dose) (FIG. 4F) collected from LXFA677 xenograft tumor-bearing mice injected with vehicle, 25 mg/kg of cetuximab or 25 mg/kg of Pb-1204. The IgG concentration (blue) and the EGFR binding (red) were measured by ELISA.

FIG. 5A is a graph depicting the level of proteolytic conversion of Pb-1204 cleavage by MT-SP1 and uPA. FIG. 5B is a photograph of SDS-PAGE analysis of Pb-1204 before and after digestion with legumain, MT-SP1 and uPA. FIG. 5C is a graph depicting the binding of cetuximab, parental Ab, Pb-1204 or uPA-activated Pb-1204 to immobilized EGFR-ECD.

FIGS. 6A and 6B depict the immunofluorescent detection of activatable anti-EGFR antibodies in liver 7 days after the mice were injected with Alexa Fluor 750-conjugated Pb-1204 (FIG. 6A) or Alexa Fluor 750-conjugated Pb-NSUB (FIG. 6B).

In FIG. 7A, lysates of cetuximab, Pb-NSUB and Pb-1204 (25 mg/kg) treated H292 xenograft tumors were generated 72 h post-treatment and human IgG light chain was analyzed by immunoblotting. In FIG. 7B, plasma from LXFA677 xenograft tumor-bearing mice injected on day 0 with 25 mg/kg of cetuximab or Pb-1204 was collected at days 1, 7, 14, 21, 28 post-dose, and the binding to immobilized EGFR-ECD (cetuximab, blue; Pb-1204, red) was measured.

FIGS. 9A and 9B are a table and graph that depict the rate of cleavage and substrate selectivity of the proteases uPA (human and mouse), MT-SP1 (human and mouse), legumain (human), tissue plasminogen activator (tPA, human) and thrombin (human) for the 1204 substrate sequence LSGRSDNH (SEQ ID NO: 13) in an IQ probe. FIGS. 9C and 9D are a series of graphs that depict the rate of cleavage of the 1204 substrate sequence by recombinant human uPA (FIG. 9C) and recombinant human MT-SP1 (FIG. 9D). The 1204 substrate sequence was present at a final concentration of 500 nM in each study.

FIG. 10B demonstrates that once activated by the appropriate protease, the 3954-1204-C225v4 activatable antibody binds EGFR at comparable levels to the parental antibody.

FIG. 16, panel C demonstrates that the fluorescent signal shown in panel A was inhibited by pre-treatment of the tissue with a 1:100 dilution of broad spectrum inhibitor cocktail set III and 50 mM EDTA. Blue staining represents DAPI nuclear staining.

FIG. 17 is a series of tables depicting that 3954-1204-C225v5 is activatable in a wide range of human tumor samples. Column 2 indicates the expression level of EGFR receptor, as detected by a commercially available anti-EGFR antibody, for the various human cancer tissue samples. Column 3 indicates the amount of active matriptase (MT-SP1), as detected by antibody A11, in the various human cancer tissue samples. Columns 4 and 5 represent an evaluation of in situ activation and binding of the EGFR activatable antibody (col. 5) as compared to cetuximab (Cetux) tissue staining (col. 4). The IHC staining that measures the amount of EGFR and A11 antibodies binding to the tissue sample was scored from 0 to 3+: 0, no staining; 1+ (i.e., "+"), weak staining; 2+ (i.e., "++"), moderate staining; and 3+ (i.e., "+++"), strong staining. The in situ imaging staining scoring is based on comparison with cetuximab antibody staining and defined as follows: 0, no staining; 1+ (i.e., "+"), weak staining as compared to parental antibody; 2+ (i.e., "++"), moderate staining as compared to parental antibody; and 3+ (i.e., "+++"), analogous staining to parental antibody.

FIG. 23, middle column of images, demonstrates co-localization of matriptase (MT-SP1) activity with EGFR expression.

DETAILED DESCRIPTION OF THE INVENTION

The present invention provides activatable monoclonal antibodies (mAbs) that specifically bind human epidermal growth factor receptor (EGFR), also known as EGF receptor, human EGF receptor-1 (HER1), erbB, erbB1, and species antigen 7 (SA-7). The activatable anti-EGFR antibodies, also referred to herein as anti-EGFR activatable antibodies or EGFR activatable antibodies, are used in methods of treating, preventing, delaying the progression of, ameliorating and/or alleviating a symptom of a disease or disorder associated with aberrant EGFR expression and/or activity. For example, the activatable anti-EGFR antibodies are used in methods of treating, preventing, delaying the progression of, ameliorating and/or alleviating a symptom of a cancer or other neoplastic condition.

The activatable anti-EGFR antibodies include an antibody or antigen-binding fragment thereof that specifically binds epidermal growth factor receptor (EGFR) coupled to a masking moiety (MM), such that coupling of the MM reduces the ability of the antibody or antigen-binding fragment thereof to bind EGFR. In a preferred embodiment, the MM is coupled via a sequence that includes a substrate for a protease, for example, a protease that is co-localized with EGFR at a treatment site in a subject. Numerous studies have demonstrated the correlation of aberrant protease levels, e.g., uPA, legumain, MT-SP1, matrix metalloproteases (MMPs), in solid tumors. (See e.g., Murthy R V, et al. "Legumain expression in relation to clinicopathologic and biological variables in colorectal cancer." Clin Cancer Res. 11 (2005): 2293-2299; Nielsen B S, et al. "Urokinase plasminogen activator is localized in stromal cells in ductal breast cancer." Lab Invest 81 (2001): 1485-1501; Mook O R, et al. "In situ localization of gelatinolytic activity in the extracellular matrix of metastases of colon cancer in rat liver using quenched fluorogenic DQ-gelatin." J Histochem Cytochem. 51 (2003): 821-829).

Figure 1A:
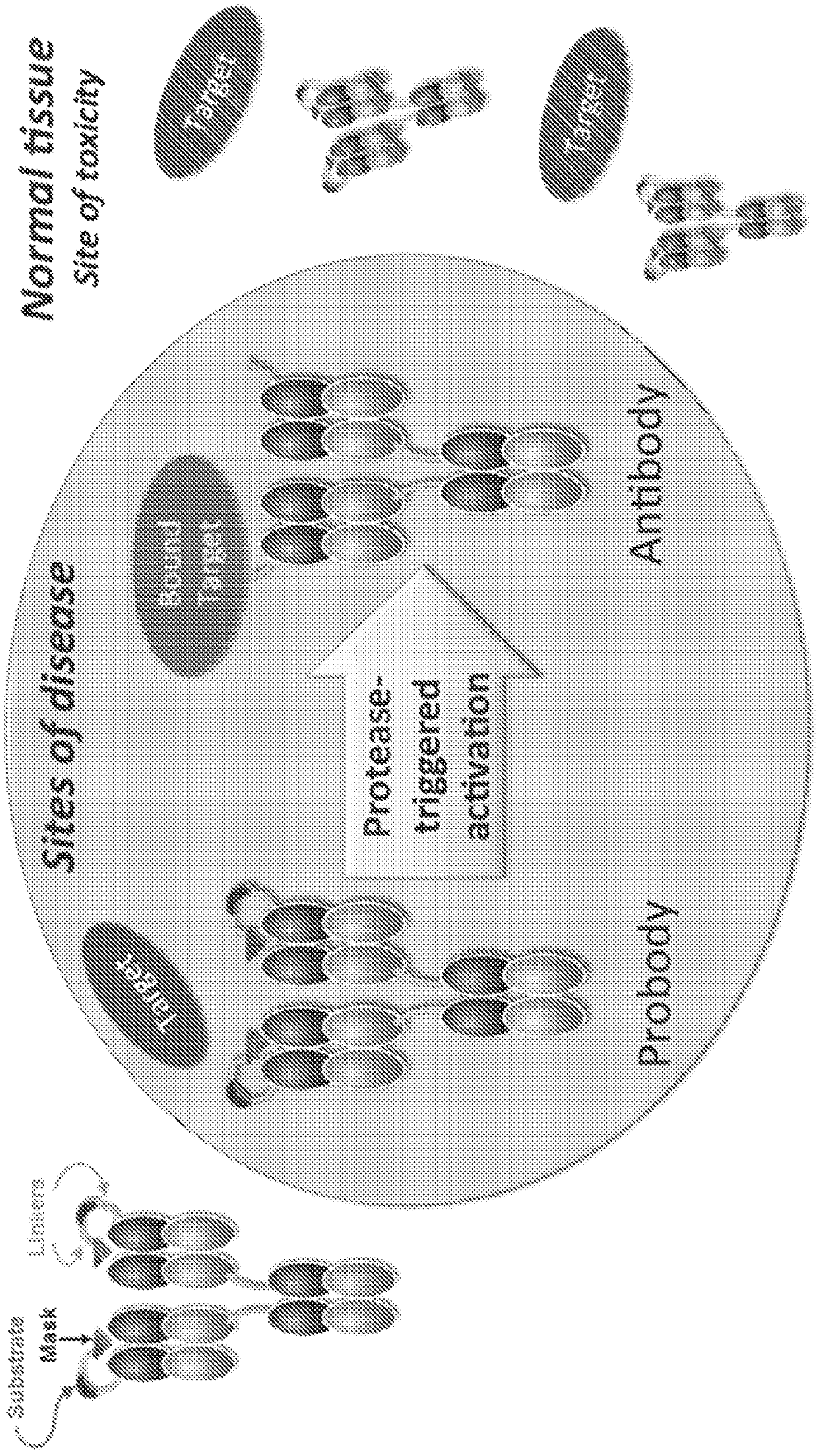
FIG. 1A is an illustration depicting an activatable antibody of the invention being masked in a first state and activated in the presence of a disease-associated protease.
Figure 1B:
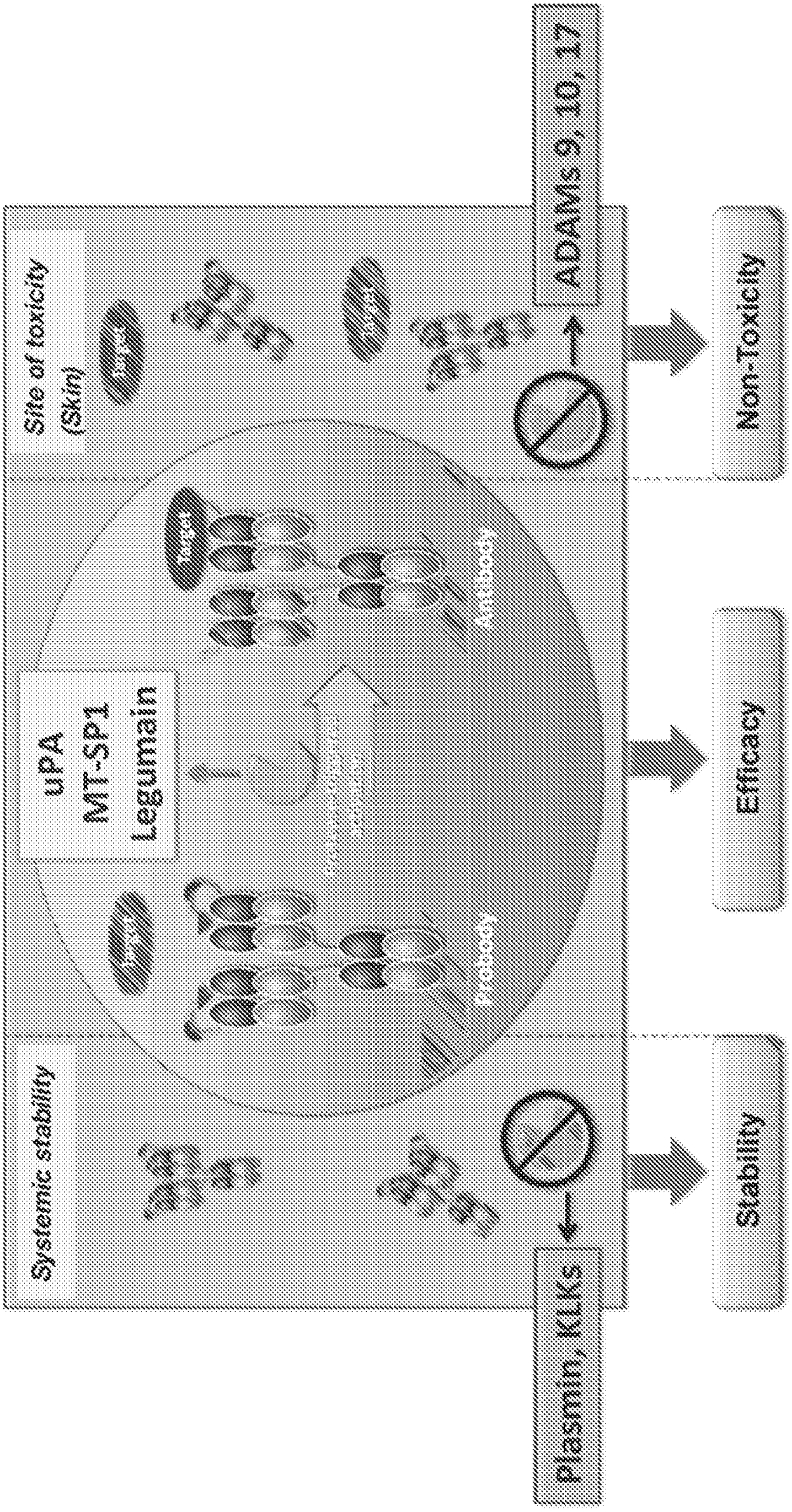
FIG. 1B is an illustration depicting the substrate selection process used to identify suitable substrates that will selectively activate the activatable anti-EGFR antibodies of the invention at the desired location.

The activatable anti-EGFR antibodies provided herein include a substrate for a protease, which is useful in leveraging the protease activity in tumor cells for targeted antibody activation at the site of treatment and/or diagnosis. A general overview of this process is shown in FIG. 1A, and a general overview of the process by which a suitable substrate for a protease such as uPA, MT-SP1, Legumain, etc., is selected is shown in FIG. 1B. The substrate selection process is used to identify substrates that have a number of desirable characteristics. For example, the selected substrates are systemically stable (i.e., stable in the systemic circulation of a subject), are generally not susceptible to cleavage by circulating proteases such as plasmin, thrombin, tissue plasminogen activator (tPA) or a kallikrein (KLK) such as KLK-5 and/or KLK-7, are non-toxic, are generally not susceptible to cleavage at potential sites of toxicity such as the skin by proteases such as ADAM 9, ADAM 10, ADAM 17 and/or kallikreins, such as KLK-5 and KLK-7, and are active at an intended site of treatment and/or diagnosis. Preferably, the identified substrates are selected for proteases that are overexpressed at an intended site of therapy and/or diagnosis but are not typically expressed at or in normal, healthy or otherwise non-diseased or damaged tissue, and then the selected substrates are subsequently counter-screened against proteases expressed in normal, e.g., non-diseased, tissue.

In some embodiments, the antibody or antigen-binding fragment thereof in the activatable anti-EGFR antibody is derived from the anti-EGFR antibody cetuximab. Cetuximab, also known as Erbitux or C225, is a chimeric (mouse/human) monoclonal antibody that specifically binds EGFR. Cetuximab is currently used in the treatment of metastatic colorectal cancer and head and neck cancer.

Preferably, the activatable anti-EGFR antibody includes a heavy chain that is or is derived from the amino acid sequence of SEQ ID NO: 26, the amino acid sequence of SEQ ID NO: 30, or the amino acid sequence of SEQ ID NO: 34.

In some embodiments, the sequence of the antibody or antigen-binding fragment thereof that binds EGFR contains at least one amino acid substitution to remove a potential site of glycosylation. For example, the antibody or antigen-binding fragment thereof that binds EGFR contains an amino acid substitution in the heavy chain and/or the light chain to remove a potential site of glycosylation. In some embodiments, the antibody or antigen-binding fragment thereof that binds EGFR has a heavy chain in which the asparagine (N) corresponding to the asparagine at position 88 of the heavy chain having amino acid sequence of SEQ ID NO: 30 is replaced with a glutamine (Q) residue to yield a heavy chain having the amino acid sequence of SEQ ID NO: 26.

In some embodiments, the antibody or antigen-binding fragment thereof that binds EGFR in the activatable antibodies can include additional modifications, particularly in the Fc region of the antibody or antigen-binding fragment thereof. For example, the Fc region of the antibody or antigen-binding fragment thereof can include one or more amino acid substitutions to remove a potential site of glycosylation and or to disrupt binding of the Fc region of its receptor. In some embodiments, the antibody or antigen-binding fragment thereof that binds EGFR has a heavy chain in which the asparagine (N) corresponding to the asparagine at position 299 of the heavy chain having amino acid sequence of SEQ ID NO: 30 is replaced with an alanine (A) residue. This mutation removes a glycosylation site in the Fc region and leads to reduced Fc receptor binding by the Fc. In some embodiments, the antibody or antigen-binding fragment thereof that binds EGFR has a heavy chain in which the asparagine (N) corresponding to the asparagine at position 88 of the heavy chain having amino acid sequence of SEQ ID NO: 30 is replaced with a glutamine (Q) residue and in which the asparagine (N) corresponding to the asparagine at position 299 of the heavy chain having amino acid sequence of SEQ ID NO: 30 is replaced with an alanine (A) residue to yield a heavy chain having the amino acid sequence of SEQ ID NO: 34.

In some embodiments, the activatable anti-EGFR antibody includes a signal peptide. The signal peptide can be linked to the activatable anti-EGFR antibody by a spacer. In some embodiments, the spacer is conjugated to the activatable antibody in the absence of a signal peptide. In some embodiments, the spacer is joined directly to the MM of the activatable antibody. In some embodiments, the spacer has amino acid sequence QGQSGQ (SEQ ID NO: 38). In some embodiments, an activatable antibody comprises a spacer of sequence QGQSGQ (SEQ ID NO: 38) joined directly to a MM sequence CISPRGCPDGPYVMY (SEQ ID NO: 14) in the structural arrangement from N-terminus to C-terminus of spacer-MM-CM-AB. In some embodiments, an activatable antibody includes a spacer joined directly to a MM sequence and includes the amino acid sequence QGQSGQCISPRGCPDGPYVMY (SEQ ID NO: 59) in the structural arrangement from N-terminus to C-terminus of spacer-MM-CM-AB.

The activatable anti-EGFR antibodies provided herein include a masking moiety. In some embodiments, the masking moiety is an amino acid sequence that is coupled, or otherwise attached, to the anti-EGFR antibody and is positioned within the activatable anti-EGFR antibody construct such that the masking moiety reduces the ability of the anti-EGFR antibody to specifically bind EGFR. Suitable masking moieties are identified using any of a variety of known techniques. For example, peptide masking moieties are identified using the methods described in U.S. Patent Application Publication No. 2009/0062142 by Daugherty et al., the contents of which are hereby incorporated by reference in their entirety.

The activatable anti-EGFR antibodies provided herein include a cleavable moiety. In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al., the contents of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

The activatable anti-EGFR antibodies described herein overcome a limitation of antibody therapeutics, particularly antibody therapeutics that are known to be toxic to at least some degree in vivo. Target-mediated toxicity constitutes a major limitation for the development of therapeutic antibodies. This is best exemplified by the skin rash that afflicts 88% of patients treated with cetuximab, an antibody that specifically binds epidermal growth factor receptor (EGFR) and has been approved for the treatment of colorectal and head and neck cancer. The activatable anti-EGFR antibodies provided herein are designed to address the toxicity associated with the inhibition of the target in normal tissues by traditional therapeutic antibodies. These activatable anti-EGFR antibodies remain masked until proteolytically activated at the site of disease. Starting with cetuximab as a parental therapeutic antibody, the activatable anti-EGFR antibodies of the invention were engineered by coupling the antibody to an inhibitory mask through a linker that incorporates a protease substrate. In studies performed in vitro studies, the binding to EGFR and the cell-based activity of the activatable anti-EGFR antibody was diminished compared to cetuximab. In studies performed in vivo studies, the activatable anti-EGFR antibody remained masked in normal tissues, but was activated and accumulated in the tumor environment. The tumor activation of the activatable anti-EGFR antibody translated into an in vivo efficacy that was equivalent to the efficacy of cetuximab.

The activatable anti-EGFR antibodies provided herein satisfy a significant clinical need. EGFR is a clinically validated target that has been shown to promote proliferation, angiogenesis and invasion/metastasis, as well as to inhibit apoptosis of tumor cells. Antibodies and small molecule tyrosine kinase inhibitors targeting EGFR have been approved for cancer treatment (Nature Rev Cancer 5 (2005) 341; Curr Opin Cell Biol 21, (2009) 177). However, current anti-EGFR therapies, also referred to as EGFR inhibitors (EGFRi), have been shown to exhibit a number of adverse events post-treatment, including for example, papulopustular rash, particularly in the face and upper trunk of human subjects; dry and itchy skin; inflammation around the nails, loss of hair on the scalp; and increased growth of eyelashes and facial hair. Cutaneous toxicities that results from treatment with EGFRi have been shown to affect 45-100% of patients. (See e.g., Segaert and Van Cutsem. Ann Oncol. 16 (9) (2005): 1425-33).

Exemplary activatable anti-EGFR antibodies of the invention include, for example, the activatable antibody referred to herein as the 3954-1204-C225v5 activatable antibody, which binds epidermal growth factor receptor (EGFR). Two sequences of the 3954-1204-C225v5 activatable anti-EGFR antibody are shown below, Sequence 1 is the sequence of a version of the 3954-1204-C225v5 activatable anti-EGFR antibody that includes a signal peptide, and Sequence 2 is the sequence of the 3954-1204-C225v5 activatable anti-EGFR antibody without the signal peptide:

```
3954-1204-C225v5 Activatable Antibody Heavy Chain Nucleotide Sequence 1:
[Signal peptide (SEQ ID NO: 60)][C225v5 (SEQ ID NO: 25)]
                                                           (SEQ ID NO: 1)
[atgtacaggatgcaactcctgtcttgcattgcactaagtcttgcacttgtcacgaattcg][c

aggtgcagctgaaacagagcggcccgggcctggtgcagccgagccagagcctgagcattacctg
```

-continued caccgtgagcggctttagcctgaccaactatggcgtgcattgggtgcgccagagcccgggcaaa ggcctggaatggctgggcgtgatttggagcggcggcaacaccgattataacaccccgtttacca gccgcctgagcattaacaaagataacagcaaaagccaggtgtttttaaaatgaacagcctgca aagccaggataccgcgatttattattgcgcgcgcgcgctgacctattatgattatgaatttgcg tattggggccagggcaccctggtgaccgtgagcgcggctagcaccaagggcccatcggtcttcc ccctggcaccctcctccaagagcacctctgggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtacaac agcacgtaccgtgtggtcagcgtcctcaccgtcctgcaccaggactggctgaatggcaaggagt acaagtgcaaggtctccaacaaagccctcccagcccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]

Italics: Signal peptide
Normal text: anti-EGFR antibody derived sequence 3954-1204-C225v5 Activatable Antibody Heavy Chain Amino Acid Sequence 1:
[Signal peptide (SEQ ID NO: 61)][C225v5 (SEQ ID NO: 26)]

(SEQ ID NO: 2)
[*MYRMQLLSCI ALSLALVTNS*] [QVQLKQSGPG LVQPSQSLSI TCTVSGFSLT

NYGVHWVRQS PGKGLEWLGV IWSGGNTDYN TPFTSRLSIN KDNSKSQVFF

KMNSLQSQDT AIYYCARALT YYDYEFAYWG QGTLVTVSAA STKGPSVFPL

APSSKSTSGG TAALGCLVKD YFPEPVTVSW NSGALTSGVH TFPAVLQSSG

LYSLSSVVTV PSSSLGTQTY ICNVNHKPSN TKVDKKVEPK SCDKTHTCPP

CPAPELLGGP SVFLFPPKPK DTLMISRTPE VTCVVVDVSH EDPEVKFNWY

VDGVEVHNAK TKPREEQYNS TYRVVSVLTV LHQDWLNGKE YKCKVSNKAL

PAPIEKTISK AKGQPREPQV YTLPPSRDEL TKNQVSLTCL VKGFYPSDIA

VEWESNGQPE NNYKTTPPVL DSDGSFFLYS KLTVDKSRWQ QGNVFSCSVM

HEALHNHYTQ KSLSLSPGK*]

Italics: Signal peptide
Normal text: anti-EGFR antibody derived sequence 3954-1204-C225v5 Activatable Antibody Light Chain Nucleotide Sequence 1:
[Signal peptide (SEQ ID NO: 60)][Spacer (SEQ ID NO: 62)][Mask
(SEQ ID NO: 63)][Linker 1 (SEQ ID NO: 64)][1204 Substrate (SEQ
ID NO: 65)][Linker 2 (SEQ ID NO: 66)][C225 (SEQ ID NO: 67)]

(SEQ ID NO: 3)
[*atgtacaggatgcaactcctgtcttgcattgcactaagtcttgcacttgtcacgaattcg*]

[caaggccagtctggccag][tgcatctcacctcgtggttgtccggacggcccatacgtcatgt ac][*ggctcgagcggtggcagcggtggctctggtggatccggt*][ctgagcggccgttccgata

-continued atcat][*ggcagtagcggtacc*][cagatcttgctgacccagagcccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Light Chain Amino Acid Sequence 1:
[Signal peptide (SEQ ID NO: 61)][Spacer (SEQ ID NO: 38)][Mask (SEQ ID NO: 14)][Linker 1 (SEQ ID NO: 23)][1204 Substrate (SEQ ID NO: 13)][Linker 2 (SEQ ID NO: 24)][C225 (SEQ ID NO: 68)]

(SEQ ID NO: 4)

[*MYRMQLLSCI ALSLALVTNS*][QGQSGQ][CISPRGCPDGPYVMY][*GSSGGSGGS*

*GGSG*][LSGRSDNH][*GSSGT*][QIL LTQSPVILSV SPGERVSFSC RASQSIGTNI

HWYQQRTNGS PRLLIKYASE SISGIPSRFS GSGSGTDFTL SINSVESEDI

ADYYCQQNNN WPTTFGAGTK LELKRTVAAP SVFIFPPSDE QLKSGTASVV

CLLNNFYPRE AKVQWKVDNA LQSGNSQESV TEQDSKDSTY SLSSTLTLSK

ADYEKHKVYA CEVTHQGLSS PVTKSFNRGE C*]

Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Heavy Chain Nucleotide Sequence 2:
[C225v5 (SEQ ID NO: 25)]

(SEQ ID NO: 25)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcaccctggtgaccgtgagcgcggctagcaccaagggcccatcggtctt cccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg -continued aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v5 Activatable Antibody Heavy Chain Amino Acid Sequence 2:
[C225v5 (SEQ ID NO: 26)]

(SEQ ID NO: 26)

[QVQLKQSGPG LVQPSQSLSI TCTVSGFSLT NYGVHWVRQS PGKGLEWLGV

IWSGGNTDYN TPFTSRLSIN KDNSKSQVFF KMNSLQSQDT AIYYCARALT

YYDYEFAYWG QGTLVTVSAA STKGPSVFPL APSSKSTSGG TAALGCLVKD

YFPEPVTVSW NSGALTSGVH TFPAVLQSSG LYSLSSVVTV PSSSLGTQTY

ICNVNHKPSN TKVDKKVEPK SCDKTHTCPP CPAPELLGGP SVFLFPPKPK

DTLMISRTPE VTCVVVDVSH EDPEVKFNWY VDGVEVHNAK TKPREEQYNS

TYRVVSVLTV LHQDWLNGKE YKCKVSNKAL PAPIEKTISK AKGQPREPQV

YTLPPSRDEL TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK*]

3954-1204-C225v5 Activatable Antibody Light Chain Nucleotide Sequence 2:
[Spacer (SEQ ID NO: 62)][Mask (SEQ ID NO: 63)][Linker 1 (SEQ ID NO: 64)][1204 Substrate (SEQ ID NO: 65)][Linker 2 (SEQ ID NO: 66)][C225 (SEQ ID NO: 67)]

(SEQ ID NO: 27)

[caaggccagtctggccag][tgcatctcacctcgtggttgtccggacggcccatacgtcatgt ac*ggctcgagcggtggcagcggtggctctggtggatccggt*][ctgagcggccgttccgataat cat][*ggcagtagcggtacc*][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg cattccgagccgctttagcggcagcggcagcggcaccgattttaccctgagcattaacagcgtg gaaagcgaagatattgcggattattattgccagcagaacaacaactggccgaccacctttggcg cgggcaccaaactggaactgaaacgtacggtggctgcaccatctgtcttcatcttcccgccatc tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]

-continued

Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v5 Activatable Antibody Light Chain Amino Acid Sequence 2:
[Spacer (SEQ ID NO: 38)][Mask (SEQ ID NO: 14)][Linker 1 (SEQ ID NO: 23)][1204 Substrate (SEQ ID NO: 13)][Linker 2 (SEQ ID NO: 24)][C225 (SEQ ID NO: 68)]

(SEQ ID NO: 28)

[QGQSGQ][CISP RGCPDGPYVMY][*GSSGGSGGSGGSG*][LSGRSDNH][*GSSGT*][QIL

LTQSPVILSV SPGERVSFSC RASQSIGTNI HWYQQRTNGS PRLLIKYASE

SISGIPSRFS GSGSGTDFTL SINSVESEDI ADYYCQQNNN WPTTFGAGTK

LELKRTVAAP SVFIFPPSDE QLKSGTASVV CLLNNFYPRE AKVQWKVDNA

LQSGNSQESV TEQDSKDSTY SLSSTLTLSK ADYEKHKVYA CEVTHQGLSS

PVTKSFNRGE C*]

Bold: Spacer
Underline: Mask
Italics and Underline: Linker 1
Bold and Underline: 1204 Substrate
Bold, Italics and Underline: Linker 2
Normal text: anti-EGFR antibody derived sequence Another exemplary activatable anti-EGFR antibody of the invention is the activatable antibody referred to herein as the 3954-1204-C225v4 activatable antibody, which binds epidermal growth factor receptor (EGFR). Two sequences of the 3954-1204-C225v4 activatable anti-EGFR antibody are shown below, Sequence 1 is the sequence of a version of the 3954-1204-C225v4 activatable anti-EGFR antibody that includes a signal peptide, and Sequence 2 is the sequence of the 3954-1204-C225v4 activatable anti-EGFR antibody without the signal peptide:

3954-1204-C225v4 Activatable Antibody Heavy Chain Nucleotide Sequence 1:
[Signal Peptide (SEQ ID NO: 60)][C225v4 (SEQ ID NO: 29)]

(SEQ ID NO: 5)

[*atgtacaggatgcaactcctgtcttgcattgcactaagtcttgcacttgtcacgaattcg*][c aggtgcagctgaaacagagcggcccgggcctggtgcagccgagccagagcctgagcattacctg caccgtgagcggctttagcctgaccaactatggcgtgcattgggtgcgccagagcccgggcaaa ggcctggaatggctgggcgtgatttggagcggcggcaacaccgattataacaccccgtttacca gccgcctgagcattaacaaagataacagcaaaagccaggtgtttttaaaatgaacagcctgca aagcaacgataccgcgatttattattgcgcgcgcgcgctgacctattatgattatgaatttgcg tattggggccagggcaccctggtgaccgtgagcgcggctagcaccaagggcccatcggtcttcc ccctggcaccctcctccaagagcacctctgggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtacaac agcacgtaccgtgtggtcagcgtcctcaccgtcctgcaccaggactggctgaatggcaaggagt acaagtgcaaggtctccaacaaagccctcccagcccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga -continued gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]

Italics: Signal peptide
Normal text: anti-EGFR antibody derived sequence 3954-1204-C225v4 Activatable Antibody Heavy Chain Amino Acid Sequence 1:
[Signal Peptide (SEQ ID NO: 61)][C225v4 (SEQ ID NO: 30)]
(SEQ ID NO: 6)
[*MYRMQLLSCI ALSLALVTNS*][QVQLKQSGPG LVQPSQSLSI TCTVSGFSLT

NYGVHWVRQS PGKGLEWLGV IWSGGNTDYN TPFTSRLSIN KDNSKSQVFF

KMNSLQSNDT AIYYCARALT YYDYEFAYWG QGTLVTVSAA STKGPSVFPL

APSSKSTSGG TAALGCLVKD YFPEPVTVSW NSGALTSGVH TFPAVLQSSG

LYSLSSVVTV PSSSLGTQTY ICNVNHKPSN TKVDKKVEPK SCDKTHTCPP

CPAPELLGGP SVFLFPPKPK DTLMISRTPE VTCVVVDVSH EDPEVKFNWY

VDGVEVHNAK TKPREEQYNS TYRVVSVLTV LHQDWLNGKE YKCKVSNKAL

PAPIEKTISK AKGQPREPQV YTLPPSRDEL TKNQVSLTCL VKGFYPSDIA

VEWESNGQPE NNYKTTPPVL DSDGSFFLYS KLTVDKSRWQ QGNVFSCSVM

HEALHNHYTQ KSLSLSPGK*]

Italics: Signal peptide
Normal text: anti-EGFR antibody derived sequence 3954-1204-C225v4 Activatable Antibody Light Chain Nucleotide Sequence 1:
[Signal peptide (SEQ ID NO: 60)][Spacer (SEQ ID NO: 62)][Mask
(SEQ ID NO: 63)][Linker 1 (SEQ ID NO: 64)][1204 Substrate (SEQ
ID NO: 65)][Linker 2 (SEQ ID NO: 66)][C225 (SEQ ID NO: 67)]
(SEQ ID NO: 3)
[*atgtacaggatgcaactcctgtcttgcattgcactaagtcttgcacttgtcacgaattcg*]

[caaggccagtctggccag][tgcatctcacctcgtggttgtccggacggcccatacgtcatgt ac][*ggctcgagcggtggcagcggtggctctggtggatccggt*][ctgagcggccgttccgata atcat][*ggcagtagcggtacc*][cagatcttgctgacccagagcccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v4 Activatable Antibody Light Chain Amino Acid Sequence 1:
[Signal peptide (SEQ ID NO: 61)][Spacer (SEQ ID NO: 38)][Mask -continued (SEQ ID NO: 14)][Linker 1 (SEQ ID NO: 23)][1204 Substrate (SEQ ID NO: 13)][Linker 2 (SEQ ID NO: 24)][C225 (SEQ ID NO: 68)]

(SEQ ID NO: 4)

[*MYRMQLLSCI ALSLALVTNS*][QGQSGQ][CISPRGCPDGPYVMY][*GSSGGSGGS GGSG*][LSGRSD NH][*GSSGT*][QIL LTQSPVILSVSPGERVSFSC RASQSIGTNI

HWYQQRTNGS PRLLIKYASE SISGIPSRFS GSGSGTDFTL SINSVESEDI

ADYYCQQNNN WPTTFGAGTK LELKRTVAAP SVFIFPPSDE QLKSGTASVV

CLLNNFYPRE AKVQWKVDNA LQSGNSQESV TEQDSKDSTY SLSSTLTLSK

ADYEKHKVYA CEVTHQGLSS PVTKSFNRGE C*]

Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v4 Activatable Antibody Heavy Chain Nucleotide Sequence 2: [C225v4 (SEQ ID NO: 29)]

(SEQ ID NO: 29)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgtttttaaaatgaacagcctg caaagcaacgataccgcgatttattattgcgcgcgcgcgctgacctattatgattatgaatttg cgtattggggccagggcaccctggtgaccgtgagcgcggctagcaccaagggcccatcggtctt cccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v4 Activatable Antibody Heavy Chain Amino Acid Sequence 2: [C225v4 (SEQ ID NO: 30)]

(SEQ ID NO: 30)

[QVQLKQSGPG LVQPSQSLSI TCTVSGFSLT NYGVHWVRQS PGKGLEWLGV

IWSGGNTDYN TPFTSRLSIN KDNSKSQVFF KMNSLQSNDT AIYYCARALT

YYDYEFAYWG QGTLVTVSAA STKGPSVFPL APSSKSTSGG TAALGCLVKD

YFPEPVTVSW NSGALTSGVH TFPAVLQSSG LYSLSSVVTV PSSSLGTQTY

-continued

ICNVNHKPSN TKVDKKVEPK SCDKTHTCPP CPAPELLGGP SVFLFPPKPK

DTLMISRTPE VTCVVVDVSH EDPEVKFNWY VDGVEVHNAK TKPREEQYNS

TYRVVSVLTV LHQDWLNGKE YKCKVSNKAL PAPIEKTISK AKGQPREPQV

YTLPPSRDEL TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK*]

3954-1204-C225v4 Activatable Antibody Light Chain Nucleotide Sequence 2:
[Spacer (SEQ ID NO: 62)][Mask (SEQ ID NO: 63)][Linker 1 (SEQ ID NO: 64)][1204 Substrate (SEQ ID NO: 65)][Linker 2 (SEQ ID NO: 66)][C225 (SEQ ID NO: 67)]

(SEQ ID NO: 27)

[caaggccagtctggccag][<u>tgcatctcacctcgtggttgtccggacggcccatacgtcatgt</u>

<u>ac</u>][<u>*ggctcgagcggtggcagcggtggctctggtggatccggt*</u>][<u>ctgagcggccgttccgata</u>

<u>atcat</u>][<u>*ggcagtagcggtacc*</u>][cagatcttgctgacccagagcccggtgattctgagcgtga gcccgggcgaacgtgtgagctttagctgccgcgcgagccagagcattggcaccaacattcattg gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v4 Activatable Antibody Light Chain Amino Acid Sequence 2:
[Spacer (SEQ ID NO: 38)][Mask (SEQ ID NO: 14)][Linker 1 (SEQ ID NO: 23)][1204 Substrate (SEQ ID NO: 13)][Linker 2 (SEQ ID NO: 24)][C225 (SEQ ID NO: 68)]

(SEQ ID NO: 28)

[QGQSGQ][<u>CISPRGCPDGPYVMY</u>][<u>*GSSGGSGGSGGSG*</u>][<u>LSGRSDNH</u>][<u>*GSSGT*</u>][QIL

LTQSPVILSV SPGERVSFSC RASQSIGTNI HWYQQRTNGS PRLLIKYASE

SISGIPSRFS GSGSGTDFTL SINSVESEDI ADYYCQQNNN WPTTFGAGTK

LELKRTVAAP SVFIFPPSDE QLKSGTASVV CLLNNFYPRE AKVQWKVDNA

LQSGNSQESV TEQDSKDSTY SLSSTLTLSK ADYEKHKVYA CEVTHQGLSS

PVTKSFNRGE C*]

Bold: Spacer
Underline: Mask
Italics and Underline: Linker 1
Bold and Underline: 1204 Substrate
Bold, Italics and Underline: Linker 2
Normal text: anti-EGFR antibody derived sequence Another exemplary activatable anti-EGFR antibody of the invention is the activatable antibody referred to herein as the 3954-1204-C225v6 activatable antibody, which binds epidermal growth factor receptor (EGFR). Two sequences of the 3954-1204-C225v6 activatable anti-EGFR antibody are shown below, Sequence 1 is the sequence of a version of the 3954-1204-C225v6 activatable anti-EGFR antibody that includes a signal peptide, and Sequence 2 is the sequence of the 3954-1204-C225v6 activatable anti-EGFR antibody without the signal peptide:

3954-1204-C225v6 Activatable Antibody Heavy Chain Nucleotide Sequence 1:
[Signal peptide (SEQ ID NO: 60)][C225v6 (SEQ ID NO: 33)]
(SEQ ID NO: 9)
[*atgtacaggatgcaactcctgtcttgcattgcactaagtcttgcacttgtcacgaattcg*][c aggtgcagctgaaacagagcggcccgggcctggtgcagccgagccagagcctgagcattacctg caccgtgagcggctttagcctgaccaactatggcgtgcattgggtgcgccagagcccgggcaaa ggcctggaatggctgggcgtgatttggagcggcggcaacaccgattataacaccccgtttacca gccgcctgagcattaacaaagataacagcaaaagccaggtgtttttaaaatgaacagcctgca aagccaggataccgcgatttattattgcgcgcgcgcgctgacctattatgattatgaatttgcg tattggggccagggcaccctggtgaccgtgagcgcggctagcaccaagggcccatcggtcttcc ccctggcaccctcctccaagagcacctctgggggcacagcggccctgggctgcctggtcaagga ctacttccccgaaccggtgacggtgtcgtggaactcaggcgccctgaccagcggcgtgcacacc ttcccggctgtcctacagtcctcaggactctactccctcagcagcgtggtgaccgtgccctcca gcagcttgggcacccagacctacatctgcaacgtgaatcacaagcccagcaacaccaaggtgga caagaaagttgagcccaaatcttgtgacaaaactcacacatgcccaccgtgcccagcacctgaa ctcctggggggaccgtcagtcttcctcttccccccaaaacccaaggacaccctcatgatctccc ggacccctgaggtcacatgcgtggtggtggacgtgagccacgaagaccctgaggtcaagttcaa ctggtacgtggacggcgtggaggtgcataatgccaagacaaagccgcgggaggagcagtacgcc agcacgtaccgtgtggtcagcgtcctcaccgtcctgcaccaggactggctgaatggcaaggagt acaagtgcaaggtctccaacaaagccctcccagcccccatcgagaaaaccatctccaaagccaa agggcagccccgagaaccacaggtgtacaccctgcccccatcccgggatgaactgaccaagaac caggtcagcctgacctgcctggtcaaaggcttctatcccagcgacatcgccgtggagtgggaga gcaatgggcagccggagaacaactacaagaccacgcctcccgtgctggactccgacggctcctt cttcctctacagcaagctcaccgtggacaagagcaggtggcagcaggggaacgtcttctcatgc tccgtgatgcatgaggctctgcacaaccactacacgcagaagagcctctccctgtctccgggta aatga]

Italics: Signal peptide
Normal text: anti-EGFR antibody derived sequence 3954-1204-C225v6 Activatable Antibody Heavy Chain Amino Acid Sequence 1:
[Signal peptide (SEQ ID NO: 61)][C225v6 (SEQ ID NO: 34)]
(SEQ ID NO: 10)
[*MYRMQLLSCI ALSLALVTNS*][QVQLKQSGPG LVQPSQSLSI TCTVSGFSLT

NYGVHWVRQS PGKGLEWLGV IWSGGNTDYN TPFTSRLSIN KDNSKSQVFF

KMNSLQSQDT AIYYCARALT YYDYEFAYWG QGTLVTVSAA STKGPSVFPL

APSSKSTSGG TAALGCLVKD YFPEPVTVSW NSGALTSGVH TFPAVLQSSG

LYSLSSVVTV PSSSLGTQTY ICNVNHKPSN TKVDKKVEPK SCDKTHTCPP

CPAPELLGGP SVFLFPPKPK DTLMISRTPE VTCVVVDVSH EDPEVKFNWY

VDGVEVHNAK TKPREEQYAS TYRVVSVLTV LHQDWLNGKE YKCKVSNKAL

-continued

PAPIEKTISK AKGQPREPQV YTLPPSRDEL TKNQVSLTCL VKGFYPSDIA

VEWESNGQPE NNYKTTPPVL DSDGSFFLYS KLTVDKSRWQ QGNVFSCSVM

HEALHNHYTQ KSLSLSPGK*]

Italics: Signal peptide
Normal text: anti-EGFR antibody derived sequence 3954-1204-C225v6 Activatable Antibody Light Chain Nucleotide Sequence 1:
[Signal peptide (SEQ ID NO: 60)][Spacer (SEQ ID NO: 62)][Mask (SEQ ID NO: 63)][Linker 1 (SEQ ID NO: 64)][1204 Substrate (SEQ ID NO: 65)][Linker 2 (SEQ ID NO: 66)][C225 (SEQ ID NO: 67)]

(SEQ ID NO: 3)

[*atgtacaggatgcaactcctgtcttgcattgcactaagtcttgcacttgtcacgaattcg*][c aaggccagtctggccag][tgcatctcacctcgtggttgtccggacggcccatacgtcatgtac]

[*ggctcgagcggtggcagcggtggctctggtggatccggt*][ctgagcggccgttccgataat cat][*ggcagtagcggtacc*][cagatcttgctgacccagagcccggtgattctgagcgtgagc ccgggcgaacgtgtgagctttagctgccgcgcgagccagagcattggcaccaacattcattggt atcagcagcgcaccaacggcagcccgcgcctgctgattaaatatgcgagcgaaagcattagcgg cattccgagccgctttagcggcagcggcagcggcaccgattttaccctgagcattaacagcgtg gaaagcgaagatattgcggattattattgccagcagaacaacaactggccgaccacctttggcg cgggcaccaaactggaactgaaacgtacggtggctgcaccatctgtcttcatcttcccgccatc tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgttag]

Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v6 Activatable Antibody Light Chain Amino Acid Sequence 1:
[Signal peptide (SEQ ID NO: 61)][Spacer (SEQ ID NO: 38)][Mask (SEQ ID NO: 14)][Linker 1 (SEQ ID NO: 23)][1204 Substrate (SEQ ID NO: 13)][Linker 2 (SEQ ID NO: 24)][C225 (SEQ ID NO: 68)]

(SEQ ID NO: 4)

[*MYRMQLLSCI ALSLALVTNS*][QGQSGQ][CISPRGCPDGPYVMY][*GSSGGSGGS*

*GGSG*][LSGRSDNH][*GSSGT*][QILLTQSPVILSV SPGERVSFSC RASQSIGTNI

HWYQQRTNGS PRLLIKYASE SISGIPSRFS GSGSGTDFTL SINSVESEDI

ADYYCQQNNN WPTTFGAGTK LELKRTVAAP SVFIFPPSDE QLKSGTASVV

CLLNNFYPRE AKVQWKVDNA LQSGNSQESV TEQDSKDSTY SLSSTLTLSK

ADYEKHKVYA CEVTHQGLSS PVTKSFNRGE C*]

Italics: Signal peptide
Bold: Spacer
Underline: Mask
Italics and Underline: Linker 1
Bold and Underline: 1204 Substrate
Bold, Italics and Underline: Linker 2
Normal text: anti-EGFR antibody derived sequence -continued 3954-1204-C225v6 Activatable Antibody Heavy Chain Nucleotide Sequence 2:
[C225v6 (SEQ ID NO: 33)]

(SEQ ID NO: 33)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgtttttaaaatgaacagcctg caaagccaggataccgcgatttattattgcgcgcgcgcgctgacctattatgattatgaatttg cgtattggggccagggcaccctggtgaccgtgagcgcggctagcaccaagggcccatcggtctt cccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtacg ccagcacgtaccgtgtggtcagcgtcctcaccgtcctgcaccaggactggctgaatggcaagga gtacaagtgcaaggtctccaacaaagccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

3954-1204-C225v6 Activatable Antibody Heavy Chain Amino Acid Sequence 2:
[C225v6 (SEQ ID NO: 34)]

(SEQ ID NO: 34)

[QVQLKQSGPG LVQPSQSLSI TCTVSGFSLT NYGVHWVRQS PGKGLEWLGV

IWSGGNTDYN TPFTSRLSIN KDNSKSQVFF KMNSLQSQDT AIYYCARALT

YYDYEFAYWG QGTLVTVSAA STKGPSVFPL APSSKSTSGG TAALGCLVKD

YFPEPVTVSW NSGALTSGVH TFPAVLQSSG LYSLSSVVTV PSSSLGTQTY

ICNVNHKPSN TKVDKKVEPK SCDKTHTCPP CPAPELLGGP SVFLFPPKPK

DTLMISRTPE VTCVVVDVSH EDPEVKFNWY VDGVEVHNAK TKPREEQYAS

TYRVVSVLTV LHQDWLNGKE YKCKVSNKAL PAPIEKTISK AKGQPREPQV

YTLPPSRDEL TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK*]

3954-1204-C225v6 Activatable Antibody Light Chain Nucleotide Sequence 2:
[Spacer (SEQ ID NO: 62)][Mask (SEQ ID NO: 63)][Linker 1 (SEQ ID NO: 64)][1204 Substrate (SEQ ID NO: 65)][Linker 2 (SEQ ID NO: 66)][C225 (SEQ ID NO: 67)]

(SEQ ID NO: 27)

[caaggccagtctggccag][tgcatctcacctcgtggttgtccggacggcccatacgtcatgt ac][*ggctcgagcggtggcagcggtggctctggtggatccggt*][ctgagcggccgttccgata atcat][*ggcagtagcggtacc*][cagatcttgctgacccagagcccggtgattctgagcgtga gcccgggcgaacgtgtgagctttagctgccgcgcgagccagagcattggcaccaacattcattg -continued gtatcagcagcgcaccaacggcagcccgcgcctgctgattaaatatgcgagcgaaagcattagc ggcattccgagccgctttagcggcagcggcagcggcaccgattttaccctgagcattaacagcg tggaaagcgaagatattgcggattattattgccagcagaacaacaactggccgaccacctttgg cgcgggcaccaaactggaactgaaacgtacggtggctgcaccatctgtcttcatcttcccgcca tctgatgagcagttgaaatctggaactgcctctgttgtgtgcctgctgaataacttctatccca gagaggccaaagtacagtggaaggtggataacgccctccaatcgggtaactcccaggagagtgt cacagagcaggacagcaaggacagcacctacagcctcagcagcaccctgacgctgagcaaagca gactacgagaaacacaaagtctacgcctgcgaagtcacccatcagggcctgagctcgcccgtca caaagagcttcaacaggggagagtgttag]

Bold: Spacer
Underline: Mask
Italics and Underline: Linker 1
Bold and Underline: 1204 Substrate
Bold, Italics and Underline: Linker 2
Normal text: anti-EGFR antibody derived sequence 3954-1204-C225v6 Activatable Antibody Light Chain Amino Acid Sequence 2:
[Spacer (SEQ ID NO: 38)][Mask (SEQ ID NO: 14)][Linker 1 (SEQ ID NO: 23)][1204 Substrate (SEQ ID NO: 13)][Linker 2 (SEQ ID NO: 24)][C225 (SEQ ID NO: 68)]

(SEQ ID NO: 28)

[QGQSGQ][CISPRGCPDGPYVMY][*GSSGGSGGSGGSG*][LSGRSDNH][*GSSGT*][QIL

LTQSPVILSV SPGERVSFSC RASQSIGTNI HWYQQRTNGS PRLLIKYASE

SISGIPSRFS GSGSGTDFTL SINSVESEDI ADYYCQQNNN WPTTFGAGTK

LELKRTVAAP SVFIFPPSDE QLKSGTASVV CLLNNFYPRE AKVQWKVDNA

LQSGNSQESV TEQDSKDSTY SLSSTLTLSK ADYEKHKVYA CEVTHQGLSS

PVTKSFNRGE C*]

Bold: Spacer
Underline: Mask
Italics and Underline: Linker 1
Bold and Underline: 1204 Substrate
Bold, Italics and Underline: Linker 2
Normal text: anti-EGFR antibody derived sequence When an activatable anti-EGFR antibody of the invention is cleaved by a protease, i.e., when the activatable anti-EGFR is in an active or cleaved state, the activated anti-EGFR antibody will retain only a portion of the amino acid sequence of the activatable antibody in an inactive or uncleaved state. The sequence of the activatable anti-EGFR in an active or cleaved state will vary depending on which protease cleaves the substrate (CM), as different proteases can have different recognition sites.

For example, the exemplary anti-EGFR antibodies of the invention, the 3954-1204-C225v5 activatable antibody, the 3954-1204-C225v4 activatable antibody, and/or the 3954-1204-C225v6 activatable antibody, each have the same light chain amino acid (referred to herein as Light Chain Amino Acid Sequence 2). When exposed to and activated by either urokinase plasminogen activator (uPA) or MT-SP1, the activated form of the anti-EGFR activatable antibody would have the following amino acid sequence:

```
Activated Form of 3954-1204-C225v5, 3954-1204-
C225v4 and/or 3954-1204-C225v6
Activatable Antibody Light Chain Amino Acid
Sequence 2 When Activated by uPA or MT-SP1:
                                    (SEQ ID NO: 69)
SDNHGSSGTQILLTQSPVILSVSPGERVSFSCRASQSIGTNIHWYQQRTN

GSPRLLIKYASESISGIPSRFSGSGSGTDFTLSINSVESEDIADYYCQQN

NNWPTTFGAGTKLELKRTVAAPSVFIFPPSDEQLKSGTASVVCLLNNFYP

REAKVQWKVDNALQSGNSQESVTEQDSKDSTYSLSSTLTLSKADYEKHKV

YACEVTHQGLSSPVTKSFNRGEC*
```

When exposed to and activated legumain, the activated form of the anti-EGFR activatable antibody would have the following amino acid sequence:

```
Activated Form of 3954-1204-C225v5, 3954-1204-
C225v4 and/or 3954-1204-C225v6
Activatable Antibody Light Chain Amino Acid
Sequence 2 When Activated by Legumain:
                                    (SEQ ID NO: 70)
HGSSGTQILLTQSPVILSVSPGERVSFSCRASQSIGTNIHWYQQRTNGSP

RLLIKYASESISGIPSRFSGSGSGTDFTLSINSVESEDIADYYCQQNNNW

PTTFGAGTKLELKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC*
```

In some embodiments, the activatable anti-EGFR antibodies described herein also include an agent conjugated to the activatable antibody. In some embodiments, the conjugated agent is a therapeutic agent, such as an antineoplastic agent. In such embodiments, the agent is conjugated to a carbohydrate moiety of the activatable antibody, preferably where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody. In some embodiments, the agent is conjugated to an amino group of the antibody or antigen-binding fragment of the activatable antibody. In some embodiments the agent is conjugated to a carboxylic acid group of the antibody or antigen-binding fragment of the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, any of the cytotoxic agents listed in Table 1. In some embodiments, the cytotoxic agent is a dolastatin or a derivative thereof (e.g. auristatin E, AFP, MMAF, MMAE, DMAF, DMAE). For example, the cytotoxic agent is monomethyl auristatin E (MMAE).

In some embodiments, the conjugated activatable antibody can be modified for site-specific conjugation through modified amino acid sequences inserted or otherwise included in the activatable antibody sequence. These modified amino acid sequences are designed to allow for controlled placement and/or dosage of the conjugated agent within a conjugated activatable anti-EGFR antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Table 1 lists some of the exemplary pharmaceutical agents that may be employed in the herein described invention but in no way is meant to be an exhaustive list.

TABLE 1

Exemplary Pharmaceutical Agents for Conjugation

| | |
|---|---|
| CYTOTOXIC AGENTS | |
| Auristatins | Turbostatin |
| Auristatin E | Phenstatins |
| Monomethyl auristatin E (MMAE) | Hydroxyphenstatin |
| Desmethyl auristatin E (DMAE) | Spongistatin 5 |
| Auristatin F | Spongistatin 7 |
| Monomethyl auristatin F (MMAF) | Halistatin 1 |
| Desmethyl auristatin F (DMAF) | Halistatin 2 |
| Auristatin derivatives, e.g., amides thereof | Halistatin 3 |
| Auristatin tyramine | Modified Bryostatins |
| Auristatin quinoline | Halocomstatins |
| Dolastatins | Pyrrolobenzimidazoles (PBI) |
| Dolastatin derivatives | Cibrostatin6 |
| Dolastatin 16 DmJ | Doxaliform |
| Dolastatin 16 Dpv | Anthracyclins analogues |
| Maytansinoids, e.g. DM-1; DM-4 | Anthracyclins analogues |
| Maytansinoid derivatives | |
| Duocarmycin | Cemadotin analogue (CemCH2-SH) |
| Duocarmycin derivatives | Pseudomonas toxin A (PE38) variant |
| Alpha-amanitin | Pseudomonas toxin A (ZZ-PE38) variant |
| Anthracyclines | ZJ-101 |
| Doxorubicin | OSW-1 |
| Daunorubicin | 4-Nitrobenzyloxycarbonyl Derivatives of O6-Benzylguanine |
| Bryostatins | Topoisomerase inhibitors |
| Camptothecin | Hemiasterlin |
| Camptothecin derivatives | Cephalotaxine |
| 7-substituted Camptothecin | Homoharringtonine |
| 10, 11-Difluoromethylenedioxy-camptothecin | Pyrrolobenzodiazepine dimers (PBDs) |
| Combretastatins | Functionalized pyrrolobenzodiazepenes |
| Debromoaplysiatoxin | Calicheamicins |
| Kahalalide-F | Podophyllotoxins |
| Discodermolide | Taxanes |
| Ecteinascidins | Vinca alkaloids |
| ANTIVIRALS | CONJUGATABLE DETECTION REAGENTS |
| Acyclovir | Fluorescein and derivatives thereof |
| Vira A | Fluorescein isothiocyanate (FITC) |
| Symmetrel | |
| ANTIFUNGALS | |
| Nystatin | |
| ADDITIONAL ANTI-NEOPLASTICS | RADIO-PHARMACEUTICALS |
| Adriamycin | $^{125}$I |
| Cerubidine | $^{131}$I |
| Bleomycin | $^{89}$Zr |
| Alkeran | $^{111}$In |
| Velban | $^{123}$I |
| Oncovin | $^{131}$I |
| Fluorouracil | $^{99}$mTc |
| Methotrexate | $^{201}$Tl |
| Thiotepa | $^{133}$xe |
| Bisantrene | $^{11}$C |
| Novantrone | $^{62}$Cu |
| Thioguanine | $^{18}$F |
| Procarabizine | $^{68}$Ga |
| Cytarabine | $^{13}$N |

TABLE 1-continued

Exemplary Pharmaceutical Agents for Conjugation

| | |
|---|---|
| ANTI-BACTERIALS | $^{15}$O |
| Aminoglycosides | $^{38}$K |
| Streptomycin | $^{82}$Rb |
| Neomycin | $^{99}$mTc (Technetium) |
| Kanamycin | HEAVY METALS |
| Amikacin | Barium |
| Gentamicin | Gold |
| Tobramycin | Platinum |
| Streptomycin B | ANTI-MYCOPLASMALS |
| Spectinomycin | Tylosine |
| Ampicillin | Spectinomycin |
| Sulfanilamide | |
| Polymyxin | |
| Chloramphenicol | |

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfosuccinimidyl 6 [3-(2-pyridyldithio)-propianamide] hexanoate (Pierce Chem. Co. Cat. #2165-G.

The linkers described above contain components that have different attributes, thus leading to conjugates with differing physio-chemical properties. For example, the linker SMPT contains a sterically hindered disulfide bond, and can form conjugates with increased stability. Disulfide linkages, are in general, less stable than other linkages because the disulfide linkage is cleaved in vitro, resulting in less conjugate available.

The reagent EDC (1-ethyl-3-(3-dimethylaminopropyl) carbodiimide hydrochloride is useful to create a carboxamide starting with a carboxylic acid and a primary or secondary amine. Thus, EDC may be used to link lysine residues in an antibody with a carboxylic acid in a linker or toxin, or to link aspartate or glutamate residues in an antibody with an amine in a linker or toxin. Such conjugation reactions utilizing EDC may be enhanced by addition of NHS (N-hydroxysuccinimide) or sulfo-NHS (N-hydroxy-3-oxysulfonylsuccinimide). Addition of NHS or sulfo-NHS to such conjugation reactions may enhance the rate, completeness, selectivity, and/or reproducibility of the conjugation reactions.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

The present invention utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101:3097-3110).

According to the present invention, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present invention, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers which are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class that can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 1.

Non-liming examples of cleavable linker sequences are provided in Table 2.

TABLE 2

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 7)<br>PRFRIIGG (SEQ ID NO: 8) |
| TGFβ | SSRHRRALD (SEQ ID NO: 11) |
| Plasminogen | RKSSIIIRMRDVVL (SEQ ID NO: 12) |
| Staphylokinase | SSSFDKGKYKKGDDA (SEQ ID NO: 31)<br>SSSFDKGKYKRGDDA (SEQ ID NO: 32) |

TABLE 2-continued

| Exemplary Linker Sequences for Conjugation | |
|---|---|
| Types of Cleavable Sequences | Amino Acid Sequence |
| Factor Xa cleavable sequences | IEGR (SEQ ID NO: 35) |
| | IDGR (SEQ ID NO: 36) |
| | GGSIDGR (SEQ ID NO: 39) |
| MMP cleavable sequences | |
| Gelatinase A | PLGLWA (SEQ ID NO: 40) |
| Collagenase cleavable sequences | |
| Calf skin collagen (α1(I) chain) | GPQGIAGQ (SEQ ID NO: 41) |
| Calf skin collagen (α2(I) chain) | GPQGLLGA (SEQ ID NO: 42) |
| Bovine cartilage collagen (α1(II) chain) | GIAGQ (SEQ ID NO: 43) |
| Human liver collagen (α1(III) chain) | GPLGIAGI (SEQ ID NO: 44) |
| Human $\alpha_2$M | GPEGLRVG (SEQ ID NO: 45) |
| Human PZP | YGAGLGVV (SEQ ID NO: 46) |
| | AGLGVVER (SEQ ID NO: 47) |
| | AGLGISST (SEQ ID NO: 48) |
| Rat $\alpha_1$M | EPQALAMS (SEQ ID NO: 49) |
| | QALAMSAI (SEQ ID NO: 50) |
| Rat $\alpha_2$M | AAYHLVSQ (SEQ ID NO: 51) |
| | MDAFLESS (SEQ ID NO: 52) |
| Rat $\alpha_1I_3$(2J) | ESLPVVAV (SEQ ID NO: 53) |
| Rat $\alpha_1I_3$(27J) | SAPAVESE (SEQ ID NO: 54) |
| Human fibroblast collagenase (autolytic cleavages) | DVAQFVLT (SEQ ID NO: 55) |
| | VAQFVLTE (SEQ ID NO: 56) |
| | AQFVLTEG (SEQ ID NO: 57) |
| | PVQPIGPQ (SEQ ID NO: 58) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacers and Cleavable Elements: In still another embodiment, it may be necessary to construct the linker in such a way as to optimize the spacing between the agent and the AB of the activatable antibody. This may be accomplished by use of a linker of the general structure:

$$W—(CH_2)n\text{-}Q$$

wherein

W is either —NH—$CH_2$— or —$CH_2$—;

Q is an amino acid, peptide; and n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present invention, when release of an agent is desired, an AB that is an antibody of a class which can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB which is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond which attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 1.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In other embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH. Exemplary hetero-bifunctional cross-linkers are referenced in Table 3.

TABLE 3

Exemplary Hetero-Bifunctional Cross Linkers
HETERO-BIFUNCTIONAL CROSS-LINKERS

| Linker | Reactive Toward | Advantages and Applications | Spacer Arm Length after crosslinking- (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |
| | Sulfhydryls | Enzyme-antibody conjugation Hapten-carrier protein conjugation | |
| Sulfo-SMCC | Primary amines | Stable maleimide reactive group | 11.6 Å |
| | Sulfhydryls | Water-soluble Enzyme-antibody conjugation | |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment: In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds which may be modified to include functional groups that can subsequently be utilized in attachment to ABs by the methods described herein. A-general formula for such an organic linker could be $$W—(CH_2)n\text{-}Q$$

wherein

W is either —NH—$CH_2$— or —$CH_2$—;

Q is an amino acid, peptide; and n is an integer from 0 to 20.

Non-Cleavable Conjugates: Alternatively, a compound may be attached to ABs which do not activate complement. When using ABs that are incapable of complement activation, this attachment may be accomplished using linkers that are susceptible to cleavage by activated complement or using linkers that are not susceptible to cleavage by activated complement.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 μM; preferably ≤100 nM and most preferably ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to EGFR, when the equilibrium binding constant ($K_d$) is ≤1 μM, preferably ≤100 nM, more preferably ≤10 nM, and most preferably ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology-A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Activatable antibodies of the invention specifically bind human epidermal growth factor receptor (EGFR). Also included in the invention are activatable antibodies that bind to the same epitope as the activatable anti-EGFR antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to EGFR. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of a monoclonal antibody of the invention is to pre-incubate the monoclonal antibody of the invention with EGFR and then add the monoclonal antibody being tested to determine if the monoclonal antibody being tested is inhibited in its ability to bind EGFR. If the monoclonal antibody being tested is inhibited then, in all likelihood, it has the same, or functionally equivalent, epitopic specificity as the monoclonal antibody of the invention.

Use of Activatable Anti-EGFR Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32 (2): 210-8 (2000), Wang W. "Lyophilization and development of solid protein pharmaceuticals." Int. J. Pharm. 203 (1-2): 1-60 (2000), Charman W N "Lipids, lipophilic drugs, and oral drug delivery-some emerging concepts." J Pharm Sci. 89 (8): 967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an activatable anti-EGFR antibody, are used to prevent, treat or otherwise ameliorate a disease or disorder associated with aberrant EGFR expression and/or activity. For example, therapeutic formulations of the invention, which include an activatable anti-EGFR antibody, are used to treat or otherwise ameliorate a cancer or other neoplastic condition.

Figure 8B:
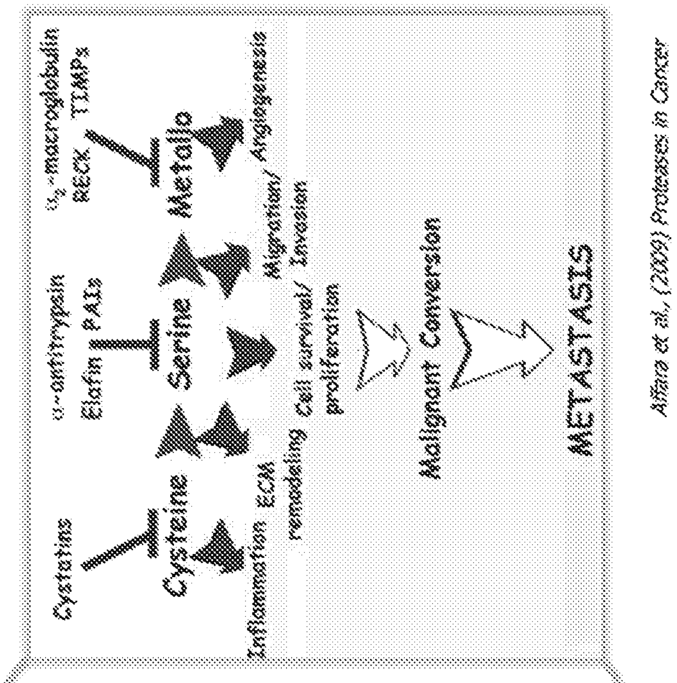
FIGS. 8A and 8B are a series of illustrations depicting the progression, invasion and metastasis of tumors that result from several interdependent processes in which proteases are implicated. These figures are adapted from Affara N I, et al. "Delineating protease functions during cancer development." Methods Mol Biol. 539 (2009): 1-32.
Figure 8A:
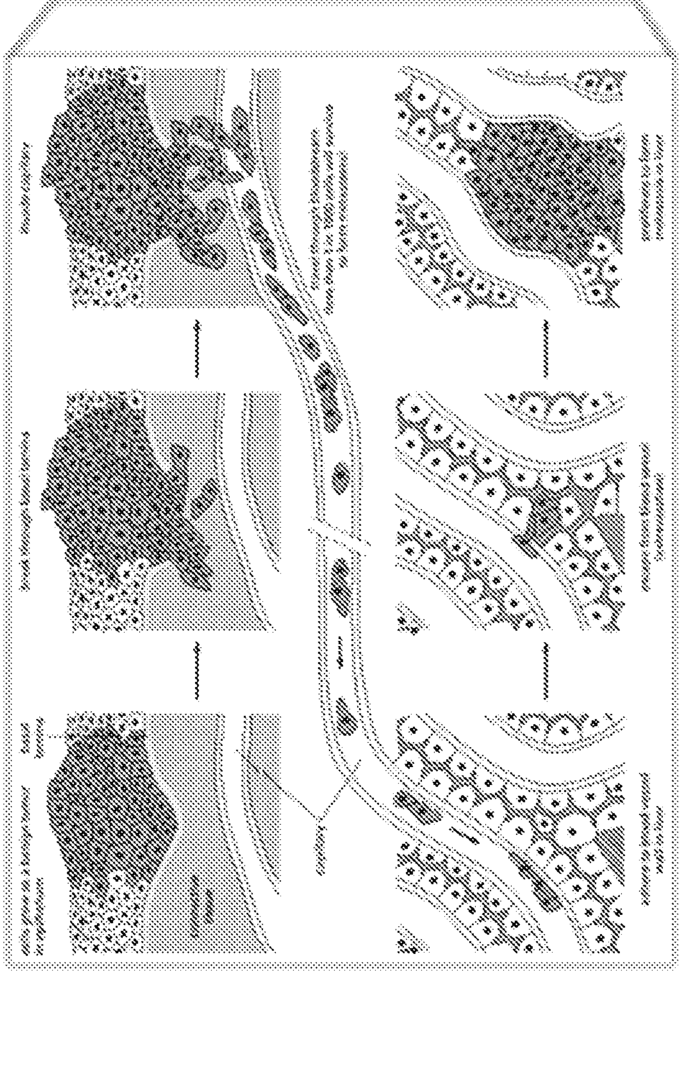
Figure 9D:
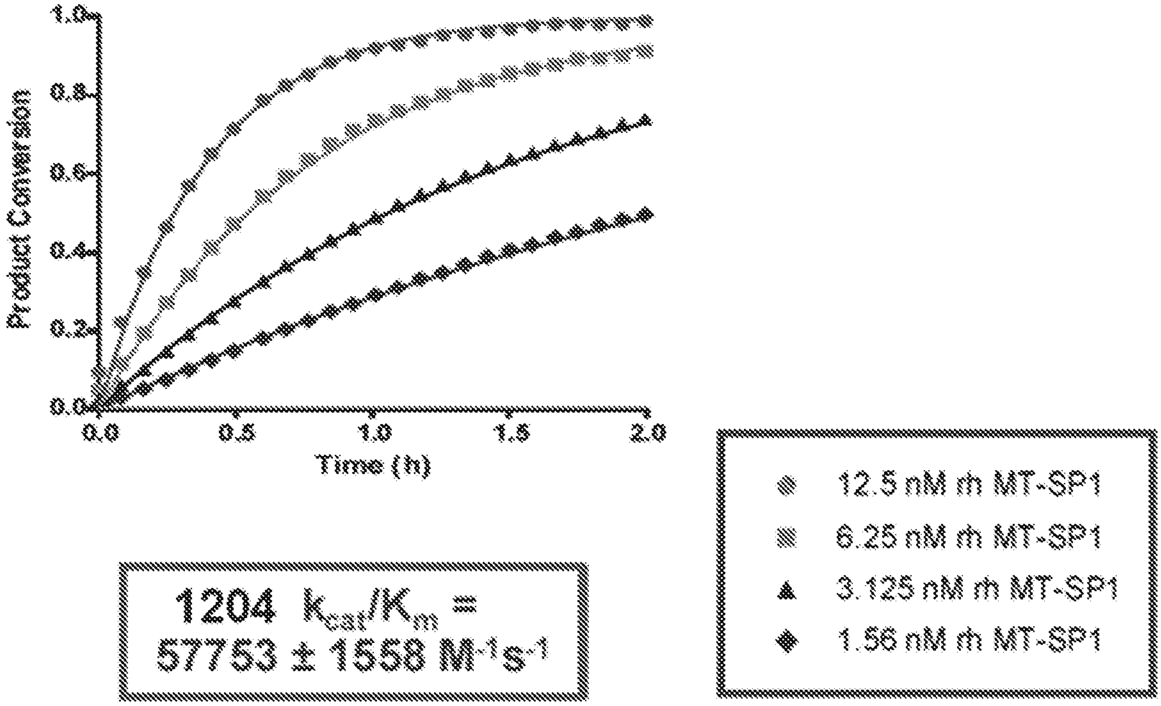
Figure 10A:
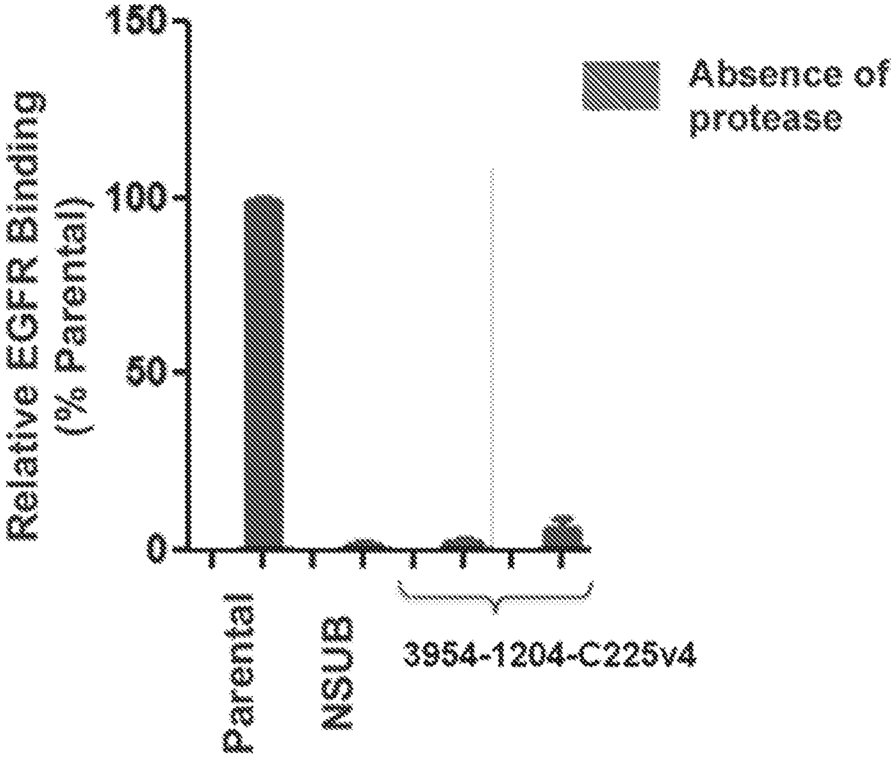
FIG. 10A is a graph depicting the relative ability of unmodified cetuximab antibody ("Parental"), the Pb-NSUB construct ("NSUB"), and the uncleaved 3954-1204-C225v4 activatable antibody to bind EGFR in the absence of protease.
Figure 10B:
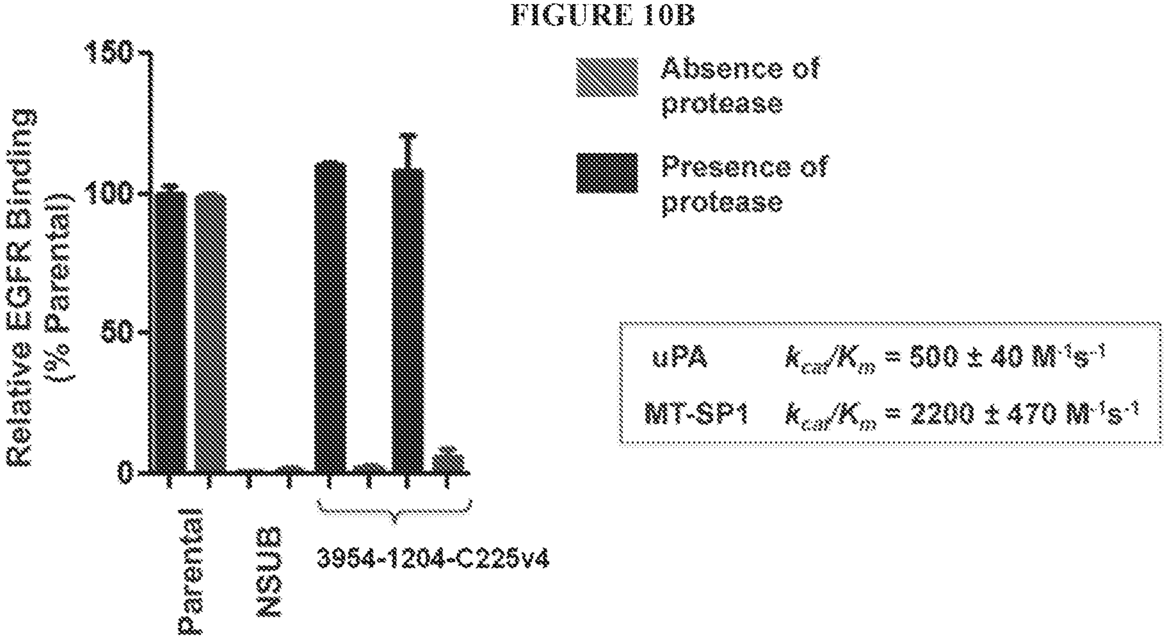
FIG. 10B is a graph that depicts the relative ability of the unmodified cetuximab antibody ("Parental"), the Pb-NSUB construct ("NSUB"), and activated, i.e., cleaved 3954-1204-C225v4 activatable antibody to bind EGFR in the presence of two proteases, human uPA and human MT-SP1.
Figure 11A:
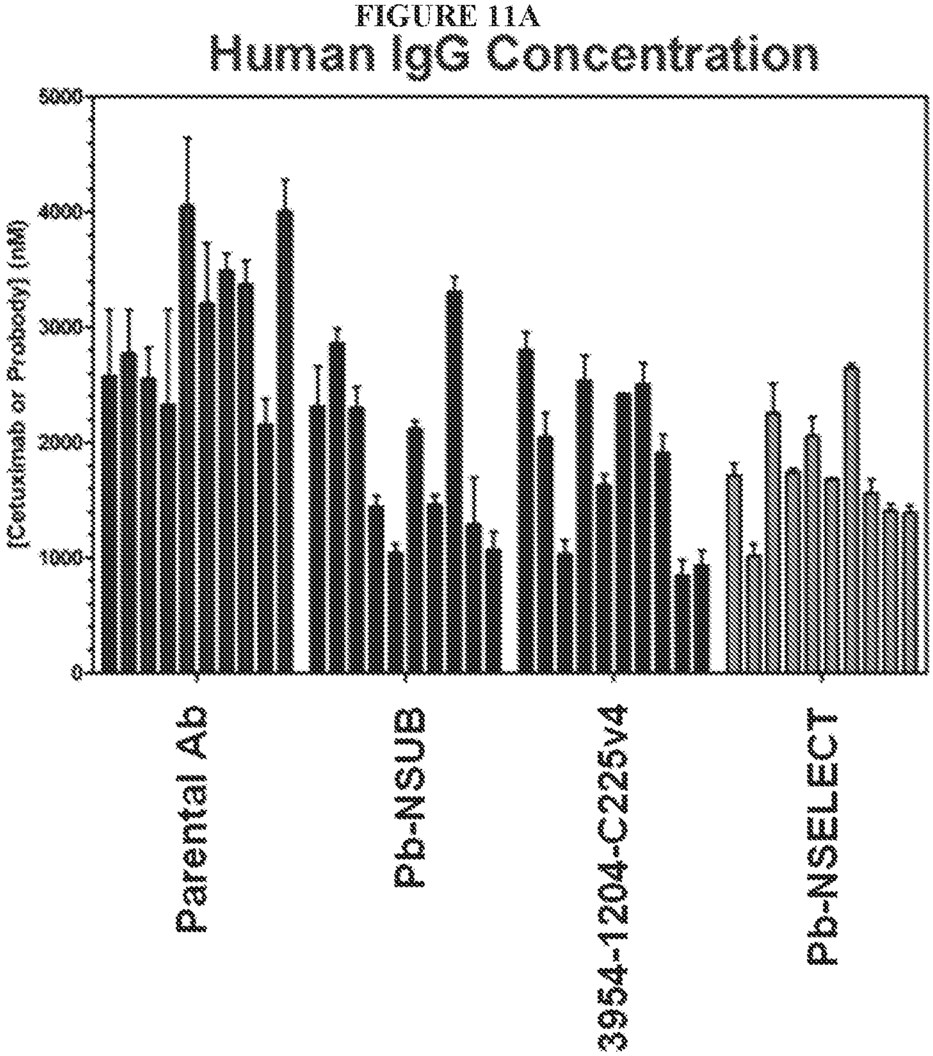
FIGS. 11A and 11B are a series of graphs depicting that the activatable anti-EGFR antibody 3954-1204-C225v4, after at least four weeks after dosing in mice, is stable in circulation and exhibits low activation in plasma, which suggests a superior toxicity profile. As used in FIGS. 11A and 11B, "Parental Ab" refers to the unmodified cetuximab antibody, the Pb-NSUB construct represents an activatable anti-EGFR antibody that includes the NSUB sequence that is not susceptible to protease cleavage, and "PB-NSELECT" is an activatable anti-EGFR antibody that includes a non-selective substrate, i.e., an amino acid sequence that is recognized by enzymes in the circulation.
Figure 11B:
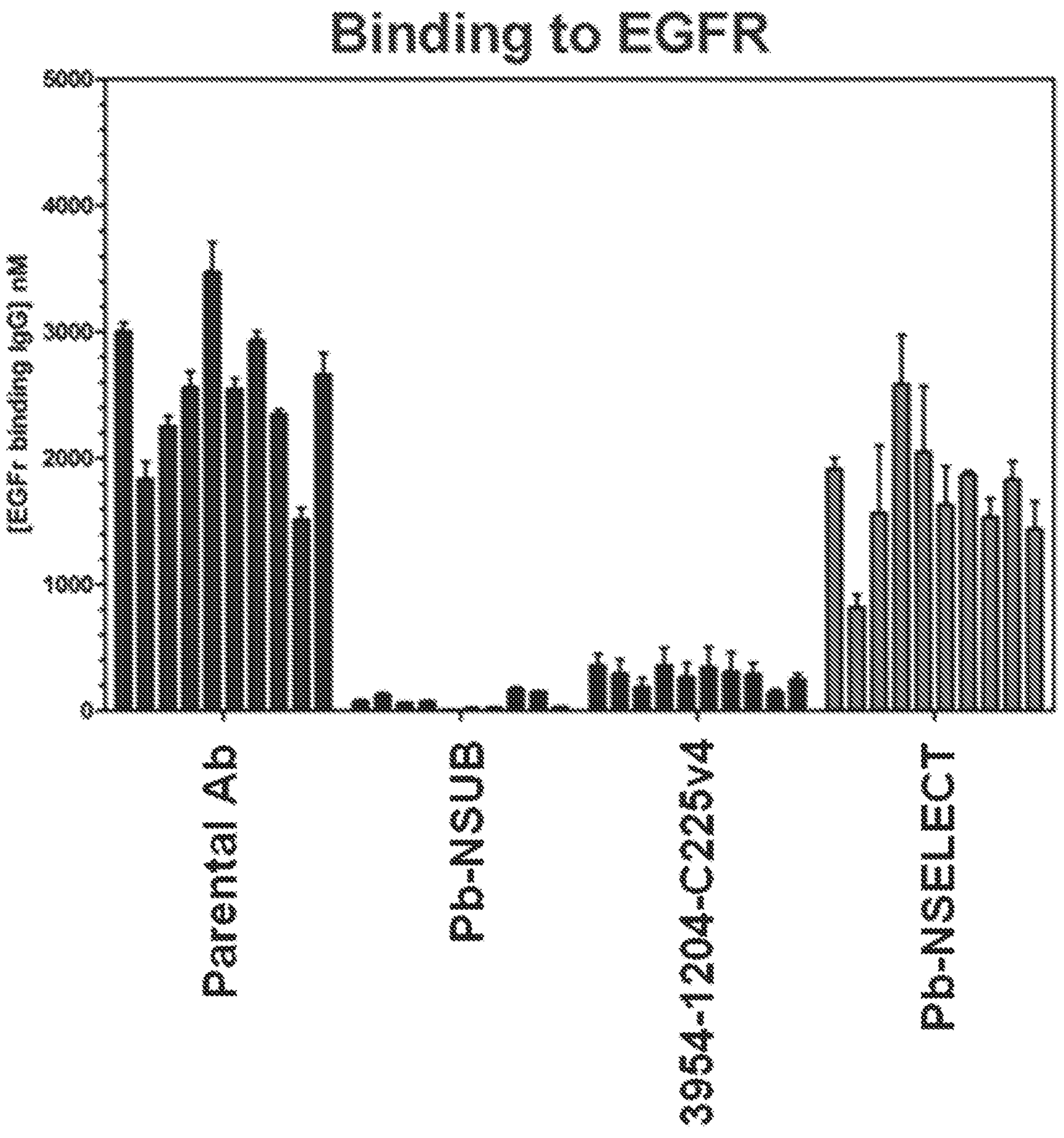

Increased proteolysis is known to be a hallmark of cancer. (See e.g., Affara N I, et al. "Delineating protease functions during cancer development." Methods Mol Biol. 539 (2009): 1-32). Progression, invasion and metastasis of tumors result from several interdependent processes in which proteases are implicated. This process is shown generally in FIGS. 8A and 8B.

Efficaciousness of prevention, amelioration or treatment is determined in association with any known method for diagnosing or treating the disease or disorder associated with aberrant EGFR expression and/or activity. Prolonging the survival of a subject or otherwise delaying the progression of the disease or disorder associated with aberrant EGFR expression and/or activity in a subject indicates that the activatable antibody confers a clinical benefit.

Activatable anti-EGFR antibodies can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where activatable antibody fragments are used, the smallest fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90:7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the activatable antibody contains a detectable label. An intact antibody, or a fragment thereof (e.g., Fab, scFv, or F (ab) 2) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, NJ, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Diagnostic and Prophylactic Formulations

The anti-EGFR antibodies and/or activatable anti-EGFR antibodies of the invention are used in diagnostic and prophylactic formulations. In one embodiment, an anti-EGFR antibody and/or activatable anti-EGFR antibody is administered to patients that are at risk of developing one or more of the aforementioned cancer or other disorders. A patient's or organ's predisposition to one or more of the aforementioned disorders can be determined using genotypic, serological or biochemical markers.

In another embodiment of the invention, an anti-EGFR antibody and/or activatable anti-EGFR antibody is administered to human individuals diagnosed with a clinical indication associated with one or more of the aforementioned disorders. Upon diagnosis, an anti-EGFR antibody and/or activatable anti-EGFR antibody is administered to mitigate or reverse the effects of the clinical indication.

Antibodies and/or activatable antibodies of the invention are also useful in the detection of EGFR in patient samples and accordingly are useful as diagnostics. For example, the anti-EGFR antibodies and/or activatable anti-EGFR antibodies of the invention are used in in vitro assays, e.g., ELISA, to detect EGFR levels in a patient sample.

In one embodiment, an anti-EGFR antibody and/or activatable anti-EGFR antibody of the invention is immobilized on a solid support (e.g., the well(s) of a microtiter plate). The immobilized antibody and/or activatable antibody serves as a capture antibody for any EGFR that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of EGFR antigen in the test sample is determined by comparison with a standard curve developed from the standard samples.

It will be appreciated that based on the results obtained using the anti-EGFR antibodies of the invention in an in vitro diagnostic assay, it is possible to stage a disease in a subject based on expression levels of the EGFR antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Anti-EGFR antibodies and/or activatable anti-EGFR antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable anti-EGFR antibodies having an enzymatically cleavable CM can be used to detect the presence or absence of an enzyme that is capable of cleaving the CM. Such activatable anti-EGFR antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated anti-EGFR antibodies (i.e., antibodies resulting from cleavage of an activatable anti-EGFR antibody) in a given cell or tissue of a given host organism. Such accumulation of activated anti-EGFR antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an anti-EGFR antibody and/or activatable anti-EGFR antibody. Suitable detectable labels are discussed in the context of the above screening methods and additional specific examples are provided below. Using an AB specific to a protein or peptide of the disease state, along with a protease whose activity is elevated in the disease tissue of interest, activatable anti-EGFR antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated anti-EGFR antibodies in the disease tissue is enhanced relative to non-disease tissues.

In another example, activatable anti-EGFR antibodies can be used to detect the presence or absence of a cleaving agent in a sample. For example, where the activatable anti-EGFR antibodies contain a CM susceptible to cleavage by an enzyme, the activatable anti-EGFR antibodies can be used to detect (either qualitatively or quantitatively) the presence of an enzyme in the sample. In another example, where the activatable anti-EGFR antibodies contain a CM susceptible to cleavage by reducing agent, the activatable anti-EGFR antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable anti-EGFR antibody that is not released following cleavage, for example, the detectable label can be a quenched fluorescent label or other label that is not detectable until cleavage has occurred. The assay can be conducted by, for example, contacting the immobilized, detectably labeled activatable anti-EGFR antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable anti-EGFR antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable anti-EGFR antibodies when cleaved. Thus, the assays can be adapted to assess the presence or absence of a cleaving agent and the presence or absence of a target of interest (EGFR). The presence or absence of the cleaving agent can be detected by the presence of and/or an increase in detectable label of the activatable anti-EGFR antibodies as described above, and the presence or absence of the target can be detected by detection of a target-AB complex e.g., by use of a detectably labeled anti-target antibody.

Activatable anti-EGFR antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable anti-EGFR antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g., horseradish peroxidase or alkaline phosphatase).

Detection of the label in a sample that has been incubated with the labeled, activatable anti-EGFR antibody indicates that the sample contains the target, i.e., EGFR, and contains a protease that is specific for the CM of the activatable anti-EGFR antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable anti-EGFR antibody. In some embodiments, the presence of the target can be confirmed using an agent that is specific for the target, e.g., another anti-EGFR antibody, or the detectable label can be competed with unlabeled EGFR. In some embodiments, unlabeled activatable anti-EGFR antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target, i.e., EGFR, and contains a protease that is specific for the CM of the activatable anti-EGFR antibody.

These techniques are also useful in kits and/or as reagents for the detection, identification or characterization of protease activity in a variety of cells, tissues, and organisms based on the protease-specific CM in the activatable anti-EGFR antibody.

In some embodiments, in situ imaging and/or in vivo imaging are useful in methods to identify which patients to treat. For example, in in situ imaging, the activatable anti-EGFR antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an anti-EGFR activatable antibody of the disclosure. For example, patients that test positive for both the target (e.g., EGFR) and a protease that cleaves the substrate in the cleavable moiety (CM) of the anti-EGFR activatable antibody being tested (e.g., accumulate activated antibodies at the disease site) are identified as suitable candidates for treatment with such an anti-EGFR activatable antibody comprising such a CM. Likewise, patients that test negative for either or both of the target (e.g., EGFR) and the protease that cleaves the substrate in the CM in the activatable antibody being tested using these methods are identified as suitable candidates for another form of therapy (i.e., not suitable for treatment with the anti-EGFR activatable antibody being tested). In some embodiments, such patients that test negative with respect to a first anti-EGFR activatable antibody can be tested with other anti-EGFR activatable antibodies comprising different CMs until a suitable anti-EGFR activatable antibody for treatment is identified (e.g., an anti-EGFR activatable antibody comprising a CM that is cleaved by the patient at the site of disease).

In some embodiments in vivo imaging is used to identify or otherwise refine a patient population suitable for treatment with an anti-EGFR activatable antibody of the disclosure. For example, patients that test positive for both the target (e.g., EGFR) and a protease that cleaves the substrate in the cleavable moiety (CM) of the anti-EGFR activatable antibody being tested (e.g., accumulate activated antibodies at the disease site) are identified as suitable candidates for treatment with such an anti-EGFR activatable antibody comprising such a CM. Likewise, patients that test negative are identified as suitable candidates for another form of therapy (i.e., not suitable for treatment with the anti-EGFR activatable antibody being tested). In some embodiments, such patients that test negative with respect to a first anti-EGFR activatable antibody can be tested with other anti-EGFR activatable antibodies comprising different CMs until a suitable anti-EGFR activatable antibody for treatment is identified (e.g., an anti-EGFR activatable antibody comprising a CM that is cleaved by the patient at the site of disease).

Pharmaceutical Compositions

The activatable anti-EGFR antibodies of the invention (also referred to herein as "active compounds"), and derivatives, fragments, analogs and homologs thereof, can be incorporated into pharmaceutical compositions suitable for administration. Such compositions typically comprise the activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Materials and Methods

Activatable anti-EGFR antibody expression and purification. The cDNA coding for the heavy chain and the light chain of each of the activatable anti-EGFR antibodies were separately cloned into a modified pcDNA3.1 mammalian expression vector (Life Technologies). CHO-S cells (Life Technologies) were transiently transfected with the plasmids for each activatable anti-EGFR antibody for 5-7 days using FreeStyle MAX transfection reagent (Life Technologies) following the manufacturer's instructions. The activatable anti-EGFR antibodies were purified using a HiTrap Mab Select Sure protein A column (GE Healthcare) coupled to an AKTA purifier (GE Healthcare). The purity and the homogeneity of purified activatable anti-EGFR antibodies were analyzed by SDS-PAGE in reducing and non-reducing conditions and size exclusion chromatography using a Superdex 200, 10/300 GL column (GE Healthcare), respectively.

Rate of activatable anti-EGFR antibody cleavage and Kcat/Km determination. Recombinant human uPA and MT-SP1 (R & D Systems; final concentrations of 1.6-100 nM) was incubated with 500 nM (uPA) and 2 μM (MT-SP1) in 50 mM Tris-HCl, pH 7.4, 150 mM NaCl, 0.05% Tween-20, 5 mM calcium chloride, (TBST) for 24 h at 37° C. The reaction was stopped by adding 5 μl of sample to 7 μl of HT Protein Express Sample Buffer (Caliper LifeSciences) and incubating for 10 min at 95° C. Samples were analyzed by capillary electrophoresis (GXII; Caliper LifeSciences) and concentrations of cleaved and uncleaved light chain were determined using LabChip GX software (Caliper LifeSciences). The kcat/Km were determined using the following equation:

$$\frac{kcat}{Km} = -\ln(1 - C)/(t * p)$$

C=relative portion of product converted (cleaved light chain/cleaved+uncleaved light chain), t=time(s) and p=protease concentration (M). The substrate concentration was maintained below the Km and in excess of the protease.

Protease digestion/activation of activatable anti-EGFR antibody. The 3954-1204-C225v4 activatable antibody, also referred to herein as Pb-1204, (100 ug) was incubated with various proteases: uPA (50 nM in PBS, pH 7.2), MT-SP1 (10 nM in PBS, pH 7.2), or legumain (30 ug/ml in 50 mM MES, 250 mM NaCl, pH 6.0) at room temperature for 4 days. For the cell proliferation and the EGFR binding assays, the uPA-cleaved Pb-1204 was purified by protein A agarose affinity chromatography. The cleavage of Pb-1204 was analyzed by SDS PAGE and capillary electrophoresis (LabChip GXII; Caliper Life Sciences).

Cell culture and proliferation assays. H292 human lung cancer cells (American Type Culture Collection) were maintained at 37° C. (5% $CO_2$) in RPMI medium supplemented with 10% fetal bovine serum (FBS). For proliferation assays, the cells were seeded at 3000 cells/well in a 96-well plate under low serum conditions (RPMI+1% FBS). The following day, antibodies or activatable anti-EGFR antibodies were added at the indicated concentrations and cells were incubated for an additional 4 days at 37° C. Cell viability was measured using Cell-Titer Glo (Promega), according to the manufacturer's instructions.

EGFR binding assay. 96-well plates (Nunc) were coated with EGFR-Fc (50 ng/well; R&D Systems) in Hank's Balanced Salt Solution (HBSS pH 7.4, 10 mM Hepes) and blocked with HBSS containing 1% BSA. The plates were incubated with the indicated concentrations of antibody or activatable anti-EGFR antibody in HBSS/1% BSA for 1 h at room temperature. The plates were then incubated with horseradish peroxidase (HRP) conjugated anti-human $F(ab')_2$ (Jackson ImmunoResearch Laboratories) in HBSS for 30 min. and the detection was performed by the addition of 3,3',5,5'-tetramethylbenzidine substrate (1-Step Ultra-TMB, Pierce) followed by an equal volume of 1M hydrochloric acid. Absorbance at 450 nm was then measured and reported as optical density (OD 450 nm).

In some cases, the relative EGFR binding was converted to an IgG concentration using a cetuximab standard curve (1 nM starting concentration, 10 point serial dilutions). The standard curve was fitted on a 4 parameter curve and the results interpolated using the Elx 800 software.

Evaluation of activatable anti-EGFR antibody distribution in vivo by optical imaging. HT29 xenograft tumor bearing mice were injected intraperitoneally with 12.5 mg/kg Alexa Fluor 750 conjugated activatable anti-EGFR antibodies. One hour before imaging the mice were injected intravenously with quenched PEGylated Cy5.5 substrate probes (2 nmol). The mice were imaged 24 h after activatable anti-EGFR antibody injection using an IVIS Spectrum/CT imaging system (Caliper LifeSciences). During the procedure, the mice were kept under gaseous anesthesia (5% isofluorane) at 37° C. Imaging at 750 nm is used to evaluate accumulation levels of the activatable anti-EGFR antibodies (e.g., 3954-1204-C225v4 or 3954-1204-C225v5 as well as the Pb-NSUB construct in which the protease substrate sequence from 3954-1204-C225v4 or 3954-1204-C225v5, respectively, has been replaced with a sequence that is not susceptible to protease cleavage), as distribution of the labeled activatable anti-EGFR antibody constructs at this wavelength is an indication of antibody activation and EGFR receptor binding. Imaging at 680 nm is used to evaluate the level of substrate cleavage by monitoring probe activation kinetics in tumor tissue. Finally, necropsy is used to evaluate biodistribution ex vivo.

Immunofluorescence. Seven days after the activatable anti-EGFR antibody injection the mice were sacrificed, and the tissues samples were excised and cryo-preserved. Samples of HT29 xenograft tumors and liver were sectioned (5 μm) at −20° C. Sections were stained with AlexaFluor488 conjugated donkey, anti-human IgG and counterstained with DAPI antifade mounting medium. The stained sections were imaged using a fluorescence microscope (Olympus IX 81) and an Imaging Software for Life Science Microscopy Cell.

Human IgG ELISA. 96 well maxisorp plates (NUNC) were coated with mouse anti-Human IgG Fc antibody (50 ng/well; Jackson ImmunoResearch) in HBSS (Invitrogen) and blocked with HBSS containing 1% BSA. Samples were added to the wells and incubated for 1 h at room temperature. The plates were then incubated with horseradish peroxidase (HRP) conjugated anti-human $F(ab')_2$ (Jackson ImmunoResearch Laboratories) in HBSS for 30 min. and the detection was performed by the addition of 3,3',5,5'-tetramethylbenzidine substrate (1-Step Ultra-TMB, Pierce) followed by an equal volume of 1M hydrochloric acid. Absorbance at 450 nm was then measured and reported as optical density (OD 450 nm). A standard curve was generated for each plate using cetuximab (1 nM starting concentration, 10 point serial). The standard curve is fitted on a 4 parameter curve and the results interpolated using the Elx 800 software.

Immunoprecipitation and Western Blotting. Tissues samples were homogenized in lysis buffer (HBSS/2% Triton X-100, Halt protease inhibitor cocktail; Thermo Fisher Scientific) using stainless steel beads containing Bullet Blender homogenization tubes (Next Advance) at a ratio of 1 g tumor/tissue per 2 ml lysis buffer. The tissue homogenate was centrifuged at 3000×g and the supernatant was further centrifuged at 20,800×g at 4° C. for 45 minutes. Tissues lysates were immediately incubated with 10 μl Goat anti-human IgG Fc Specific magnetic beads (Bangs Laboratories, Inc.), overnight at 4° C. Beads were washed and then eluted by denaturation in (5 minutes, 95° C.) in LDS Sample Buffer (Invitrogen) containing beta-Mercaptoethanol (Sigma, St. Louis, MO). The samples were electrophoresed, transferred to nitrocellulose, blotted using HRP-conjugated mouse anti-human IgG Fc (Jackson ImmunoResearch). The bands were visualized using the SuperSignal Pico Chemiluminescent Substrate (Thermo Fisher Scientific) and the ImageQuant LAS 4000 (GE Healthcare).

In vivo efficacy studies. In vivo studies, conducted at Jackson Laboratory were reviewed and approved by the Institutional Animal Care and Use Committee (IACUC). In vivo studies conducted at Oncotest GmbH where reviewed approved by the Regierungs-präsidium Freiburg, Germany and conducted according to the guidelines of the German Animal Welfare Act.

In Vivo Xenograft Studies. In one set of xenograft studies at Jackson Laboratory, 6-8 week old female NU/J (JAX #2019) mice were inoculated subcutaneously in the right hind flank with $5\times10^6$ NCI-H292 cells (ATCC) suspended 1:1 with Matrigel™ in serum free media. Clinical observations, body weights and digital caliper tumor volume measurements were made 3× weekly once tumors become measureable. Animals were tumor size rank matched in cohorts (12 mice/group) with average tumor volumes of ~150 $mm^3$-200 $mm^3$ and treatments were started. Animals were treated intravenously weekly for 4 weeks. Tumors were measured with calipers twice a week for the duration of the study. Plasma was collected in $K_2$EDTA from 3 mice per group at 1 h, 8 h, 24 h, 72 h, the blood collection was alternated between mice within a cohort. Four mice per group were euthanized on Day 3 and tumors were collected and snap frozen for analysis.

Another set of xenograft studies, using the LXFA677 xenograft model, was established at Oncotest GmbH from primary patient material after informed consent. Xenografts were subcutaneously grown in athymic NMRI nu/nu mice and randomized after reaching tumor volumes of 100-300 $mm^3$. Mice (12/group) were treated with antibodies once a week intraperitoneally and tumors were measured with calipers twice weekly. Blood was collected in 3 mice per group once weekly and the blood collection was alternated between mice within a cohort. Four mice per group were euthanized on Day 3 and tumors were collected and snap frozen for analysis.

Immunohistochemistry: Samples of xenograft tumors and liver were sectioned (5 μm). Slides were deparaffinized and rehydrated in distilled water followed by retrieval with Citrate Buffer pH 6.0 (Thermo Scientific). Endogenous peroxidase was quenched with 0.3% Hydrogen Peroxide. Sections were blocked with the Avidin/Biotin blocking kit (Vector Laboratories) followed by 3% BSA. The sections were stained with Biotin-conjugated donkey, anti-human IgG (Jackson) antibodies utilizing the ABC Elite Detection kit (Vector Laboratories) and visualized with DAB (Pierce Scientific). The slides were counterstained with Hematoxylin, dehydrated, cleared and cover-slipped. The stained sections were imaged using a bright field scope (Leica DM750) and LAS EZ software (Leica Application Suite).

Pharmacokinetics: Plasma pharmacokinetic parameters were derived from cetuximab or activatable anti-EGFR antibody concentrations using a non-compartment analysis with sparse sampling (Phoenix WinNonlin, v 5.2; Pharsight; Mountain View, CA) with pooling of individual animal concentrations for each group at each time point. Values are reported as population estimates with a standard error of the estimate.

Example 2. Preparation of Activatable Anti-EGFR Antibodies

Figure 2A:
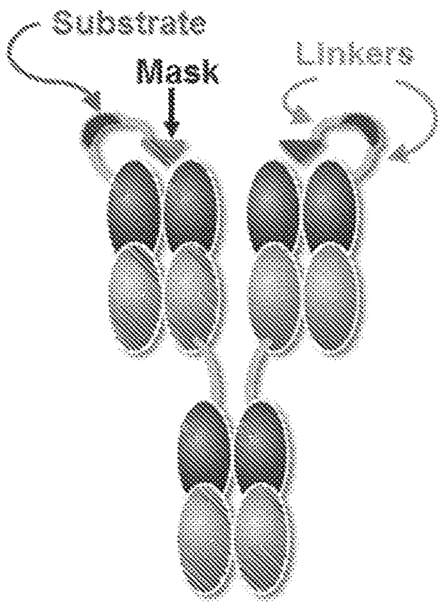
FIG. 2A is a schematic representation of an activatable antibody.
Figure 2B:
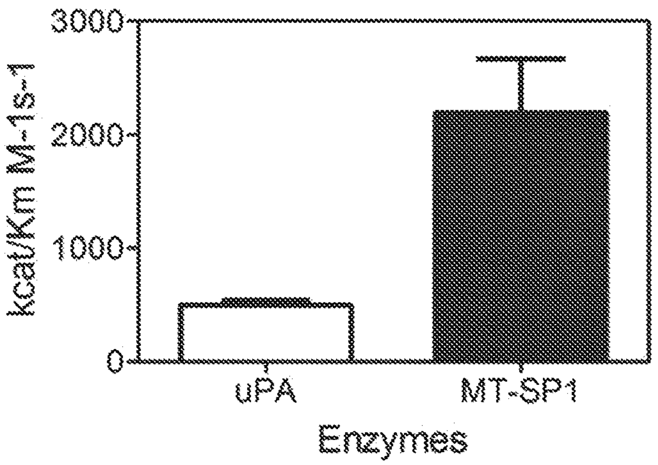
FIGS. 2B-2D are a series of graphs depicting the in vitro characterization of an anti-EGFR activatable antibody referred to herein as “Pb-1204” or 3954-1204-C225v4 activatable antibody.

The activatable anti-EGFR antibodies described herein include an antibody or antigen-binding fragment that is derived from the anti-EGFR antibody cetuximab. Cetuximab is a well characterized therapeutic antibody approved for the treatment of colorectal and head and neck cancer. One cetuximab-based activatable anti-EGFR antibody, referred to herein as Pb-1204, was engineered by adding a 21 amino acid long binding peptide, i.e., the masking moiety, to the N-terminus of the light chain (FIG. 2A). The mask was attached to the antibody through a 26 amino acid long linker carrying an 8 residue long sequence that is an uPA, MT-SP1 or legumain specific substrate sequence. The efficiency, cleavage rate and selectivity of various proteases (uPA, MT-SP1, tissue plasminogen activator (tPA) and/or thrombin) with respect to the substrate within the Pb-1204 activatable antibody (referred to herein as the 1204 substrate or simply 1204) is shown in FIGS. 9A-9D.

Figure 2C:
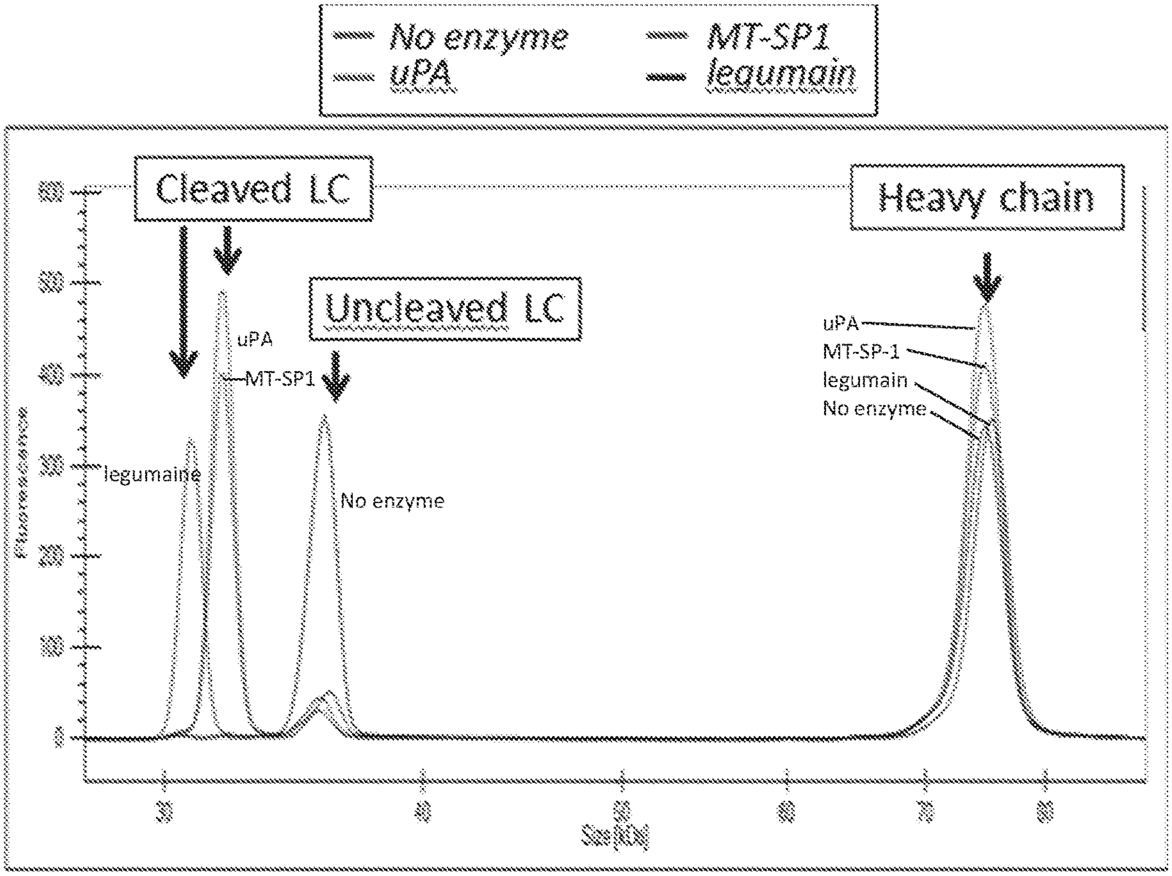
Figure 2D:
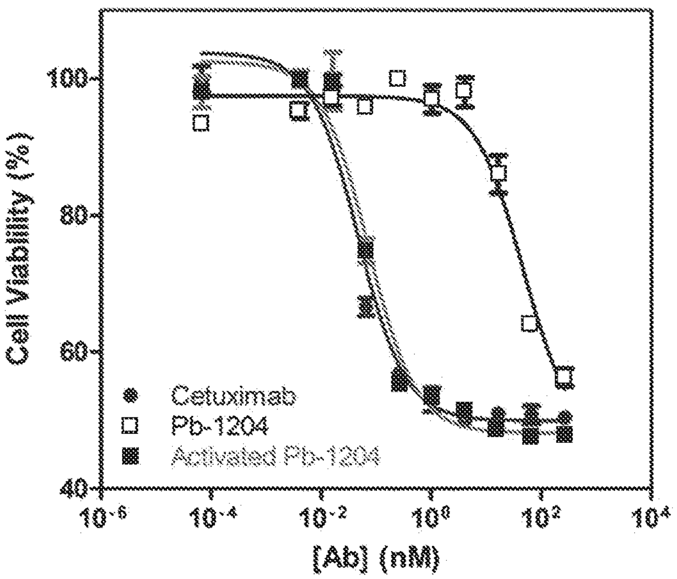
Figure 5A:
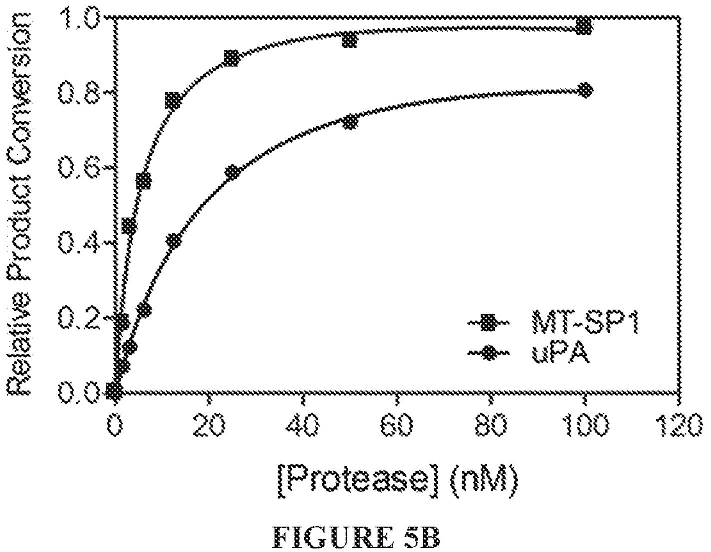
FIGS. 5A-5C are a series of graphs showing further in vitro characterization of activatable anti-EGFR antibodies.
Figure 5B:
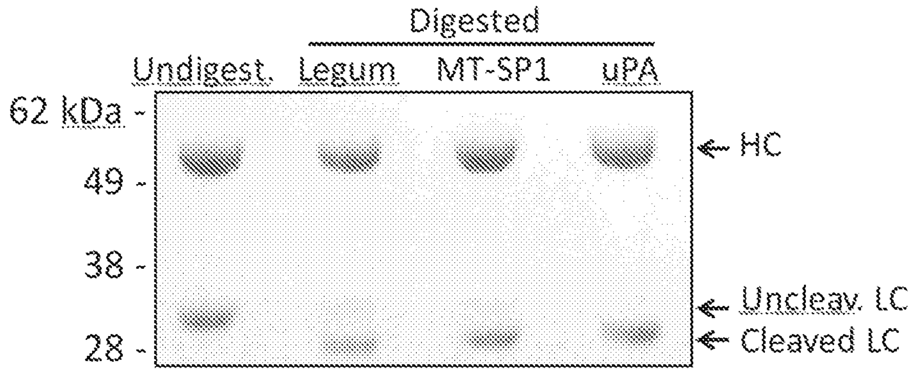

The efficiency and the specificity of cleavage of Pb-1204 by different proteases were evaluated. Pb-1204 was efficiently cleaved by human MT-SP1 (2200 M−1 s−1±470 M−1 s−1) human uPA (530 M−1 s−1±40 M−1 s−1) and legumain. However Pb-1204 was not cleaved by tPA or plasmin, ADAM 9, 10, and 17, kallikrein 5 and 7. Pb-1204 was digested to near completion and analyzed by SDS-PAGE, capillary electrophoresis and N-terminal sequencing (FIGS. 2C and 5B). The N-terminal sequence of the cleaved products demonstrated the predicted cleavage sites for the three proteases. MT-SP1 and uPA cleaved the Pb-1204 substrate sequence at the same P1 site and yielded light chain products of the same molecular weight. The cleavage by legumain yielded a slower migrating light chain that was shorter by 3 amino acids.

Example 3. In Vitro Activity of Activatable Anti-EGFR Antibodies

Figure 5C:
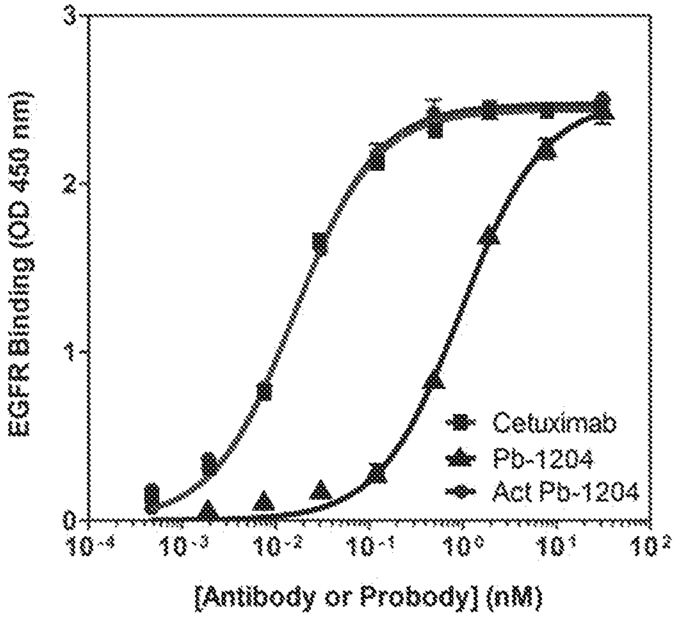

The relative in vitro activity of cetuximab, Pb-1204 and Pb-1204 digested to completion with uPA was evaluated next. The binding of Pb-1204 to EGFR was reduced by 23-fold relative to cetuximab showing an apparent $K_d$ of 0.36 nM compared to 0.02 nM respectively (FIG. 5C). The apparent $K_d$ of the fully activated Pb-1204 and cetuximab were identical (0.02 nM). The inhibitory activity of Pb-204 on H292 cell proliferation was reduced by 990-fold relative to cetuximab ($IC_{50}$ 46.6 nM and 0.05 nM respectively; FIG.

2D). Once activated, Pb-1204 showed an inhibitory activity comparable to cetuximab ($IC_{50}$ 0.07 nM).

Example 4. In Vivo Distribution of Activatable Anti-EGFR Antibodies

Figure 3A:
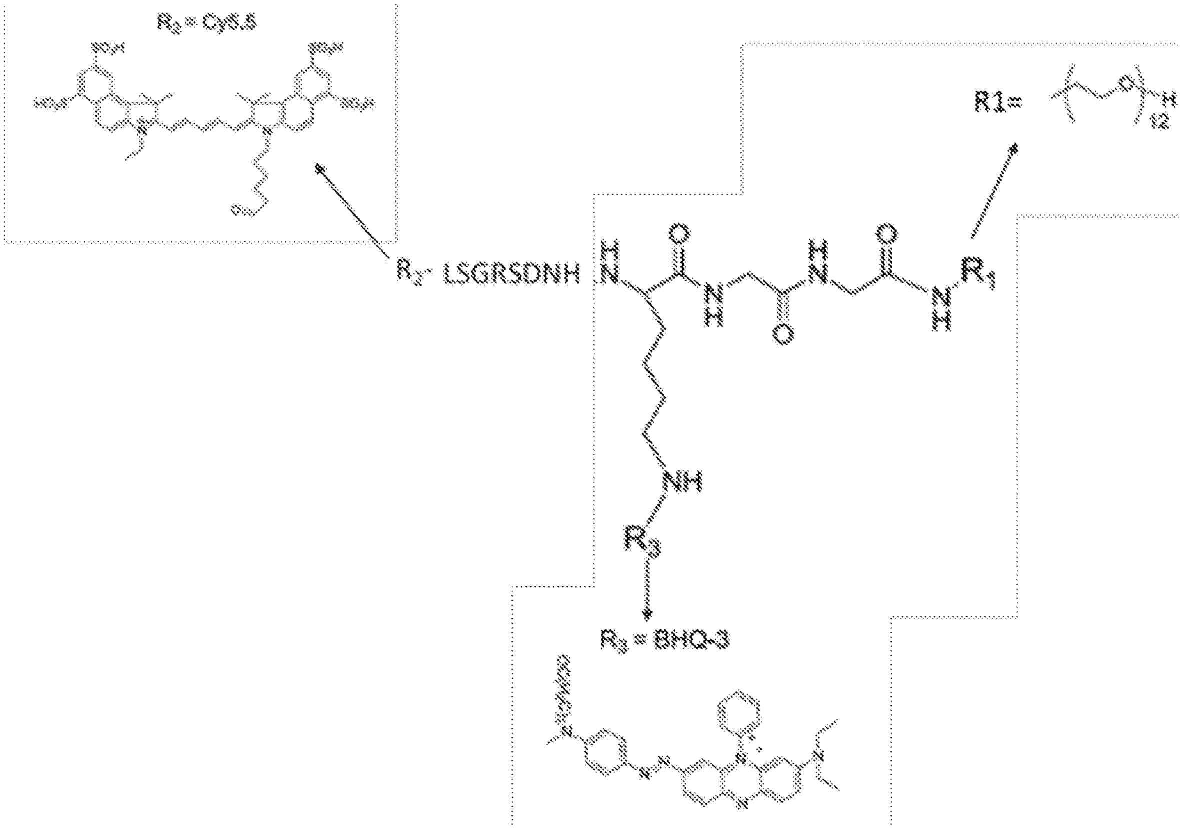
FIG. 3A is a schematic representation of the chemical structure of the near-infrared quenched probe Cy5.5-1204-Q.
Figure 3B:
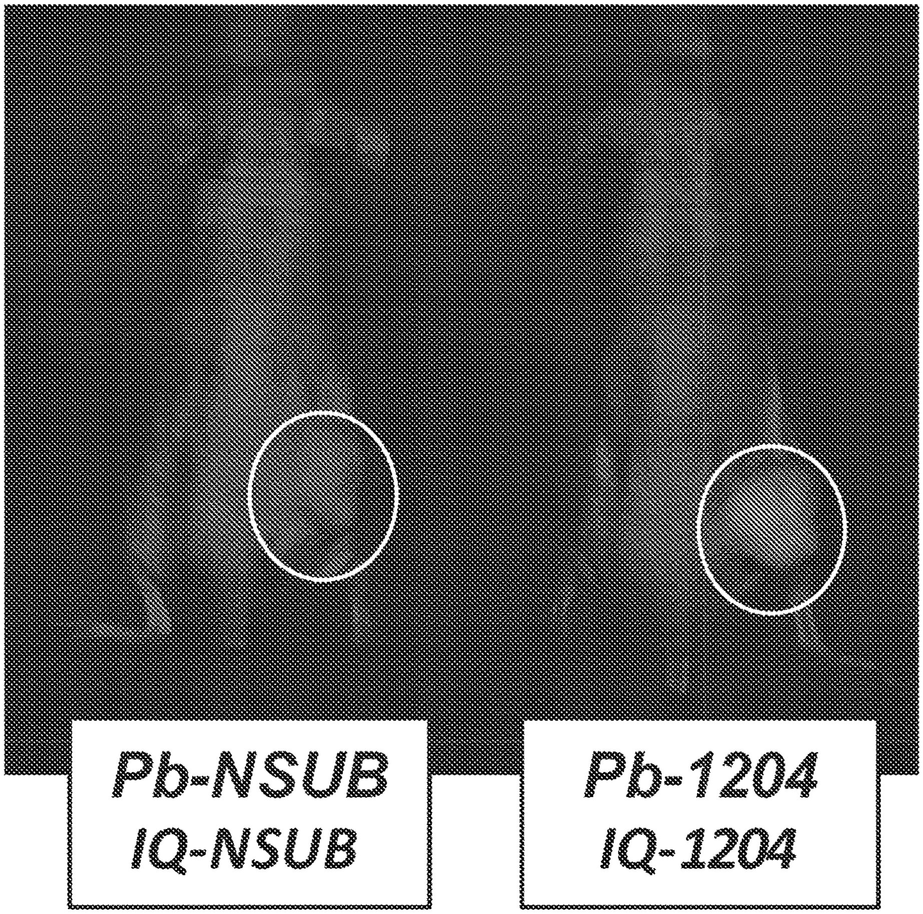
FIGS. 3B-3H are a series of illustrations depicting how the activatable anti-EGFR antibody referred to herein as Pb-1204 accumulates in xenograft tumors.
Figure 3C:
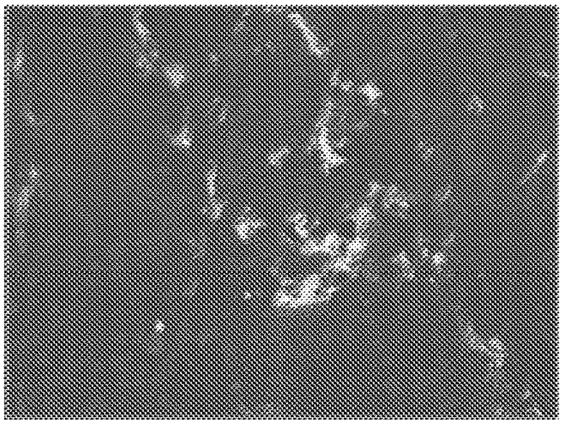
Figure 3D:
Figure 3E:
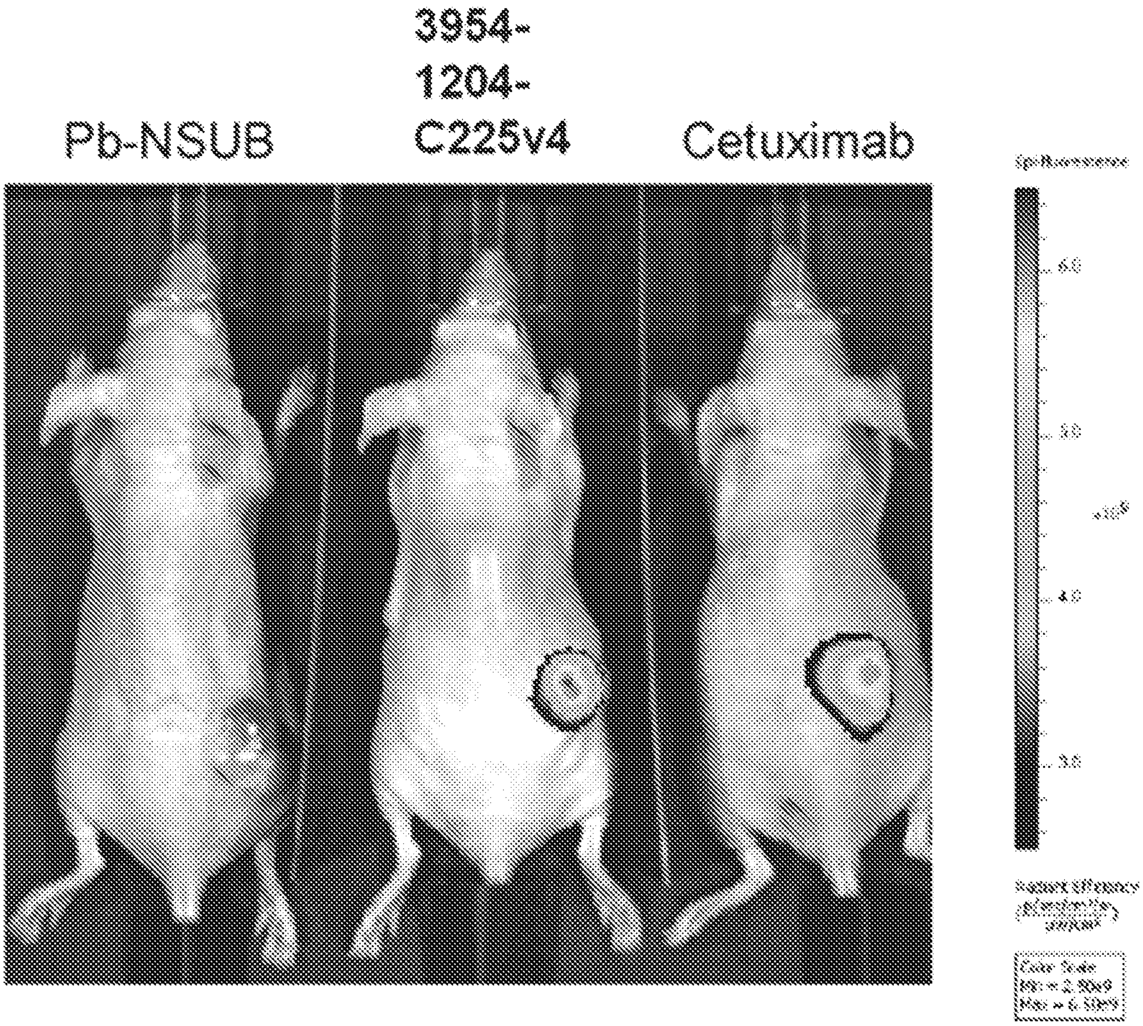
Figure 3F:
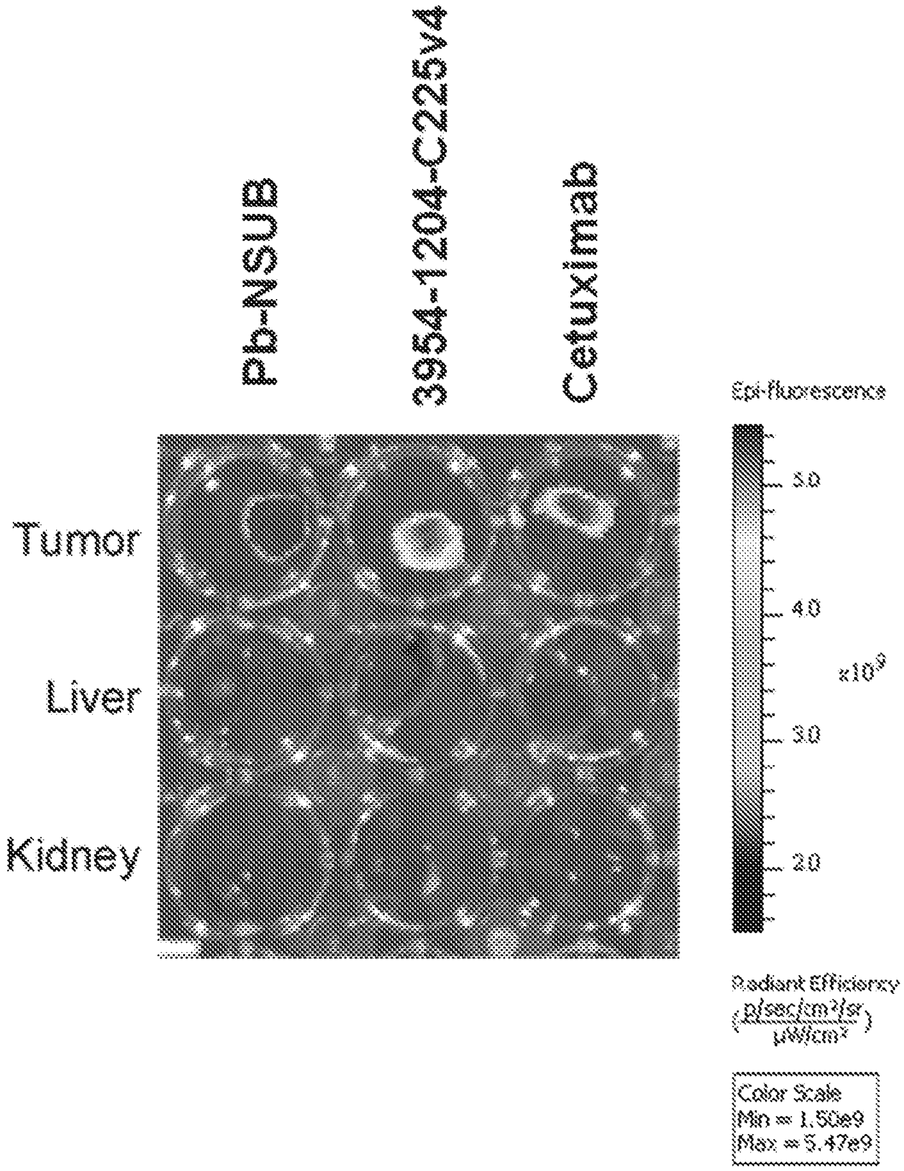
Figure 3G:
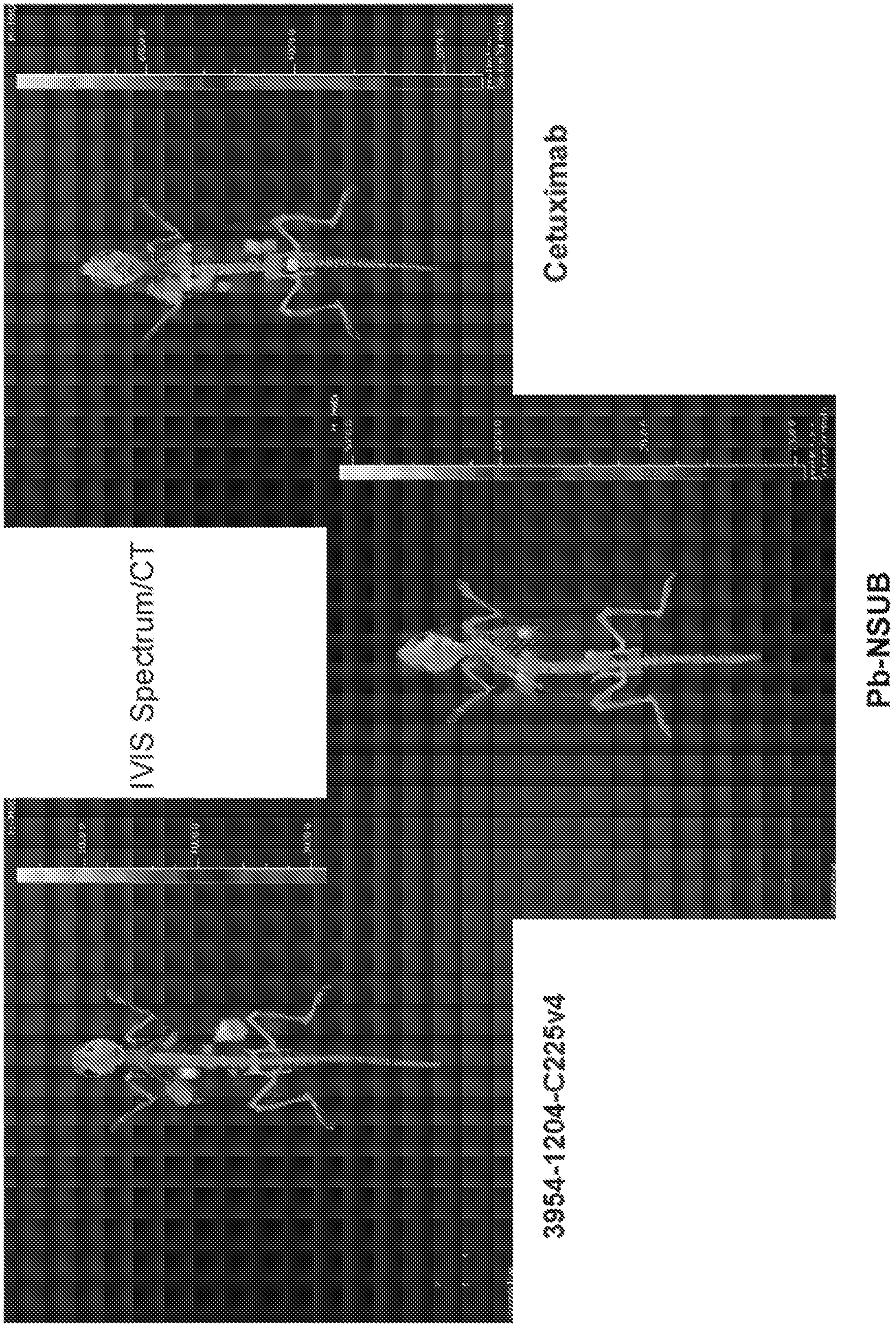
Figure 3H:
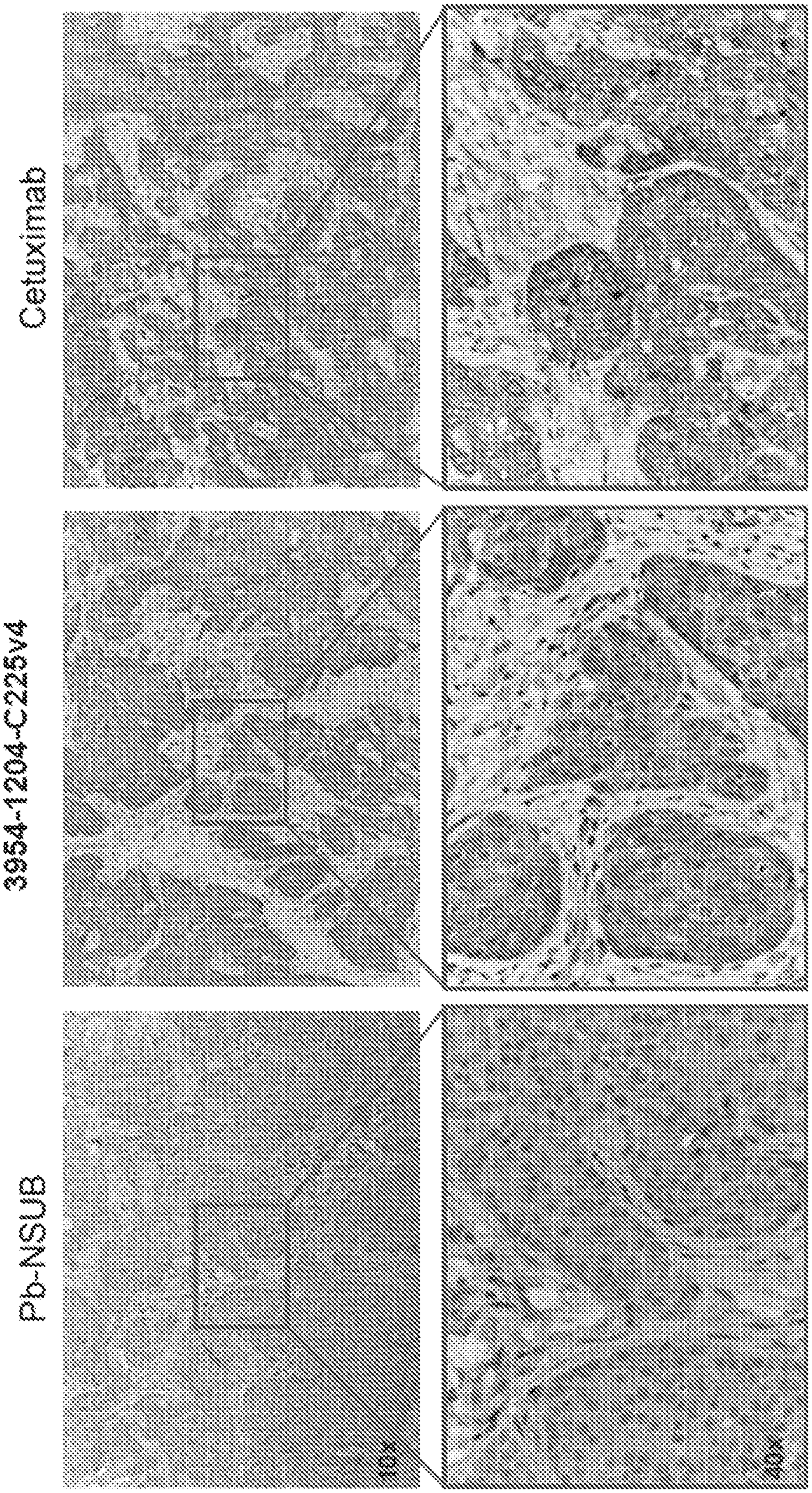
Figure 6A:
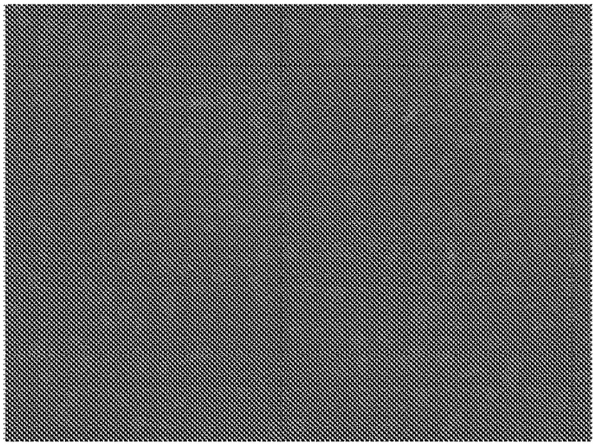
FIGS. 6A and 6B are illustrations depicting how Pb-1204 is not activated in normal liver.
Figure 6B:
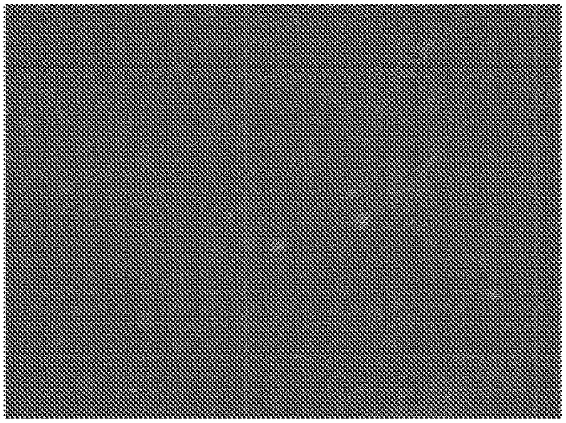

To assess the in vivo distribution of the proteolytic activity susceptible of cleaving Pb-1204, near-infrared fluorescence self-quenched imaging (IQ) probes were used. An IQ probe bearing the substrate sequence of Pb-1204 (IQ-1204; FIG. 3A) and a negative control IQ probe bearing a peptide linker without a substrate sequence (IQ-NSUB) were injected in HT29 tumor bearing mice. The term "NSUB" used herein refers to an amino acid substrate sequence that includes glycine and serine residues, but is not susceptible to protease cleavage. One hour after the injection of IQ-1204, the imaging showed fluorescence restricted to the tumor site (FIG. 3B). The simultaneous imaging of these mice 48 hours after the injection with a fluorescently labeled Pb-1204 demonstrated a fluorescence distribution identical to IQ-1204 and restricted to the tumor. No fluorescence was detected in the animals injected with the IQ-NSUB and fluorescently labeled Pb-NSUB negative controls. Seven days after injection, the localization of the activatable anti-EGFR antibody in tumor and liver samples from treated mice using immunofluorescence staining was evaluated. Tumors of animals injected with Pb-1204 demonstrated membranous fluorescent staining on epithelial cells, whereas no staining was detected in tumors from mice injected with Pb-NSUB (FIGS. 3C and 3D). No staining was detected in liver samples from animals treated with Pb-1204 or Pb-NSUB (FIGS. 6A and 6B). These results indicate that the proteolytic activity associated with the tumor site specifically cleaves the 1204 substrate sequence. The cleavage of the substrate sequence allows the antibody to bind to its target and accumulate at the tumor site.

Example 5. Analysis of Activatable Anti-EGFR Antibodies in Xenograft Models

Figure 4A:
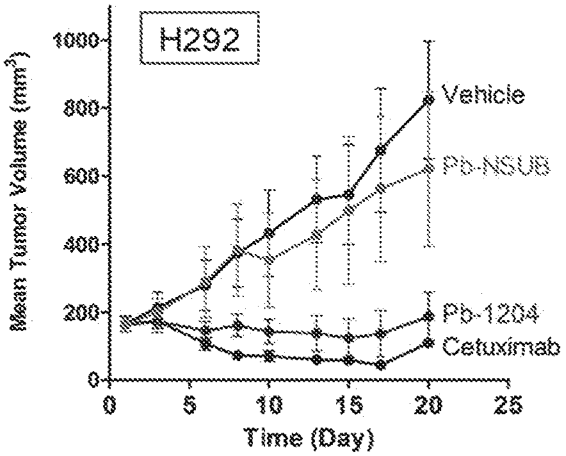
FIGS. 4A-4F are a series of graphs depicting the ability of the activatable anti-EGFR antibody referred to herein as Pb-1204 to inhibit tumor growth in xenograft models.
Figure 4D:
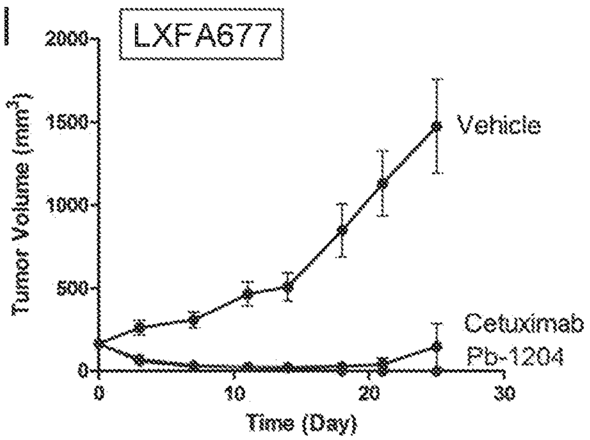
Figure 4B:
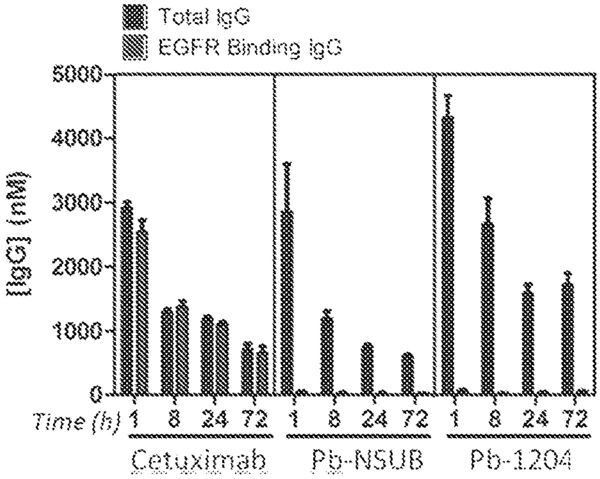
Figure 4E:
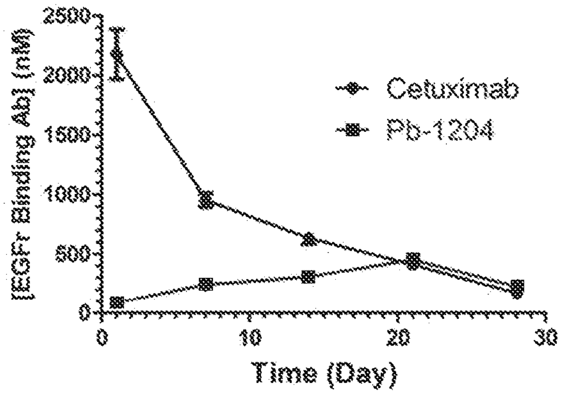
Figure 4C:
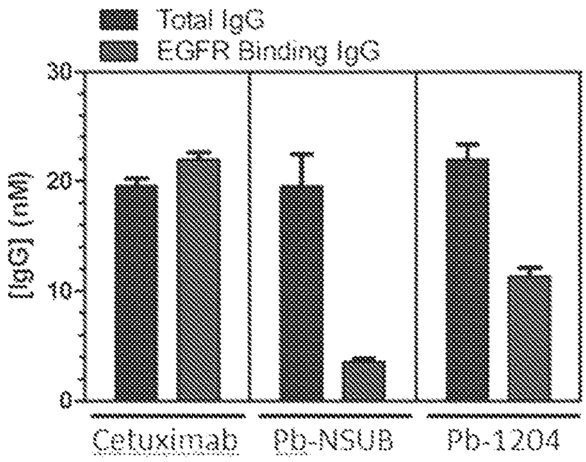
Figure 4F:
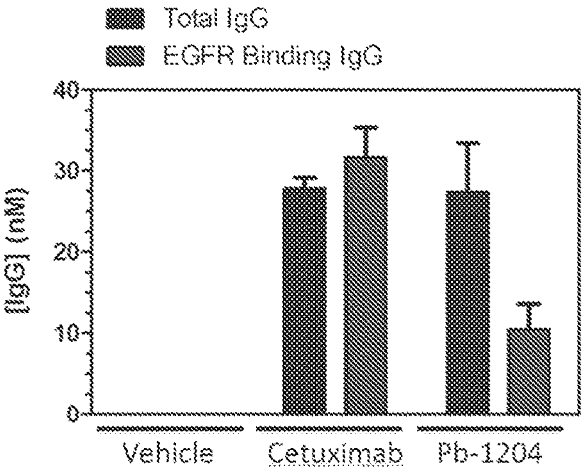

The effect of Pb-1204 on EGFR-dependent tumor growth was investigated using the NSCLC xenograft model H292. Tumor regression was seen in the Pb-1204 treated group and the cetuximab control treated group (FIG. 4A). The mean tumor volume between these treatment groups was not statistically different at study termination (day 20) suggesting that Pb-1204 was as effective as cetuximab. No statistically significant tumor reduction was seen in mice treated with Pb-NSUB control. In a subset of mice (n=4), plasma samples were collected at different times up to 72 hours at which point the mice were sacrificed and the tumors were excised. Despite the circulating concentration of Pb-1204 being higher than the cetuximab and Pb-NSUB concentrations, the resulting EGFR binding activity of Pb-1204 (2.2%+0.2) and Pb-NSUB (3.9%+0.3) was marginal compared to cetuximab (95.6%±3.5; FIG. 4B). The concentrations of Pb-1204, Pb-NSUB and cetuximab found in the tumor were equivalent. The western blot analysis of lysates from these tumors showed that a significant fraction of the Pb-1204 had been activated, whereas the Pb-NSUB remained intact and unactivated. As expected the EGFR binding activity of Pb-1204 (51.6%±0.8) found in the tumors was greater than its activity in plasma or to the binding activity of Pb-NSUB (18.2%±0.3; FIG. 4C).

Figure 7A:
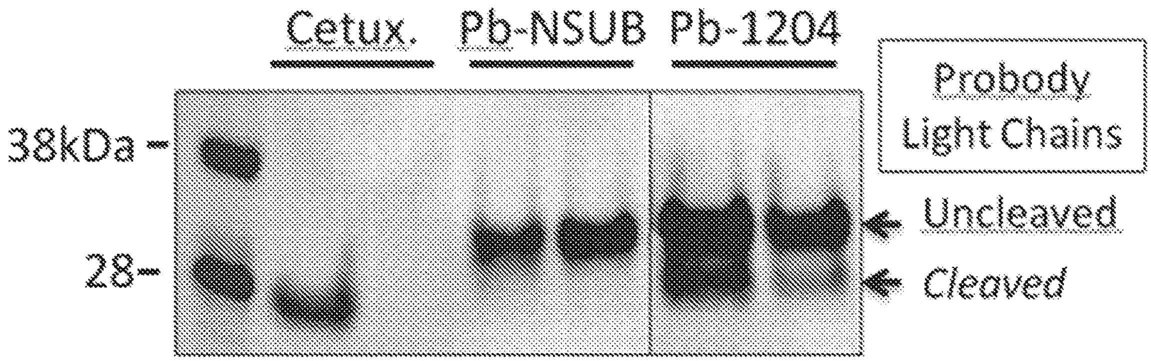
FIGS. 7A and 7B are an illustration and a graph depicting tumor activation and PK of cetuximab and Pb-1204 in tumor bearing mice.
Figure 7B:
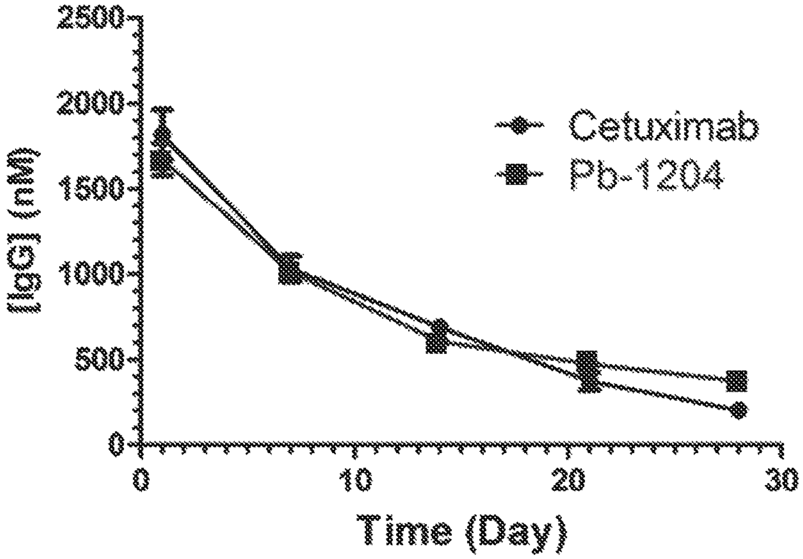

Next, the activity of a single dose of Pb-1204 relative to cetuximab was determined in a patient derived non-small cell lung cancer tumor xenograft model (LXFA677). The activatable anti-EGFR antibody and the antibody were equally efficacious at inhibiting the tumor growth. At day 21, cetuximab had inhibited tumor growth by 96% and Pb-1204 by 100% (FIG. 4D). The plasma concentrations of cetuximab and Pb-1204 were equivalent throughout the study (FIG. 7B) with identical exposures (3331 μg/ml×day). The concentration EGFR binding activity in plasma was equivalent to the concentration of the antibody for cetuximab. However, for Pb-1204, the concentration of the EGFR binding activity was greatly diminished compared to the total concentration of circulating activatable anti-EGFR antibody. The exposure (day 1-28) for the EGFR binding activity of the Pb-1204 (1214 μg/ml×day) represented 36% of the exposure for the total activatable anti-EGFR antibody circulating concentration. Seventy two hours after treatment, the tumors from a subset of mice (n=4) were excised and evaluated for activatable anti-EGFR antibody and antibody concentration and activity. The average concentration of Pb-1204 in the tumor was equivalent to the concentration of cetuximab. A considerable fraction (35±4%) of the activatable anti-EGFR antibody found in the tumors demonstrated EGFR binding activity.

In summary, through the development of two bacterial display screening platforms, an inhibitory binding peptide for cetuximab, i.e., a mask, and a novel peptide substrate for the proteases MT-SP1, uPA and legumain was identified. The parental antibody was modified to link the inhibitory peptide to the N-terminus of the light chain trough a flexible peptide linker bearing the novel peptide substrate. This activatable anti-EGFR antibody was named Pb-1204. The in vitro characterization of Pb-1204 showed that the masking peptide considerably inhibited the activity of the activatable anti-EGFR antibody compared to cetuximab. The substrate containing linker allows for specific activation of the activatable anti-EGFR antibody by MT-SP1, uPA and legumain, and once activated, the activatable anti-EGFR antibody demonstrated an activity equal to cetuximab. In vivo, Pd-1204 remained stable in circulation and in normal tissues but was efficiently activated in xenograft tumors. The specific tumor activation of Pb-1204 led to an anti-tumor efficacy that was equivalent to cetuximab.

Thus, the activatable anti-EGFR antibodies described herein are useful in improving the therapeutic window of a majority of antibody therapeutics demonstrating target mediated toxicity. In addition, the use of the activatable anti-EGFR antibody expands the cancer target landscape by allowing the development of cancer therapeutics directed toward targets that cannot be considered with traditional antibodies due to associated toxicities.

Figure 12:
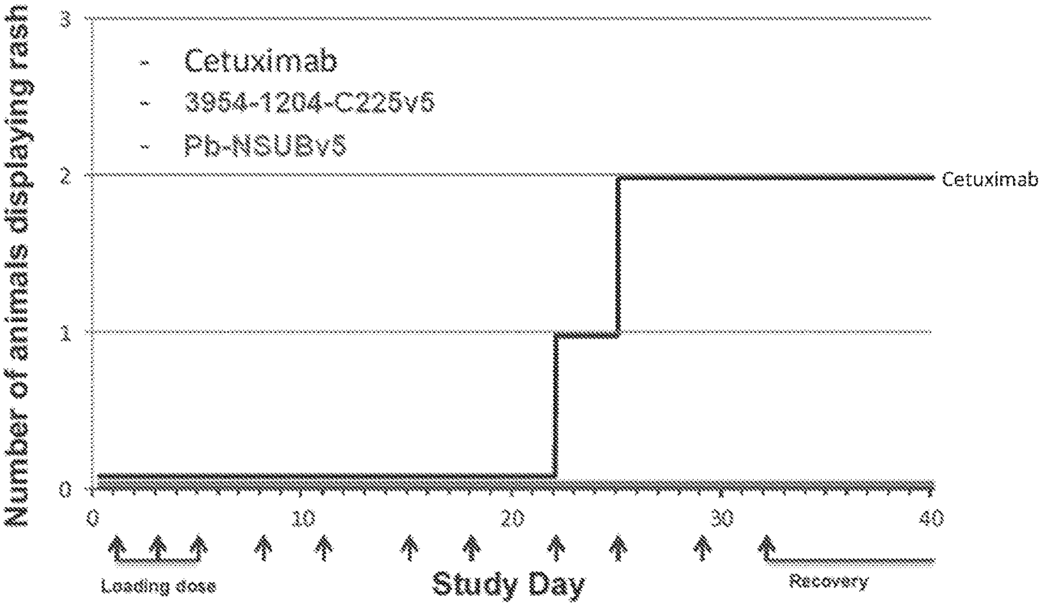
FIG. 12 is a graph depicting the number of non-human primates displaying a skin rash following administration with cetuximab, Pb-NSUBv5 (i.e., 3954-NSUB-C225v5) or 3954-1204-C225v5.
Figure 13A:
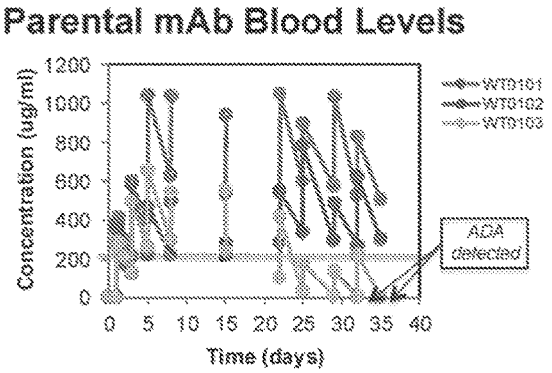
FIGS. 13A-13D are a series of graphs comparing the level of cetuximab and 3954-1204-C225v5 detected in the blood of the cynomolgus monkeys that received 25 mg/kg weekly dosing after the initial 40 mg/kg loading dose.
Figure 13B:
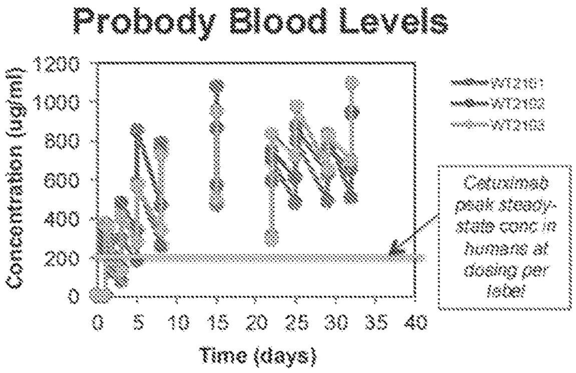
Figure 13C:
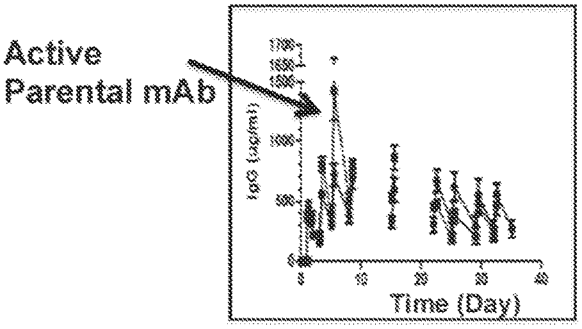
Figure 13D:
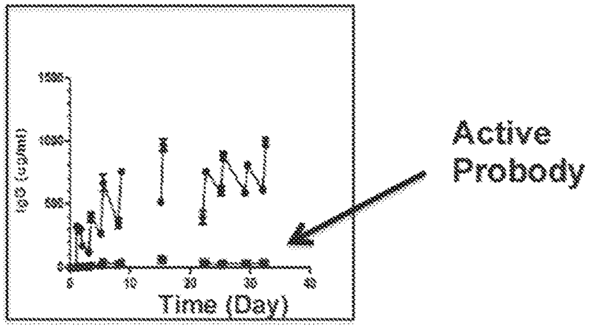

Example 6. Analysis of Activatable Anti-EGFR Antibodies in Non-Human Primate Models Among the toxicities seen in humans and non-human primates administered cetuximab is skin rash, including papulopustular rash of face and upper trunk, and dry and itchy skin. In the studies described herein, the activatable anti-EGFR antibody 3954-1204-C225v5 was evaluated using a non-human primate animal model. Briefly, three groups of 3 female cynomolgus monkeys were dosed intravenously (IV) with cetuximab (i.e., unmodified cetuximab), 3954-1204-C225v5, or Pb-NSUB (i.e., 3954-NSUB-C225v5, an activatable anti-EGFR antibody that includes the NSUB sequence that is not susceptible to protease cleavage), respectively. A 40 mg/kg loading dose was administered (three 2-hour infusions spread over 5 days), followed by a 25 mg/kg dose that was administered weekly (two 2-hour infusions per week). The animals were dosed over a 5-week period (last dose was administered on day 32), followed by a 4-week treatment-free recovery phase. All animals examined daily for skin rash. All animals were also subject to clinical chemistry and hematology analysis as well as TK and immunogenicity. As shown in FIG. 12 and Table 4, the animals that were administered the activatable anti-EGFR antibody 3954-1204-C225v5 exhibited no detectable rash as compared to those that were administered cetuximab. In addition, the animals that were administered the activatable anti-EGFR antibody 3954-1204-C225v5 exhibited reduced dermatological toxicity as compared to those that were administered cetuximab.

TABLE 4

Summary of Dermatological Toxicity Results Observed in Non-Human Primates

| 25 mg/kg Groups | Animal No. | Study day 22 | 25 | 27 | 29 | 32 | 35 | 40 |
|---|---|---|---|---|---|---|---|---|
| Cetuximab | WT0101 | 1 | 1 | 1 | 2 | 2 | 2 | 2 |
| | WT0102 (a) | 0 | 0-1 | 0 | 0-1 | 0-1 | 0-1 | 0 |
| | WT0103 | 1 | 1 | 1 | 2 | 2 | 2 | 1 |
| Pb-NSUB | WT1101 | 0 | 0 | 0 | 0 | 0 | 0 | 0 |
| | WT1102 | 0 | 0 | 0 | 0 | 0 | 0 | 0 |
| | WT1103 | 0 | 0 | 0 | 0 | 0 | 0 | 0 |
| 3954-1204-C225v4 | WT2101 | 0 | 0 | 0 | 0 | 0 | 0 | 0 |
| | WT2102 | 0 | 0 | 0 | 0 | 0 | 0 | 0 |
| | WT2103 | 0 | 0 | 0 | 0 | 0 | 0 | 0 |

0 = No erythema
1 = Slight erythema
2 = Well-defined erythema
3 = Moderate of severe erythema
4 = Severe erythema of slight eschar formation
(a) = The "redness" noted on this animal was not typical of the "rash" noted in the other two animals.

A comparison of the level of cetuximab and 3954-1204-C225v5 detected in the blood of the cynomolgus monkeys that received 25 mg/kg weekly dosing after the initial 40 mg/kg loading dose is shown in FIGS. 13A-13D.

IHC analysis of human IgG in the skin of the cynomolgus monkeys indicated significant binding of cetuximab in skin but no detectable binding of anti-EGFR activatable antibody 3954-1204-C225v5 in skin.

Figure 19:
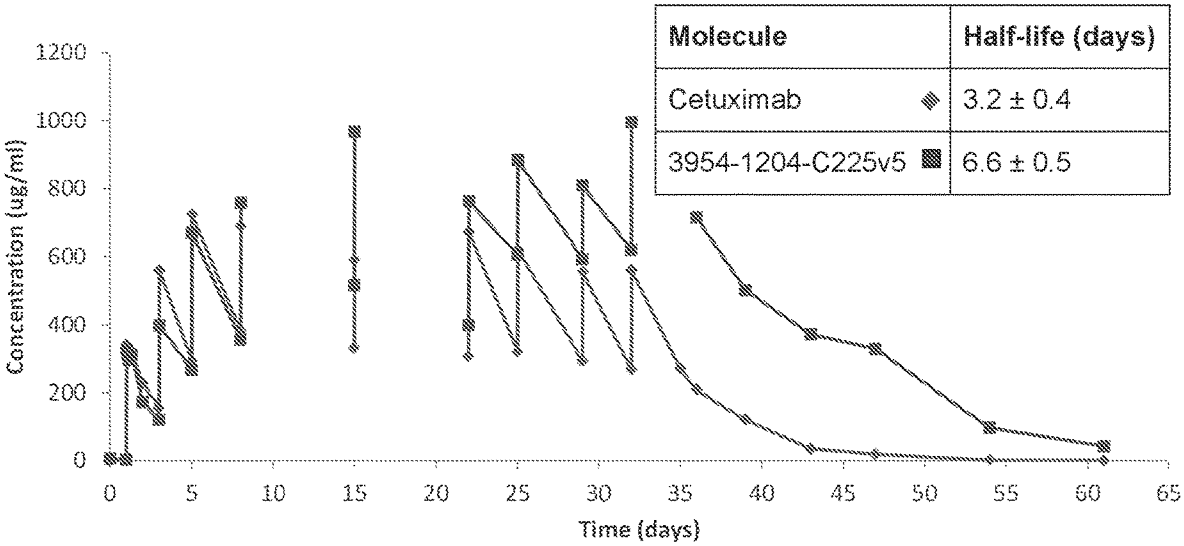
FIG. 19 is a graph depicting the half-life of the anti-EGFR activatable antibody 3954-1204-C225v5 as compared to the half-life of cetuximab.

A pharmacokinetic study comparing serum concentrations over time indicated that the half-life of anti-EGFR activatable antibody 3954-1204-C225v5 was 6.6±0.5 days while the half-life of cetuximab was 3.2±0.4 days. An exemplary study showing the half-life of the anti-EGFR activatable antibody 3954-1204-C225v5 as compared to the half-life of cetuximab is shown in FIG. 19. The half-life of cetuximab was similar to previously reported values. The pharmacokinetics of the anti-EGFR activatable antibody 3954-1204-C225v5 is consistent with lack of systemic antigen-mediated clearance (EGFR in normal tissues).

Example 7. Imaging and Immunohistochemistry Staining of Tumor Tissues with A11 Active Site Antibodies The studies described herein were designed to demonstrate that a target protease of the activatable anti-EGFR antibodies described herein, specifically the MT-SP1 protease, is active in tumor tissue.

Figure 14A:
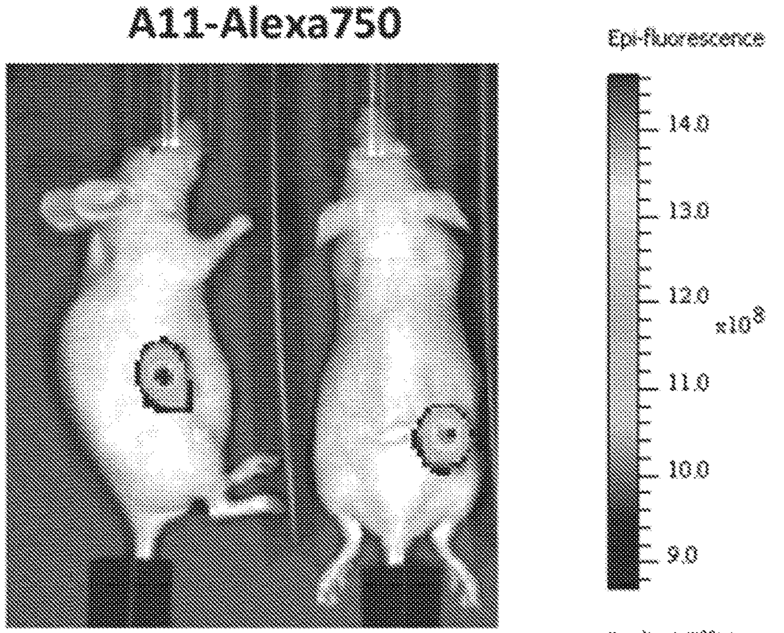
FIGS. 14A-14C are a series of photographs of fluorescent imaging in H292 xenograft tumors with an antibody that specifically recognizes the active site of MT-SP1 (antibody A11).
Figure 14B:
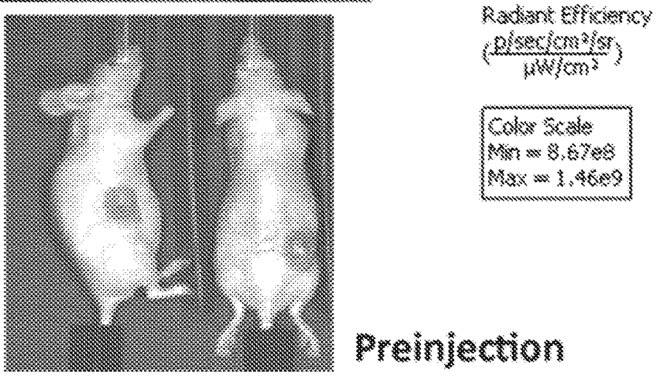
Figure 14C:
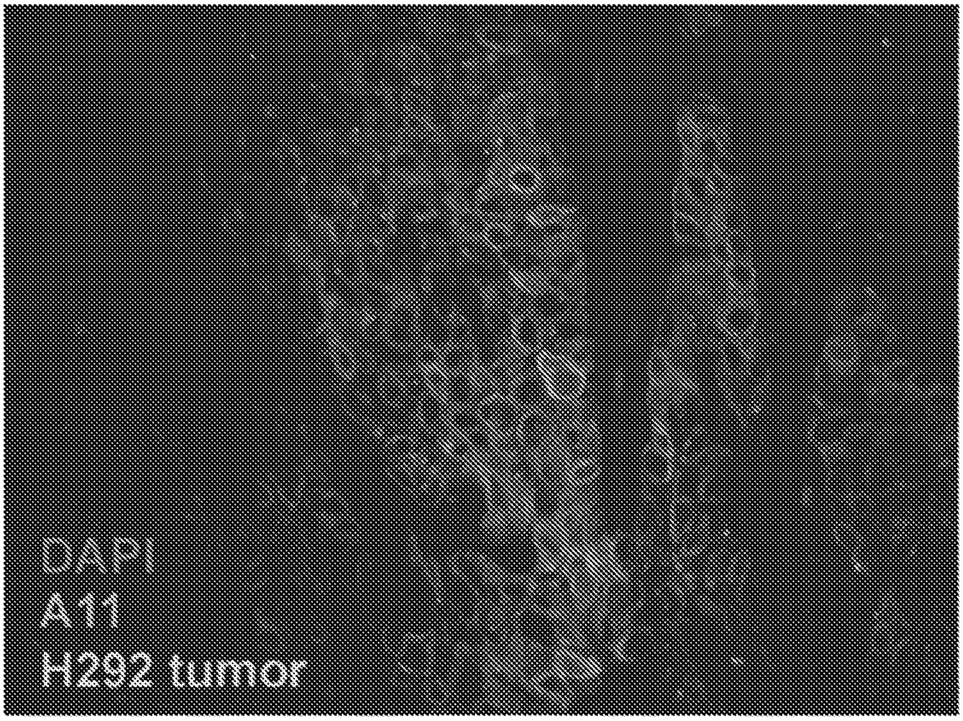

As shown in FIGS. 14A-14C, in vivo imaging and immunohistochemistry (IHC) staining of tumor tissues with A11 active site antibodies (Darragh et al., "Tumor detection by imaging proteolytic activity." Cancer Res. 70 (2010): 1505-1512) confirmed the presence of active MT-SP1 in the H292 xenograft model. A11 is an antibody that specifically binds to the active site of the MT-SP1 protease, also known as matriptase.

Example 8. In Situ Imaging of Anti-EGFR Activatable Antibodies

The present Example describes the use of in situ imaging of the activation and binding of an anti-EGFR activatable antibody of the disclosure. The results indicate that anti-EGFR activatable antibodies of the disclosure can be activated by proteases expressed by a tissue and bind EGFR targets on that tissue.

Figure 15:
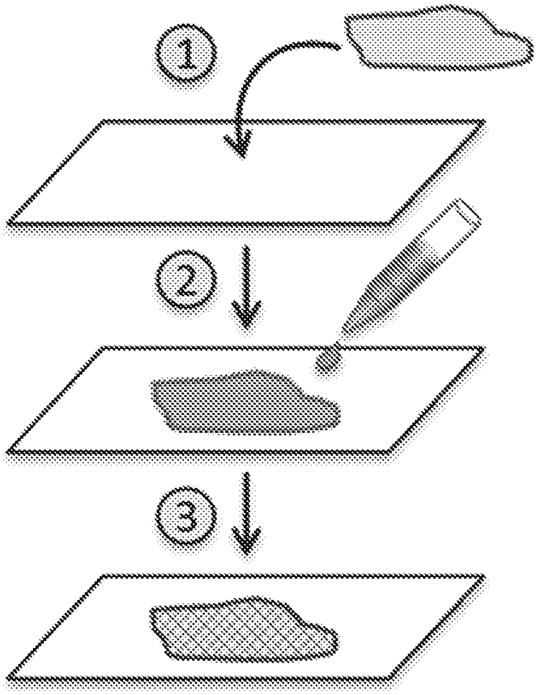
FIG. 15 is a schematic overview of in situ imaging of an activatable antibody: 1. A tissue section is laid over the slide. 2. The slide is covered with solution containing labeled activatable antibody and incubated. 3. After extensive washing, binding of activated antibody is visualized.

In situ imaging of activatable antibodies represents a unique approach to characterize protease activity in cells and tissues. This technology enables validation of activatable antibody activation and binding to a target in histological sections of cells and tissues expressing proteases capable of cleaving the activatable antibody. A schematic of such an in situ approach is presented in FIG. 15.

In situ imaging of the activation and binding of an anti-EGFR activatable antibody (also referred to herein as in situ imaging) by a cell or tissue capable of cleaving the activatable antibody at a site co-localized with the target recognized by the activated antibody was conducted as follows: Frozen tissue sections were laid over glass slides. A solution containing labeled anti-EGFR activatable antibodies (labeled, e.g., with a fluorescent tag) was applied on the tissue and incubated, e.g., for 1 hour at room temperature (about 22-24° C.) in an incubation buffer of 50 mM Tris-HCl buffer pH 7.4, containing 150 mM NaCl, 100 μM $ZnCl_2$, 5 mM $CaCl_2$) and 0.05% Tween 20; activatable antibody at a concentration of about 1 μg/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 μg/ml to about 10 μg/ml). The tissue was then extensively washed to remove non-bound material and detectable label was measured. For example, when a fluorescent tag was used, the tissue was submitted to fluorescent microscopy. Detection of activated antibody on the tissue indicated that the tissue expressed proteases that cleaved the activatable antibody and also expressed EGFR targets to which the activated antibody bound.

Figure 16:
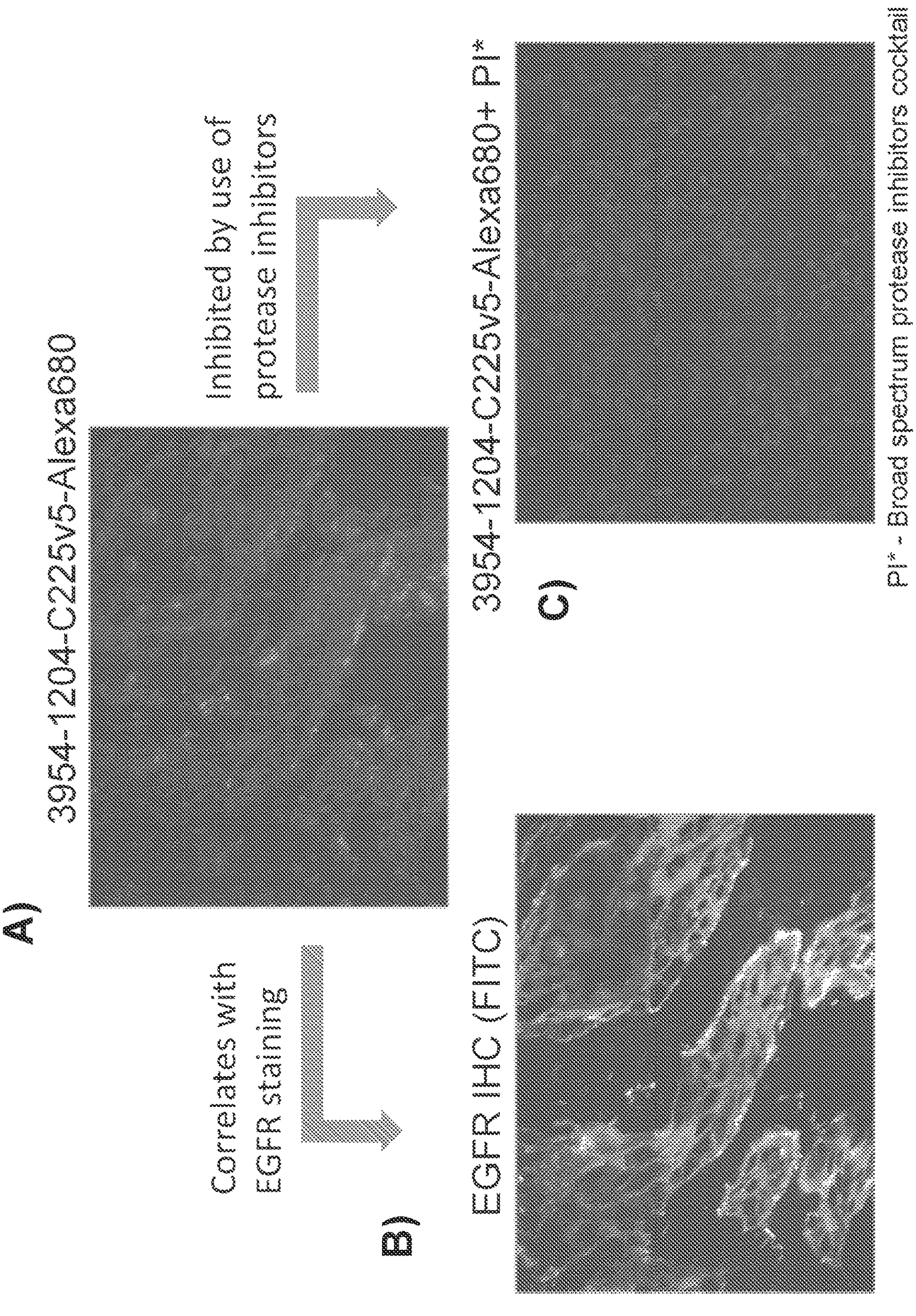
FIG. 16 is a series of photographs showing the ability of anti-EGFR activatable antibody 3954-1204-C225v5 to be activated and to bind frozen human cancer tissues using in situ imaging. The red fluorescent tissue image in FIG. 16, panel A demonstrates binding of C225v5 antibody activated by tissue-derived proteolytic cleavage of the anti-EGFR activatable antibody. The identical pattern of tissue staining was detected by exposing a commercially available anti-EGFR antibody to the tissue, as shown in FIG. 16, panel B.

The ability of anti-EGFR activatable antibody 3954-1204-C225v5 to be activated and to bind frozen human lung cancer tissue was evaluated using in situ imaging. The activatable antibody was labeled with Alexa Fluor 680 (Invitrogen) to produce labeled activatable antibody 3954-1204-C225v5-AF680. The labeled activatable antibody was incubated with a frozen human lung cancer tissue sample as described above. The results are shown in FIG. 16, panel A. The red fluorescent tissue image demonstrates binding of C225v5 antibody activated by tissue-derived proteolytic cleavage of the anti-EGFR activatable antibody. The identical pattern of tissue staining was detected by exposing an EGFR antibody (monoclonal rabbit anti-EGFR antibody, Cell Signaling) to the tissue, as shown in FIG. 16, panel B. The fluorescent signal shown in panel A was inhibited by pre-treatment of the tissue with a 1:100 dilution of broad spectrum inhibitor cocktail set III (539134, EMD Millipore, Billerica, MA) and 50 mM EDTA, as shown in FIG. 16, panel C. Blue staining represents DAPI nuclear staining.

FIG. 17 demonstrates that 3954-1204-C225v5 is activatable in a wide range of human tumor samples. Column 2 indicates the expression level of EGFR receptor, as detected by an EGFR antibody (monoclonal rabbit anti-EGFR antibody, Cell Signaling), for the various human cancer tissue samples. Column 3 indicates the amount of active matriptase (MT-SP1), as detected by antibody A11, in the various human cancer tissue samples. Columns 4 and 5 represent an evaluation of in situ activation and binding of the EGFR activatable antibody (col. 5) as compared to cetuximab (Cetux) tissue staining (col. 4). The staining that measures the amount of EGFR, A11 and cetuximab antibodies binding to the tissue sample was scored from 0 to 3+: 0, no staining; 1+ (i.e., "+"), weak staining; 2+ (i.e., "++"), moderate staining; and 3+ (i.e., "+++"), strong staining. The activatable antibody in situ imaging staining scoring is based on comparison with cetuximab antibody staining and defined as follows: 0, no staining; 1+ (i.e., "+"), weak staining as compared to parental antibody; 2+ (i.e., "++"), moderate staining as compared to parental antibody; and 3+ (i.e., "+++"), analogous staining to parental antibody. As shown in FIG. 17, high levels of active matriptase have been observed in 8 of 9 samples from colorectal cancer (CRC) tumors, and high levels of active matriptase have been observed in samples from 5 of 10 lung cancer (NSCLC) tumors. No active matriptase was observed in samples from adjacent healthy lung tissue.

These data suggest the utility of in situ imaging in methods of effectively and efficiently identifying or otherwise refining a patient population suitable for treatment with an anti-EGFR activatable antibody of the disclosure, such as activatable antibody 3954-1204-C225v5. For example, patients that test positive for both the target (e.g., EGFR) and the protease that cleaves the substrate in the cleavable moiety (CM) of the anti-EGFR activatable antibody (e.g., MT-SP1) using these in situ imaging techniques could be identified as suitable candidates for treatment with the anti-EGFR activatable antibody being tested. Likewise, patients that test negative for either or both of the target (e.g., EGFR) and the protease that cleaves the substrate in the CM (e.g., MT-SP1) using these in situ imaging techniques are identified as suitable candidates for another form of therapy (i.e., not suitable for treatment with the anti-EGFR activatable antibody being tested). In some embodiments, such patients can be tested with other anti-EGFR activatable antibodies until a suitable anti-EGFR activatable antibody for treatment is identified (e.g., an anti-EGFR activatable antibody comprising a CM that is cleaved by the patient at the site of disease).

Example 9. Activatable Antibodies Conjugated to an Agent

The present Example demonstrates the ability of an activatable antibody-agent conjugate of the disclosure to inhibit tumor growth.

Activatable antibody 3954-1204-C225v5 was conjugated to monomethyl auristatin E (MMAE), a synthetic antimitotic tubulin polymerization inhibitor via a Val-Cit-based linker (K-lock C5-vc-PAB; Concortis Biosystems Corp., San Diego, CA), to generate activatable antibody-agent conjugate 3954-1204-C225v5-MMAE. The in vivo efficacy of 3954-1204-C225v5-MMAE relative to 3954-1204-C225v5 and to cetuximab was tested using the H292 lung cancer cell line xenograft mouse model. The H292 xenograft model was established by inoculating 6-8 week old female NU/J (JAX #2019) mice subcutaneously in the right hind flank with $5\times10^6$ NCI-H292 cells (ATCC) suspended 1:1 with Matrigel™ in serum-free media. Tumor volume measurements were made 3 times (3×) weekly once tumors became measureable. Animals were tumor-size rank-matched in cohorts (8 mice/group) with average tumor volumes of ~150 $mm^3$-200 $mm^3$, and treatments were administered to the groups 1 time on day 0 as follows: (a) 12.5 mg/kg 3954-1204-C225v5-MMAE, applied intravenously; (b) 2.5 mg/kg 3954-1204-C225v5-MMAE, applied intravenously; (c) 12.5 mg/kg rituxan-MMAE (i.e., rituximab MMAE; rituximab is available from Genentech, So. San Francisco, CA), applied intravenously; (d) 12.5 mg/kg 3954-1204-C225v5, applied intraperitoneally; (e) 12.5 mg/kg cetuximab, applied intraperitoneally; or (f) 12.5 mg/kg IVIg, applied intraperitoneally. Tumors were measured with calipers twice weekly for the duration of the study.

Figure 18:
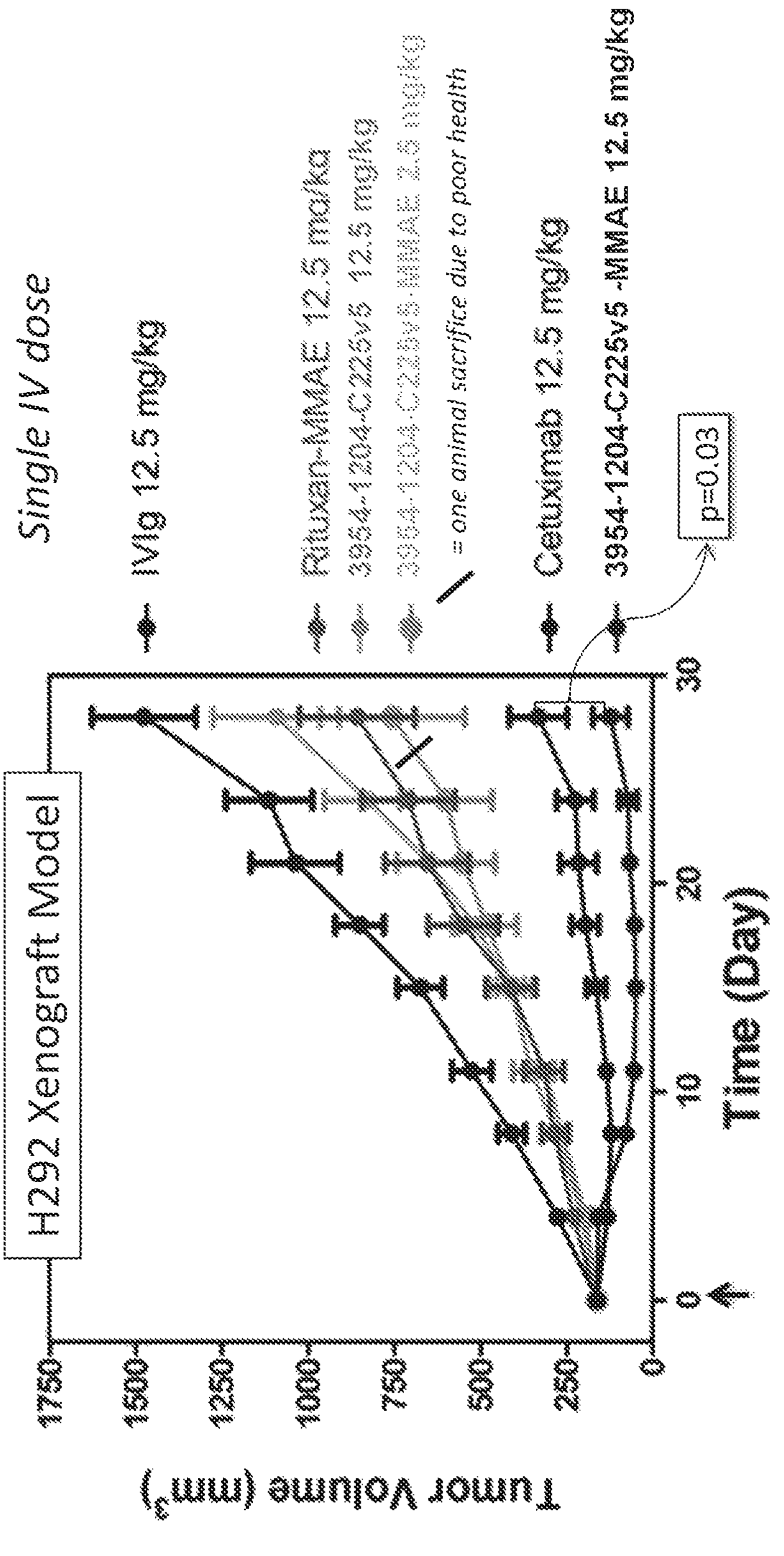
FIG. 18 is a graph depicting the ability of the anti-EGFR activatable antibody-agent conjugate 3954-1204-C225v5-MMAE to inhibit tumor growth.

As shown in FIG. 18, a single injection of 12.5 mg/kg activatable antibody-agent conjugate 3954-1204-C225v5-MMAE demonstrated significant efficacy compared to 12.5 mg/kg IVIg (92% tumor reduction; p=0.0000003), as did a single injection of 12.5 mg/kg cetuximab (78% tumor reduction; p=0.000006) 28 days after administration. The efficacy of 3954-1204-C225v5-MMAE was significantly higher than that of cetuximab at this dose (p=0.03) at day 28. A reduced efficacy was recorded for a lower dose (2.5 mg/kg) of 3954-1204-C225v5-MMAE (p=0.007) and as well as for a dose of 12.5 mg/kg rituxan-MMAE (p=0.008) at day 28. No statistically significant efficacy was observed for activatable antibody 3954-1204-C225v5 at 12.5 mg/kg (p=0.06 at day 28).

An additional dose fractionation study in the same H292 xenograft tumor model was run to compare the activity of cetuximab, activatable antibody 3954-1204-C225v5-MMAE administered at a single dose of 12.5 mg/kg or administered twice weekly (at Days 0, 3, 7, 10 and 14) doses of 2.5 mg/kg each for a total of 5 doses (total of 12.5 mg/kg activatable antibody administered over the study). This dose fractionation study used the same control (12.5 mg/kg IVIg) and methods described above for the H292 xenograft model, EGFR binding assay, and cell culture and proliferation assays. In this dose fractionation study, the activatable antibody 3954-1204-C225v5-MMAE was well tolerated, as evidenced by the lack of weight loss in treated mice. A single control animal was euthanized on Day 23 with body weight loss >20%, but all other animals survived through Day 35.

Significant anti-tumor activity was seen in all activatable antibody 3954-1204-C225v5-MMAE and cetuximab treated groups as shown in Table 5 below, where values greater than 100% represent tumor shrinkage.

TABLE 5

Tumor growth inhibition relative to control-treated group.

| Treatment | Tumor Growth Inhibition (%) | | | | |
|---|---|---|---|---|---|
| | Day 7 | Day 14 | Day 21 | Day 28 | Day 35 |
| IVIG 25 mg/kg | 0% | 0% | 0% | 0% | 0% |
| Cetuximab 12.5 mg/kg | 91% | 102% | 90% | 74% | 61% |
| Cetuximab 2.5 mg/kg × 5 | 82% | 98% | 93% | 87% | 77% |

TABLE 5-continued

| Tumor growth inhibition relative to control-treated group. | | | | | |
|---|---|---|---|---|---|
| | Tumor Growth Inhibition (%) | | | | |
| Treatment | Day 7 | Day 14 | Day 21 | Day 28 | Day 35 |
| 3954-1204-C225v5-MMAE 12.5 mg/kg | 104% | 124% | 112% | 112% | 109% |
| 3954-1204-C225v5-MMAE 2.5 mg/kg × 5 | 39% | 107% | 107% | 107% | 107% |

Cetuximab as a single dose of 12.5 mg/kg produced tumor stasis or tumor regression in 8/8 mice; however, the effect was short lived with 6/8 mice showing evidence of tumor regrowth on Day 35. Cetuximab as a fractionated dose of 2.5 mg/kg likewise produced tumor stasis or regression in all animals followed by regrowth in 5/8 mice by Day 35. Administration of the activatable antibody 3954-1204-C225v5-MMAE as a single dose of 12.5 mg/kg had a more pronounced anti-tumor effect, resulting in tumor regressions in 7/7 mice, with no evidence of tumor regrowth by Day 35. Twice weekly administration of 2.5 mg/kg 3954-1204-C225v5-MMAE yielded tumor regressions in 8/8 mice, only one of which showed evidence of tumor regrowth on Day 35. Statistical analysis of the Day 35 tumor volumes showed that both regimens using 3954-1204-C225v5-MMAE were significantly more efficacious than the fractionated dose of cetuximab (one way ANOVA $p<0.005$ in each case). The same was true when comparing to the cetuximab single dose group. There was no significant difference on Day 35 between the activities of the two regimens using 3954-1204-C225v5-MMAE ($p=0.22$ using a two-tailed t-test).

In conclusion, the activatable anti-EGFR antibody-agent conjugate 3954-1204-C225v5-MMAE showed robust and durable efficacy in the H292 tumor model, with activity superior to a matching dose of cetuximab. The activatable antibody-agent conjugate 3954-1204-C225v5-MMAE was equally effective when administered as a single dose of 12.5 mg/kg or a repeated dose of 2.5 mg/kg given twice weekly for a total of 5 doses.

Example 10. In Vitro Characterization of an Activatable Antibody Conjugated to an Agent This Example describes the ability of an activatable antibody-agent conjugate of the disclosure to retain binding to EGFR and inhibit proliferation of H292 cells in culture.

Anti-EGFR activatable antibody 3954-1204-C225v5 was conjugated to monomethylauristatin E (MMAE), a synthetic anti-mitotic tubulin polymerization inhibitor as described in the Examples herein, to generate activatable antibody-agent conjugate 3954-1204-C225v5-MMAE. The average drug to antibody ratio (DAR) was 3.44.

The abilities of the following compounds to bind EGFR in an ELISA-based assay and to inhibit H292 cell proliferation in cell culture were determined: Anti-EGFR activatable antibody-agent conjugate 3954-1204-C225v5-MMAE; anti-EGFR activatable antibody-agent conjugate 3954-1204-C225v5-MMAE activated by uPA; anti-EGFR activatable antibody 3954-1204-C225v5; anti-EGFR activatable antibody 3954-1204-C225v5 activated by uPA; and anti-EGFR antibody C225v5. Activation of activatable antibody and activatable antibody-agent conjugate was effected by digestion overnight at 37° C. with active site-titrated uPA (500 nM) in Tris pH 8.5; activation was measured by CE analysis (LabChip GXII). uPA-activated activatable antibody and uPA-activated activatable antibody-agent conjugate were purified using protein A and then stored at 4° C. prior to the study.

Figure 20A:
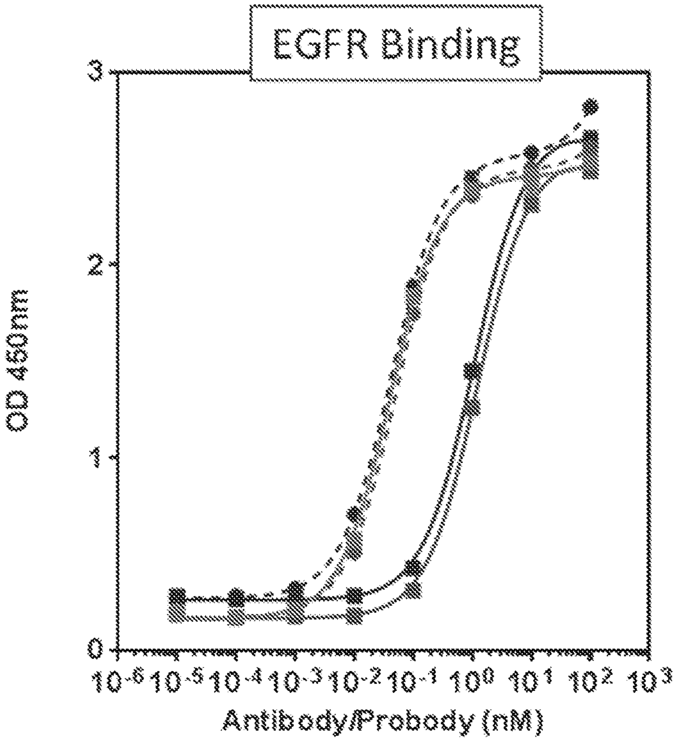
FIGS. 20A and 20B are a series of graphs depicting that lysine conjugation of MMAE increases 3954-1204-C225v5 potency while maintaining masking and activation potential. The conjugation of MMAE to 3954-1204-C225v5 does not alter its binding to EGFR. The conjugation of MMAE to 3954-1204-C225v5 increases its cell killing activity.

For the ELISA-based binding experiments, EGFR-Fc (R&D Systems) was coated to the wells of a 96-well ELISA plate. A 1:3 serial dilution of the compounds was applied to the plate and allowed to bind. Bound antibody was visualized with an anti-human $F(ab')_2$ IgG-HRP conjugate (Jackson ImmunoResearch Laboratories) and developed with the chromogenic substrate TMB. FIG. 20A demonstrates that conjugation of MMAE to the activatable antibody did not interfere with the ability of the masking moiety to inhibit binding of the activatable antibody to EGFR. In addition, conjugation of MMAE to the uPA-activated activatable antibody did not alter the activated antibody's ability to bind to EGFR.

Figure 20B:
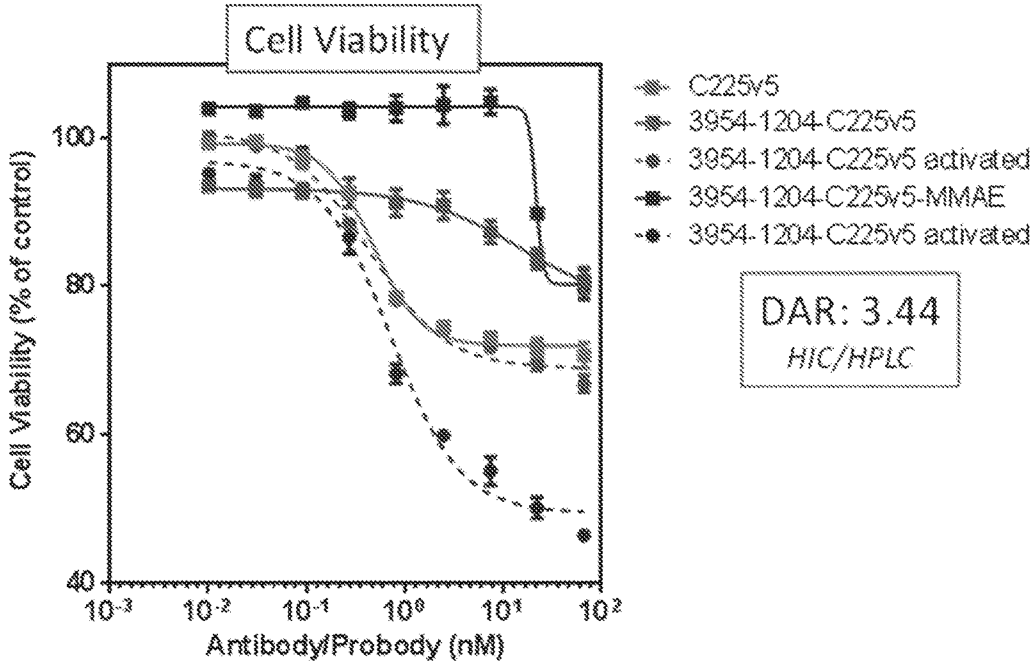

For the cell proliferation assay, the human lung cancer cell line H292 was obtained from ATCC. H292 cells were grown in complete media (RPMI-1640 supplemented with 10% fetal bovine serum) at 37° C. in an atmosphere of 5% CO2 in air. H292 cells were harvested during the logarithmic growth period, resuspended in complete medium, and plated at a density of 10,000 cells per well in a 96-well white wall chimney plate. Following overnight incubation, a 10-point 1:3 serial dilution, starting at 10 μg/ml and ending in essentially 0 μg/ml of each compound was added to cells in culture in replicates. Cells were cultured for 3 days and cell viability was measured using CellTiterGlo (Promega) following manufacturer's protocol and a luminometer (Tecan). Data were analyzed using Prism GraphPad. FIG. 20B demonstrates that conjugation of MMAE to the uPA-activated activatable antibody increases the activated antibody's cell-killing activity. In addition, conjugation of MMAE to the activatable antibody did not interfere with the ability of the masking moiety to inhibit cell killing by the uncleaved activatable antibody.

Example 11. In Situ Imaging of Anti-EGFR Activatable Antibodies

The present Example describes the use of an in situ imaging approach to screen a patient's tissue samples for the activation and binding of an anti-EGFR activatable antibody. The results indicate that anti-EGFR activatable antibodies of the disclosure can be activated by proteases expressed by a cancer patient's tissue and bind to EGFR receptor on that tissue.

Figure 21:
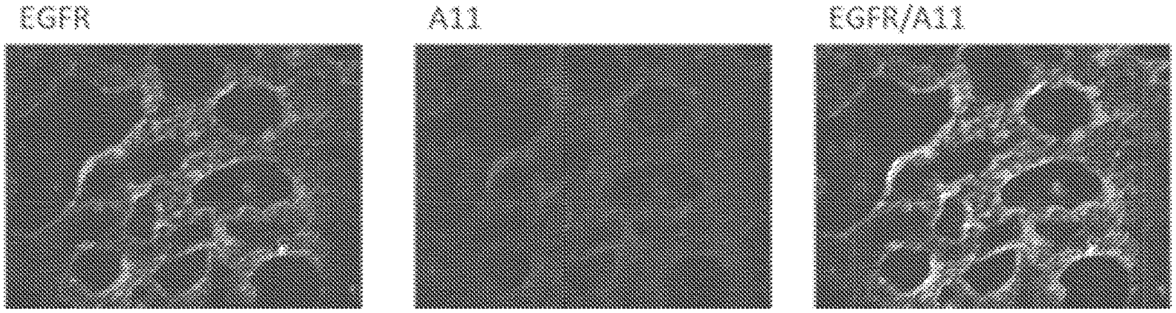
FIG. 21 is an illustration depicting the co-localization of EGFR and A11 in human colorectal cancer liver metastasis tissue samples.
Figure 22:
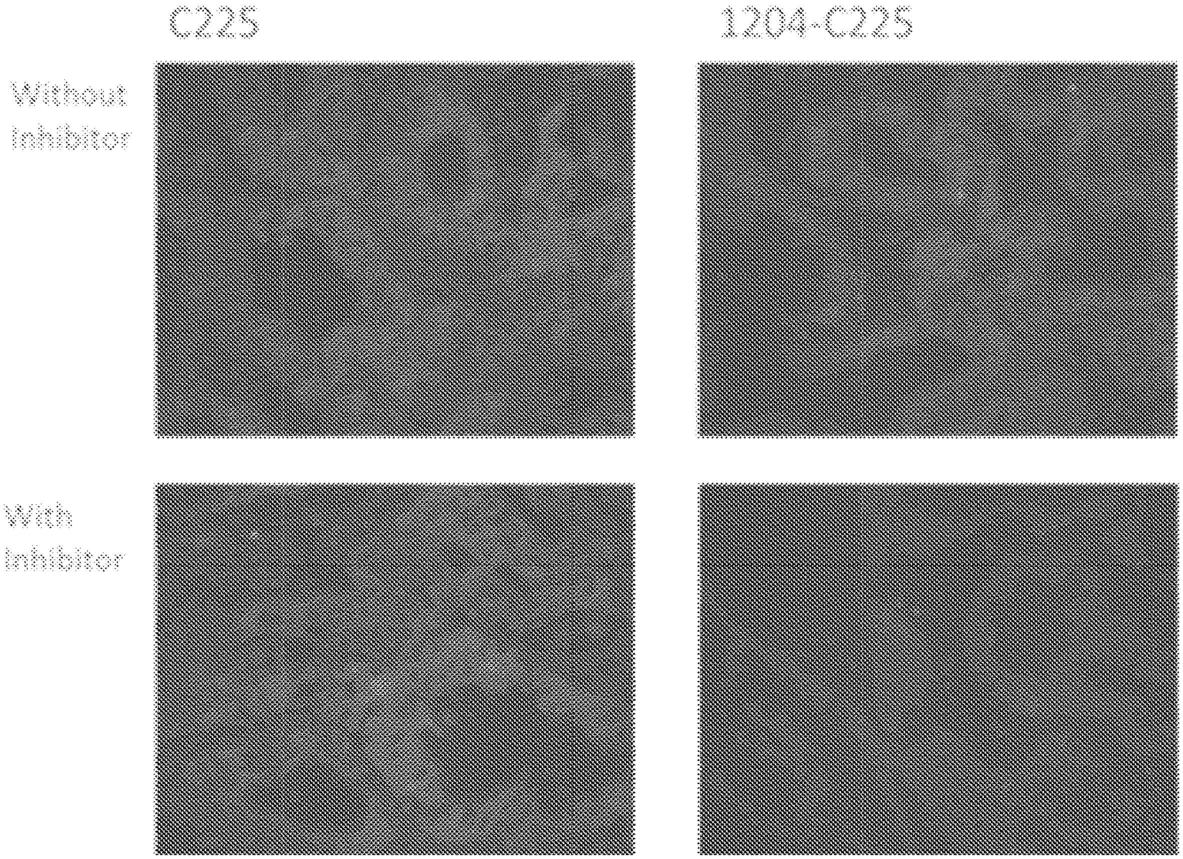
FIG. 22 is an illustration depicting the ability of human colorectal cancer liver metastasis tissues to activate and bind anti-EGFR activatable antibodies.

Human colorectal cancer, non-small cell lung cancer (NSCLC) and liver metastasis tissue samples were profiled for EGFR and MT-SP1 expression by treating frozen tissue with labeled EGFR and A11 antibodies at 1 μg/ml and 5 μg/ml concentrations, respectively for 1 hour (FIG. 21 and Tables 6-8). Furthermore, the ability of anti-EGFR activatable antibody 3954-1204-C225V5 to be activated and to bind human tumor or liver metastasis tissues was evaluated using in situ imaging. The activatable antibody was labeled with Alexa Fluor® 680 (Invitrogen) as described above. The resultant activatable antibody 3954-1204-C225V5-AF680 (also referred to as 1204-C225v5 or 1204-C225) was incubated with frozen patient tissue samples according to the protocol of in situ imaging described herein. FIG. 22 illustrates the ability of colorectal cancer liver metastasis tissues to activate and bind anti-EGFR activatable antibodies. The results on the ability of cancer patient's tissue samples to activate and bind anti-EGFR activatable antibodies are summarized in the Tables 6-8. The IHC staining that measures the amount of EGFR and A11 antibodies binding to the tissue sample was scored from 0 to 3+: 0, no staining; 1+ (i.e., "+"), weak staining; 2+ (i.e., "++"), moderate staining; and 3+ (i.e., "+++"), strong staining. The in situ imaging staining scoring is based on comparison with cetuximab antibody staining and defined as follows: 0, no staining; 1+ (i.e., "+"), weak staining as compared to parental antibody; 2+ (i.e., "+"), moderate staining as compared to parental antibody; and 3+ (i.e., "+++"), analogous staining to parental antibody.

TABLE 6

Screening for EGFR and MT-SP1 expression and in situ imaging of 3954-1204-C225 activatable antibody in colorectal cancer patients tumor tissues.

| | IHC* | | IHZ** | | | | | | |
|---|---|---|---|---|---|---|---|---|---|
| Patient # | EGFR | MT-SP1 | Cetux-imab | Activatable Antibody | Tumor type | Stage | Grade | AJCC 7th edition | Treatment |
| 5577 | +++ | +++ | ++ | ++ | Adenocarcinoma | N/A | G2 Moderately Differentiated | N/A | UNKNOWN |
| 5579 | +++ | − | ++ | ++ | Adenocarcinoma | N/A | G3 Poorly Differentiated | (pT4, pN2, pM1) | UNKNOWN |
| 5638 | ++ | + | ++ | ++ | Adenocarcinoma | Stage IIA | G2 Moderately Differentiated | (pT3, pN0, pMn/a) | UNKNOWN |
| 5640 | ++ | ++ | ++ | +++ | Adenocarcinoma | Stage IIA | G2 Moderately Differentiated | IIA (pT3, pN0, pMn/a) | UNKNOWN |
| 5642 | ++ | + | +++ | + | Adenocarcinoma | Stage IIA | G3 Poorly Differentiated | II (pT3, pN0, pMn/a) | UNKNOWN |
| 5650 | ++ | + | ++ | ++ | Adenocarcinoma | Stage IIIB | G2 Moderately Differentiated | IIIB (pT3, pN0, pMn/a) | UNKNOWN |
| 5652 | +++ | +++ | +++ | ++ | Adenocarcinoma | Stage IIA | G2 Moderately Differentiated | (pT3, pN0, pMn/a) | UNKNOWN |
| 5656 | +++ | ++ | +++ | +++ | Adenocarcinoma | Stage IIB | G2 Moderately Differentiated | (pT3c/d, pN1, pMn/a) | UNKNOWN |
| 5658 | + | ++ | ++ | +++ | Adenocarcinoma | Stage IIIB | G3 Poorly Differentiated | (pT3, pN1, pMn/a) | UNKNOWN |
| 5660 | +++ | +++ | ++ | +++ | Adenocarcinoma | Stage I | G2 Moderately Differentiated | (pT2, pN0, pMn/a) | UNKNOWN |
| 5662 | − | − | − | − | Adenocarcinoma | Stage IIA | G2 Moderately Differentiated | (pT3, pN0, pMn/a) | UNKNOWN |
| 5663 | + | − | + | − | Adenocarcinoma | Stage IIA | G3 Poorly Differentiated | (pT3, pN0, pMn/a) | UNKNOWN |
| 5665 | ++ | + | ++ | ++ | Adenocarcinoma | N/A | N/A | (pT4, pN1, pMn/a) | UNKNOWN |

*The IHC staining scored from 0 to 3+ that measures the amount of antibody binding: 0, no staining; 1+, weak staining; 2+, moderate staining; and 3+, strong staining.
**The IHZ staining scoring is based on comparison with parental antibody staining: 0, no staining; 1+, weak staining as compared to parental antibody; 2+, moderate staining as compared to parental antibody; and 3+, analogous staining to parental antibody.

TABLE 7

Screening for EGFR and MT-SP1 expression and in situ imaging of 3954-1204-C225 activatable antibody in human colorectal cancer liver metastasis tissues.

| | IHC* | | IHZ** | | | | | | |
|---|---|---|---|---|---|---|---|---|---|
| Patient # | EGFR | MT-SP1 | Cetuximab | Activatable Antibody w/ 1204 | Tumor type | Stage | Grade | AJCC 7th edition | Treatment |
| 10398 | ++ | ++ | ++ | + | Metastatic Adenocarcinoma | N/A | N/A | N/A | N/A |
| 10404 | +++ | ++ | +++ | +++ | Metastatic Adenocarcinoma | Stage IV | N/A | N/A | Yes-N/A |
| 10444 | +++ | + | ++ | +++ | Metastatic Adenocarcinoma | Stage IV | N/A | N/A | Yes-N/A |
| 10465 | ++ | ++ | ++ | ++ | Metastatic Adenocarcinoma | Stage IV | N/A | N/A | Yes-N/A |
| 10470 | ++ | ++ | ++ | ++ | Metastatic Adenocarcinoma | Stage IV | N/A | N/A | FOLFIRI Avastin |
| 10484 | − | ++ | − | − | Metastatic Adenocarcinoma | Stage IV | N/A | N/A | FOLFOX |
| 10498 | ++/+ | ++ | ++ | +++ | Metastatic Adenocarcinoma | N/A | N/A | N/A | Chemo-FOLFIRI Radiation-Pelvic XRT |
| 10510 | ++ | +++ | + | +++ | Metastatic Adenocarcinoma | Stage IV | N/A | N/A | Chemo-5FU Leucovorin Radiation-Pelvic XRT |
| 10515 | + | ++ | + | +/− | Metastatic Adenocarcinoma | N/A | N/A | N/A | FOLFIRI Avastin |
| 10517 | ++ | + | ++/+ | +++/++ | Metastatic Adenocarcinoma | Stage IV | N/A | N/A | FOLFOX |
| 10519 | ++ | + | ++ | +++ | Metastatic | | G2, | N/A | Folfox |

TABLE 7-continued

Screening for EGFR and MT-SP1 expression and in situ imaging of 3954-1204-C225 activatable antibody in human colorectal cancer liver metastasis tissues.

| | IHC* | | IHZ** | | | | | | |
|---|---|---|---|---|---|---|---|---|---|
| Patient # | EGFR | MT-SP1 | Cetuximab | Activatable Antibody w/ 1204 | Tumor type | Stage | Grade | AJCC 7th edition | Treatment |
| | | | | | Adenocarcinoma | | Moderately Differentiated | | (Previous) CPT11, Leucovorin, 5FU (Current) |

*The IHC staining scored from 0 to 3+ that measures the amount of antibody binding: 0, no staining; 1+, weak staining; 2+, moderate staining; and 3+, strong staining.

**The IHZ staining scoring is based on comparison with parental antibody staining: 0, no staining; 1+, weak staining as compared to parental antibody; 2+, moderate staining as compared to parental antibody; and 3+, analogous staining to parental antibody.

TABLE 8

Screening for EGFR and MT-SP1 expression and in situ imaging of 3954-1204-C225 activatable antibody in NSCLC patients tissues.

| | IHC* | | IHZ** | | | | | | |
|---|---|---|---|---|---|---|---|---|---|
| Patient # | EGFR | MT-SP1 | Cetuximab | Activatable Antibody | Tumor type | Stage | Grade | AJCC 7th edition | Treatment |
| 5648 | – | – | – | – | ADENO-CARCINOMA | Stage I | G2 Moderately differentiated | IB (pT2, pN0 (0/12), pM n/a) | UN-KNOWN |
| 5608 | – | +++ | – | – | ADENO-CARCINOMA | Stage I | G2 Moderately differentiated | IB (pT2, pN0(0/12), pM n/a) | NONE |
| 5624 | – | – | – | – | Squamous Cell Carcinoma | Stage I | G2 Moderately differentiated | IB (pT2a, pN0, pMn/a) | NONE |
| 5613 | + | – | ++ | + | squamous cell carcinoma | Stage I | G3 Poorly differentiated | IB (pT2a, pN0, M n/a). | NONE |
| 5614 | +++ | ++ | +++ | ++ | Squamous Cell Carcinoma | Stage I | G3 Poorly differentiated | IB (pT2, pN0(0/12), pM n/a) | NONE |
| 5633 | + | +/– | + | + | ADENO-CARCINOMA | Stage I | G2 Moderately differentiated | IA (pT1b, pN0, pMnia) | YES-N/A |
| 5636 | + | + | + | + | Large Cell Carcinoma | Stage I | G3 Poorly differentiated | IA (pT1a, pN0, pMn/a) | NONE |
| 5630 | + | + | + | – | Squamous Cell Carcinoma | Stage I | G2 Moderately differentiated | IB (pT2a, pN0, pMn/a) | NONE |
| 5618 | +++ | + | +++ | +++ | Squamous Cell Carcinoma | Stage I | G2 Moderately differentiated | IB (pT2, pN0, pMn/a) | NONE |
| 5619 | + | +/– | ++ | + | ADENO-CARCINOMA | Stage II | G2 Moderately differentiated | IIB (pT2,pN1, pM n/a) | NONE |
| 5627 | ++ | – | ++ | | Squamous Cell Carcinoma | Stage II | G2 Moderately differentiated | IIB (pT2b, pN1, pM n/a) | NONE |
| 5629 | +++ | – | +++ | ++ | ADENO-CARCINOMA | Stage II | G2 Moderately differentiated | IIB (pT2b, pN1, pMn/a) | NONE |
| 5646 | +/– | + | + | + | LARGE CELL NEURO-ENDOCRINE CARCINOMA | Stage II | G3 Poorly differentiated | IIB (pT2, pN1, pMX). | UN-KNOWN |
| 5654 | +/– | ++ | – | – | LARGE CELL NEURO-ENDOCRINE CARCINOMA | Stage II | G3 poorly differentiated | IIA (pT2, pN0, pMn/a) | UN-KNOWN |
| 5607 | – | + | – | – | ADENO-CARCINOMA | Stage III | G3 Poorly differentiated | IIIA (pT2, pN0, pMn/a) | NONE |
| 5610 | – | – | – | – | Squamous Cell Carcinoma | Stage III | G2 Moderately differentiated | IIIA (pT3, pN1) | NONE |
| 5615 | + | – | ++ | + | squamous cell carcinoma | Stage III | G3 Poorly differentiated | IIIA (pT3, pN1, M n/a) | NONE |
| 5620 | +/– | – | – | – | Large Cell Basaloid Carcinoma | Stage III | G3 Poorly differentiated | IIIA (pT3, pN1, pMn/a) | NONE |

TABLE 8-continued

Screening for EGFR and MT-SP1 expression and in situ imaging of 3954-1204-C225 activatable antibody in NSCLC patients tissues.

| | IHC* | | IHZ** | | | | | | |
|---|---|---|---|---|---|---|---|---|---|
| Patient # | EGFR | MT-SP1 | Cetuximab | Activatable Antibody | Tumor type | Stage | Grade | AJCC 7th edition | Treatment |
| 5621 | +++ | ++ | +++ | ++ | SQUAMOUS CELL CARCINOMA | Stage III | G2 Moderately differentiated | IIIA (pT4, pN0, M n/a). | NONE |
| 5625 | +++ | ++ | +++ | ++ | Squamous Cell Carcinoma | Stage III | G2 Moderately differentiated | IIIA (pT4, pN2, pM n/a) | YES-N/A |

*The IHC staining scored from 0 to 3+ that measures the amount of antibody binding: 0, no staining; 1+, weak staining; 2+, moderate staining; and 3+, strong staining.
**The IHZ staining scoring is based on comparison with parental antibody staining: 0, no staining; 1+, weak staining as compared to parental antibody; 2+, moderate staining as compared to parental antibody; and 3+, analogous staining to parental antibody.

Example 12. Quantification of In Situ Imaging of Anti-EGFR Activatable Antibodies The present Example describes in situ imaging of the activation and binding of an anti-EGFR activatable antibody to biological tissues ex vivo in combination with anti-EGFR antibody IHC and A11 antibody IHC. The use of commercially available anti-EGFR antibody IHC allows one to normalize the staining of parental antibody (e.g. cetuximab) and anti-EGFR activatable antibody to the quantity of EGFR expression in a tissue. Co-staining with EGFR antibodies also enables qualitative quantification of in situ imaging of anti-EGFR activatable antibodies relative to the cetuximab staining normalized to EGFR expression. Quantification of the fluorescent signal can be performed using bioanalytical software for research imaging, such as MetaMorph. The staining of tissue with antibody that specifically recognizes the active site of MT-SP1 (antibody A11) can also be performed to monitor the activity of MT-SP1, an enzyme that proteolytically cleaves the substrate of activatable antibodies 3954-1204-C225v4, 3954-1204-C225v5, and 3954-1204-C225v6.

Quantification of in situ imaging of anti-EGFR activatable antibody cleavage by a cell or tissue performed in combination with EGFR IHC was conducted as follows: Frozen tissue sections were laid over glass slides and rinsed in 1×PBS-T. A solution containing labeled anti-EGFR activatable antibodies (labeled, e.g., with a fluorescent tag) was applied on the tissue and incubated, e.g., for 1 hour at room temperature in an incubation buffer of 50 mM Tris-HCl buffer pH 7.4, containing 150 mM NaCl, 100 μM $ZnCl_2$, 5 mM $CaCl_2$) and 0.05% Tween 20; activatable antibody at a concentration of about 1 μg/ml. The tissue was then rinsed in 1×PBS-T to remove non-bound material, and endogenous IgG was blocked with 3% BSA. Sections were incubated with commercially available anti-Rabbit, anti-EGFR antibodies and labeled A11 antibodies (labeled, e.g., with a fluorescent tag), e.g., for 1 hour at room temperature. After rinsing, secondary antibody Anti-Rabbit IgG labeled with a fluorescent tag was applied and incubated on the sections e.g., for 30 minutes at room temperature at a concentration of 5 μg/ml to amplify the primary antibody. Sections were rinsed and detectable label was measured. For example, when a fluorescent tag was used, the tissue was submitted to fluorescent microscopy. The ability of anti-EGFR activatable antibody to be activated and to bind to the receptor in situ was quantified by the following equation:

$$PbA = \frac{(Ab\,EGFR \cdot Pb \text{ in situ imaging})}{(Pb\,EGFR \cdot Ab \text{ in situ imaging})} \cdot 100\%$$

PbA=% of anti-EGFR activatable antibody activation and binding as compared to parental antibody (e.g. cetuximab), Ab EGFR=staining intensity of EGFR IHC on the section with cetuximab binding, Pb EGFR=staining intensity of EGFR IHC on the section with anti-EGFR activatable antibody in situ imaging, Ab in situ imaging=intensity of cetuximab binding, Pb in situ imaging=intensity of anti-EGFR activatable antibody binding.

Figure 23:
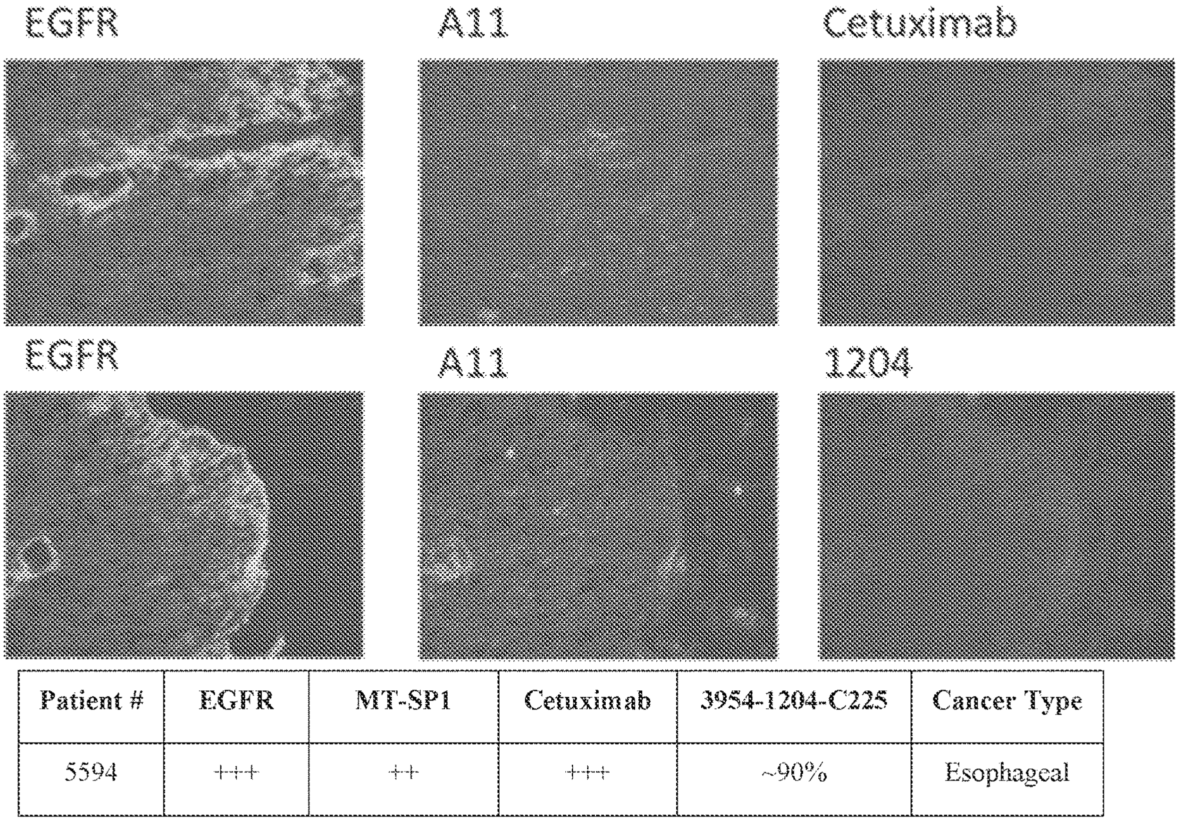
FIG. 23 is a series of photographs showing the triple staining of in situ imaging, EGFR IHC and A11 IHC. The upper row of images demonstrates the staining performed on a single tissue slice, demonstrating (left to right): EGFR expression, activity of matriptase (MT-SP1) and binding of cetuximab under in situ imaging conditions. The lower row of images demonstrates the staining performed on a single tissue slice, demonstrating (left to right): EGFR expression, activity of matriptase (MT-SP1) and in situ imaging of anti-EGFR activatable antibody 3954-1204-C225v5. The right column of images in FIG. 23 compares binding of cetuximab (upper image) and of anti-EGFR activatable antibody activated by tissue-derived proteolytic cleavage (lower image) under in situ imaging conditions. The identical pattern of tissue staining was detected by exposing a commercially available anti-EGFR antibody to the tissue, as shown in FIG. 23, left column of images.

Human esophageal and pancreatic cancer tissue samples were profiled for EGFR and MT-SP1 expression; the ability of anti-EGFR activatable antibody 3954-1204-C225v5 to be activated and to bind human tumor was evaluated using in situ imaging. The activatable antibody was labeled with Alexa Fluor® 680 (Invitrogen) as described above. The resultant activatable antibody 3954-1204-C225v5-AF680 was incubated with frozen patient tissue samples according to the protocol of in situ imaging described herein. Furthermore, EGFR and Alexa Fluor® 750 labeled A11 antibodies were used by treating frozen tissue with at 1 μg/ml and 5 μg/ml concentrations, respectively for 1 hour. FIG. 23 illustrates the ability of esophageal cancer tissues to activate and bind anti-EGFR activatable antibodies. The results on the ability of esophageal and pancreatic cancer patients' tissue samples to activate and bind anti-EGFR activatable antibodies are summarized in Table 9. The IHC staining that measures the amount of Cetuximab, EGFR and A11 antibodies binding to the tissue sample was scored from 0 to 3+: 0, no staining; 1+ (i.e., "+"), weak staining; 2+ (i.e., "++"), moderate staining; and 3+ (i.e., "+++"), strong staining. The in situ imaging of anti-EGFR activatable antibodies staining was quantified based on comparison with cetuximab antibody staining normalized to EGFR staining and calculated by the equation described above.

TABLE 9

Screening for EGFR and MT-SP1 expression and in situ imaging of 3954-1204-C225 activatable antibody in esophageal and pancreatic cancer patients tumor tissues.

| | IHC | | in situ imaging | | |
|---|---|---|---|---|---|
| Patient # | EGFR | MT-SP1 | Cetuximab | 3954-1204-C225 | Disease Diagnosis |
| 5586 | ++ | ++ | ++ | ~55% | Esophageal cancer |
| 5594 | +++ | ++ | +++ | ~90% | Esophageal cancer |
| 5595 | ++ | ++ | +++ | ~80% | Esophageal cancer |
| 5606 | +++ | +++ | +++ | ~100% | Esophageal cancer |
| 5641 | +++ | ++ | ++ | ~90% | Esophageal cancer |
| 5587 | ++ | +++ | ++ | ~100% | Pancreatic cancer |

TABLE 9-continued

Screening for EGFR and MT-SP1 expression and in situ imaging of 3954-1204-C225 activatable antibody in esophageal and pancreatic cancer patients tumor tissues.

| | IHC | | in situ imaging | | |
|---|---|---|---|---|---|
| Patient # | EGFR | MT-SP1 | Cetuximab | 3954-1204-C225 | Disease Diagnosis |
| 5617 | + | + | + | ~80% | Pancreatic cancer |
| 5623 | ++ | ++ | ++ | ~75% | Pancreatic cancer |
| 13007 | ++ | ++ | ++ | ~100% | Pancreatic cancer |
| 13011 | − | + | − | − | Pancreatic cancer |

*The IHC and Cetuximab staining scored from 0 to 3+ that measures the amount of antibody binding: 0, no staining; 1+, weak staining; 2+, moderate staining; and 3+, strong staining.

**The 3954-1204-C225 in situ imaging scoring is based on comparison with parental antibody staining normalized to the EGFR IHC staining and identified as % of activation: 0, no activation; 100% activation resulting in staining analogous to staining to parental antibody.

FIG. 23 is a series of photographs showing the triple staining of in situ imaging, EGFR IHC and A11 IHC. The upper row of images demonstrates the staining performed on a single tissue slice, demonstrating (left to right): EGFR expression, activity of matriptase (MT-SP1) and binding of cetuximab under in situ imaging conditions. The lower row of images demonstrates the staining performed on a single tissue slice, demonstrating (left to right): EGFR expression, activity of matriptase (MT-SP1) and in situ imaging of anti-EGFR activatable antibody 3954-1204-C225v5. The right column of images in FIG. 23 compares binding of cetuximab (upper image) and of anti-EGFR activatable antibody activated by tissue-derived proteolytic cleavage (lower image) under in situ imaging conditions. The identical pattern of tissue staining was detected by exposing a commercially available anti-EGFR antibody to the tissue, as shown in FIG. 23, left column of images. FIG. 23, middle column of images, demonstrates co-localization of matriptase (MT-SP1) activity with EGFR expression. As used herein, the term “co-localization” is not intended to imply any overlay or other overlap of the EGFR and/or A11 staining, and the term “co-localization” is used to indicate the presence of MT-SP1 activity in EGFR-expressing patient tissue. Overall, these data demonstrate about 90% activation of anti-EGFR antibody 3954-1204-C255v5 by the human esophageal cancer tissue sample.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A nucleic acid molecule encoding an activatable antibody that in an activated state binds Epidermal Growth Factor Receptor (EGFR), wherein the activatable antibody comprises:

an antibody or an antigen binding fragment thereof (AB) that specifically binds to EGFR, wherein the AB comprises (i) a heavy chain amino acid sequence selected from the group consisting of SEQ ID NO: 26, SEQ ID NO: 30 and SEQ ID NO: 34 and a light chain amino acid sequence comprising SEQ ID NO: 68, or (ii) a heavy chain amino acid sequence selected from the group consisting of SEQ ID NO: 2, SEQ ID NO: 6 and SEQ ID NO: 10 and a light chain amino acid sequence comprising SEQ ID NO: 68;

a masking moiety (MM) that inhibits binding of the AB of the activatable antibody in an uncleaved state to EGFR, wherein the masking moiety comprises the amino acid sequence CISPRGCPDGPYVMY (SEQ ID NO: 14); and a cleavable moiety (CM) coupled to the AB, wherein the CM is a polypeptide that functions as a substrate for a protease, and wherein the CM comprises the amino acid sequence LSGRSDNH (SEQ ID NO: 13), wherein the activatable antibody in the uncleaved state has a structural arrangement from N-terminus to C-terminus as follows: MM-CM-AB or AB-CM-MM.

2. The nucleic acid molecule of claim 1, further comprising a nucleic acid encoding a signal peptide.

3. The nucleic acid molecule of claim 2, wherein the nucleic acid encoding the signal peptide is operably linked to the nucleic acid encoding the activatable antibody via a nucleic acid encoding a spacer.

4. The nucleic acid molecule of claim 3, wherein the nucleic acid encoding the spacer encodes an amino acid sequence that comprises QGQSGQ (SEQ ID NO: 38).

5. A vector comprising the nucleic acid molecule of claim 1.

6. A method of producing an activatable antibody by culturing a cell under conditions that lead to expression of the activatable antibody, wherein the cell comprises the vector of claim 5.

7. A method of manufacturing an activatable antibody that in an activated state binds Epidermal Growth Factor Receptor (EGFR), the method comprising:

(a) culturing a cell comprising the nucleic acid molecule of claim 1 under conditions that lead to expression of the activatable antibody, and (b) recovering the activatable antibody.

8. The nucleic acid molecule of claim 1, wherein the antigen binding fragment thereof is selected from the group consisting of a Fab fragment, a F(ab')2 fragment, a scFv, and a scAb.

9. The nucleic acid molecule of claim 1, wherein the activatable antibody comprises a first linking peptide (LP1) and a second linking peptide (LP2), and wherein the activatable antibody in an uncleaved state has the structural arrangement from N-terminus to C-terminus as follows: MM-LP1-CM-LP2-AB or AB-LP2-CM-LP1-MM.

10. The nucleic acid molecule of claim 9, wherein at least one of LP1 or LP2 comprises an amino acid sequence selected from the group consisting of (GS)n, (GGS)n, (GSGGS)n (SEQ ID NO: 15) and (GGGS)n (SEQ ID NO: 16), where n is an integer of at least one.

11. The nucleic acid molecule of claim 9, wherein at least one of LP1 or LP2 comprises an amino acid sequence selected from the group consisting of GGSG (SEQ ID NO: 17), GGSGG (SEQ ID NO: 18), GSGSG (SEQ ID NO: 19), GSGGG (SEQ ID NO: 20), GGGSG (SEQ ID NO: 21), GSSSG (SEQ ID NO: 22), GSSGGSGGSGGSG (SEQ ID NO: 23), GSSGT (SEQ ID NO: 24), or GSSG (SEQ ID NO: 37).

12. The nucleic acid molecule of claim 1, wherein the activatable antibody in an uncleaved state comprises a spacer, wherein the spacer is joined directly to the MM and has the structural arrangement from N-terminus to C-terminus of spacer-MM-CM-AB, wherein the spacer comprises the amino acid sequence QGQSGQ (SEQ ID NO: 38).

13. The nucleic acid molecule of claim 1, wherein the activatable antibody is conjugated to an agent.

14. The nucleic acid molecule of claim 13, wherein the agent is a dolastatin, an auristatin or a derivative thereof, a maytansinoid or a derivative thereof, a duocarmycin or a derivative thereof, or a calicheamicin or a derivative thereof.

15. The nucleic acid molecule of claim 13, wherein the agent is conjugated to the AB via a linker.

16. The nucleic acid molecule of claim 1, wherein the activatable antibody further comprises a detectable moiety.

17. A nucleic acid molecule encoding an activatable antibody that in an activated state binds Epidermal Growth Factor Receptor (EGFR), wherein the activatable antibody comprises:

an antibody or an antigen binding fragment thereof (AB) that specifically binds to EGFR, wherein the AB comprises a combination of heavy and light chains selected from the group consisting of:

(a) a heavy chain comprising amino acid sequence of SEQ ID NO: 26 and a light chain comprising the amino acid sequence of SEQ ID NO: 28;

(b) a heavy chain comprising amino acid sequence of SEQ ID NO: 2 and a light chain comprising the amino acid sequence of SEQ ID NO: 4;

(c) a heavy chain comprising amino acid sequence of SEQ ID NO: 6 and a light chain comprising the amino acid sequence of SEQ ID NO: 4;

(d) a heavy chain comprising amino acid sequence of SEQ ID NO 30 and a light chain comprising the amino acid sequence of SEQ ID NO: 28;

(e) a heavy chain comprising amino acid sequence of SEQ ID NO: 10 and a light chain comprising the amino acid sequence of SEQ ID NO: 4; and (f) a heavy chain comprising amino acid sequence of SEQ ID NO: 34 and a light chain comprising the amino acid sequence of SEQ ID NO: 28;

a masking moiety (MM) that inhibits binding of the AB of the activatable antibody in an uncleaved state to EGFR, wherein the masking moiety comprises the amino acid sequence CISPRGCPDGPYVMY (SEQ ID NO: 14); and a cleavable moiety (CM) coupled to the AB, wherein the CM is a polypeptide that functions as a substrate for a protease, and wherein the CM comprises the amino acid sequence LSGRSDNH (SEQ ID NO: 13), wherein the activatable antibody in the uncleaved state has a structural arrangement from N-terminus to C-terminus as follows: MM-CM-AB or AB-CM-MM.

18. The nucleic acid molecule of claim 17, wherein the activatable antibody comprises a heavy chain comprising amino acid sequence of SEQ ID NO: 26 and a light chain comprising the amino acid sequence of SEQ ID NO: 28.

19. The nucleic acid molecule of claim 17, wherein the activatable antibody comprises a heavy chain comprising amino acid sequence of SEQ ID NO: 30 and a light chain comprising the amino acid sequence of SEQ ID NO: 28.

20. The nucleic acid molecule of claim 17, wherein the activatable antibody comprises a heavy chain comprising amino acid sequence of SEQ ID NO: 34 and a light chain comprising the amino acid sequence of SEQ ID NO: 28.

* * * * *

SEQUENCE LISTING

```
Sequence total quantity: 70
SEQ ID NO: 1            moltype = DNA  length = 1410
FEATURE                 Location/Qualifiers
source                  1..1410
                        mol_type = other DNA
                        organism = synthetic construct
SEQUENCE: 1
atgtacagga tgcaactcct gtcttgcatt gcactaagtc ttgcacttgt cacgaattcg  60
caggtgcagc tgaaacagag cggcccgggc ctggtgcagc cgagccagag cctgagcatt  120
acctgcaccg tgagcggctt tagcctgacc aactatggcg tgcattgggt gcgccagagc  180
ccgggcaaag gcctggaatg gctgggcgtg atttggagcg gcggcaacac cgattataac  240
accccgttta ccagccgcct gagcattaac aaagataaca gcaaaagcca ggtgtttttt  300
aaaatgaaca gcctgcaaag ccaggatacc gcgatttatt attgcgcgcg cgcgctgacc  360
tattatgatt atgaatttgc gtattggggc cagggcaccc tggtgaccgt gagcgcggct  420
agcaccaagg gcccatcggt cttccccctg gcaccctcct ccaagagcac ctctgggggc  480
acagcggccc tgggctgcct ggtcaaggac tacttccccg aaccggtgac ggtgtcgtgg  540
aactcaggcg ccctgaccag cggcgtgcac accttcccgg ctgtcctaca gtcctcagga  600
ctctactccc tcagcagcgt ggtgaccgtg ccctccagca gcttgggcac ccagacctac  660
atctgcaacg tgaatcacaa gcccagcaac accaaggtgg acaagaaagt tgagcccaaa  720
tcttgtgaca aaactcacac atgcccaccg tgcccagcac ctgaactcct ggggggaccg  780
tcagtcttcc tcttcccccc aaaacccaag gacaccctca tgatctcccg gacccctgag  840
gtcacatgcg tggtggtgga cgtgagccac gaagaccctg aggtcaagtt caactggtac  900
gtggacggcg tggaggtgca taatgccaag acaaagccgc gggaggagca gtacaacagc  960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgaactg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                    1410

SEQ ID NO: 2            moltype = AA  length = 469
FEATURE                 Location/Qualifiers
source                  1..469
                        mol_type = protein
                        organism = synthetic construct
SEQUENCE: 2
MYRMQLLSCI ALSLALVTNS QVQLKQSGPG LVQPSQSLSI TCTVSGFSLT NYGVHWVRQS  60
PGKGLEWLGV IWSGGNTDYN TPFTSRLSIN KDNSKSQVFF KMNSLQSQDT AIYYCARALT  120
YYDYEFAYWG QGTLVTVSAA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPELLGGP SVFLFPPKPK DTLMISRTPE VTCVVVDVSH EDPEVKFNWY  300
VDGVEVHNAK TKPREEQYNS TYRVVSVLTV LHQDWLNGKE YKCKVSNKAL PAPIEKTISK  360
```

```
AKGQPREPQV YTLPPSRDEL TKNQVSLTCL VKGFYPSDIA VEWESNGQPE NNYKTTPPVL  420
DSDGSFFLYS KLTVDKSRWQ QGNVFSCSVM HEALHNHYTQ KSLSLSPGK              469

SEQ ID NO: 3            moltype = DNA  length = 846
FEATURE                 Location/Qualifiers
source                  1..846
                        mol_type = other DNA
                        organism = synthetic construct
SEQUENCE: 3
atgtacagga tgcaactcct gtcttgcatt gcactaagtc ttgcacttgt cacgaattcg  60
caaggccagt ctggccagtg catctcacct cgtggttgtc cggacggccc atacgtcatg  120
tacggctcga gcggtggcag cggtggctct ggtggatccg gtctgagcgg ccgttccgat  180
aatcatggca gtagcggtac ccagatcttg ctgacccaga gcccggtgat tctgagcgtg  240
agcccgggcg aacgtgtgag ctttagctgc cgcgcgagcc agagcattgg caccaacatt  300
cattggtatc agcagcgcac caacggcagc ccgcgcctgc tgattaaata tgcgagcgaa  360
agcattagcg gcattccgag ccgctttagc ggcagcggca gcggcaccga ttttaccctg  420
agcattaaca gcgtggaaag cgaagatatt gcggattatt attgccagca gaacaacaac  480
tggccgacca cctttggcgc gggcaccaaa ctggaactga aacgtacggt ggctgcacca  540
tctgtcttca tcttcccgcc atctgatgag cagttgaaat ctggaactgc ctctgttgtg  600
tgcctgctga ataacttcta tcccagagag gccaaagtac agtggaaggt ggataacgcc  660
ctccaatcgg gtaactccca ggagagtgtc acagagcagg acagcaagga cagcacctac  720
agcctcagca gcaccctgac gctgagcaaa gcagactacg agaaacacaa agtctacgcc  780
tgcgaagtca cccatcaggg cctgagctcg cccgtcacaa agagcttcaa caggggagag  840
tgttag                                                             846

SEQ ID NO: 4            moltype = AA  length = 281
FEATURE                 Location/Qualifiers
source                  1..281
                        mol_type = protein
                        organism = synthetic construct
SEQUENCE: 4
MYRMQLLSCI ALSLALVTNS QGQSGQCISP RGCPDGPYVM YGSSGGSGGS GGSGLSGRSD  60
NHGSSGTQIL LTQSPVILSV SPGERVSFSC RASQSIGTNI HWYQQRTNGS PRLLIKYASE  120
SISGIPSRFS GSGSGTDFTL SINSVESEDI ADYYCQQNNN WPTTFGAGTK LELKRTVAAP  180
SVFIFPPSDE QLKSGTASVV CLLNNFYPRE AKVQWKVDNA LQSGNSQESV TEQDSKDSTY  240
SLSSTLTLSK ADYEKHKVYA CEVTHQGLSS PVTKSFNRGE C                     281

SEQ ID NO: 5            moltype = DNA  length = 1410
FEATURE                 Location/Qualifiers
source                  1..1410
                        mol_type = other DNA
                        organism = synthetic construct
SEQUENCE: 5
atgtacagga tgcaactcct gtcttgcatt gcactaagtc ttgcacttgt cacgaattcg  60
caggtgcagc tgaaacagag cggcccgggc ctggtgcagc cgagccagag cctgagcatt  120
acctgcaccg tgagcggctt tagcctgacc aactatggcg tgcattgggt gcgccagagc  180
ccgggcaaag gcctggaatg gctgggcgtg atttggagcg gcggcaacac cgattataac  240
accccgttta ccagccgcct gagcattaac aaagataaca gcaaaagcca ggtgtttttt  300
aaaatgaaca gcctgcaaag caacgatacc gcgatttatt attgcgcgcg cgcgctgacc  360
tattatgatt atgaatttgc gtattggggc cagggcaccc tggtgaccgt gagcgcggct  420
agcaccaagg gcccatcggt cttccccctg gcaccctcct ccaagagcac ctctgggggc  480
acagcggccc tgggctgcct ggtcaaggac tacttccccg aaccggtgac ggtgtcgtgg  540
aactcaggcg ccctgaccag cggcgtgcac accttcccgg ctgtcctaca gtcctcagga  600
ctctactccc tcagcagcgt ggtgaccgtg ccctccagca gcttgggcac ccagacctac  660
atctgcaacg tgaatcacaa gcccagcaac accaaggtgg acaagaaagt tgagcccaaa  720
tcttgtgaca aaactcacac atgcccaccg tgcccagcac ctgaactcct ggggggaccg  780
tcagtcttcc tcttcccccc aaaacccaag gacaccctca tgatctcccg gacccctgag  840
gtcacatgcg tggtggtgga cgtgagccac gaagaccctg aggtcaagtt caactggtac  900
gtggacggcg tggaggtgca taatgccaag acaaagccgc gggaggagca gtacaacagc  960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgaactg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                   1410

SEQ ID NO: 6            moltype = AA  length = 469
FEATURE                 Location/Qualifiers
source                  1..469
                        mol_type = protein
                        organism = synthetic construct
SEQUENCE: 6
MYRMQLLSCI ALSLALVTNS QVQLKQSGPG LVQPSQSLSI TCTVSGFSLT NYGVHWVRQS  60
PGKGLEWLGV IWSGGNTDYN TPFTSRLSIN KDNSKSQVFF KMNSLQSNDT AIYYCARALT  120
YYDYEFAYWG QGTLVTVSAA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPELLGGP SVFLFPPKPK DTLMISRTPE VTCVVVDVSH EDPEVKFNWY  300
```

```
VDGVEVHNAK TKPREEQYNS TYRVVSVLTV LHQDWLNGKE YKCKVSNKAL PAPIEKTISK  360
AKGQPREPQV YTLPPSRDEL TKNQVSLTCL VKGFYPSDIA VEWESNGQPE NNYKTTPPVL  420
DSDGSFFLYS KLTVDKSRWQ QGNVFSCSVM HEALHNHYTQ KSLSLSPGK             469

SEQ ID NO: 7           moltype = AA  length = 8
FEATURE                Location/Qualifiers
source                 1..8
                       mol_type = protein
                       organism = synthetic construct
SEQUENCE: 7
PRFKIIGG                                                          8

SEQ ID NO: 8           moltype = AA  length = 8
FEATURE                Location/Qualifiers
source                 1..8
                       mol_type = protein
                       organism = synthetic construct
SEQUENCE: 8
PRFRIIGG                                                          8

SEQ ID NO: 9           moltype = DNA  length = 1410
FEATURE                Location/Qualifiers
source                 1..1410
                       mol_type = other DNA
                       organism = synthetic construct
SEQUENCE: 9
atgtacagga tgcaactcct gtcttgcatt gcactaagtc ttgcacttgt cacgaattcg  60
caggtgcagc tgaaacagag cggcccgggc ctggtgcagc cgagccagag cctgagcatt  120
acctgcaccg tgagcggctt tagcctgacc aactatggcg tgcattgggt gcgccagagc  180
ccgggcaaag gcctggaatg gctgggcgtg atttggagcg gcggcaacac cgattataac  240
accccgttta ccagccgcct gagcattaac aaagataaca gcaaaagcca ggtgtttttt  300
aaaatgaaca gcctgcaaag ccaggatacc gcgatttatt attgcgcgcg cgcgctgacc  360
tattatgatt atgaatttgc gtattggggc cagggcaccc tggtgaccgt gagcgcggct  420
agcaccaagg gcccatcggt cttccccctg gcaccctcct ccaagagcac ctctgggggc  480
acagcggccc tgggctgcct ggtcaaggac tacttccccg aaccggtgac ggtgtcgtgg  540
aactcaggcg ccctgaccag cggcgtgcac accttcccgg ctgtcctaca gtcctcagga  600
ctctactccc tcagcagcgt ggtgaccgtg ccctccagca gcttgggcac ccagacctac  660
atctgcaacg tgaatcacaa gcccagcaac accaaggtgg acaagaaagt tgagcccaaa  720
tcttgtgaca aaactcacac atgcccaccg tgcccagcac ctgaactcct ggggggaccg  780
tcagtcttcc tcttcccccc aaaacccaag gacaccctca tgatctcccg gacccctgag  840
gtcacatgcg tggtggtgga cgtgagccac gaagaccctg aggtcaagtt caactggtac  900
gtggacggcg tggaggtgca taatgccaag acaaagccgc gggaggagca gtacgccagc  960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgaactg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                  1410

SEQ ID NO: 10          moltype = AA  length = 469
FEATURE                Location/Qualifiers
source                 1..469
                       mol_type = protein
                       organism = synthetic construct
SEQUENCE: 10
MYRMQLLSCI ALSLALVTNS QVQLKQSGPG LVQPSQSLSI TCTVSGFSLT NYGVHWVRQS  60
PGKGLEWLGV IWSGGNTDYN TPFTSRLSIN KDNSKSQVFF KMNSLQSQDT AIYYCARALT  120
YYDYEFAYWG QGTLVTVSAA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPELLGGP SVFLFPPKPK DTLMISRTPE VTCVVVDVSH EDPEVKFNWY  300
VDGVEVHNAK TKPREEQYAS TYRVVSVLTV LHQDWLNGKE YKCKVSNKAL PAPIEKTISK  360
AKGQPREPQV YTLPPSRDEL TKNQVSLTCL VKGFYPSDIA VEWESNGQPE NNYKTTPPVL  420
DSDGSFFLYS KLTVDKSRWQ QGNVFSCSVM HEALHNHYTQ KSLSLSPGK             469

SEQ ID NO: 11          moltype = AA  length = 9
FEATURE                Location/Qualifiers
source                 1..9
                       mol_type = protein
                       organism = synthetic construct
SEQUENCE: 11
SSRHRRALD                                                         9

SEQ ID NO: 12          moltype = AA  length = 14
FEATURE                Location/Qualifiers
source                 1..14
                       mol_type = protein
                       organism = synthetic construct
```

```
SEQUENCE: 12
RKSSIIIRMR DVVL                                                     14

SEQ ID NO: 13           moltype = AA  length = 8
FEATURE                 Location/Qualifiers
source                  1..8
                        mol_type = protein
                        organism = synthetic construct
SEQUENCE: 13
LSGRSDNH                                                            8

SEQ ID NO: 14           moltype = AA  length = 15
FEATURE                 Location/Qualifiers
source                  1..15
                        mol_type = protein
                        organism = synthetic construct
SEQUENCE: 14
CISPRGCPDG PYVMY                                                    15

SEQ ID NO: 15           moltype = AA  length = 5
FEATURE                 Location/Qualifiers
source                  1..5
                        mol_type = protein
                        organism = synthetic construct
SEQUENCE: 15
GSGGS                                                               5

SEQ ID NO: 16           moltype = AA  length = 4
FEATURE                 Location/Qualifiers
source                  1..4
                        mol_type = protein
                        organism = synthetic construct
SEQUENCE: 16
GGGS                                                                4

SEQ ID NO: 17           moltype = AA  length = 4
FEATURE                 Location/Qualifiers
source                  1..4
                        mol_type = protein
                        organism = synthetic construct
SEQUENCE: 17
GGSG                                                                4

SEQ ID NO: 18           moltype = AA  length = 5
FEATURE                 Location/Qualifiers
source                  1..5
                        mol_type = protein
                        organism = synthetic construct
SEQUENCE: 18
GGSGG                                                               5

SEQ ID NO: 19           moltype = AA  length = 5
FEATURE                 Location/Qualifiers
source                  1..5
                        mol_type = protein
                        organism = synthetic construct
SEQUENCE: 19
GSGSG                                                               5

SEQ ID NO: 20           moltype = AA  length = 5
FEATURE                 Location/Qualifiers
source                  1..5
                        mol_type = protein
                        organism = synthetic construct
SEQUENCE: 20
GSGGG                                                               5

SEQ ID NO: 21           moltype = AA  length = 5
FEATURE                 Location/Qualifiers
source                  1..5
                        mol_type = protein
                        organism = synthetic construct
SEQUENCE: 21
GGGSG                                                               5

SEQ ID NO: 22           moltype = AA  length = 5
FEATURE                 Location/Qualifiers
source                  1..5
                        mol_type = protein
```

```
                         organism = synthetic construct
SEQUENCE: 22
GSSSG                                                                  5

SEQ ID NO: 23            moltype = AA  length = 13
FEATURE                  Location/Qualifiers
source                   1..13
                         mol_type = protein
                         organism = synthetic construct
SEQUENCE: 23
GSSGGSGGSG GSG                                                         13

SEQ ID NO: 24            moltype = AA  length = 5
FEATURE                  Location/Qualifiers
source                   1..5
                         mol_type = protein
                         organism = synthetic construct
SEQUENCE: 24
GSSGT                                                                  5

SEQ ID NO: 25            moltype = DNA  length = 1350
FEATURE                  Location/Qualifiers
source                   1..1350
                         mol_type = other DNA
                         organism = synthetic construct
SEQUENCE: 25
caggtgcagc tgaaacagag cggcccgggc ctggtgcagc cgagccagag cctgagcatt  60
acctgcaccg tgagcggctt tagcctgacc aactatggcg tgcattgggt gcgccagagc  120
ccgggcaaag gcctggaatg gctgggcgtg atttggagcg gcggcaacac cgattataac  180
accccgttta ccagccgcct gagcattaac aaagataaca gcaaaagcca ggtgtttttt  240
aaaatgaaca gcctgcaaag ccaggatacc gcgatttatt attgcgcgcg cgcgctgacc  300
tattatgatt atgaatttgc gtattggggc cagggcaccc tggtgaccgt gagcgcggct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgaactg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                   1350

SEQ ID NO: 26            moltype = AA  length = 449
FEATURE                  Location/Qualifiers
source                   1..449
                         mol_type = protein
                         organism = synthetic construct
SEQUENCE: 26
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 27            moltype = DNA  length = 786
FEATURE                  Location/Qualifiers
source                   1..786
                         mol_type = other DNA
                         organism = synthetic construct
SEQUENCE: 27
caaggccagt ctggccagtg catctcacct cgtggttgtc cggacggccc atacgtcatg  60
tacggctcga gcggtggcag cggtggctct ggtggatccg gtctgagcgg ccgttccgat  120
aatcatggca gtagcggtac ccagatcttg ctgacccaga gcccggtgat tctgagcgtg  180
agcccgggcg aacgtgtgag ctttagctgc cgcgcgagcc agagcattgg caccaacatt  240
cattggtatc agcagcgcac caacggcagc ccgcgcctgc tgattaaata tgcgagcgaa  300
agcattagcg gcattccgag ccgctttagc ggcagcggca gcggcaccga ttttaccctg  360
agcattaaca gcgtggaaag cgaagatatt gcggattatt attgccagca gaacaacaac  420
tggccgacca cctttggcgc gggcaccaaa ctggaactga aacgtacggt ggctgcacca  480
```

```
tctgtcttca tcttcccgcc atctgatgag cagttgaaat ctggaactgc ctctgttgtg  540
tgcctgctga ataacttcta tcccagagag gccaaagtac agtggaaggt ggataacgcc  600
ctccaatcgg gtaactccca ggagagtgtc acagagcagg acagcaagga cagcacctac  660
agcctcagca gcaccctgac gctgagcaaa gcagactacg agaaacacaa agtctacgcc  720
tgcgaagtca cccatcaggg cctgagctcg cccgtcacaa agagcttcaa caggggagag  780
tgttag                                                             786

SEQ ID NO: 28          moltype = AA  length = 261
FEATURE                Location/Qualifiers
source                 1..261
                       mol_type = protein
                       organism = synthetic construct
SEQUENCE: 28
QGQSGQCISP RGCPDGPYVM YGSSGGSGGS GGSGLSGRSD NHGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 29          moltype = DNA  length = 1350
FEATURE                Location/Qualifiers
source                 1..1350
                       mol_type = other DNA
                       organism = synthetic construct
SEQUENCE: 29
caggtgcagc tgaaacagag cggcccgggc ctggtgcagc cgagccagag cctgagcatt  60
acctgcaccg tgagcggctt tagcctgacc aactatggcg tgcattgggt gcgccagagc  120
ccgggcaaag gcctggaatg gctgggcgtg atttggagcg gcggcaacac cgattataac  180
accccgttta ccagccgcct gagcattaac aaagataaca gcaaaagcca ggtgtttttt  240
aaaatgaaca gcctgcaaag caacgatacc gcgatttatt attgcgcgcg cgcgctgacc  300
tattatgatt atgaatttgc gtattggggc cagggcaccc tggtgaccgt gagcgcggct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgaactg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                  1350

SEQ ID NO: 30          moltype = AA  length = 449
FEATURE                Location/Qualifiers
source                 1..449
                       mol_type = protein
                       organism = synthetic construct
SEQUENCE: 30
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 31          moltype = AA  length = 15
FEATURE                Location/Qualifiers
source                 1..15
                       mol_type = protein
                       organism = synthetic construct
SEQUENCE: 31
SSSFDKGKYK KGDDA                                                   15

SEQ ID NO: 32          moltype = AA  length = 15
FEATURE                Location/Qualifiers
source                 1..15
                       mol_type = protein
                       organism = synthetic construct
SEQUENCE: 32
SSSFDKGKYK RGDDA                                                   15
```

```
SEQ ID NO: 33          moltype = DNA  length = 1350
FEATURE                Location/Qualifiers
source                 1..1350
                       mol_type = other DNA
                       organism = synthetic construct
SEQUENCE: 33
caggtgcagc tgaaacagag cggcccgggc ctggtgcagc cgagccagag cctgagcatt  60
acctgcaccg tgagcggctt tagcctgacc aactatggcg tgcattgggt gcgccagagc  120
ccgggcaaag gcctggaatg gctgggcgtg atttggagcg gcggcaacac cgattataac  180
accccgttta ccagccgcct gagcattaac aaagataaca gcaaaagcca ggtgtttttt  240
aaaatgaaca gcctgcaaag ccaggatacc gcgatttatt attgcgcgcg cgcgctgacc  300
tattatgatt atgaatttgc gtattggggc cagggcaccc tggtgaccgt gagcgcggct  360
agcaccaagg gcccatcggt cttcccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacgccagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgaactg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                   1350

SEQ ID NO: 34          moltype = AA  length = 449
FEATURE                Location/Qualifiers
source                 1..449
                       mol_type = protein
                       organism = synthetic construct
SEQUENCE: 34
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYAS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 35          moltype = AA  length = 4
FEATURE                Location/Qualifiers
source                 1..4
                       mol_type = protein
                       organism = synthetic construct
SEQUENCE: 35
IEGR                                                               4

SEQ ID NO: 36          moltype = AA  length = 4
FEATURE                Location/Qualifiers
source                 1..4
                       mol_type = protein
                       organism = synthetic construct
SEQUENCE: 36
IDGR                                                               4

SEQ ID NO: 37          moltype = AA  length = 4
FEATURE                Location/Qualifiers
source                 1..4
                       mol_type = protein
                       organism = synthetic construct
SEQUENCE: 37
GSSG                                                               4

SEQ ID NO: 38          moltype = AA  length = 6
FEATURE                Location/Qualifiers
source                 1..6
                       mol_type = protein
                       organism = synthetic construct
SEQUENCE: 38
QGQSGQ                                                             6

SEQ ID NO: 39          moltype = AA  length = 7
```

```
FEATURE                 Location/Qualifiers
source                  1..7
                        mol_type = protein
                        organism = synthetic construct
SEQUENCE: 39
GGSIDGR                                                     7

SEQ ID NO: 40           moltype = AA  length = 6
FEATURE                 Location/Qualifiers
source                  1..6
                        mol_type = protein
                        organism = synthetic construct
SEQUENCE: 40
PLGLWA                                                      6

SEQ ID NO: 41           moltype = AA  length = 8
FEATURE                 Location/Qualifiers
source                  1..8
                        mol_type = protein
                        organism = synthetic construct
SEQUENCE: 41
GPQGIAGQ                                                    8

SEQ ID NO: 42           moltype = AA  length = 8
FEATURE                 Location/Qualifiers
source                  1..8
                        mol_type = protein
                        organism = synthetic construct
SEQUENCE: 42
GPQGLLGA                                                    8

SEQ ID NO: 43           moltype = AA  length = 5
FEATURE                 Location/Qualifiers
source                  1..5
                        mol_type = protein
                        organism = synthetic construct
SEQUENCE: 43
GIAGQ                                                       5

SEQ ID NO: 44           moltype = AA  length = 8
FEATURE                 Location/Qualifiers
source                  1..8
                        mol_type = protein
                        organism = synthetic construct
SEQUENCE: 44
GPLGIAGI                                                    8

SEQ ID NO: 45           moltype = AA  length = 8
FEATURE                 Location/Qualifiers
source                  1..8
                        mol_type = protein
                        organism = synthetic construct
SEQUENCE: 45
GPEGLRVG                                                    8

SEQ ID NO: 46           moltype = AA  length = 8
FEATURE                 Location/Qualifiers
source                  1..8
                        mol_type = protein
                        organism = synthetic construct
SEQUENCE: 46
YGAGLGVV                                                    8

SEQ ID NO: 47           moltype = AA  length = 8
FEATURE                 Location/Qualifiers
source                  1..8
                        mol_type = protein
                        organism = synthetic construct
SEQUENCE: 47
AGLGVVER                                                    8

SEQ ID NO: 48           moltype = AA  length = 8
FEATURE                 Location/Qualifiers
source                  1..8
                        mol_type = protein
                        organism = synthetic construct
SEQUENCE: 48
AGLGISST                                                    8
```

```
SEQ ID NO: 49          moltype = AA  length = 8
FEATURE                Location/Qualifiers
source                 1..8
                       mol_type = protein
                       organism = synthetic construct
SEQUENCE: 49
EPQALAMS                                                    8

SEQ ID NO: 50          moltype = AA  length = 8
FEATURE                Location/Qualifiers
source                 1..8
                       mol_type = protein
                       organism = synthetic construct
SEQUENCE: 50
QALAMSAI                                                    8

SEQ ID NO: 51          moltype = AA  length = 8
FEATURE                Location/Qualifiers
source                 1..8
                       mol_type = protein
                       organism = synthetic construct
SEQUENCE: 51
AAYHLVSQ                                                    8

SEQ ID NO: 52          moltype = AA  length = 8
FEATURE                Location/Qualifiers
source                 1..8
                       mol_type = protein
                       organism = synthetic construct
SEQUENCE: 52
MDAFLESS                                                    8

SEQ ID NO: 53          moltype = AA  length = 8
FEATURE                Location/Qualifiers
source                 1..8
                       mol_type = protein
                       organism = synthetic construct
SEQUENCE: 53
ESLPVVAV                                                    8

SEQ ID NO: 54          moltype = AA  length = 8
FEATURE                Location/Qualifiers
source                 1..8
                       mol_type = protein
                       organism = synthetic construct
SEQUENCE: 54
SAPAVESE                                                    8

SEQ ID NO: 55          moltype = AA  length = 8
FEATURE                Location/Qualifiers
source                 1..8
                       mol_type = protein
                       organism = synthetic construct
SEQUENCE: 55
DVAQFVLT                                                    8

SEQ ID NO: 56          moltype = AA  length = 8
FEATURE                Location/Qualifiers
source                 1..8
                       mol_type = protein
                       organism = synthetic construct
SEQUENCE: 56
VAQFVLTE                                                    8

SEQ ID NO: 57          moltype = AA  length = 8
FEATURE                Location/Qualifiers
source                 1..8
                       mol_type = protein
                       organism = synthetic construct
SEQUENCE: 57
AQFVLTEG                                                    8

SEQ ID NO: 58          moltype = AA  length = 8
FEATURE                Location/Qualifiers
source                 1..8
                       mol_type = protein
                       organism = synthetic construct
SEQUENCE: 58
PVQPIGPQ                                                    8
```

```
SEQ ID NO: 59          moltype = AA  length = 21
FEATURE                Location/Qualifiers
source                 1..21
                       mol_type = protein
                       organism = synthetic construct
SEQUENCE: 59
QGQSGQCISP RGCPDGPYVM Y                                            21

SEQ ID NO: 60          moltype = DNA  length = 60
FEATURE                Location/Qualifiers
source                 1..60
                       mol_type = other DNA
                       organism = synthetic construct
SEQUENCE: 60
atgtacagga tgcaactcct gtcttgcatt gcactaagtc ttgcacttgt cacgaattcg  60

SEQ ID NO: 61          moltype = AA  length = 20
FEATURE                Location/Qualifiers
source                 1..20
                       mol_type = protein
                       organism = synthetic construct
SEQUENCE: 61
MYRMQLLSCI ALSLALVTNS                                              20

SEQ ID NO: 62          moltype = DNA  length = 18
FEATURE                Location/Qualifiers
source                 1..18
                       mol_type = other DNA
                       organism = synthetic construct
SEQUENCE: 62
caaggccagt ctggccag                                                18

SEQ ID NO: 63          moltype = DNA  length = 45
FEATURE                Location/Qualifiers
source                 1..45
                       mol_type = other DNA
                       organism = synthetic construct
SEQUENCE: 63
tgcatctcac ctcgtggttg tccggacggc ccatacgtca tgtac                  45

SEQ ID NO: 64          moltype = DNA  length = 39
FEATURE                Location/Qualifiers
source                 1..39
                       mol_type = other DNA
                       organism = synthetic construct
SEQUENCE: 64
ggctcgagcg gtggcagcgg tggctctggt ggatccggt                         39

SEQ ID NO: 65          moltype = DNA  length = 24
FEATURE                Location/Qualifiers
source                 1..24
                       mol_type = other DNA
                       organism = synthetic construct
SEQUENCE: 65
ctgagcggcc gttccgataa tcat                                         24

SEQ ID NO: 66          moltype = DNA  length = 15
FEATURE                Location/Qualifiers
source                 1..15
                       mol_type = other DNA
                       organism = synthetic construct
SEQUENCE: 66
ggcagtagcg gtacc                                                   15

SEQ ID NO: 67          moltype = DNA  length = 645
FEATURE                Location/Qualifiers
source                 1..645
                       mol_type = other DNA
                       organism = synthetic construct
SEQUENCE: 67
cagatcttgc tgacccagag cccggtgatt ctgagcgtga gcccgggcga acgtgtgagc  60
tttagctgcc gcgcgagcca gagcattggc accaacattc attggtatca gcagcgcacc  120
aacggcagcc cgcgcctgct gattaaatat gcgagcgaaa gcattagcgg cattccgagc  180
cgctttagcg gcagcggcag cggcaccgat tttaccctga gcattaacag cgtggaaagc  240
gaagatattg cggattatta ttgccagcag aacaacaact ggccgaccac ctttggcgcg  300
ggcaccaaac tggaactgaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
```

-continued

```
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 68          moltype = AA  length = 214
FEATURE                Location/Qualifiers
source                 1..214
                       mol_type = protein
                       organism = synthetic construct
SEQUENCE: 68
QILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 69          moltype = AA  length = 223
FEATURE                Location/Qualifiers
source                 1..223
                       mol_type = protein
                       organism = synthetic construct
SEQUENCE: 69
SDNHGSSGTQ ILLTQSPVIL SVSPGERVSF SCRASQSIGT NIHWYQQRTN GSPRLLIKYA  60
SESISGIPSR FSGSGSGTDF TLSINSVESE DIADYYCQQN NNWPTTFGAG TKLELKRTVA  120
APSVFIFPPS DEQLKSGTAS VVCLLNNFYP REAKVQWKVD NALQSGNSQE SVTEQDSKDS  180
TYSLSSTLTL SKADYEKHKV YACEVTHQGL SSPVTKSFNR GEC                    223

SEQ ID NO: 70          moltype = AA  length = 220
FEATURE                Location/Qualifiers
source                 1..220
                       mol_type = protein
                       organism = synthetic construct
SEQUENCE: 70
HGSSGTQILL TQSPVILSVS PGERVSFSCR ASQSIGTNIH WYQQRTNGSP RLLIKYASES  60
ISGIPSRFSG SGSGTDFTLS INSVESEDIA DYYCQQNNNW PTTFGAGTKL ELKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220
```